United States Patent …

(12) United States Patent
Sakurada et al.

(10) Patent No.: US 9,969,724 B2
(45) Date of Patent: May 15, 2018

(54) FACTOR IXA INHIBITORS

(71) Applicants: Isao Sakurada, Tokyo (JP); Tomokazu Hirabayashi, Tokyo (JP); Yoshitaka Maeda, Tokyo (JP); Hiroshi Nagasue, Tokyo (JP); Takashi Mizuno, Tokyo (JP); Jiayi Xu, Rahway, NJ (US); Ting Zhang, Rahway, NJ (US); Cameron Smith, Lawrenceville, NJ (US); Dann Parker, Rahway, NJ (US)

(72) Inventors: Isao Sakurada, Tokyo (JP); Tomokazu Hirabayashi, Tokyo (JP); Yoshitaka Maeda, Tokyo (JP); Hiroshi Nagasue, Tokyo (JP); Takashi Mizuno, Tokyo (JP); Jiayi Xu, Marlboro, NJ (US); Ting Zhang, Princeton Junction, NJ (US); Cameron Smith, Montgomery Village, MD (US); Dann Parker, Cranford, NJ (US)

(73) Assignees: Merck Sharp & Dohme Corp., Rahway, NJ (US); Mochida Pharmaceutical Co., Ltd., Tokyo (JP)

( * ) Notice: Subject to any disclaimer, the term of this patent is extended or adjusted under 35 U.S.C. 154(b) by 32 days.

(21) Appl. No.: 15/303,310

(22) PCT Filed: Apr. 10, 2015

(86) PCT No.: PCT/US2015/025229
§ 371 (c)(1),
(2) Date: Oct. 11, 2016

(87) PCT Pub. No.: WO2015/160636
PCT Pub. Date: Oct. 22, 2015

(65) Prior Publication Data
US 2017/0129880 A1    May 11, 2017

Related U.S. Application Data

(60) Provisional application No. 61/980,363, filed on Apr. 16, 2014.

(51) Int. Cl.
| | |
|---|---|
| A61K 31/506 | (2006.01) |
| C07D 413/14 | (2006.01) |
| C07D 471/04 | (2006.01) |
| C07D 413/04 | (2006.01) |
| C07D 417/14 | (2006.01) |
| C07D 498/04 | (2006.01) |
| C07D 519/00 | (2006.01) |
| A61K 31/423 | (2006.01) |
| A61K 31/428 | (2006.01) |
| A61K 31/437 | (2006.01) |

(Continued)

(52) U.S. Cl.
CPC .......... *C07D 413/14* (2013.01); *A61K 31/423* (2013.01); *A61K 31/428* (2013.01); *A61K 31/437* (2013.01); *A61K 31/4439* (2013.01); *A61K 31/497* (2013.01); *A61K 31/501* (2013.01); *A61K 31/506* (2013.01); *A61K 31/52* (2013.01); *A61K 45/06* (2013.01); *C07D 413/04* (2013.01); *C07D 417/14* (2013.01); *C07D 471/04* (2013.01); *C07D 498/04* (2013.01); *C07D 519/00* (2013.01)

(58) Field of Classification Search
None
See application file for complete search history.

(56) References Cited

U.S. PATENT DOCUMENTS

| 5,254,556 A | 10/1993 | Janssen et al. |
|---|---|---|
| 7,235,575 B2 | 6/2007 | Lam et al. |

(Continued)

FOREIGN PATENT DOCUMENTS

| WO | WO2013056060 A1 | 4/2013 |
|---|---|---|
| WO | WO2015160634 A1 | 10/2015 |

OTHER PUBLICATIONS

Al-Horani, et al., Potent Direct Inhibitors of Factor Xa Based on the Tetrahydroisoquinoline Scaffold, Eur J. Med Chem., 2012, 771-783, 54.

(Continued)

*Primary Examiner* — Deepak R Rao
*Assistant Examiner* — Laura M Daniel
(74) *Attorney, Agent, or Firm* — Nicole M. Beeler; John C. Todaro

(57) ABSTRACT

In its many embodiments, the present invention provides a novel class of benzamide compounds represented by Formula (I) or pharmaceutically acceptable salts or solvates thereof, or pharmaceutical compositions comprising one or more said compounds or pharmaceutically acceptable salts or solvates thereof, and methods for using said compounds or pharmaceutically acceptable salts or solvates thereof for treating or preventing a thromboses, embolisms, hypercoagulability or fibrotic changes.

20 Claims, No Drawings

(51) Int. Cl.
    *A61K 31/4439*    (2006.01)
    *A61K 31/497*     (2006.01)
    *A61K 31/501*     (2006.01)
    *A61K 31/52*      (2006.01)
    *A61K 45/06*      (2006.01)

(56) References Cited

U.S. PATENT DOCUMENTS

2006/0247238 A1    11/2006    Zbinden et al.
2008/0300251 A1    12/2008    Sattigeri et al.

OTHER PUBLICATIONS

International Search Report and Written Opinion for PCT/US2015/025229 dated Jul. 6, 2015; 6 pages.
Pubchem—CID 20718874, Created Dec. 5, 2007; 12 pages.

FACTOR IXA INHIBITORS

CROSS REFERENCE TO RELATED APPLICATIONS

This application is a U.S. National Phase application under 35 U.S.C. § 371 of PCT Application No. PCT/US15/025229 filed Apr. 10, 2015, which claims priority from U.S. Provisional Application Ser. No. 61/980,363, filed Apr. 16, 2014.

FIELD OF THE INVENTION

The invention relates to novel compounds of the Formula (I) having antithrombotic activity which, in particular, inhibit blood clotting factor IXa, to processes for their preparation and to use thereof as medicaments.

BACKGROUND OF THE INVENTION

Factor IXa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commences after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors.

The intrinsic pathway requires the clotting factors V, VIII, IX, X, XI and XII and also prekallikrein, high molecular weight kininogen, calcium ions and phospholipids from platelets.

The intrinsic pathway is initiated when prekallikrein, high molecular weight kininogen, factor XI and XII bind to a negatively charged surface. This point in time is designated as the contact phase. Exposure to vessel wall collagen is the primary stimulus of the contact phase. The result of the processes of the contact phase is the conversion of prekallikrein to kallikrein, which in turn activates factor XII. Factor XIIa hydrolyzes further prekallikrein to kallikrein, such that activation is the result. With increasing activation of factor XII, activation of factor XI occurs, which leads to a release of bradykinin, a vasodilator. As a result, the ending of the initial phase of vasoconstriction occurs. Bradykinin is formed from high molecular weight kininogen. In the presence of $Ca^{2+}$ ions, factor XIa activates factor IX. Factor IX is a proenzyme, which contains vitamin K-dependent, γ-carboxyglutamic acid (GLA) residues. The serine protease activity becomes noticeable after binding of $Ca^{2+}$ to these GLA residues. A number of the serine proteases of the blood clotting cascade (factors II, VII, IX and X) contain such vitamin K-dependent GLA residues. Factor IXa cleaves factor X and leads to activation to factor Xa. The prerequisite for the formation of factor IXa is the formation of a tenase complex from $Ca^{2+}$ and the factors VIIIa, IXa and X on the surface of activated platelets. One of the reactions of activated platelets is the presentation of phosphatidylserine and phosphatidylinositol along the surfaces. The exposure of these phospholipids first makes the formation of the tenase complex possible. Factor VIII in this process has the function of a receptor for the factors IXa and X. Factor VIII is therefore a cofactor in the clotting cascade. The activation of factor VIII with formation of factor VIIIa, the actual receptor, needs only a minimal amount of thrombin. With increase in the concentration of thrombin, factor VIIIa is finally cleaved further and inactivated by thrombin. This dual activity of thrombin in relation to factor VIII leads to a self-restriction of tenase complex formation and thus to a limitation of blood clotting.

The extrinsic pathway requires a tissue factor (TF) and clotting factors V, VII, VIII, IX and X. In the case of a vessel injury, the tissue factor (TF) accumulates with the clotting factor VII and the latter is activated. The complex of TF and clotting factor VII has two substrates, clotting factors X and IX.

Clotting factor IX can be activated by means of the intrinsic pathway and the extrinsic pathway. The activation of factor IXa is thus a central point of intersection between the two pathways of activation of clotting.

Factor IXa has an important role in blood clotting. Defects in factor IXa lead to hemophilia B, while increased concentrations of factor IXa in the blood lead to a significantly increased risk of thrombosis formation (Weltermann A, et al., J Thromb Haemost. 2003; 1: 28-32). The regulation of factor IXa activity can reduce thrombus formation in animal models (Feuerstein G Z, et al., Thromb Haemost. 1999; 82: 1443-1445). Vijaykumar et al., *Bioorganic & Medicinal Chemistry Letters* (2006), 16 (10), 2796-2799, discloses hydroxy pyrazole based factor IXa inhibitors.

Recently, compounds that antagonize Factor IXa antagonism have been disclosed in, for example, PCT Publication No. WO 2008/031508, PCT Publication No. WO 2008/031509, PCT Publication No. WO 2007/070826 pamphlet, PCT Publication No. WO 2008/076805 pamphlet, PCT Publication No. WO 2009/143039, PCT Publication No. WO 2010/065717, PCT Publication No. WO 2011/017296, PCT Publication No. WO 2011/025565, PCT Publication No. WO 20013/009527. However, these publications do not disclose the Benzamide derivatives of the instant invention.

In the development of pharmaceuticals, strict criteria are required for not only target pharmacological activity but also absorption, distribution, metabolism, excretion, and the like. It is also necessary to study drug interactions, desensitization or tolerance, digestive absorption in oral administration, the rate of transfer to the small intestine, the rate of absorption and first-pass effect, an organ barrier, protein binding, induction of a drug-metabolizing enzyme, an excretion pathway and body clearance, a method of administration (an application site, a method, and purpose), and the like. It is very difficult to discover a drug that satisfies all of these requirements.

These comprehensive problems in drug development might also exist for Factor IXa antagonists, and Factor IXa antagonists have not yet been released onto the market. More specifically, known compounds having a Factor IXa antagonism may also include problems in terms of usefulness and safety. For example, these compounds may have low absorption, and oral administration of these compounds may be difficult; these compounds also may exhibit inhibitory activity of the human ether-a-go-go related gene (hERG) channel, which may cause arrhythmia, and pharmacokinetics of these compounds might not satisfactory.

Accordingly, a compound in which these problems are solved and which has high activity has been desired.

SUMMARY OF THE INVENTION

In its many embodiments, the present invention provides a novel class of benzamide compounds represented by Formula (I) or an analogue, or pharmaceutically acceptable salts or solvates thereof, or pharmaceutical compositions comprising one or more said compounds or pharmaceutically acceptable salts or solvates thereof, and methods for using said compounds or pharmaceutically acceptable salts or solvates thereof for treating or preventing a thromboses, embolisms, hypercoagulability or fibrotic changes.

The compounds of the Formula (I) according to the invention are suitable for prophylactic and for therapeutic administration to humans who suffer from diseases which accompany thromboses, embolisms, hypercoagulability or fibrotic changes. They can be employed for secondary prevention and are suitable both for acute and for long-term therapy.

[1] In the first aspect, the present invention provides the compounds represented by Formula (I):

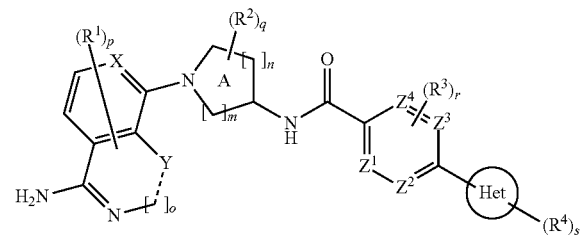

or a pharmaceutically acceptable salt thereof;
wherein: m is an integer of 1 to 2; n is an integer of 1 to 2; o is an integer of 0 or 1; p is an integer of 0 to 5; q is an integer of 0 to 4; r is an integer of 0 to 4; s is an integer of 0 to 4; X is a nitrogen atom or CH; Y is an oxygen atom, a sulfur atom or NH (when o=0), a nitrogen atom or CH (when o=1);

$Z_1$, $Z_2$, $Z_3$, $Z_4$ are each independently a nitrogen atom or CH;

each $R^1$ is independently a halogen atom, a cyano group, a $C_{1-6}$ alkyl group, a halogenated $C_{1-6}$ alkyl group, a hydroxyl $C_{1-6}$ alkyl group, a $C_{3-12}$ cycloalkyl group, a $C_{1-6}$ alkoxy group, a halogenated $C_{1-6}$ alkoxy group, a $C_{2-7}$ alkanoyl group or a group of —$NR^A R^B$;

$R^A$ and $R^B$ are each independently a hydrogen atom, a $C_{1-6}$ alkyl group, or a $C_{2-7}$ alkanoyl group;

each $R^2$ is independently a hydroxyl group, a $C_{1-6}$ alkyl group, a halogenated $C_{-6}$ alkyl group, a hydroxyl $C_{1-6}$ alkyl group, a $C_{1-6}$ alkoxy group, a halogenated $C_{1-6}$ alkoxy group, a $C_{6-14}$ aryl group, a heteroaryl group or oxo;

each $R^3$ is independently a halogen atom, a cyano group, a $C_{1-6}$ alkyl group, a halogenated $C_{1-6}$ alkyl group, a $C_{3-12}$ cycloalkyl group, a $C_{1-6}$ alkoxy group, or a halogenated $C_{1-6}$ alkoxy group;

each $R^4$ is independently a halogen atom, a cyano group, a $C_{1-6}$ alkyl group, a $C_{3-12}$ cycloalkyl group, a halogenated $C_{1-6}$ alkyl group, a hydroxy $C_{1-6}$ alkyl group, a cyanated $C_{1-6}$ alkyl group, a $C_{1-6}$ alkoxy group, a $C_{1-6}$ alkoxy $C_{1-6}$ alkyl group, a halogenated $C_{1-6}$ alkoxy group, a $C_{2-7}$ alkanoyl group, a $C_{1-6}$ alkylthio group, a $C_{1-6}$ alkylsulfonyl group, a group of —$NR^A R^B$ and oxo;

a dotted line in a bicyclic substructure of Formula (I) represented by Formula (II):

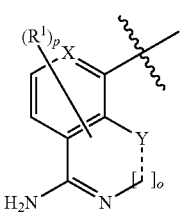

represents a single bond when o is 0, or a double bond when o is 1;
and

is heteroaryl.

In another aspect, the present invention provides processes and intermediates for making the compounds represented by the Formula (I) or pharmaceutically acceptable salts thereof.

In another aspect, compounds represented by the Formula (I) or a pharmaceutical acceptable salt or a solvate thereof can be useful for treating or preventing a disorder or disease mediated by factor IXa, or a thromboembolic disorder (each disorder being a "Condition").

In another aspect, the present invention provides pharmaceutical compositions comprising at least one compound of the Formula (I) or a pharmaceutically acceptable salt thereof. The composition can be useful for treating or preventing a Condition.

In another aspect, the present invention provides a method for treating a Condition, the method comprising administering to a patient an effective amount of at least one compound of Formula (I) or a pharmaceutically acceptable salt thereof.

In another aspect, the present invention provides the use of the compounds represented by the Formula (I) or pharmaceutically acceptable salts thereof for the manufacture of a medicament for treating a Condition.

In another aspect, the compounds represented by the Formula (I) or pharmaceutically acceptable salts thereof are suitable for prophylactic and for therapeutic administration to humans who suffer from diseases which accompany thromboses, embolisms, hypercoagulability or fibrotic changes. They can be employed for secondary prevention and are suitable both for acute and for long-term therapy.

DETAILED DESCRIPTION OF THE INVENTION

In an embodiment, the present invention provides compounds of the Formula (I) and/or pharmaceutically acceptable salts, and prodrugs thereof. The compounds of Formula (I) can be useful for treating or preventing a Condition in a patient.

As used in the compounds represented by the Formula (I) above embodiment [1], and throughout this disclosure, the following terms, unless otherwise indicated, shall be understood to have the following meanings:

In the explanation of the compound according to the present invention, for example, "$C_{x-y}$" indicates that the number of constituent carbon atoms, which is the number of carbon atoms in a linear, branched, or cyclic group unless otherwise indicated, is x to y. Therefore, as for an acyclic group, "$C_{1-6}$" means a "linear or branched chain with the number of constituent carbon atoms of 1 to 6". As for a cyclic group, "$C_{3-6}$" means a "cyclic group with the number of ring-constituting carbon atoms of 3 to 6". As for a group having an acyclic group and a cyclic group, "$C_{1-6}$" means a "group with the total number of carbon atoms of 1 to 6".

Except where noted, the term "halogen atom" as used herein refers to a fluorine atom, a chlorine atom, a bromine atom or an iodine atom.

Except where noted, the term "halogenated" as used herein refers to a substituent is optionally substituted with one to five "halogen atom".

Except where noted, the term "cyanated" as used herein refers to a substituent is optionally substituted with one to five "cyano group".

Except where noted, the term "$C_{1-6}$ alkyl group" as used herein refers to a linear or branched, saturated hydrocarbon having from 1 to 6 carbon atoms. Representative $C_{1-6}$ alkyl groups can be linear or branched, including, but not limited to, methyl, ethyl, propyl, isopropyl, butyl, isobutyl, sec-butyl, tert-butyl, pentyl, isopentyl, neopentyl, tert-pentyl, 1-methylbutyl, 2-methylbutyl, 3-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Commonly used abbreviations for "alkyl group" are used throughout the specification, e.g. methyl may be represented by conventional abbreviations including "Me" or "CH$_3$" or a symbol that is an extended bond as the terminal group,

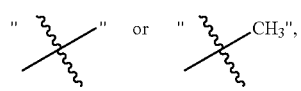

e.g. ethyl may be represented by "Et" or "—CH$_2$CH$_3$", or a symbol that is an extended bond as the terminal group, e.g.

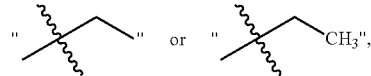

normalpropyl may be represented by "nPr" or "—CH$_2$CH$_2$CH$_3$", or a symbol that is an extended bond as the terminal group, e.g.

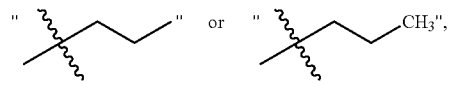

isopropyl may be represented by "iPr" or "—CH(CH$_3$)$_2$", or a symbol that is an extended bond as the terminal group, e.g.

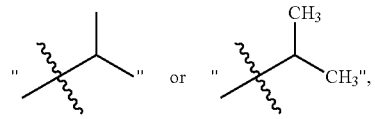

normalbutyl may be represented by "nBu" or "—CH$_2$CH$_2$CH$_2$CH$_3$", or a symbol that is an extended bond as the terminal group, e.g.

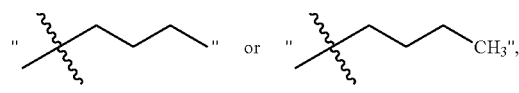

iso-butyl may be represented by "isoBu" or "—CH$_2$CH(CH$_3$)$_2$", or a symbol that is an extended bond as the terminal group, e.g.,

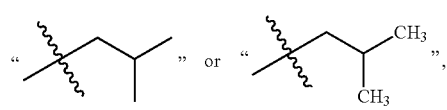

secondary-butyl may be represented by "secBu" or "—CH(CH$_3$)(CH$_2$CH$_3$)", or a symbol that is an extended bond as the terminal group, e.g.

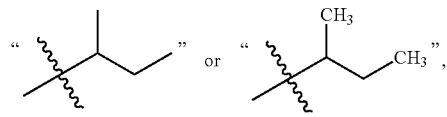

tertiary-butyl may be represented by "tertBu" or "—C(CH$_3$)$_3$", or a symbol that is an extended bond as the terminal group, e.g.

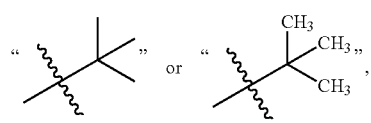

etc.

"$C_{1-6}$ alkyl" for example, means linear or branched chain alkyl groups, including all isomers, having the specified number of carbon atoms.

Except where noted, the term "halogenated $C_{1-6}$ alkyl group" as used herein refers to a group in which the "$C_{1-6}$ alkyl group" is optionally substituted with 1 to 5 halogen atom(s). Representative halogenated $C_{1-6}$ alkyl groups can be linear or branched and include,—but are not limited to, trifluoromethyl, difluoromethyl, fluoromethyl, 2,2,2-trifluoroethyl, 1,1,2,2-tetrafluoroethyl, pentafluoroethyl and the like.

Except where noted, the term "cyanated $C_{1-6}$ alkyl group" as used herein refers to a group in which the "$C_{1-6}$ alkyl group" is optionally substituted with 1 to 5 cyano group(s). Representative cyanated $C_{1-6}$ alkyl groups can be linear or branched and include—, but are not limited to, cyanomethyl, cyanoethyl, cyanopropyl, cyanocyclopropyl, and the like.

Except where noted, the term "hydroxy $C_{1-6}$ alkyl group" as used herein refers to a group in which the "$C_{1-6}$ alkyl group" is optionally substituted with one to five "hydroxy group (—OH)". Representative hydroxy $C_{1-6}$ alkyl groups can be linear or branched and include,—but are not limited to, hydroxymethyl, hydroxyethyl, hydroxypropyl, 2-hydroxy-2-methyl-ethyl, and the like.

Except where noted, the term "$C_{1-6}$ alkoxy group" as used herein refers to a group in which the "$C_{1-6}$ alkyl group" is substituted with an oxygen atom, and is represented by "RO—" (R=$C_{1-6}$ alkyl group). Representative $C_{1-6}$ alkoxy groups can be linear or branched and include, but are not limited to, methoxy, ethoxy, propoxy, isopropoxy, butoxy, isobutoxy, sec-butoxy, tert-butoxy, pentyloxy, isopentyloxy, neopentyloxy, tert-pentyloxy, 1-methylbutoxy, 2-methylbutoxy, 1,2-dimethylpropoxy, 1-ethylpropoxy, hexyloxy, isohexyloxy, 1-methylpentyloxy, 2-methylpentyloxy, 3-methylpentyloxy, 1,1-dimethylbutyloxy, 1,2-dimethylbutyloxy, 2,2-dimethylbutyloxy, 1,3-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy, 1-ethyl-2-methylpropyloxy, and the like.

Except where noted, the term "halogenated $C_{1-6}$ alkoxy group" as used herein refers to a group in which the "$C_{1-6}$ alkyl group" in the "$C_{1-6}$ alkoxy group" is optionally substituted with 1 to 5 halogen atom(s). Representative halogenated $C_{1-6}$ alkoxy groups can be linear or branched and include, but are not limited to, trifluoromethoxy, difluoromethoxy, fluoromethoxy, 2,2,2-trifluoroethoxy, 1,1,2,2-tetrafluoroethoxy, pentafluoroethoxy, and the like.

Except where noted, the term "$C_{1-6}$alkoxy-$C_{1-6}$alkyl group" as used herein refers to a group in which the "$C_{1-6}$ alkyl group" is optionally substituted with one to five "$C_{1-6}$alkoxy" group(s). Representative $C_{1-6}$ alkoxy-$C_{1-6}$ alkyl groups can be linear or branched and include, but are not limited to, methoxymethyl, methoxyethyl, methoxypropyl, ethoxymethyl, ethoxyethyl, ethoxypropyl, dimethoxymethyl, diethoxymethyl, and the like.

Except where noted, the term "$C_{2-7}$ alkanoyl group" as used herein refers to a group in which the "$C_{1-6}$ alkyl group" is substituted with a carbonyl group (C=O), and is represented by "RCO—" (R=$C_{1-6}$ alkyl group). Representative $C_{2-7}$ alkanoyl groups can be linear or branched and include, but are not limited to, acetyl, propionyl, butyryl, isobutyryl, valeryl, isovaleryl, pivaloyl, hexanoyl, heptanoyl, and the like.

Except where noted, the term "$C_{1-6}$ alkylthio group" as used herein refers to a group in which the "$C_{1-6}$ alkyl group" is substituted with a sulfur atom, and is represented by "RS—" (R=$C_{1-6}$ alkyl group). Representative $C_{1-6}$ alkylthio groups can be linear or branched and include, but are not limited to, methylthio, ethylthio, propylthio, isopropylthio, butylthio, isobutylthio, sec-butylthio, tert-butylthio, pentylthio, isopentylthio, neopentylthio, tert-pentylthio, 1-methylbutylthio, 2-methylbutylthio, 1,2-dimethylpropylthio, 1-ethylpropylthio, hexylthio, isohexylthio, 1-methylpentylthio, 2-methylpentylthio, 3-methylpentylthio, 1,1-dimethylbutylthio, 1,2-dimethylbutylthio, 2,2-dimethylbutylthio, 1,3-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio, 1-ethyl-2-methylpropylthio, and the like.

Except where noted, the term "$C_{1-6}$ alkylsulfonyl group" as used herein refers to a group in which the "$C_{1-6}$ alkyl group" is substituted with a sulfonyl group (—$SO_2$—), and is represented by "$RSO_2$—" (R=$C_{1-6}$ alkyl group). Representative $C_{1-6}$ alkylsulfonyl groups can be linear or branched and include, but are not limited to, methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, tert-pentylsulfonyl, neopentylsulfonyl, 2-methylbutylsulfonyl, 1,2-dimethylpropylsulfonyl, 1-ethylpropylsulfonyl, hexylsulfonyl, and the like.

Except where noted, the term "$C_{6-14}$ aryl group" as used herein refers to aromatic hydrocarbon ring having from 6 to 14 carbon atoms, and is represented by "Ar—". "$C_{6-14}$ aryl group" includes a monocyclic or ring-fused $C_{6-14}$ aryl group. Representative $C_{6-14}$ aryl groups include, but are not limited to, phenyl, 1-naphthyl, 2-naphthyl, anthryl, phenanthryl, acenaphthyl, and the like.

Examples of the "heterocyclic group" as used herein refers to a heteroaryl group, a partly hydrogenated heteroaryl group, and a saturated or unsaturated non-aromatic heterocyclic group.

The term "cyclic" used in "heterocyclic" means a monovalent group obtained by removing any hydrogen atom from a ring having a three to fourteen membered monocyclic ring or fused ring containing, in addition to carbon atoms, at least one (preferably one to four) heteroatom(s) arbitrarily selected from nitrogen atom, oxygen atom, and sulfur atom.

Except where noted, the term "heteroaryl group" as used herein refers to an aromatic heterocycle ring system having a six to fourteen membered monocycle or fused ring containing, in addition to carbon atoms, at least one heteroatom(s) selected from a nitrogen atom, oxygen atom, and sulfur atom. "Heteroaryl group" includes monocyclic or ring-fused heteroaryl group.

The "monocyclic heteroaryl group" preferably has five to seven ring members and representative monocyclic heteroaryl groups include, but are not limited to, pyrrolyl, furyl, thienyl, imidazolyl, pyrazolyl, oxazolyl, isoxazolyl, thiazolyl, isothiazolyl, 1,2,3-triazolyl, 1,2,4-triazolyl, 1,3,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,3,5-triazinyl, 2H-1,2,3-thiadiazinyl, 4H-1,2,4-thiadiazinyl, 6H-1,3,4-thiadiazinyl, 1,4-diazepinyl, 1,4-oxazepinyl, pyridine-2(1H)-one-yl, pyridazin-3(2H)-one-yl, pyrimidin-2(1H)-one, and the like.

The "ring-fused heteroaryl group" preferably has eight to twelve ring members and includes a monovalent group obtained by removing any hydrogen atom from a fused ring formed by fusing the five to seven membered heterocyclic ring and a monocyclic aryl group or a monocyclic heteroaryl group, and the like. The hydrogen atom is optionally removed from any of the fused rings.

The representative ring-fused heteroaryl groups include, but are not limited to, indolyl, isoindolyl, benzofuranyl, isobenzofuranyl, benzothienyl, isobenzothienyl, benzoxazolyl, 1,2-benzisoxazolyl, benzothiazolyl, 1,2-benzisothiazolyl, 1H-benzo[d]imidazolyl, 1H-indazolyl, 1H-benzotriazolyl, 2,1,3-benzothiadiazinyl, chromenyl, isochromenyl, 4H-1,4-benzoxazinyl, 4H-1,4-benzothiazinyl, quinolyl, isoquinolyl, cinnolinyl, quinazolinyl, quinoxalinyl, phthalazinyl, benzoxazepinyl, benzoazepinyl, benzodiazepinyl, naphthyridinyl, purinyl, pteridinyl, carbazolyl, carbolinyl, acridinyl, phenoxazinyl, phenothiazinyl, phenazinyl, phenoxathiinyl, thianthrenyl, phenanthridinyl, phenanthrolinyl, indolizinyl, thieno[3,2-c]pyridyl, thiazolo[5,4-c]pyridyl, pyrrolo[1,2-b]pyridazinyl, pyrazolo[1,5-a]pyridyl, imidazo[1,2-a]pyridyl, imidazo[1,5-a]pyridyl, imidazo[4,5-b]pyridine, imidazo[1,2-b]pyridazinyl, imidazo[1,5-a]pyrimidinyl, 1,2,4-triazolo[4,3-a]pyridyl, 1,2,4-triazolo[4,3-b]pyridazinyl, 1H-pyrazolo[3,4-b]pyridyl, 1,2,4-triazolo[1,5-a]pyrimidinyl, and the like.

The representative partly hydrogenated heteroaryl groups include, but are not limited to, indolinyl, dihydrobenzofuranyl, dihydrobenzoxazolyl, dihydrobenzothiazolyl, chromanyl, isochromanyl, 3,4-dihydro-2H-1,4-benzoxazinyl, 3,4-dihydro-2H-1,4-benzothiazinyl, tetrahydroquinolyl, tetrahydroisoquinolyl, tetrahydroquinoxalinyl, 1,3-benzodioxanyl, 1,4-benzodioxanyl, 1,3-benzodioxolyl, tetrahydrobenzoxazepinyl, tetrahydrobenzoazepinyl, and 6,7,8,9-tetrahydro-5H-cyclohepta[b]pyridyl.

The "partly hydrogenated ring-fused heteroaryl group" is preferably one having eight to twelve ring members, namely a monovalent group obtained by removing any hydrogen atom from a ring which is partly hydrogenated in the fused ring formed by fusing the five to seven membered heterocyclic ring and a monocyclic aryl group or a monocyclic heteroaryl group. The hydrogen atom to be removed is optionally a hydrogen atom in the aryl group or in the heterocyclic moiety or a hydrogen atom in the hydrogenated moiety. In the case of tetrahydroquinolyl, examples of the partially hydrogenated ring-condensed heteroaryl group include 5,6,7,8-tetrahydroquinolyl and 1,2,3,4-tetrahydroquinolyl. Depending on the position in these groups from which the hydrogen atom is removed, -2-yl, -3-yl, -4-yl, -5-yl, -6-yl, -7-yl, and -8-yl are exemplified in the case of 5,6,7,8-tetrahydroquinolyl, and in the case of 1,2,3,4-tetrahydroquinolyl, -1-yl, -2-yl, -3-yl, -4-yl, -5-yl, -6-yl, -7-yl, and -8-yl are exemplified.

Except where noted, the term "non aromatic heterocyclic group" as used herein refers to "saturated or unsaturated three to fourteen membered heterocycle" which ring systems having three to fourteen carbon atoms which one, two, three or four identical or different heteroatoms from the group consisting of an oxygen atom, a nitrogen atom or a sulfur atom can replace the respective carbon atoms. Representative non aromatic heterocyclic groups include, but are not limited to, aziridinyl, azetidinyl, oxiranyl, thiranyl, oxetanyl, thietanyl, pyrolidinyl, 2-azabicyclo[2.2.1]heptanyl, 7-azabicyclo[2.2.1]heptanyl, tetrahydrofuryl, dihydrofuryl, thiolanyl, pyrazolinyl, pyrazolidinyl, imidazolidinyl, piperidinyl, dihydropyranyl, tetrahydropyranyl (oxanyl), tetrahydrothiopyranyl, piperazinyl, dioxanyl, oxazolinyl, isoxazolinyl, 1,3-oxazolidinyl, oxazolidinyl, isoxazolidinyl, thiazolinyl, isothiazolinyl, 1,3-thiazolidinyl, isothiazolidinyl, oxadiazolinyl, 1,3,4-oxadiazolidinyl, morpholinyl, thiomorpholinyl, quinuclidinyl, azepanyl, diazepinyl, oxepanyl and the like.

Except where noted, the term "$C_{3-12}$ cycloalkyl group" as used herein refers to monocyclic or bicyclic hydrocarbons which ring systems having three to twelve carbon atoms in the ring. The representative partly $C_{3-12}$ cycloalkyl groups include, but are not limited to, cyclopropyl, cyclobutyl, cyclopentyl, cyclohexyl, cycloheptyl, cyclooctyl, bicyclo[4.2.0]octyl, octahydroindenyl, decahydronaphthalenyl, decahydroazulenyl, decahydrobenzocycloheptenyl, dodecahydroheptalenyl, spiro[2.5]octanyl, spiro[3.4]octanyl, spiro[3.5]nonanyl, bicyclo[3.1.1]heptanyl, bicyclo[2.2.1]heptanyl, bicyclo[2.2.2]octanyl, and the like.

Except where noted, the term "halogenated $C_{1-6}$alkoxy group" as used herein refers to a group in which $C_{1-6}$alky group in the "$C_{1-6}$alkoxy group" is optionally substituted with 1 to 5 halogen atom(s). Representative $C_{1-6}$alkoxy groups can be linear or branched and include,—but are not limited to, trifluoromethoxy, difluoromethoxy, fluoromethoxy, 2,2,2-trifluoroethoxy, 1,1,2,2-tetrafluoroethoxy, pentafluoroethoxy, and the like.

Except where noted, the term "$C_{2-6}$ alkenyl group" as used herein refers to a monovalent group obtained by removing any hydrogen atom from carbon atoms of an alkene group. The term "alkene group" means linear and branched hydrocarbons having from 2 to 6 carbon atoms with a carbon-carbon double bond. Representative $C_{2-6}$ alkenyl groups include—but are not limited to, vinyl, allyl, isopropenyl, 2-methylallyl, butenyl, pentenyl, isopentenyl, hexenyl, and the like. Representative $C_{2-6}$ cycloalkenyl groups include 1-cyclopropen-1-yl, 2-cyclopropen-1-yl, 1-cyclobuten-1-yl, 1-cyclopenten-1-yl, 2-cyclopenten-1-yl, 3-cyclopenten-1-yl, 1-cyclohexen-1-yl, 2-cyclohexen-1-yl, 3-cyclohexen-1-yl, 2,4-cyclopentadien-1-yl, 2,5-cyclohexadien-1-yl, and the like.

Except where noted, the term "$C_{2-6}$ alkynyl group" as used herein refers to a monovalent group obtained by removing any hydrogen atom from carbon atoms of an alkyne group. The term "alkyne group" means linear and branched hydrocarbons having from 2 to 6 carbon atoms with a carbon-carbon triple bond. Representative $C_{2-6}$ alkynyl groups include, but are not limited to, ethynyl, 1-propynyl, 2-propynyl, butynyl, pentynyl, hexynyl, and the like.

Except where noted, the term "$C_{7-20}$ aralkyl group," as used herein refers to a group in which a "$C_{1-6}$ alkyl group" is substituted with a "$C_{6-14}$ aryl group". Representative $C_{7-20}$ aralkyl groups include, but are not limited to, benzyl, phenethyl, 3-phenylpropyl, 1-naphthylmethyl, 2-naphthylmethyl, 2-(1-naphthyl)ethyl, 2-(2-naphthyl)ethyl, 1-indanylmethyl, 2-indanylmethyl, 1,2,3,4-tetrahydronaphthalen-1-ylmethyl, 1,2,3,4-tetrahydronaphthalen-2-ylmethyl, and the like.

Except where noted, the term "heterocyclic $C_{1-6}$ alkyl group" as used herein refers to a group in which a "heterocyclic group" is substituted with a "$C_{1-6}$ alkyl group". Representative heterocyclic $C_{1-6}$ alkyl groups include, but are not limited to, pyrrolylmethyl, furylmethyl, thienylmethyl, imidazolylmethyl, pyrazolylmethyl, oxazolylmethyl, isoxazolylmethyl, thiazolylmethyl, isothiazolylmethyl, 1,2,3-triazolylmethyl, 1,2,4-triazolylmethyl, 1,2,3-oxadiazolylmethyl, 1,2,4-oxadiazolylmethyl, 1,3,4-oxadiazolylmethyl, furazanylmethyl, 1,2,3-thiadiazolylmethyl, 1,2,4-thiadiazolylmethyl, 1,3,4-thiadiazolylmethyl, tetrazolylmethyl, pyridylmethyl, pyridazinylmethyl, pyrimidinylmethyl, pyrazinylmethyl, 1,2,3-triazinylmethyl, 1,2,4-triazinylmethyl, 1,3,5-triazinylmethyl, 2H-1,2,3-thiadiazinylmethyl, 4H-1,2,4-thiadiazinylmethyl, 6H-1,3,4-thiadiazinylmethyl, 1,4-diazepinylmethyl, 1,4-oxazepinylmethyl, indolylmethyl, isoindolylmethyl, benzofuranylmethyl, isobenzofuranylmethyl, benzothienylmethyl, isobenzothienylmethyl, benzoxazolylmethyl, 1,2-benzisoxazolylmethyl, benzothiazolylmethyl, 1,2-benzisothiazolylmethyl, 1H-benzimidazolylmethyl, 1H-indazolylmethyl, 1H-benzotriazolylmethyl, 2,1,3-benzothiadiazinylmethyl, chromenylmethyl, isochromenylmethyl, 4H-1,4-benzoxazinylmethyl, 4H-1,4-benzothiazinylmethyl, quinolylmethyl, isoquinolylmethyl, cinnolinylmethyl, quinazolinylmethyl, quinoxalinylmethyl, phthalazinylmethyl, benzoxazepinylmethyl, benzoazepinylmethyl, benzodiazepinylmethyl, naphthyridinylmethyl, purinylmethyl, pteridinylmethyl, carbazolylmethyl, carbolinylmethyl, acridinylmethyl, phenoxazinylmethyl, phenothiazinylmethyl, phenazinylmethyl, phenoxathiinylmethyl, thianthrenylmethyl, phenanthridinylmethyl, phenanthrolinylmethyl, indolizinylmethyl, thieno[3,2-c]pyridylmethyl, thiazolo[5,4-c]pyridylmethyl, pyrrolo[1,2-b]pyridazinylmethyl, pyrazolo[1,5-a]pyridylmethyl, imidazo[1,2-a]pyridylmethyl, imidazo[1,5-a]pyridylmethyl, imidazo[1,2-b]pyridazinylmethyl, imidazo[1,5-a]pyrimidinylmethyl, 1,2,4-triazolo[4,3-a]pyridylmethyl, 1,2,4-triazolo[4,3-b]pyridazinylmethyl, 1H-pyrazolo[3,4-b]pyridylmethyl, 1,2,4-triazolo[1,5-a]pyrimidinylmethyl, indolinylmethyl, dihydrobenzofuranylmethyl, chromanylmethyl, tetrahydroquinolylmethyl, tetrahydroisoquinolylmethyl, 1,4-benzodioxanylmethyl, 1,3-benzodioxolylmethyl, aziridinylmethyl, azetidinylmethyl, oxiranylmethyl, thiranylmethyl, oxetanylmethyl, thietanylmethyl, pyrolidinylmethyl, tetrahydrofurylmethyl, dihydrofurylmethyl, thiolanylmethyl, pyrazolinylmethyl, pyrazolidinylmethyl, imidazolidinylmethyl, piperidinylmethyl, dihydropyranylmethyl, tetrahydropyranylmethyl, tetrahydrothiopyranylmethyl, piperazinylmethyl, dioxanylmethyl, oxazolinylmethyl, isoxazolinylmethyl, 1,3-oxazolidinylmethyl, oxazolidinylmethyl, isoxazolidinylmethyl, thiazolinylmethyl, isothiazolinylmethyl, 1,3-thiazolidinylmethyl, isothiazolidinylmethyl, oxadiazolinylmethyl, 1,3,4-oxadiazolidinylmethyl, morpholinylmethyl, thiomorpholinylmethyl, quinuclidinylmethyl, azepanylmethyl, diazepinylmethyl, oxepanylmethyl, and the like.

Except where noted, the term "halogenated $C_{6-14}$ aryl group" as used herein refers to a group in which the "$C_{6-14}$ aryl" is substituted with 1 to 5 halogen atom(s). Representative halogenated $C_{6-14}$ aryl groups include, but are not limited to, fluoro benzene, chloro benzene, bromo benzene, iodo benzene, difluoro benzene, dichloro benzene, dibromo benzene, diiodo benzene, trifluoro benzene, trichloro benzene, tribromo benzene, triiodo benzene, chloro fluoro benzene, bromo chloro benzene, chloro iodo benzene, bromo fluoro benzene, fluoro iodo benzene, and the like.

Except where noted, the term "halogenated $C_{7-20}$ aralkyl group" as used herein refers to a group in which the "$C_{7-20}$ aralkyl" is substituted with 1 to 5 halogen atom(s). Representative halogenated $C_{7-20}$ aralkyl groups include, but are not limited to, fluorobenzyl, chlorobenzyl, bromobenzyl, iodobenzyl, difluorobenzyl, dichlorobenzyl, dibromobenzyl, diiodobenzyl, trifluorobenzyl, trichlorobenzyl, tribromobenzyl, triiodobenzyl, chloro fluoro benzyl, bromo chloro benzyl, chloro iodo benzyl, bromo fluoro benzyl, fluoro iodo benzyl, and the like.

Except where noted, the term "halogenated heterocycle group" as used herein refers to a group in which the "heterocycle" is substituted with 1 to 5 halogen atom(s). Representative halogenated heterocycle groups include, but are not limited to, chloropyrrolyl, bromofuryl, bromothienyl, chloroimidazolyl, chloropyrazolyl, chloro-1,2,3-triazolyl, chloro-1,2,4-triazolyl, chloro-1,3,4-triazolyl, chloropyridyl, chloropyridazinyl, chloropyrimidinyl, chloro pyrazinyl, chloro pyridine-2(1H)-one-yl, chloropyridazin-3(2H)-one-yl, chloropyrimidin-2(1H)-one, bromoindolyl, chlorobenzofuranyl, bromo-1H-benzo[d]imidazolyl, bromo-imidazo[4,5-b]pyridine, bromo-1,2,4-triazolo[4,3-a]pyridyl, chloroaziridinyl, chloroazetidinyl, chlorooxiranyl, chlorotetrahydrofuryl, chloropiperidinyl, chloropiperazinyl, chlorooxazolinyl, chlorooxazolidinyl, and the like.

Except where noted, the term "halogenated heterocyclic $C_{1-6}$alkyl group" as used herein refers to a group in which the "$C_{1-6}$alkyl" is substituted with the "halogenated heterocycle group". Representative halogenated heterocyclic $C_{1-6}$alkyl groups include, but are not limited to, chloropyrrolylmethyl, bromofurylmethyl, bromothienylmethyl, chloroimidazolylmethyl, chloropyrazolylmethyl, chloro-1,2,3-triazolylmethyl, chloro-1,2,4-triazolylmethyl, chloro-1,3,4-triazolylmethyl, chloropyridylmethyl, chloropyridazinylmethyl, chloropyrimidinylmethyl, chloro pyrazinylmethyl, chloro pyridine-2(1H)-one-yl methyl, chloropyridazin-3(2H)-one-yl methyl, chloropyrimidin-2(1H)-one methyl, bromoindolylmethyl, chlorobenzofuranylmethyl, bromo-1H-benzo[d]imidazolylmethyl, bromo-imidazo[4,5-b]pyridinemethyl, bromo-1,2,4-triazolo[4,3-a]pyridylmethyl, chloroaziridinylmethyl chloroazetidinylmethyl, chlorooxiranylmethyl, chlorotetrahydrofuryl methyl, chloropiperidinyl methyl, chloropiperazinyl methyl, chlorooxazolinyl methyl, chlorooxazolidinyl methyl, and the like.

Except where noted, the term "cyanated $C_{6-14}$ aryl group" as used herein refers to a group in which the "$C_{6-14}$ aryl" is substituted with 1 to 5 cyano group (s). Representative cyanated $C_{6-14}$ aryl groups include, but are not limited to, such as 2-cyanophenyl, 2,3-dicyanophenyl, 2,4,6-tricyanophenyl, 1-cyanonaphtyl, 2-cyanonaphtyl, and the like.

Except where noted, the term "cyanated $C_{7-20}$ aralkyl group" as used herein refers to a group in which the "$C_{7-20}$ aralkyl" is substituted with 1 to 5 cyano group (s). Representative cyanated $C_{7-20}$ aralkyl groups include, but are not limited to, 2-cyanobenzyl, 2,3-dicyanobenzyl, 2,4,6-tricyanobenzyl, and the like.

Except where noted, the term "cyanated heterocycle group" as used herein refers to a group in which the "heterocycle" is substituted with 1 to 5 cyano group (s). Representative cyanated heterocycle groups include, but are not limited to, 2-cyano-pyrrolyl, 2-cyano-furyl, 2-cyano-thienyl, 4-cyano-imidazolyl, 3-cyano-pyrazolyl, 4-cyano-1,2,3-triazolyl, 3-cyano-1,2,4-triazolyl, 2-cyano-1,3,4-triazolyl, 2-cyano pyridyl, 2-cyano pyridazinyl, 4-cyano pyrimidinyl, 2-cyano pyrazinyl, 3-cyano pyridine-2(1H)-one-yl, 3-cyano pyridazin-3(2H)-one-yl, 3-cyano pyrimidin-2(1H)-one, 3-cyano indolyl, 3-cyano benzofuranyl, 5-cyano-1H-benzo[d]imidazolyl, cyano-imidazo[4,5-b]pyridine, cyano-1,2,4-triazolo[4,3-a]pyridyl, 2-cyano aziridinyl, 2-cyano azetidinyl, 2-cyano oxiranyl, 3-cyano tetrahydrofuryl, 4-cyano piperidinyl, 2-cyano piperazinyl, cyano oxazolinyl, cyano oxazolidinyl, and the like.

Except where noted, the term "cyanated heterocyclic $C_{1-6}$alkyl, group" as used herein refers to a group in which the "$C_{1-6}$alkyl" is substituted with the "cyanated heterocyclic group". Representative cyanated heterocyclic $C_{1-6}$alkyls include, but are not limited to, 2-cyano-pyrrolylmethyl, 2-cyano-furylmethyl, 2-cyano-thienylmethyl, 4-cyano-imidazolylmethyl, 3-cyano-pyrazolylmethyl, 4-cyano-1,2,3-triazolylmethyl, 3-cyano-1,2,4-triazolylmethyl, 2-cyano-1,3,4-triazolylmethyl, 2-cyano pyridylmethyl, 2-cyano pyridazinylmethyl, 4-cyano pyrimidinylmethyl, 2-cyano pyrazinylmethyl, 3-cyano pyridine-2(1H)-one-yl-methyl, 3-cyano pyridazin-3(2H)-one-yl-methyl, 3-cyano pyrimidin-2(1H)-one-methyl, 3-cyano indolyl methyl, 3-cyanobenzofuranyl methyl, 5-cyano-1H-benzo[d]imidazolyl methyl, cyano-imidazo[4,5-b]pyridine methyl, cyano-1,2,4-triazolo[4,3-a]pyridylmethyl, 2-cyano aziridinylmethyl, 2-cyano azetidinylmethyl, 2-cyano oxiranylmethyl, 3-cyano tetrahydrofurylmethyl, 4-cyano piperidinylmethyl, 2-cyano piperazinylmethyl, cyano oxazolinylmethyl, cyano oxazolidinylmethyl, and the like.

Except where noted herein, the "alkyl groups" in the "$C_{1-6}$alkyl groups", "halogenated $C_{1-6}$ alkyl group", "cyanated $C_{1-6}$ alkyl group", "hydroxyl $C_{1-6}$ alkyl group", "$C_{1-6}$ alkoxy group", "halogenated $C_{1-6}$ alkoxy group", "$C_{2-7}$ alkanoyl group", "$C_{1-6}$ alkylthio group", "$C_{1-6}$ alkylsulfonyl group", or "$C_{1-6}$ alkoxy $C_{1-6}$ alkyl group" may be optionally substituted with one to three substituents on any one or more carbon atoms, with halogen atom, $C_{1-6}$ alkyl, halogenated $C_{1-6}$ alkyl, —NH$_2$, —NH($C_{1-6}$ alkyl), —N($C_{1-6}$ alkyl)$_2$, —NO$_2$, oxo, cyano, —N$_3$, —OH, $C_{1-6}$ alkoxyl, $C_{3-12}$ cycloalkyl, $C_{2-6}$ alkenyl, $C_{2-6}$ alkynyl, $C_{1-6}$ alkylthio, $C_{1-6}$ alkylsulfonyl, —SH, $C_{1-6}$ alkylthio-$C_{1-6}$ alkyl, $C_{1-6}$ alkylsulfonyl-$C_{1-6}$ alkyl, —$C_{1-6}$alkyl-SH, —NHC(O)$C_{1-6}$ alkyl, —C(=NH)NH$_2$, halogenated $C_{1-6}$alkoxyl, CHO, $C_{2-7}$ alkanoyl, —COOH, —COO($C_{1-6}$alkyl), hydroxyl $C_{1-6}$ alkyl, $C_{1-6}$ alkoxyl-$C_{1-6}$ alkyl, $C_{2-7}$ alkanoyl-$C_{1-6}$ alkyl, $C_{1-6}$ alkyl-COO—$C_{1-6}$ alkyl, $C_{1-6}$ alkyl-CHO, $C_{1-6}$ alkyl-COOH, —OC$_{2-7}$ alkanoyl, —NHC(O)OH, —NHCOO—$C_{1-6}$ alkyl, $C_{6-14}$aryl, $C_{7-20}$ aralkyl, heteroaryl, non aromatic heterocycle, heterocyclic $C_{1-6}$ alkyl, halogenated $C_{6-14}$ aryl, halogenated $C_{7-20}$ aralkyl, halogenated heterocycle, halogenated heterocyclic $C_{1-6}$ alkyl, cyanated $C_{6-14}$ aryl, cyanated $C_{7-20}$ aralkyl, cyanated heterocycle and cyanated heterocyclic $C_{1-6}$ alkyl, where such substitution results in formation of a stable compound.

Except where noted, the "$C_{6-14}$ aryl group" may be unsubstituted or substituted with one or more of $C_{1-6}$ alkyl group, hydroxyl group, $C_{1-6}$ alkoxy group, halogen atom, amino group or —NR$_A$R$_B$ (R$^A$ and R$^B$ are each independently a hydrogen atom, a $C_{1-6}$ alkyl group, a halogenated $C_{1-6}$ alkyl group or a $C_{2-7}$ alkanoyl group).

Except where noted, the "$C_{6-14}$ aryl groups" and the "$C_{3-12}$ cycloalkyl groups" may be unsubstituted, or substituted on any one or more carbon atoms, with halogen atom, $C_{1-6}$ alkyl, halogenated $C_{1-6}$ alkyl, —NH$_2$, —NH($C_{1-6}$ alkyl), —N($C_{1-6}$ alkyl)$_2$, —NO$_2$, oxo, cyano, —N$_3$, —OH, $C_{1-6}$ alkoxyl, $C_{3-12}$ cycloalkyl, $C_{2-6}$ alkenyl, $C_{2-6}$ alkynyl, $C_{1-6}$ alkylthio, $C_{1-6}$ alkylsulfonyl, —SH, $C_{1-6}$ alkylthio-$C_{1-6}$ alkyl, $C_{1-6}$ alkylsulfonyl-$C_{1-6}$ alkyl, —$C_{1-6}$alkyl-SH, —NHC(O)$C_{1-6}$ alkyl, —C(=NH)NH$_2$, halogenated $C_{1-6}$alkoxyl, CHO, $C_{2-7}$ alkanoyl, —COOH, —COO($C_{1-6}$ alkyl), hydroxyl $C_{1-6}$ alkyl, $C_{1-6}$ alkoxyl-$C_{1-6}$ alkyl, $C_{2-7}$ alkanoyl-$C_{1-6}$ alkyl, $C_{1-6}$ alkyl-COO—$C_{1-6}$ alkyl, $C_{1-6}$ alkyl-CHO, $C_{1-6}$ alkyl-COOH, —OC$_{2-7}$ alkanoyl, —NHC(O)OH, —NHCOO—$C_{1-6}$ alkyl, $C_{6-14}$aryl, $C_{7-20}$ aralkyl, heteroaryl, non aromatic heterocycle, heterocyclic $C_{1-6}$ alkyl, halogenated $C_{6-14}$ aryl, halogenated $C_{7-20}$ aralkyl, halogenated heterocycle, halogenated heterocyclic $C_{1-6}$ alkyl, cyanated $C_{6-14}$ aryl, cyanated $C_{7-20}$ aralkyl, cyanated heterocycle and cyanated heterocyclic $C_{1-6}$ alkyl, where such substitution results in formation of a stable compound.

Except where noted, the "heteroaryl group", the "non aromatic heterocycle group" and the "partly hydrogenated ring-fused heteroaryl group" may be unsubstituted, or substituted on any one or more carbon atoms, with halogen atom, $C_{1-6}$ alkyl, halogenated $C_{1-6}$ alkyl, —NH$_2$, —NH($C_{1-6}$ alkyl), —N($C_{1-6}$ alkyl)$_2$, —NO$_2$, oxo, cyano, —N$_3$, —OH, $C_{1-6}$ alkoxyl, $C_{3-12}$ cycloalkyl, $C_{2-6}$ alkenyl, $C_{2-6}$ alkynyl, $C_{1-6}$ alkylthio, $C_{1-6}$ alkylsulfonyl, —SH, $C_{1-6}$ alkylthio-$C_{1-6}$ alkyl, $C_{1-6}$ alkylsulfonyl-$C_{1-6}$ alkyl, —$C_{1-6}$alkyl-SH, —NHC(O)$C_{1-6}$ alkyl, —C(=NH)NH$_2$, halogenated $C_{1-6}$alkoxyl, CHO, $C_{2-7}$ alkanoyl, —COOH, —COO($C_{1-6}$ alkyl), hydroxyl $C_{1-6}$ alkyl, $C_{1-6}$ alkoxyl-$C_{1-6}$ alkyl, $C_{2-7}$ alkanoyl-$C_{1-6}$ alkyl, $C_{1-6}$ alkyl-COO—$C_{1-6}$ alkyl, $C_{1-6}$ alkyl-CHO, $C_{1-6}$ alkyl-COOH, —OC$_{2-7}$ alkanoyl, —NHC(O)OH, —NHCOO—$C_{1-6}$ alkyl, $C_{6-14}$ aryl, $C_{7-20}$ aralkyl, heteroaryl, non aromatic heterocycle, heterocyclic $C_{1-6}$ alkyl, halogenated $C_{6-14}$ aryl, halogenated $C_{7-20}$ aralkyl, halogenated heterocycle, halogenated heterocyclic $C_{1-6}$ alkyl, cyanated $C_{6-14}$ aryl, cyanated $C_{7-20}$ aralkyl, cyanated heterocycle and cyanated heterocyclic $C_{6-14}$alkyl, or independently or additionally substituted with 1 substituent on any one or more nitrogen atoms, with $C_{1-6}$ alkyl, oxo, $C_{3-12}$ cycloalkyl, $C_{2-6}$ alkenyl, $C_{2-6}$ alkynyl, $C_{6-14}$ aryl, —$C_{2-7}$ alkanoyl, —C(O)NHC$_{1-6}$ alkyl, —C(O) NH$_2$, —$C_{1-6}$ alkyl-C(O)NH$_2$, —$C_{1-6}$ alkoxy-C(O)NH$_2$, or independently or additionally substituted with 1 substituent on any one or more sulfur atoms, with $C_{1-6}$ alkyl, oxo, $C_{3-12}$ cycloalkyl, $C_{2-6}$ alkenyl, $C_{2-6}$ alkynyl, $C_{6-14}$ aryl, where such substitution results in formation of a stable compound.

Except where noted, structures containing substituent variables such as variable "R" below:

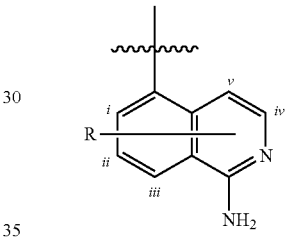

which are depicted as not being attached to any one particular bicycle carbon atom, represent structures in which the variable can be optionally attached to any bicycle carbon atom. For example, variable R shown in the above structure can be attached to any one of 6 bicycle carbon atoms i, ii, iii, iv or v.

Functional groups of the intermediates used, for example amino or carboxyl groups, can be masked here by suitable protective groups. Suitable protective groups for amino functions are, for example, para methoxy benzyl, benzyl, t-butoxycarbonyl, benzyloxycarbonyl, phthalolyl, trityl or tosyl protective group. Suitable protective groups for the carboxyl function are, for example, alkyl, aryl or arylalkyl esters. Protective groups can be introduced and removed by techniques which are well-known or described here (see Greene, T. W., et. al., *Protective Groups in Organic Synthesis* (2007), 4th Ed., Wiley, New York, or Kocienski, P., *Protecting Groups* (1994), Thieme). The term protective group can also include polymer-bound protective groups. Such masked compounds according to Formula (I), in which, for example, the functional groups of the radicals R$^1$, R$^2$, R$^3$, R$^4$ or R$^5$ can optionally also be masked, can, although optionally themselves not pharmacologically active, optionally be converted after administration to mammals by metabolization to the pharmacologically active compounds according to the invention.

When any variable (e.g., aryl, R$^1$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

In the embodiments described below of the present invention, unless otherwise noted, the definitions of m, n, o, p, q, r, s, X, Y, $R^1$, $R^2$, $R^3$, $R^4$, $R^5$, a substructure of bicycle represented by Formula (II), a substructure of ring A represented by Formula (III), Het and a substructure of ring B represented by Formula (V) shown in the each descriptions are the same as defined above for the Formula (I).

In the embodiments, compounds having Factor IXa antagonistic activity (determined by, for example, pharmacological examples described below: a measurement of fluorescence value using microtiter plate reader, ARVO 1420 Multilabel Counter) of 5 μM or less, preferably 1 μM or less, more preferably 500 nM or less, and the most preferably 100 nM or less in terms of an $IC_{50}$ value are preferably used.

In the embodiments described in this description, "agent" or "drug" means a material which is used for improvement of disease or symptom, not only for treatment of disease or symptom.

In all the above embodiments, when the term "compound" is used, the term also refers to pharmaceutically acceptable salts thereof.

The compounds of the present invention have asymmetric carbon atoms. Accordingly, the compounds of the present invention include mixtures of various stereoisomers, such as geometrical isomers, tautomers, such as keto- and enol-tautomers, or amidino- and imidino-tautomers, and optical isomers, and isolated isomers. For example, the compounds of Formula (I), Formula (I-a) and Formula (VII) may have (R) and (S) optical isomers at a substructure of ring A represented by Formula (III).

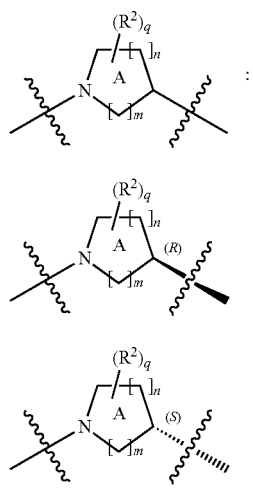

A specific example of (R) isomer compound is, for example, (R)—N-(1-(3-Amino-4-chlorobenzo[d]isoxazol-7-yl)pyrrolidin-3-yl)-2-chloro-4-(4H-1,2,4-triazol-4-yl)benzamide (EXAMPLE 9). Racemic compounds, for example, N-(1-(3-Aminobenzo[d]isoxazol-7-yl)pyrrolidin-3-yl)-2-chloro-4-(4H-1,2,4-triazol-4-yl)benzamide (EXAMPLE 1) can be separated into (R) isomer compounds and (S) isomer compounds by using a method of separation, for example, High Performance Liquid Chromatography (HPLC) with chriral columns. (R) isomer compounds and (S) isomer compounds may be synthesized by using asymmetric synthesis with appropriate starting materials. The isolation and the purification of such stereoisomers can be performed by those skilled in the art with a known technique such as optical resolution using preferential crystallization or column chromatography, or asymmetric synthesis.

Absolute stereochemistry may be determined by X-ray crystallography of crystalline products or crystalline intermediates which are derivatized, if necessary, with a reagent containing a stereogenic center of known configuration.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids.

The compounds represented by Formula (I) of the present invention may form acid addition salts. Alternatively, these compounds may form salts with a base according to the type of substituent. These salts are not particularly limited as long as the salts are pharmaceutically acceptable salts. Specific examples of the salts include acid addition salts with a mineral acid such as hydrochloric acid, hydrobromic acid, hydroiodic acid, sulfuric acid, nitric acid, or phosphoric acid; an organic carboxylic acid such as an aliphatic monocarboxylic acid, e.g., formic acid, acetic acid, trifluoroacetic acid (TFA), propionic acid, butyric acid, valeric acid, enanthic acid, capric acid, myristic acid, palmitic acid, stearic acid, lactic acid, sorbic acid, or mandelic acid, an aromatic monocarboxylic acid, e.g., benzoic acid or salicylic acid, an aliphatic dicarboxylic acid, e.g., oxalic acid, malonic acid, succinic acid, fumaric acid, maleic acid, malic acid, or tartaric acid, and an aliphatic tricarboxylic acid e.g., citric acid; an organic sulfonic acid such as an aliphatic sulfonic acid, e.g., methanesulfonic acid, ethanesulfonic acid, trifluoromethanesulfonic acid, or 2-hydroxyethanesulfonic acid, or an aromatic sulfonic acid, e.g., benzenesulfonic acid or p-toluenesulfonic acid; or an acidic amino acid, e.g., aspartic acid or glutamic acid; salts with a metal such as an alkali metal, e.g., sodium or potassium, or an alkaline earth metal, e.g., magnesium or calcium; salts with an organic base such as methylamine, ethylamine, ethanolamine, pyridine, lysine, arginine, or ornithine; and ammonium salts.

These salts can be obtained by a known method, for example, by mixing a compound of the present invention with an equivalent amount and a solution containing a desired acid, base, or the like, and then collecting the desired salt by filtering the salt or distilling off the solvent.

The compounds of the present invention and salts thereof can form solvates with a solvent such as water, ethanol, or glycerol.

The salts of a compound of the present invention include monosalts and di-salts. The compounds of the present invention can form an acid addition salt and a salt with a base at the same time according to the type of substituent of the side chain.

Furthermore, the present invention includes hydrates, pharmaceutically acceptable various solvates, and crystal polymorphism of the compounds represented by Formula (I) of the present invention. The present invention is not limited to the compounds described in examples below and includes all compounds represented by Formula (I) of the present invention and pharmaceutically acceptable salts thereof.

Prodrugs and solvates of the compounds of the invention are also contemplated herein. A discussion of prodrugs is provided in T. Higuchi and V. Stella, Pro-drugs as Novel Delivery Systems, 14, 1987, of the A.C.S. Symposium Series, and in Bioreversible Carriers in Drug Design, 1987, Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or a solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Nobel Delivery Systems," Vol. 14 of the A.C.S. Symposium Series, and in Bioreversible Carriers in Drug Design, ed. Edward B. Roche, American Pharmaceutical Associatiion and Pergamon Press, 1987.

For example, if a compound of Formula (I) or a pharmaceutically acceptable salt, hydrate or a solvate of the compound contains an alcohol functional group, a prodrug can be formed by the replacement of the hydrogen atom of the alcohol group with a group such as, for example, ($C_{2-7}$ alkanoyl)oxymethyl, 1-(($C_{2-7}$ alkanoyl)oxy)ethyl, 1-methyl-1-(($C_{2-7}$ alkanoyl)oxy)ethyl, ($C_{1-6}$ alkoxy)carbonyloxymethyl, N—($C_{1-6}$ alkoxy)carbonylaminomethyl, succinoyl, $C_{2-7}$ alkanoyl, α-amino$C_{1-4}$ alkanyl, arylacyl and α-aminoacyl, or α-aminoacyl-α-aminoacyl, where each α-aminoacyl group is independently selected from the naturally occurring L-aninoacids, —P(O)(OH)$_2$, —P(O)(O$C_{1-6}$alkyl)$_2$ or glycosyl (the radical resulting from the removal of a hydroxyl group of the hemiacetal from of a carbohydrate), and the like.

For example, if a compound of Formula (I) incorporates an amine functional group or imine functional group, for example, such as a part of amidino group, a prodrug can be formed by the replacement of a hydrogen atom of the amine group or imine group with a group such as, for example, hydroxyl group, RO—, R-carbonyl, RO-carbonyl, NRR'-carbonyl where R and R' are each independently hydrogen atom, $C_{1-6}$ alkyl, $C_{3-12}$ cycloalkyl, $C_{6-14}$ aryl, $C_{7-20}$ alalkyl, or R-carbonyl is a natural α-aminoacyl or natural β-aminoacyl, —CH(O$Y^2$)$Y^3$ wherein $Y^2$ is $C_{1-6}$ alkyl and $Y^3$ is $C_{1-6}$ alkyl, $C_{2-7}$ alkanoyl, amino $C_{1-6}$ alkyl or N—$C_{1-6}$ alkyl amino, N,N-di $C_{1-6}$ alkylamino, —CH($Y^4$)$Y^5$ wherein $Y^4$ is H or methyl and $Y^5$ is N—$C_{1-6}$ alkyl amino, N,N-di $C_{1-6}$ alkylamino, morpholino-1-yl, piperidin-1-yl or pyrrolidin-1-yl and the like.

For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$ alkyl esters and —$C_{1-6}$ alkyl substituted with phenyl esters.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Benzamide Compounds of the Invention

In another aspect, $R^1$ is a halogen atom, a cyano group, a $C_{1-6}$ alkyl group, a halogenated $C_{1-6}$ alkyl group, a hydroxyl $C_{1-6}$ alkyl group, a $C_{3-12}$ cycloalkyl group, a $C_{1-6}$ alkoxy group, a halogenated $C_{1-6}$ alkoxy group or a group of —N$R^A R^B$($R^A$ and $R^B$ are each independently a hydrogen atom, a $C_{1-6}$ alkyl group or a $C_{2-7}$ alkanoyl group).

In a further aspect, $R^1$ is a halogen atom, a cyano group, a $C_{1-6}$ alkyl group, a halogenated $C_{1-6}$ alkyl group, a hydroxyl $C_{1-6}$ alkyl group, a $C_{3-12}$ cycloalkyl group, a $C_{1-6}$ alkoxy group or a halogenated $C_{1-6}$ alkoxy group.

In a further aspect, $R^1$ is a halogen atom, a cyano group, a $C_{1-6}$ alkyl group or a halogenated $C_{1-6}$ alkyl group. Specifically, examples thereof include a fluorine atom, a chlorine atom, a cyano, methyl and difluoromethyl.

In another aspect, $R^2$ is a hydroxyl group, a $C_{1-6}$ alkyl group, a halogenated $C_{1-6}$ alkyl group, a hydroxyl $C_{1-6}$ alkyl group, a $C_{6-14}$ aryl group or a heteroaryl group.

In a further aspect, $R^2$ is a hydroxyl group, a $C_{1-6}$ alkyl group, a halogenated $C_{1-6}$ alkyl group, a hydroxyl $C_{1-6}$ alkyl group or a $C_{6-14}$ aryl group.

In a further aspect, $R^2$ is a hydroxyl group, a $C_{1-6}$ alkyl group or a $C_{6-14}$ aryl group. Specifically, examples thereof include a hydroxyl, methyl and phenyl.

In another aspect, $R^3$ is a halogen atom, a cyano group, a $C_{1-6}$ alkyl group, a halogenated $C_{1-6}$ alkyl group, a $C_{1-6}$ alkoxy group or a halogenated $C_{1-6}$ alkoxy group.

In a further aspect, $R^3$ is a halogen atom, a cyano group, a $C_{1-6}$ alkyl group or a halogenated $C_{1-6}$ alkyl group.

In a further aspect, $R^3$ is a halogen atom or a $C_{1-6}$ alkyl group. Specifically, examples thereof include a fluorine atom, a chlorine atom and methyl.

In another aspect, $R^4$ is a halogen atom, a cyano group, a $C_{1-6}$ alkyl group, a $C_{3-12}$ cycloalkyl group, a halogenated $C_{1-6}$ alkyl group, a hydroxy $C_{1-6}$ alkyl group, a cyanated $C_{1-6}$ alkyl group, a $C_{1-6}$ alkoxy group, a $C_{1-6}$ alkoxy $C_{1-6}$ alkyl group, a halogenated $C_{1-6}$ alkoxy group, a $C_{2-7}$ alkanoyl group, a group of $-NR^A R^B$ ($R^A$ and $R^B$ each independently represent a group selected from a hydrogen atom, a $C_{1-6}$ alkyl group or a $C_{2-7}$ alkanoyl group) or oxo.

In a further aspect $R^4$ is a halogen atom, a cyano group, a $C_{1-6}$ alkyl group, a $C_{3-12}$ cycloalkyl group, a halogenated $C_{1-6}$ alkyl group, a hydroxy $C_{1-6}$ alkyl group, a cyanated $C_{1-6}$ alkyl group, a $C_{1-6}$ alkoxy group, a $C_{1-6}$ alkoxy $C_{1-6}$ alkyl group, a halogenated $C_{1-6}$ alkoxy group, a $C_{2-7}$ alkanoyl group or oxo.

In a further aspect $R^4$ is a cyano group, a $C_{1-6}$ alkyl group, a $C_{3-12}$ cycloalkyl group, a halogenated $C_{1-6}$ alkyl group, a hydroxy $C_{1-6}$ alkyl group, a $C_{1-6}$ alkoxy group or oxo. More specifically, examples thereof include cyano, methyl, cyclopropyl, methoxy, difluolomethyl, trifluoromethyl, hydroxymethyl, hydroxyethyl and oxo.

In another aspect, a substructure of ring A represented by Formula (III):

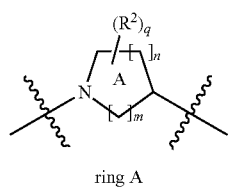

ring A (III)

is a non aromatic heterocyclic group selected from

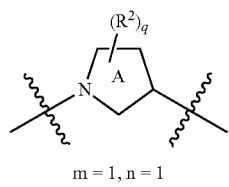

m = 1, n = 1

(III-a)

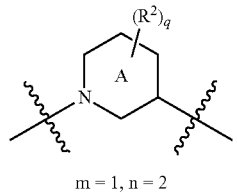

m = 1, n = 2

(III-b)

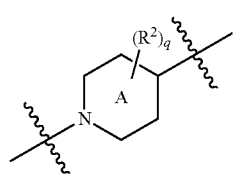

m = 2, n = 1

(III-c)

(in a substructure of ring A represented by Formula (III), Formula (III-a) means m is 1 and n is 1; Formula (III-b) means m is 1 and n is 2; Formula (III-c) means m is 2 and n is 1).

In a further aspect, a substructure of ring A represented by Formula (III) is

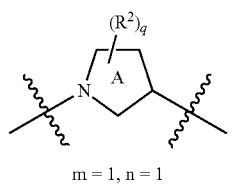

m = 1, n = 1

(III-a)

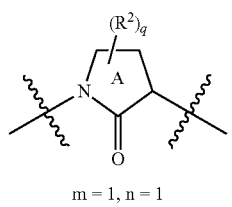

m = 1, n = 1

(III-a-2)

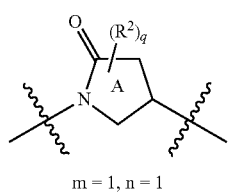

m = 1, n = 1

(III-a-3)

(in a substructure of ring A represented by Formula (III), each of Formula (III-a), (III-a-2) or (III-a-3) mean m is 1 and n is 1).

In a further aspect, a substructure of ring A represented by Formula (III) represents a group selected from

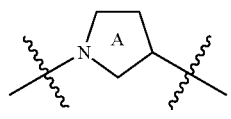

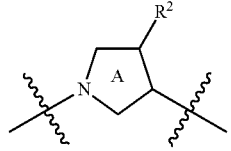

(in a substructure of ring A represented by Formula (III), m is 1 and n is 1). Specifically, examples thereof include

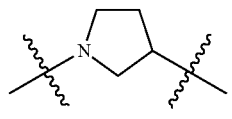

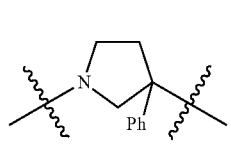

-continued
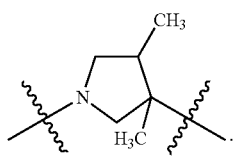
In another aspect,
is a heteroaryl ring selected from
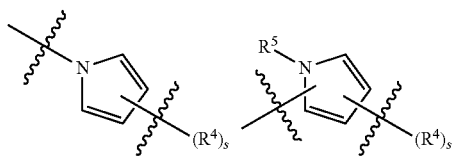
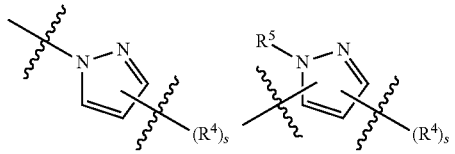
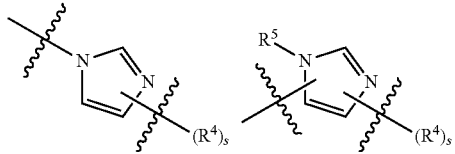
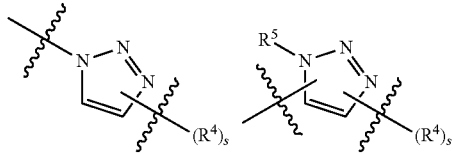
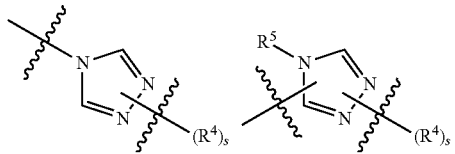
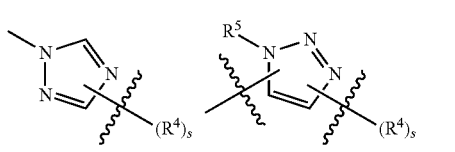
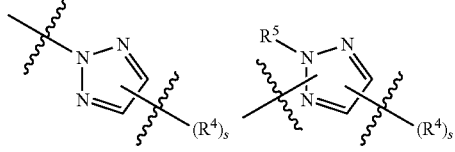
-continued
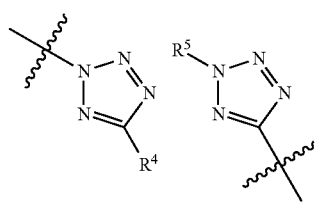
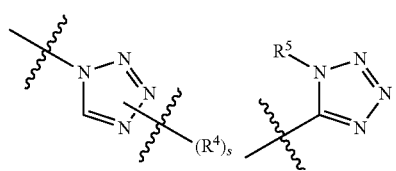
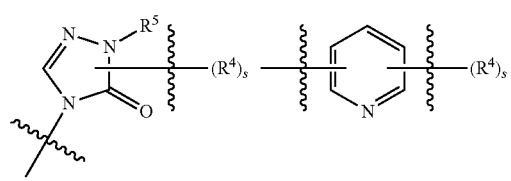
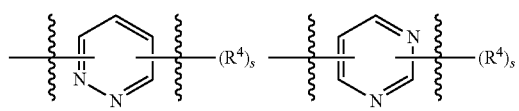
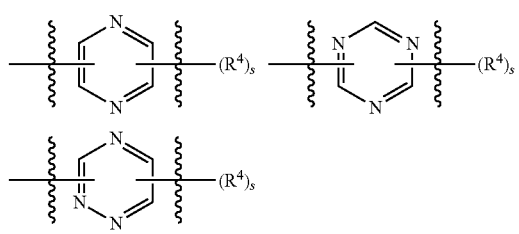
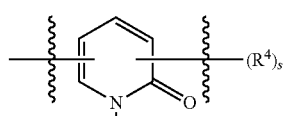
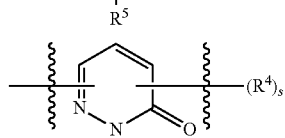
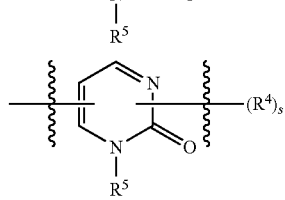
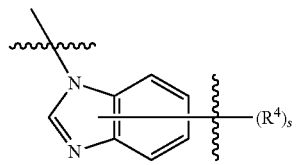
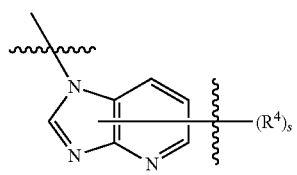

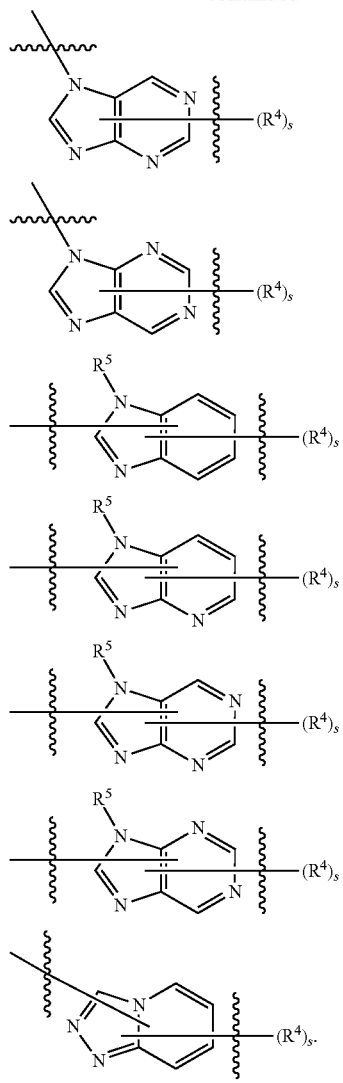
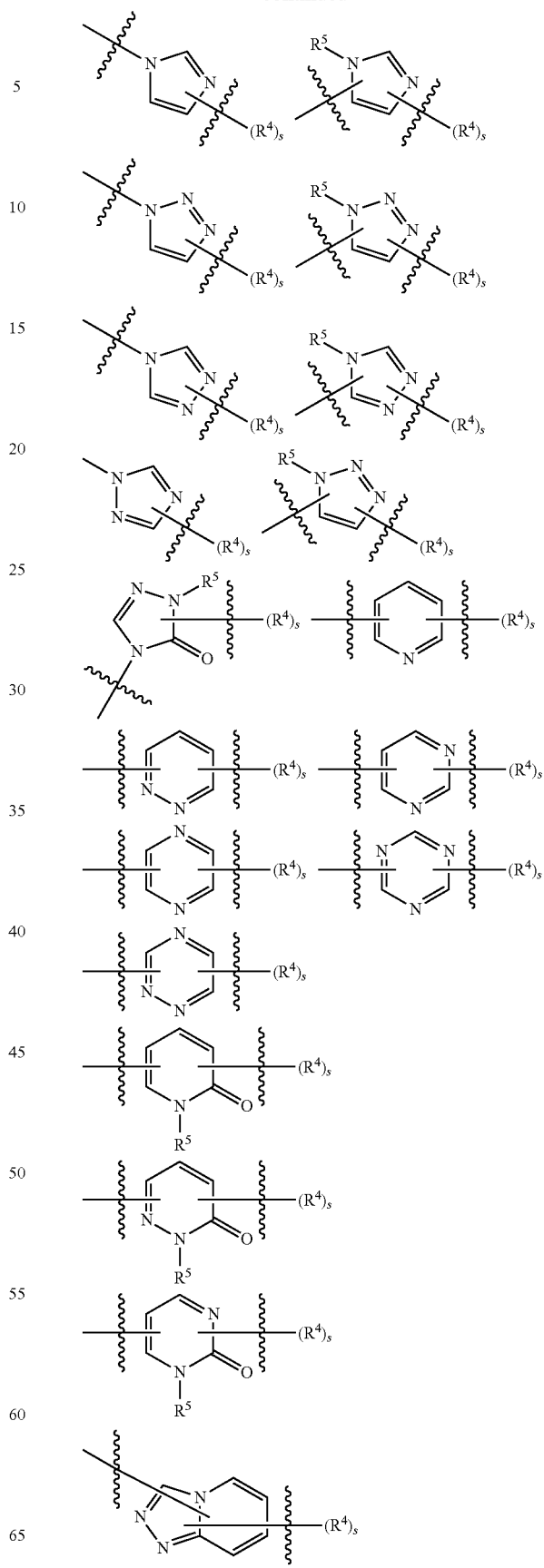
In a further aspect,
is a heteroaryl ring selected from
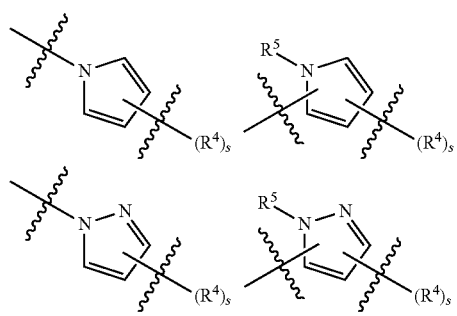

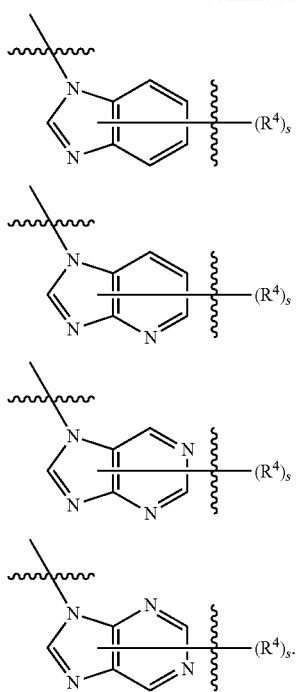
In a further aspect
is selected from
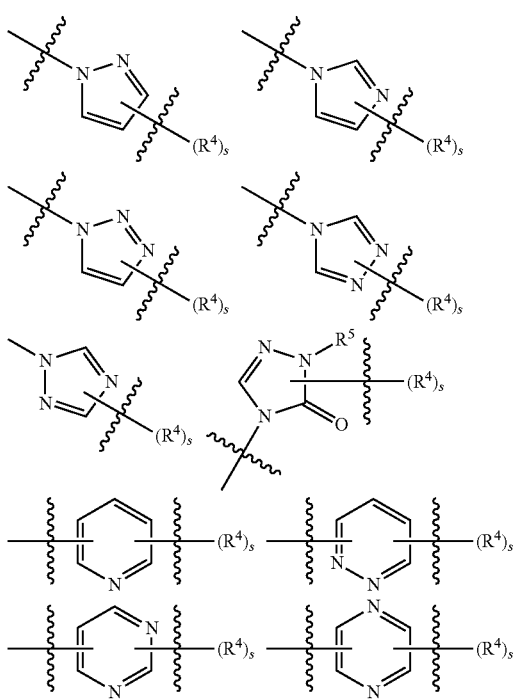
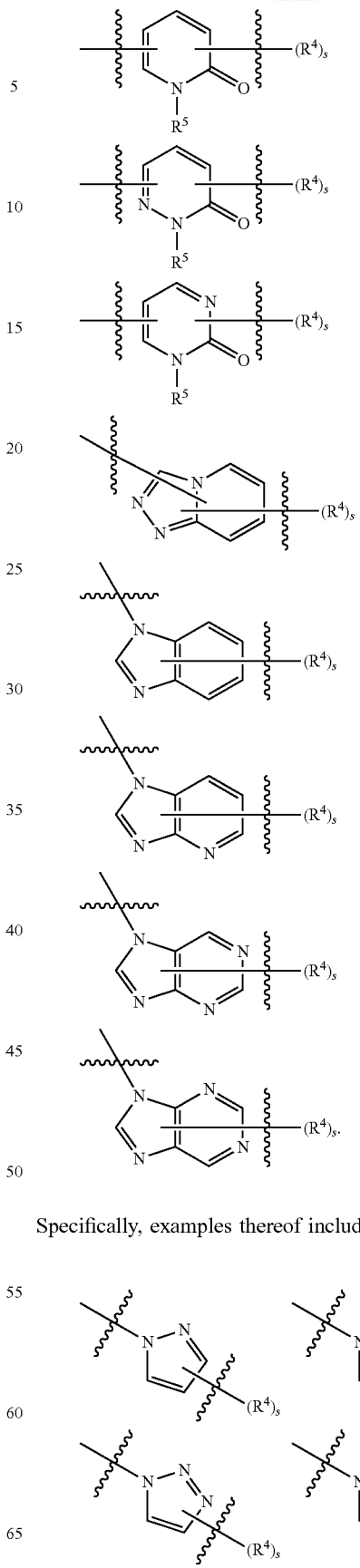
Specifically, examples thereof include
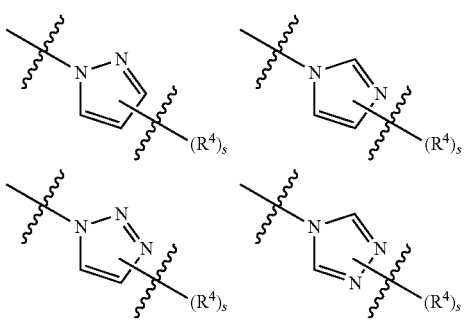

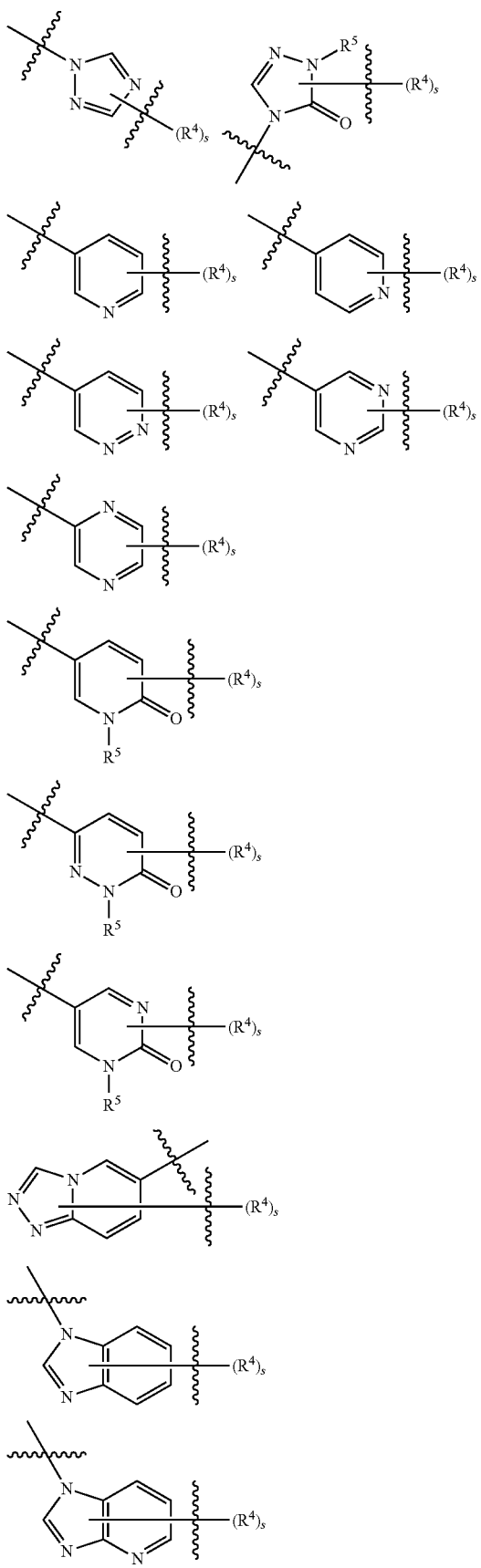

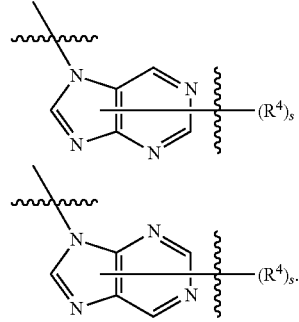

In another aspect, $R^5$ is a hydrogen atom, a $C_{1-6}$ alkyl group, a halogenated $C_{1-6}$ alkyl group, a hydroxyl $C_{1-6}$ alkyl group, a $C_{1-6}$ alkoxy $C_{1-6}$ alkyl group or a cyanated $C_{1-6}$ alkyl group.

In a further aspect, $R^5$ is a hydrogen atom, a $C_{1-6}$ alkyl group, a halogenated $C_{1-6}$ alkyl group, a hydroxyl $C_{1-6}$ alkyl group or a $C_{1-6}$ alkoxy $C_{1-6}$ alkyl group.

In a further aspect, $R^5$ is a hydrogen atom, a $C_{1-6}$ alkyl group, a halogenated $C_{1-6}$ alkyl group or a hydroxyl $C_{1-6}$ alkyl group. Specifically, examples thereof include a hydrogen atom, methyl, difluoromethyl, 2,2,2-trifluoroethyl and hydroxyethyl.

In another aspect, p is an integer of 0 to 3.

In a further aspect, p is an integer of 0 to 2.

In another aspect, q is an integer of 0 to 3.

In a further aspect, q is an integer of 0 to 2.

In another aspect, r is an integer of 0 to 3.

In a further aspect, r is an integer of 0 to 2.

In another aspect, s is an integer of 0 to 3.

In a further aspect, s is an integer of 0 to 2.

In a further aspect, s is 0 or 1.

In another aspect, combinations of m and n are (m=1, n=1), (m=1, n=2), or (m=2, n=2).

In a further aspect, a combination of m and n is (m=1, n=1).

In another aspect, a bicyclic substructure of Formula (I) represented by Formula (II):

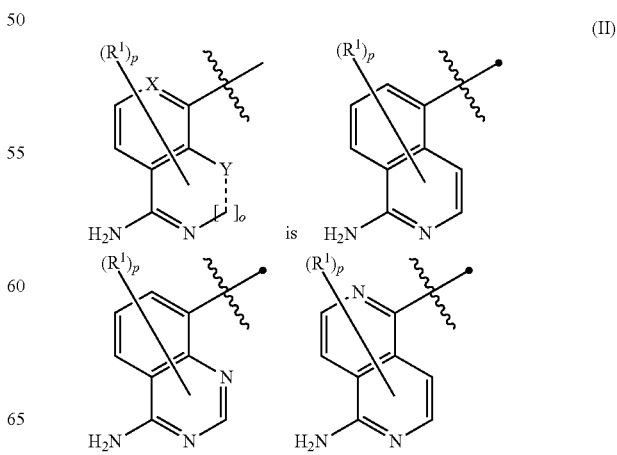

-continued
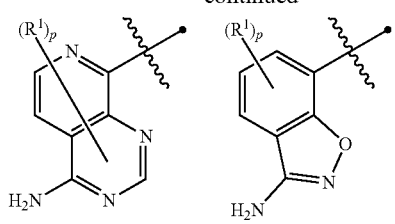
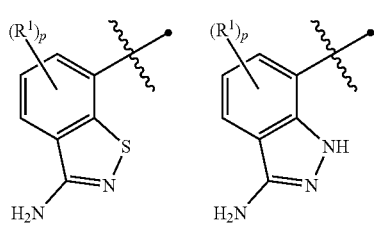
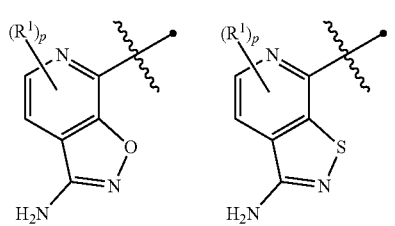
In a further aspect, the bicyclic substructure of Formula (I) represented by Formula (II) is
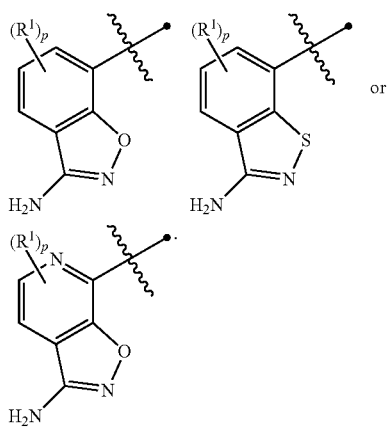
In a further aspect, the bicyclic substructure of Formula (I) represented by Formula (II) is
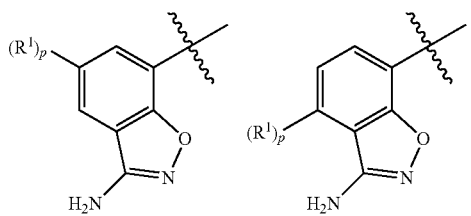
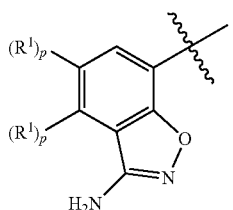
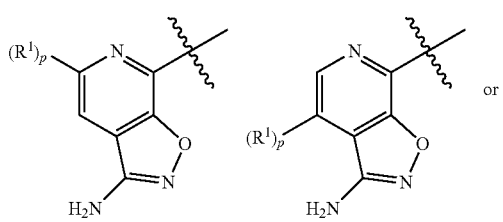
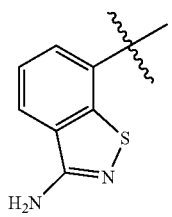 or
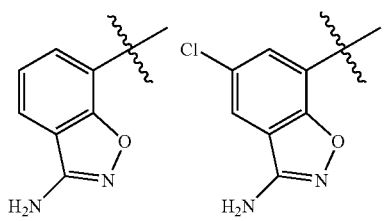
Specifically, examples thereof include
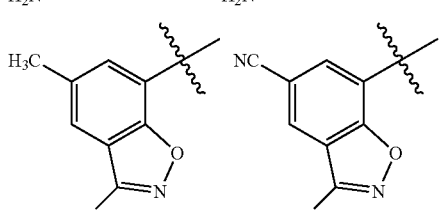
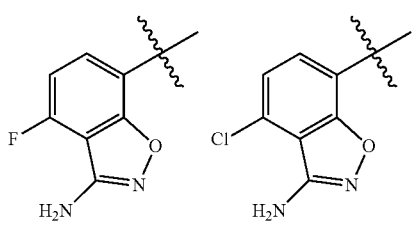

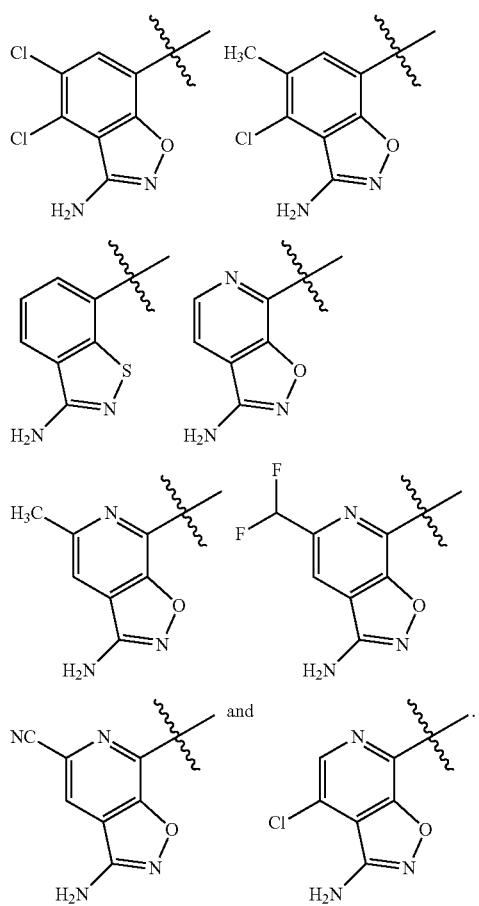
In another aspect, a substructure of ring B represented by Formula (V):
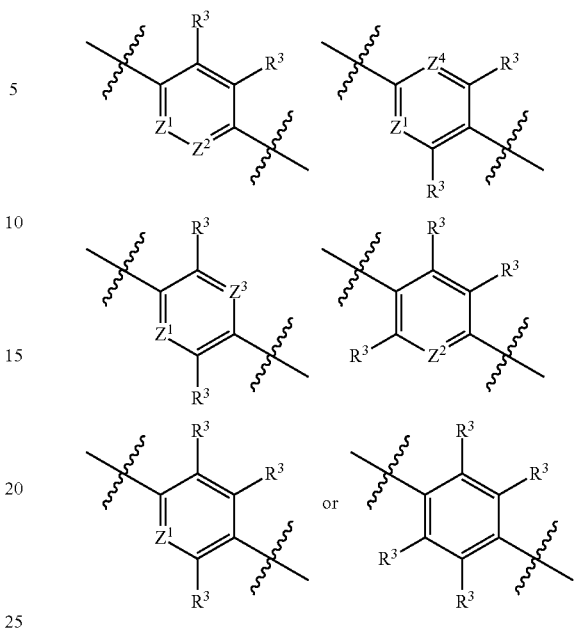
wherein $Z_1$, $Z_2$, $Z_3$, $Z_4$ are each independently a nitrogen atom or CH.
In a further aspect, substructure of a substructure of ring B represented by Formula (V) is
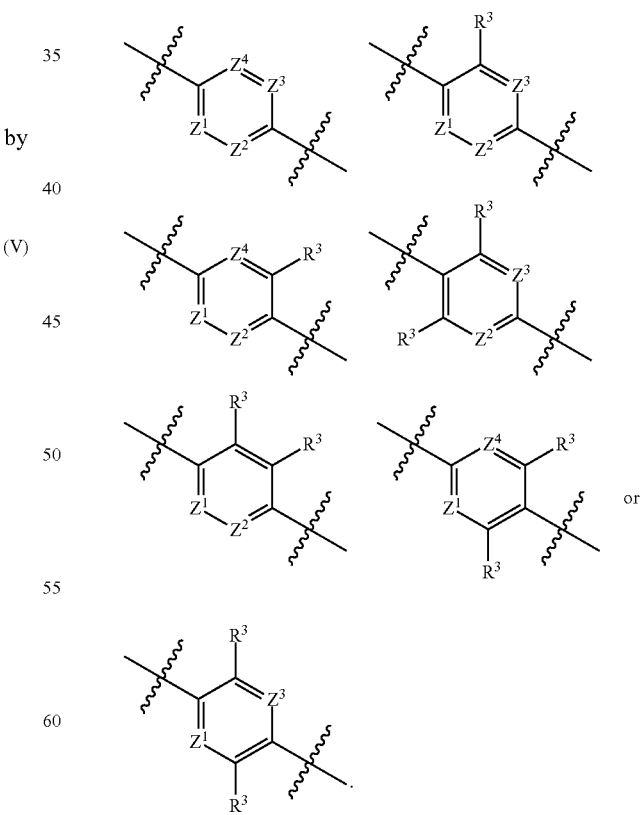
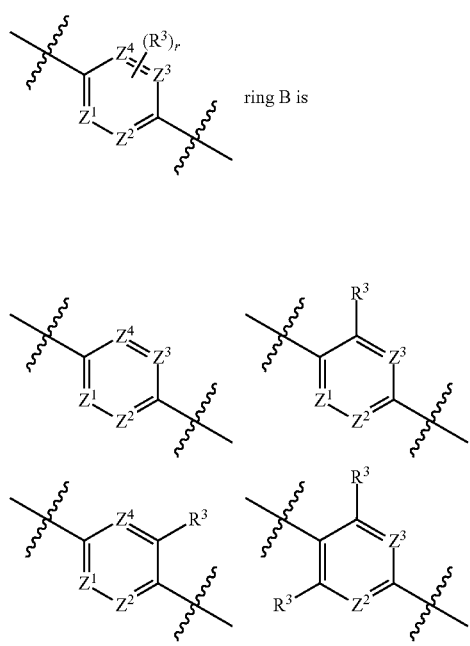
In a further aspect, substructure of a substructure of ring B represented by Formula (V) is

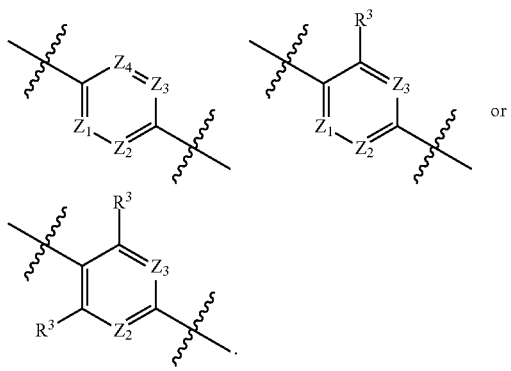

Specifically, examples thereof include

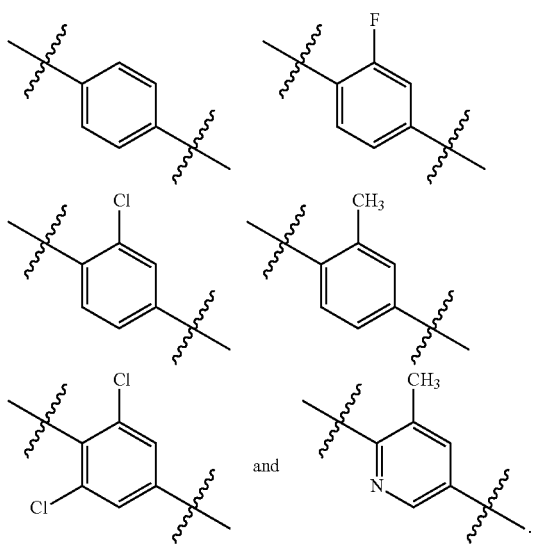

In the second aspect, the present invention provides the compounds represented by Formula (I-a):

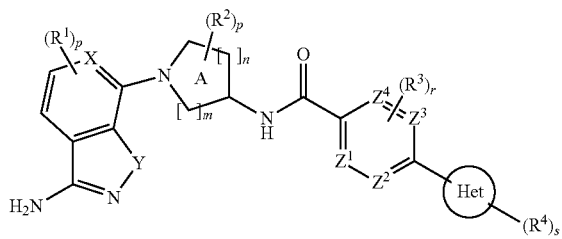

or pharmaceutically acceptable salts thereof,
wherein: m is an integer of 1 to 2; n is an integer of 1 to 2; p is an integer of 0 to 3; q is an integer of 0 to 4; r is an integer of 0 to 4; s is an integer of 0 to 4;

X is a nitrogen atom or CH; Y is an oxygen atom, a sulfur atom or NH;

$Z_1$, $Z_2$, $Z_3$ and $Z_4$ are each independently a nitrogen atom or CH;

each $R^1$ is independently a halogen atom, a cyano group, a $C_{1-6}$ alkyl group, a halogenated $C_{1-6}$ alkyl group, a hydroxyl $C_{1-6}$ alkyl group, a $C_{3-12}$ cycloalkyl group, a $C_{1-6}$ alkoxy group, a halogenated $C_{1-6}$ alkoxy group, a $C_{2-7}$ alkanoyl group or a group of —$NR^AR^B$;

$R^A$ and $R^B$ are each independently a hydrogen atom, a $C_{1-6}$ alkyl group or a $C_{2-7}$ alkanoyl group;

each $R^2$ is independently a hydroxyl group, a $C_{1-6}$ alkyl group, a halogenated $C_{-6}$ alkyl group, a hydroxyl $C_{1-6}$ alkyl group, a $C_{1-6}$ alkoxy group, a halogenated $C_{1-6}$ alkoxy group, a $C_{6-14}$ aryl group, a heteroaryl group or oxo;

each $R^3$ is independently a halogen atom, a cyano group, a $C_{1-6}$ alkyl group, a halogenated $C_{1-6}$ alkyl group, a $C_{3-12}$ cycloalkyl group, a $C_{1-6}$ alkoxy group or a halogenated $C_{1-6}$ alkoxy group;

each $R^4$ is independently a halogen atom, a cyano group, a $C_{1-6}$ alkyl group, a $C_{3-12}$ cycloalkyl group, a halogenated $C_{1-6}$ alkyl group, a hydroxy $C_{1-6}$ alkyl group, a cyanated $C_{1-6}$ alkyl group, a $C_{1-6}$ alkoxy group, a $C_{1-6}$ alkoxy $C_{1-6}$ alkyl group, a halogenated $C_{1-6}$ alkoxy group, a $C_{2-7}$ alkanoyl group, a $C_{1-6}$ alkylthio group, a $C_{1-6}$ alkylsulfonyl group, a group of —$NR^AR^B$ or oxo;

and

is heteroaryl.

In another aspect, in the compounds represented by Formula (I-a), preferably, p is an integer of 0 to 2, q is an integer of 0 to 2, r is an integer of 0 to 2, s is an integer of 0 to 3, $R^1$ is a halogen atom, a cyano group, a $C_{1-6}$ alkyl group, a halogenated $C_{1-6}$ alkyl group, a hydroxyl $C_{1-6}$ alkyl group, a $C_{3-12}$ cycloalkyl group, a $C_{1-6}$ alkoxy group, a halogenated $C_{1-6}$ alkoxy group, or a group of —$NR^AR^B$ ($R^A$ and $R^B$ each independently represent a group selected from a hydrogen atom, a $C_{1-6}$ alkyl group or a $C_{2-7}$ alkanoyl group), $R^2$ is $R^2$ is a hydroxyl group, a $C_{1-6}$ alkyl group, a halogenated $C_{1-6}$ alkyl group, a hydroxyl $C_{1-6}$ alkyl group, a $C_{6-14}$ aryl group, or a heteroaryl group, $R^3$ is a halogen atom and $C_{1-6}$ alkyl group. $R^4$ is a halogen atom, a cyano group, a $C_{1-6}$ alkyl group, a $C_{3-12}$ cycloalkyl group, a halogenated $C_{1-6}$ alkyl group, a hydroxy $C_{1-6}$ alkyl group, a cyanated $C_{1-6}$ alkyl group, a $C_{1-6}$ alkoxy group, a $C_{1-6}$ alkoxy $C_{1-6}$ alkyl group, a halogenated $C_{1-6}$ alkoxy group, a $C_{2-7}$ alkanoyl group, a group of —$NR^AR^B$($R^A$ and $R^B$ each independently represent a group selected from a hydrogen atom, a $C_{1-6}$ alkyl group or a $C_{2-7}$ alkanoyl group) or oxo, $R^5$ is a hydrogen atom, a $C_{1-6}$ alkyl group, a halogenated $C_{1-6}$ alkyl group, a hydroxyl $C_{1-6}$ alkyl group, a $C_{1-6}$ alkoxy $C_{1-6}$ alkyl group, or a cyanated $C_{1-6}$ alkyl group, a substructure of bicycle represented by Formula (VI) is the

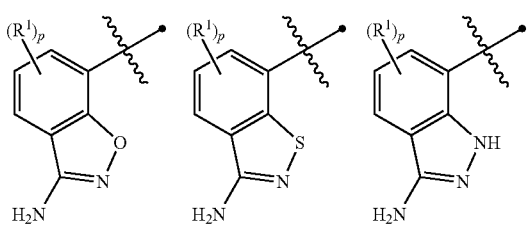

-continued
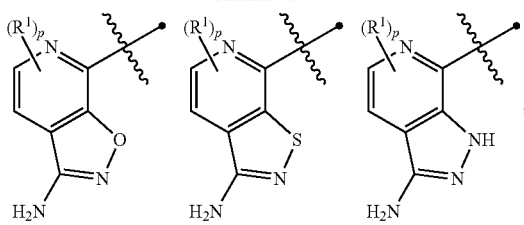
a substructure of ring A is
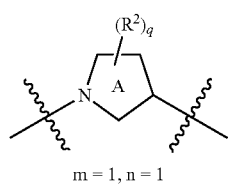
(III-a)
m = 1, n = 1
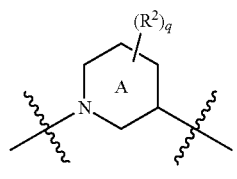
(III-b)
m = 1, n = 2
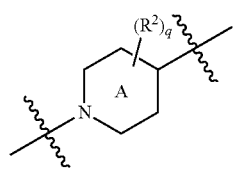
(III-c)
m = 2, n = 1
(in a substructure of ring A represented by Formula (III), Formula (III-a) means m is 1 and n is 1; Formula (III-b) means m is 1 and n is 2; Formula (III-c) means m is 2 and n is 1), a substructure of ring B is
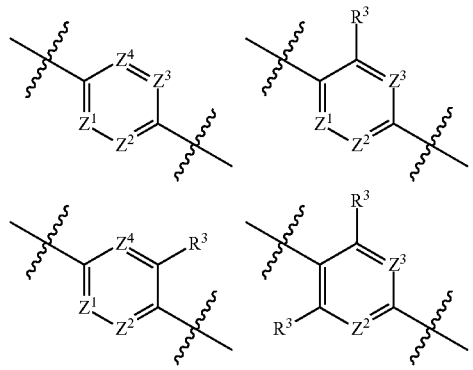
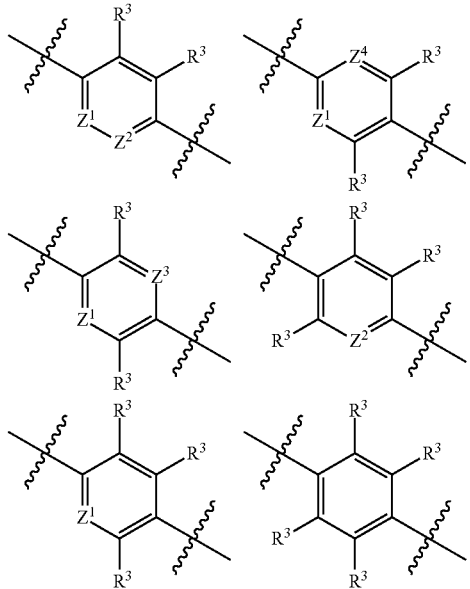
and
a substructure of
is a heteroaryl ring selected from
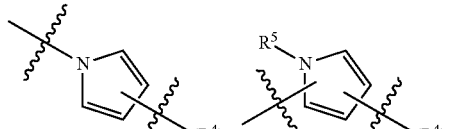
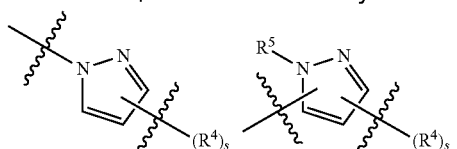
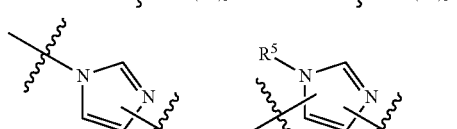
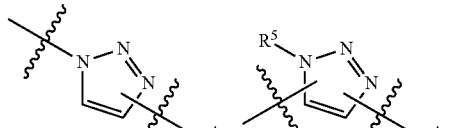
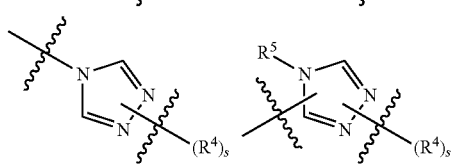

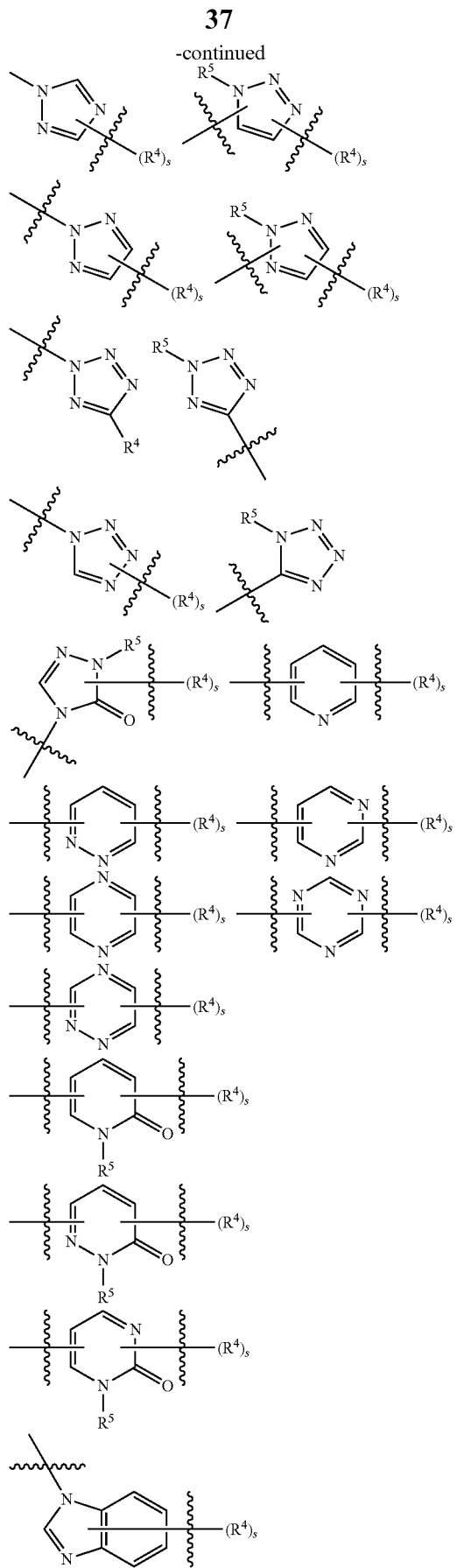
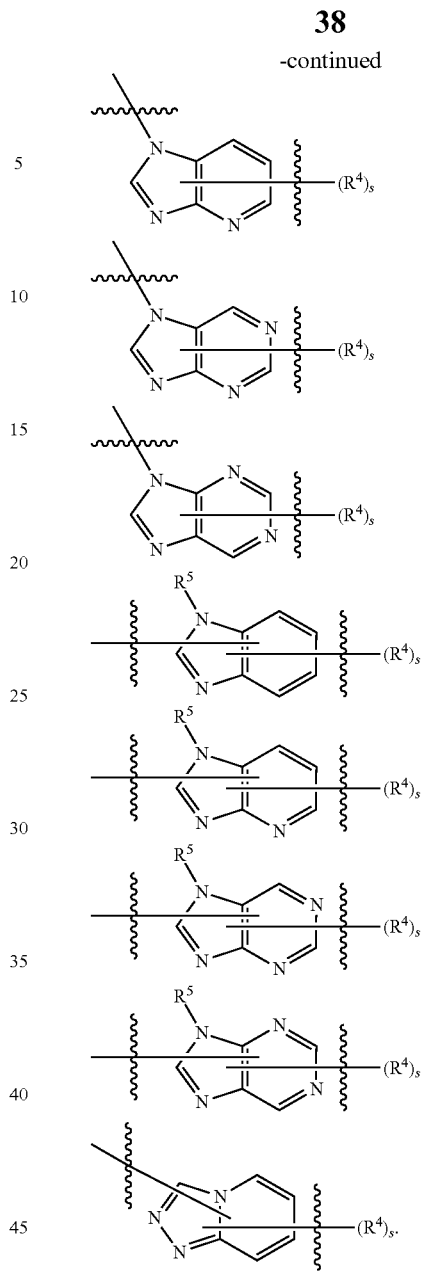

In another aspect, in the compounds represented by Formula (I-a), p is an integer of 0 to 1, q is an integer of 0 or 2, r is an integer of 0 to 2, s is an integer of 0 to 3, $R^1$ is a halogen atom, a cyano group, a $C_{1-6}$ alkyl group, a halogenated $C_{1-6}$ alkyl group, a hydroxyl $C_{1-6}$ alkyl group, a $C_{3-12}$ cycloalkyl group, a $C_{1-6}$ alkoxy group, or a halogenated $C_{1-6}$ alkoxy group; $R^2$ is a hydroxyl group, a $C_{1-6}$ alkyl group, a halogenated $C_{1-6}$ alkyl group, a hydroxyl $C_{1-6}$ alkyl group, or a $C_{6-14}$ aryl group; $R^3$ is a halogen atom, a cyano group, a $C_{1-6}$ alkyl group, or a halogenated $C_{1-6}$ alkyl group; $R^4$ is a halogen atom, a cyano group, a $C_{1-6}$ alkyl group, a $C_{3-12}$ cycloalkyl group, a halogenated $C_{1-6}$ alkyl group, a hydroxy $C_{1-6}$ alkyl group, a cyanated $C_{1-6}$ alkyl group, a $C_{1-6}$ alkoxy group, a $C_{1-6}$ alkoxy $C_{1-6}$ alkyl group, a halogenated $C_{1-6}$ alkoxy group, a $C_{2-7}$ alkanoyl group or oxo; $R^5$ is a hydrogen atom, a $C_{1-6}$ alkyl group, a halogenated $C_{1-6}$ alkyl group, a hydroxyl $C_{1-6}$ alkyl group, or a $C_{1-6}$ alkoxy $C_{1-6}$ alkyl group, a substructure of bicycle represented by Formula (VI) is

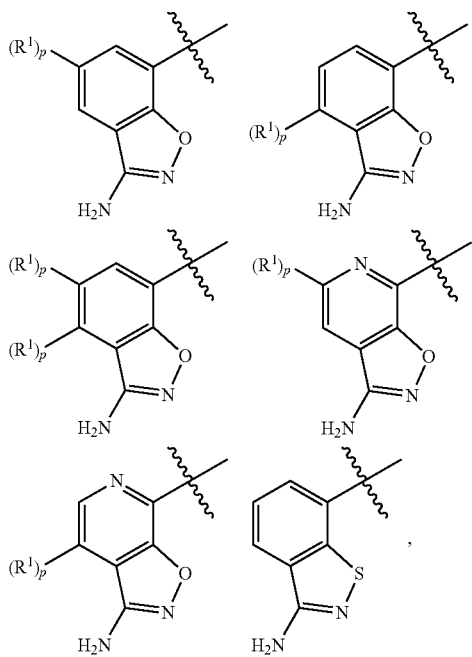
a substructure of ring A represented by Formula (III) and the combination of m and n are
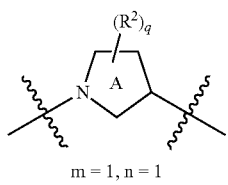
(III-a)
m = 1, n = 1
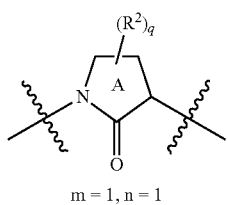
(III-a-2)
m = 1, n = 1
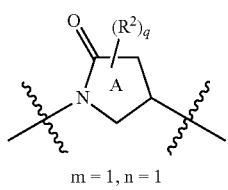
(III-a-3)
m = 1, n = 1
(in a substructure of ring A represented by Formula (III), each of Formula (III-a), (III-a-2) or (III-a-3) mean m is 1 and n is 1), a substructure of ring B represented by Formula (V) is
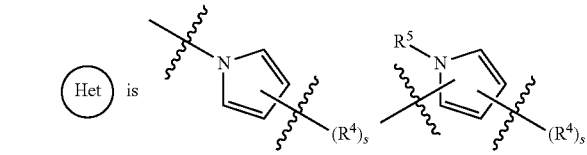
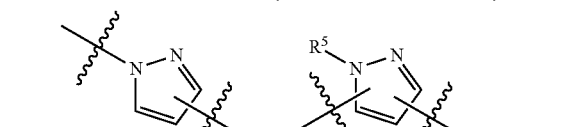
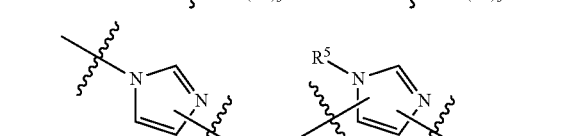
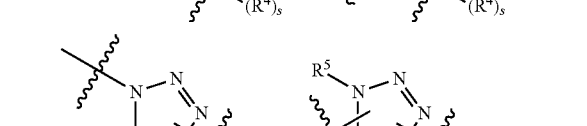
and a substructure of
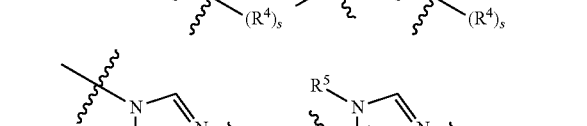

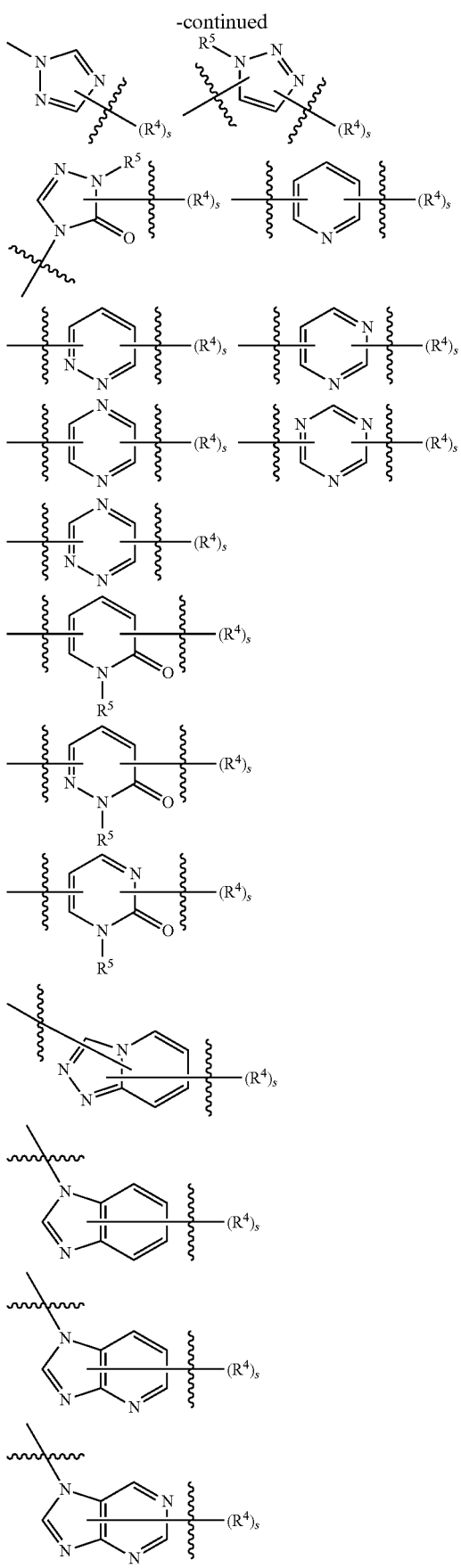

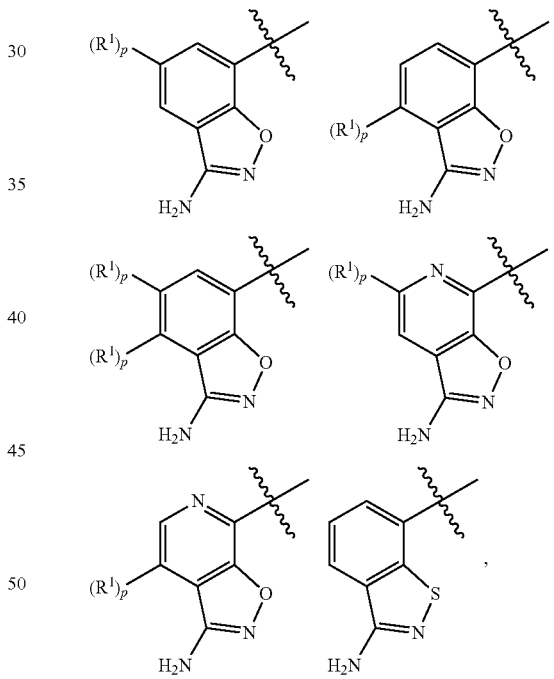

In another aspect, in the compounds represented by Formula (I-a), p is an integer of 0 or 1, q is an integer of 0 to 2, r is an integer of 0 to 2, s is an integer of 0 to 3, $R^1$ is a halogen atom, a cyano group, a $C_{1-6}$ alkyl group, or a halogenated $C_{1-6}$ alkyl group; $R^2$ is a hydroxyl group, a $C_{1-6}$ alkyl group, or a $C_{6-14}$ aryl group; $R^3$ is a halogen atom and $C_{1-6}$ alkyl group; $R^4$ is a cyano group, a $C_{1-6}$ alkyl group, a $C_{3-12}$ cycloalkyl group, a halogenated $C_{1-6}$ alkyl group, a hydroxy $C_{1-6}$ alkyl group, a $C_{1-6}$ alkoxy group or oxo; $R^5$ is a hydrogen atom, a $C_{1-6}$ alkyl group, a halogenated $C_{1-6}$ alkyl group, or a hydroxyl $C_{1-6}$ alkyl group; a substructure of bicycle represented by Formula (VI) is In a further aspect, substructure of a substructure of ring B represented by Formula (V) is

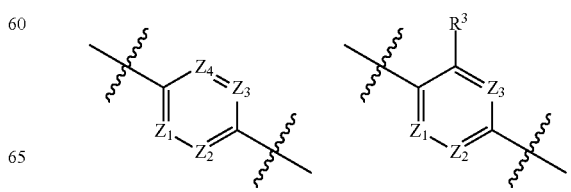

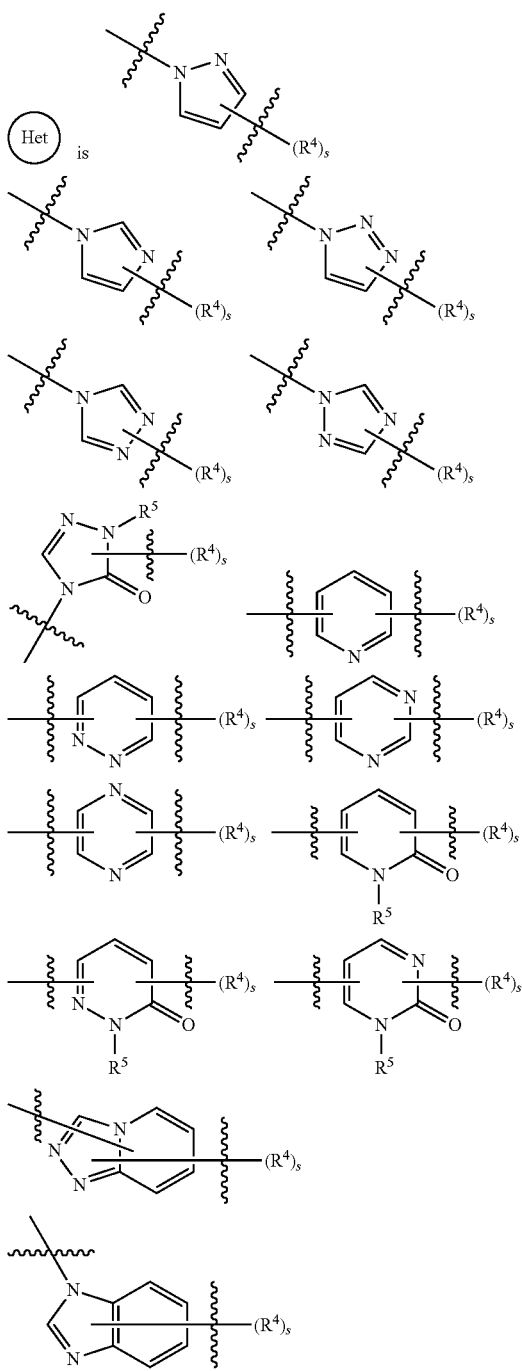

and a substructure of

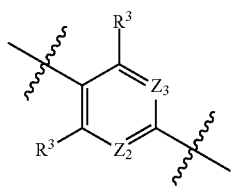 is

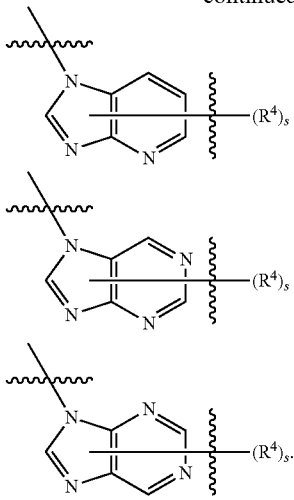

In the third aspect, the present invention provides compounds, or optical isomers thereof, or a solvate thereof, or a pharmaceutically acceptable salt thereof selected from:

N-(1-(3-Aminobenzo[d]isoxazol-7-yl)pyrrolidin-3-yl)-2-chloro-4-(4H-1,2,4-triazol-4-yl)benzamide (EXAMPLE 1);

N-(1-(3-Aminobenzo[d]isoxazol-7-yl)-3-methylpyrrolidin-3-yl)-2,6-dichloro-4-(4H-1,2,4-triazol-4-yl)benzamide (EXAMPLE 2);

N-(1-(3-Aminobenzo[d]isoxazol-7-yl)-3-phenylpyrrolidin-3-yl)-2,6-dichloro-4-(4H-1,2,4-triazol-4-yl)benzamide (EXAMPLE 3);

N-(1-(3-Aminobenzo[d]isothiazol-7-yl)pyrrolidin-3-yl)-2,6-dichloro-4-(4H-1,2,4-triazol-4-yl)benzamide (EXAMPLE 4);

N-(1-(3-Aminoisoxazolo[5,4-c]pyridin-7-yl)pyrrolidin-3-yl)-2-chloro-4-(4H-1,2,4-triazol-4-yl)benzamide (EXAMPLE 5);

N-(1-(3-Amino-5-methylbenzo[d]isoxazol-7-yl)pyrrolidin-3-yl)-2,6-dichloro-4-(3-methyl-1H-1,2,4-triazol-1-yl)benzamide (EXAMPLE 6);

N-((3R*,4S*)-1-(3-Aminobenzo[d]isoxazol-7-yl)-3,4-dimethylpyrrolidin-3-yl)-2,6-dichloro-4-(4H-1,2,4-triazol-4-yl)benzamide (EXAMPLE 7);

N-((3S*,4S*)-1-(3-Aminobenzo[d]isoxazol-7-yl)-4-hydroxypyrrolidin-3-yl)-2,6-dichloro-4-(4H-1,2,4-triazol-4-yl)benzamide (EXAMPLE 8);

(R)—N-(1-(3-Amino-4-chlorobenzo[d]isoxazol-7-yl)pyrrolidin-3-yl)-2-chloro-4-(4H-1,2,4-triazol-4-yl)benzamide (EXAMPLE 9);

(R)—N-(1-(3-Amino-5-chlorobenzo[d]isoxazol-7-yl)pyrrolidin-3-yl)-2-chloro-4-(4H-1,2,4-triazol-4-yl)benzamide (EXAMPLE 10);

(R)—N-(1-(3-Amino-4-chloroisoxazolo[5,4-c]pyridin-7-yl)pyrrolidin-3-yl)-2-chloro-4-(3-methyl-1H-1,2,4-triazol-1-yl)benzamide (EXAMPLE 11);

(R)—N-(1-(3-Amino-4-chloro-5-methylbenzo[d]isoxazol-7-yl)pyrrolidin-3-yl)-2-chloro-4-(4H-1,2,4-triazol-4-yl)benzamide (EXAMPLE 12);

(R)—N-(1-(3-Amino-4-fluorobenzo[d]isoxazol-7-yl)pyrrolidin-3-yl)-2-chloro-4-(4H-1,2,4-triazol-4-yl)benzamide (EXAMPLE 13);

(R)—N-(1-(3-Amino-4,5-dichlorobenzo[d]isoxazol-7-yl)pyrrolidin-3-yl)-2-chloro-4-(4H-1,2,4-triazol-4-yl)benzamide (EXAMPLE 14);

N-(1-(3-Amino-5-chlorobenzo[d]isoxazol-7-yl)-3-methyl-pyrrolidin-3-yl)-2-chloro-4-(3-methyl-1H-1,2,4-triazol-1-yl)benzamide (EXAMPLE 15);

(R)—N-(1-(3-Amino-5-chlorobenzo[d]isoxazol-7-yl)pyrrolidin-3-yl)-2-chloro-4-(3-(hydroxymethyl)-1H-1,2,4-triazol-1-yl)benzamide (EXAMPLE 16);

(R)—N-(1-(3-Amino-5-chlorobenzo[d]isoxazol-7-yl)pyrrolidin-3-yl)-2-chloro-4-(3-cyclopropyl-1H-1,2,4-triazol-1-yl)benzamide (EXAMPLE 17);

(R)—N-(1-(3-Amino-4-chlorobenzo[d]isoxazol-7-yl)pyrrolidin-3-yl)-2-fluoro-4-(1H-1,2,4-triazol-1-yl)benzamide (EXAMPLE 18);

(R)—N-(1-(3-Amino-4-chlorobenzo[d]isoxazol-7-yl)pyrrolidin-3-yl)-2-methyl-4-(1H-1,2,4-triazol-1-yl)benzamide (EXAMPLE 19);

(R)—N-(1-(3-Amino-4-chloroisoxazolo[5,4-c]pyridin-7-yl)pyrrolidin-3-yl)-2-chloro-4-(pyrimidin-5-yl)benzamide (EXAMPLE 20);

(R)—N-(1-(3-Amino-4-chloroisoxazolo[5,4-c]pyridin-7-yl)pyrrolidin-3-yl)-2-chloro-4-(2-methoxypyrimidin-5-yl)benzamide (EXAMPLE 21);

(R)—N-(1-(3-Amino-4-chloroisoxazolo[5,4-c]pyridin-7-yl)pyrrolidin-3-yl)-2-chloro-4-(2-cyanopyrimidin-5-yl)benzamide (EXAMPLE 22);

(R)—N-(1-(3-Amino-4-chlorobenzo[d]isoxazol-7-yl)pyrrolidin-3-yl)-2-chloro-4-(3-(2-hydroxyethyl)-1H-1,2,4-triazol-1-yl)benzamide (EXAMPLE 23);

(R)—N-(1-(3-Amino-4-chloroisoxazolo[5,4-c]pyridin-7-yl)pyrrolidin-3-yl)-2-chloro-4-(1H-1,2,4-triazol-1-yl)benzamide (EXAMPLE 24);

(R)—N-(1-(3-Amino-4-chlorobenzo[d]isoxazol-7-yl)pyrrolidin-3-yl)-2-chloro-4-(5-(hydr oxymethyl)pyridin-3-yl)benzamide (EXAMPLE 25);

(R)—N-(1-(3-Amino-4-chlorobenzo[d]isoxazol-7-yl)pyrrolidin-3-yl)-2-chloro-4-(4-(2-hydroxyethyl)-1H-pyrazol-1-yl)benzamide (EXAMPLE 26);

(R)—N-(1-(3-Amino-4-chloroisoxazolo[5,4-c]pyridin-7-yl)pyrrolidin-3-yl)-2-chloro-4-(4-(2-hydroxyethyl)-1H-imidazol-1-yl)benzamide (EXAMPLE 27);

(R)—N-(1-(3-Amino-4-chloroisoxazolo[5,4-c]pyridin-7-yl)pyrrolidin-3-yl)-2-chloro-4-(3-(difluoromethyl)-4H-1,2,4-triazol-4-yl)benzamide (EXAMPLE 28);

(R)—N-(1-(3-Amino-4-chloroisoxazolo[5,4-c]pyridin-7-yl)pyrrolidin-3-yl)-4-(1H-benzo[d]imidazol-1-yl)-2-chlorobenzamide (EXAMPLE 29);

(R)—N-(1-(3-Amino-4-chloroisoxazolo[5,4-c]pyridin-7-yl)pyrrolidin-3-yl)-2-chloro-4-(pyridazin-4-yl)benzamide (EXAMPLE 30);

(R)—N-(1-(3-Amino-4-chloroisoxazolo[5,4-c]pyridin-7-yl)pyrrolidin-3-yl)-2-chloro-4-(5-(2-hydroxyethyl)pyridin-3-yl)benzamide (EXAMPLE 31);

(R)—N-(1-(3-Amino-4-chloroisoxazolo[5,4-c]pyridin-7-yl)pyrrolidin-3-yl)-2-chloro-4-(1H-imidazo[4,5-b]pyridin-1-yl)benzamide (EXAMPLE 32);

(R)—N-(1-(3-Amino-4-chloroisoxazolo[5,4-c]pyridin-7-yl)pyrrolidin-3-yl)-2-chloro-4-(pyrazin-2-yl)benzamide (EXAMPLE 33);

(R)—N-(1-(3-Amino-5-cyanobenzo[d]isoxazol-7-yl)pyrrolidin-3-yl)-2-chloro-4-(3-methyl-1H-1,2,4-triazol-1-yl)benzamide (EXAMPLE 34);

(R)—N-(1-(3-Amino-4-chloroisoxazolo[5,4-c]pyridin-7-yl)pyrrolidin-3-yl)-2-chloro-4-(6-oxo-1-(2,2,2-trifluoroethyl)-1,6-dihydropyridin-3-yl)benzamide (EXAMPLE 35);

(R)—N-(1-(3-Amino-4-chloroisoxazolo[5,4-c]pyridin-7-yl)pyrrolidin-3-yl)-4-(4H-1,2,4-triazol-4-yl)benzamide (EXAMPLE 36);

(R)—N-(1-(3-Amino-4-chloroisoxazolo[5,4-c]pyridin-7-yl)pyrrolidin-3-yl)-2-chloro-4-(1-(difluoromethyl)-6-oxo-1,6-dihydropyridin-3-yl)benzamide (EXAMPLE 37);

(R)-4-([1,2,4]Triazolo[4,3-a]pyridin-6-yl)-N-(1-(3-amino-4-chloroisoxazolo[5,4-c]pyridin-7-yl)pyrrolidin-3-yl)-2-chlorobenzamide (EXAMPLE 38);

(R)—N-(1-(3-Amino-5-(difluoromethyl)isoxazolo[5,4-c]pyridin-7-yl)pyrrolidin-3-yl)-2-chloro-4-(3-methyl-1H-1,2,4-triazol-1-yl)benzamide (EXAMPLE 39);

(R)—N-(1-(3-Amino-4-chloroisoxazolo[5,4-c]pyridin-7-yl)pyrrolidin-3-yl)-2-chloro-4-(1-methyl-6-oxo-1,6-dihydropyridazin-3-yl)benzamide (EXAMPLE 40);

(R)—N-(1-(3-Amino-5-cyanoisoxazolo[5,4-c]pyridin-7-yl)pyrrolidin-3-yl)-2-chloro-4-(3-methyl-1H-1,2,4-triazol-1-yl)benzamide (EXAMPLE 41);

(R)—N-(1-(3-Amino-5-methylisoxazolo[5,4-c]pyridin-7-yl)pyrrolidin-3-yl)-2-chloro-4-(4-(2-hydroxyethyl)-1H-1,2,3-triazol-1-yl)benzamide (EXAMPLE 42);

(R)—N-(1-(3-Amino-4-chloroisoxazolo[5,4-c]pyridin-7-yl)pyrrolidin-3-yl)-2-chloro-4-(3-(trifluoromethyl)-4H-1,2,4-triazol-4-yl)benzamide (EXAMPLE 43);

(R)—N-(1-(3-Amino-4-chloroisoxazolo[5,4-c]pyridin-7-yl)pyrrolidin-3-yl)-2-chloro-4-(1-methyl-2-oxo-1,2-dihydropyrimidin-5-yl)benzamide (EXAMPLE 44);

(R)—N-(1-(3-Amino-4-chloroisoxazolo[5,4-c]pyridin-7-yl)pyrrolidin-3-yl)-2-chloro-4-(1-methyl-5-oxo-1,5-dihydro-4H-1,2,4-triazol-4-yl)benzamide (EXAMPLE 45);

(R)—N-(1-(3-Amino-4-chloroisoxazolo[5,4-c]pyridin-7-yl)pyrrolidin-3-yl)-2-chloro-4-(5-oxo-1,5-dihydro-4H-1,2,4-triazol-4-yl)benzamide (EXAMPLE 46);

(R)—N-(1-(3-Amino-4-chloroisoxazolo[5,4-c]pyridin-7-yl)pyrrolidin-3-yl)-2-chloro-4-(1-(2-hydroxyethyl)-5-oxo-1,5-dihydro-4H-1,2,4-triazol-4-yl)benzamide (EXAMPLE 47);

(R)—N-(1-(3-Amino-4-chloroisoxazolo[5,4-c]pyridin-7-yl)pyrrolidin-3-yl)-2-chloro-4-(9H-purin-9-yl)benzamide (EXAMPLE 48);

(R)—N-(1-(3-Amino-5-methylisoxazolo[5,4-c]pyridin-7-yl)pyrrolidin-3-yl)-2,6-dichloro-4-(1-methyl-5-oxo-1,5-dihydro-4H-1,2,4-triazol-4-yl)benzamide (EXAMPLE 49);

(R)—N-(1-(3-Amino-4-chloroisoxazolo[5,4-c]pyridin-7-yl)pyrrolidin-3-yl)-2-chloro-4-(5-oxo-1-(2,2,2-trifluoroethyl)-1,5-dihydro-4H-1,2,4-triazol-4-yl)benzamide (EXAMPLE 50);

(R)—N-(1-(3-Amino-4-chloroisoxazolo[5,4-c]pyridin-7-yl)pyrrolidin-3-yl)-2-chloro-4-(7H-purin-7-yl)benzamide (EXAMPLE 51);

(R)—N-(1-(3-Amino-4-chloroisoxazolo[5,4-c]pyridin-7-yl)pyrrolidin-3-yl)-3-chloro-5-(3-methyl-1H-1,2,4-triazol-1-yl)picolinamide (EXAMPLE 52) or (R)—N-(1-(3-Amino-4-chlorobenzo[d]isoxazol-7-yl)pyrrolidin-3-yl)-2-chloro-4-(2-(hydroxymethyl)pyridin-4-yl)benzamide (EXAMPLE 53).

In the fourth aspect, the present invention provides intermediate compounds represented by Formula (VII):

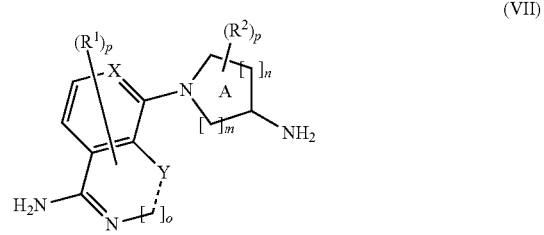

or pharmaceutically acceptable salts or solvates thereof;

wherein: m is an integer of 1 to 2; n is an integer of 1 to 2; o is an integer of 0 or 1; p is an integer of 0 to 5; q is an integer of 0 to 4; X is a nitrogen atom or CH; Y is an oxygen atom, a sulfur atom or NH (when o=0), a nitrogen atom or CH (when o=1);

each $R^1$ is independently a halogen atom, a cyano group, a $C_{1-6}$ alkyl group, a halogenated $C_{1-6}$ alkyl group, a hydroxyl $C_{1-6}$ alkyl group, a $C_{3-12}$ cycloalkyl group, a $C_{1-6}$ alkoxy group, a halogenated $C_{1-6}$ alkoxy group, a $C_{2-7}$ alkanoyl group or a group of —$NR^AR^B$; $R^A$ and $R^B$ are each independently a hydrogen atom, a $C_{1-6}$ alkyl group or a $C_{2-7}$ alkanoyl group;

each $R^2$ is independently a hydroxyl group, a $C_{1-6}$ alkyl group, a halogenated $C_{-6}$ alkyl group, a hydroxyl $C_{1-6}$ alkyl group, a $C_{1-6}$ alkoxy group, a halogenated $C_{1-6}$ alkoxy group, a $C_{6-14}$ aryl group, a heteroaryl group or oxo.

In another aspect, in the compounds represented by Formula (VII). A bicyclic substructure of Formula (VII) is a bicycle represented by Formula (VI):

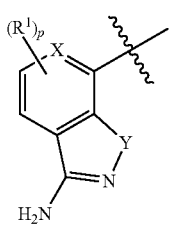

bicycle is

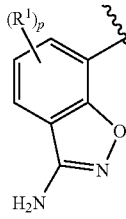 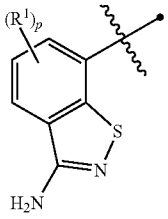 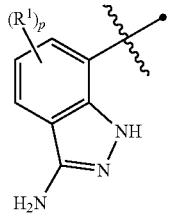

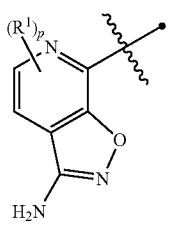 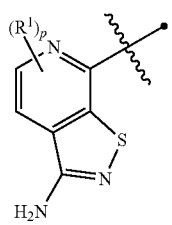 or

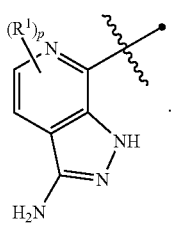

In a further aspect, a substructure of a bicycle represented by Formula (II) is

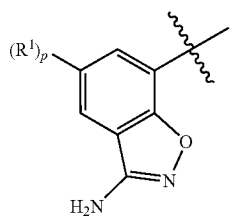 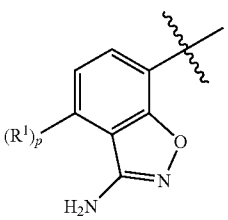 or

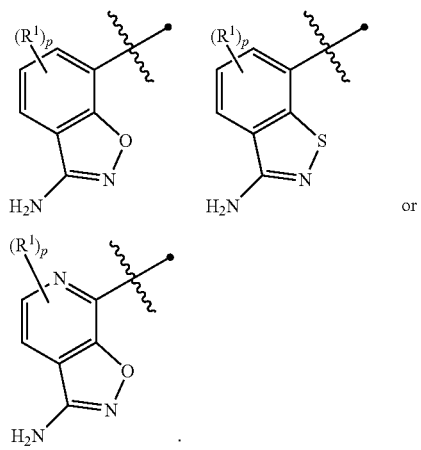

In a further aspect, a substructure of a bicycle represented by Formula (II) is

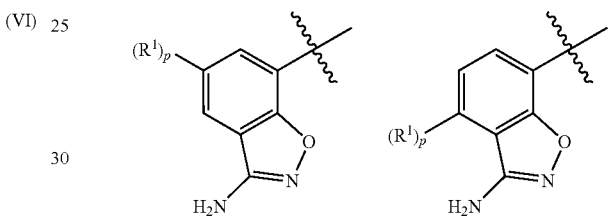

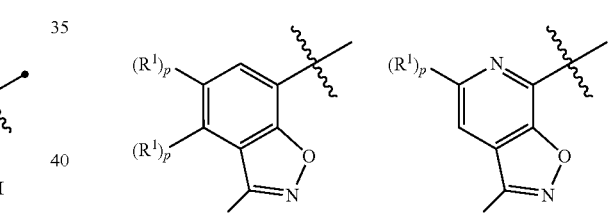

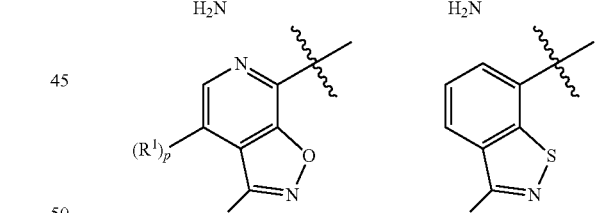

or 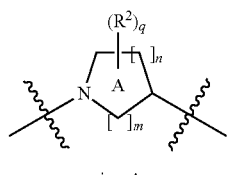.

In another aspect, in the compounds represented by Formula (VIII), m, n and a substructure of ring A represented by Formula (III):

(III)

ring A is a non aromatic heterocyclic group selected from

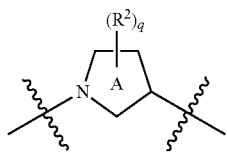

m = 1, n = 1

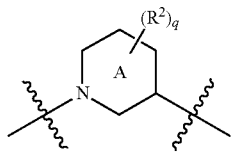

m = 1, n = 2 or

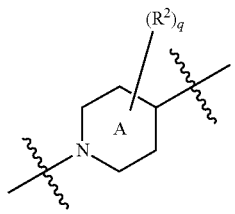

m = 2, n = 1

(in a substructure of ring A represented by Formula (III), Formula (III-a) means m is 1 and n is 1; Formula (III-b) means m is 1 and n is 2; Formula (III-c) means m is 2 and n is 1).

In a further aspect, a substructure of ring A represented by Formula (III) is (III-a)

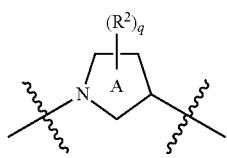

m = 1, n = 1

(III-a-2)

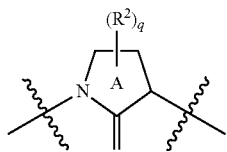

m = 1, n = 1 or (III-a-3)

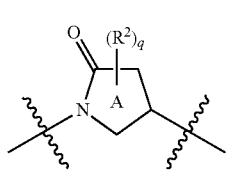

m = 1, n = 1

(in a substructure of ring A represented by Formula (III), each of Formula (III-a), (III-a-2) or (III-a-3) mean m is 1 and n is 1).

In a further aspect, a substructure of ring A represented by Formula (III) represents a group selected from

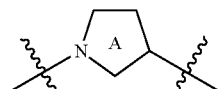

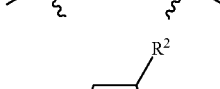

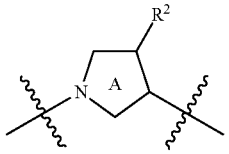

or

(in a substructure of ring A represented by Formula (III), m is 1 and n is 1).

In another aspect, in the compounds represented by Formula (VIII), o is an integer of 0 to 1, p is an integer of 0 to 3, q is an integer of 0 to 4; $R^1$ is a halogen atom, a cyano group, a $C_{1-6}$ alkyl group, a halogenated $C_{1-6}$ alkyl group, a hydroxyl $C_{1-6}$ alkyl group, a $C_{3-12}$ cycloalkyl group, a $C_{1-6}$ alkoxy group, a halogenated $C_{1-6}$ alkoxy group, or a group of —$NR^A R^B$ ($R^A$ and $R^B$ each independently represent a group selected from a hydrogen atom, a $C_{1-6}$ alkyl group or a $C_{2-7}$ alkanoyl group); $R^2$ is a hydroxyl group, a $C_{1-6}$ alkyl group, a halogenated $C_{1-6}$ alkyl group, a hydroxyl $C_{1-6}$ alkyl group, a $C_{6-14}$ aryl group, or a heteroaryl group; a substructure of bicycle represented by Formula (II) is

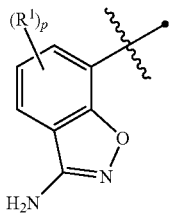

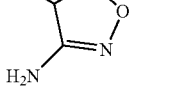

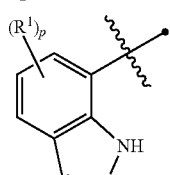

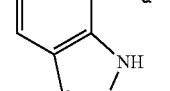

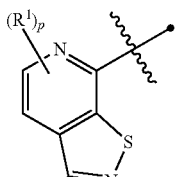

or

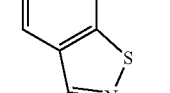

a substructure of ring A represented by Formula (III) and the definition of m and n are

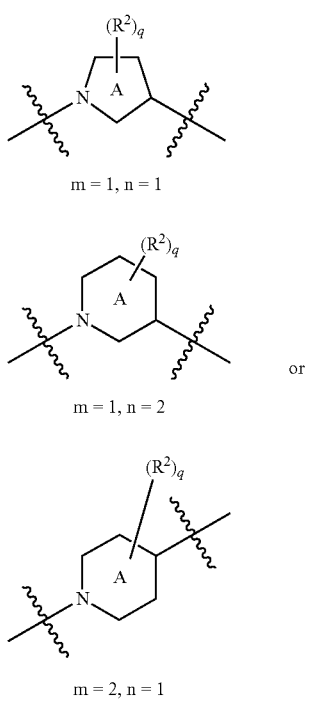

m = 1, n = 1 (III-a)

m = 1, n = 2 (III-b)

or m = 2, n = 1 (III-c)

(in a substructure of ring A represented by Formula (III), Formula (III-a) means m is 1 and n is 1; Formula (III-b) means m is 1 and n is 2; Formula (III-c) means m is 2 and n is 1).

In another aspect, in the compounds represented by Formula (VIII), o is an integer of 0, p is an integer of 0 to 3, q is an integer of 0 to 4; $R^1$ is a halogen atom, a cyano group, a $C_{1-6}$ alkyl group, a halogenated $C_{1-6}$ alkyl group, a hydroxyl $C_{1-6}$ alkyl group, a $C_{3-12}$ cycloalkyl group, a $C_{1-6}$ alkoxy group, or a halogenated $C_{1-6}$ alkoxy group; $R^2$ is a hydroxyl group, a $C_{1-6}$ alkyl group, a halogenated $C_{1-6}$ alkyl group, a hydroxyl $C_{1-6}$ alkyl group, or a $C_{6-14}$ aryl group; a substructure of bicycle represented by Formula (II) is

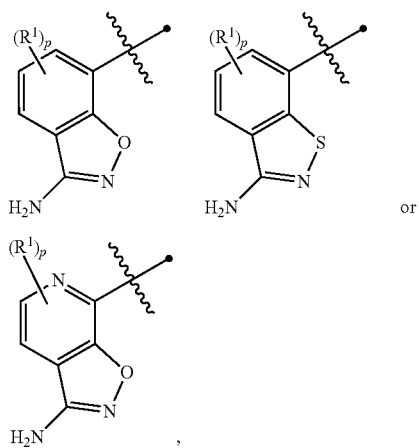

or

, a substructure of ring A represented by Formula (III) and the definition of m and n are

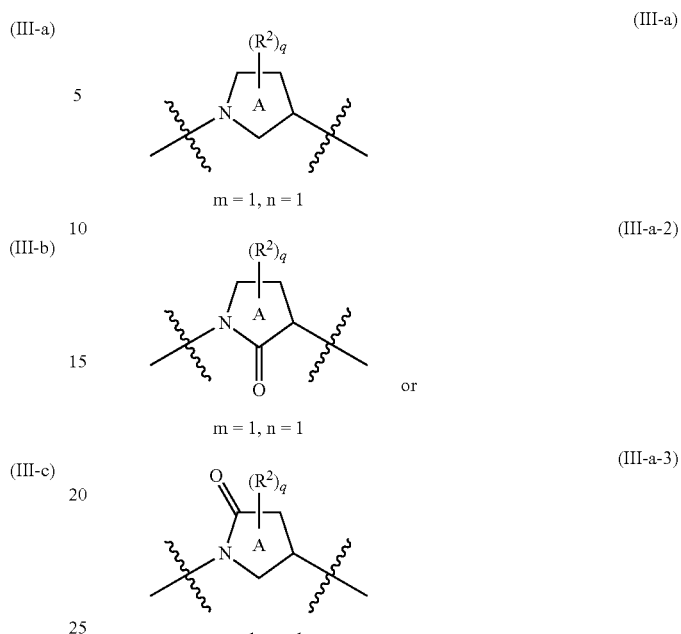

m = 1, n = 1 (III-a)

m = 1, n = 1 (III-a-2)

or m = 1, n = 1 (III-a-3)

(in a substructure of ring A represented by Formula (III), each of Formula (III-a), (III-a-2) or (III-a-3) mean m is 1 and n is 1).

In another aspect, in the compounds represented by Formula (VIII), o is an integer of 0, p is an integer of 0 to 3, q is an integer of 0 to 4; $R^1$ is a halogen atom, a cyano group, a $C_{1-6}$ alkyl group, or a halogenated $C_{1-6}$ alkyl group; $R^2$ is a hydroxyl group, a $C_{1-6}$ alkyl group, or a $C_{6-14}$ aryl group; a substructure of bicycle represented by Formula (II) is

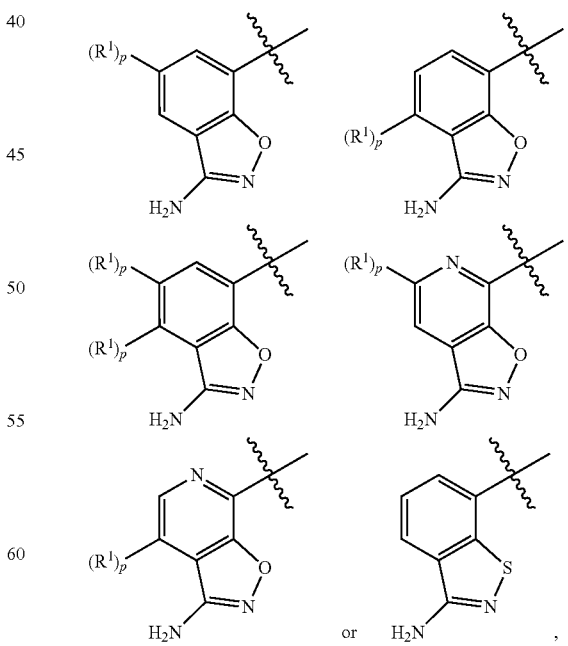

or

, a substructure of ring A represented by Formula (III) and the definition of m and n are

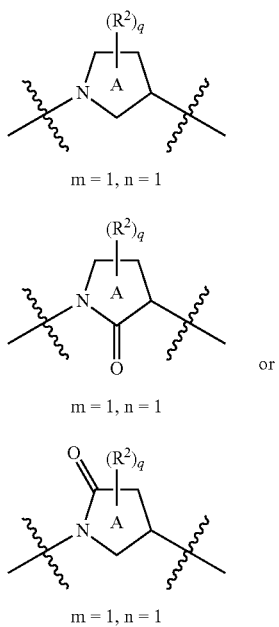

(in a substructure of ring A represented by Formula (III), each of Formula (III-a), (III-a-2) or (III-a-3) mean m is 1 and n is 1).

In the fifth aspect, the present invention provides intermediate compounds, or optical isomers thereof, or a solvate thereof, or a pharmaceutically acceptable salt thereof selected from:

7-(3-aminopyrrolidin-1-yl)benzo[d]isoxazol-3-amine (Intermediate of EXAMPLE 1);
7-(3-amino-3-methylpyrrolidin-1-yl)benzo[d]isoxazol-3-amine (Intermediate of EXAMPLE 2);
7-(3-amino-3-phenylpyrrolidin-1-yl)benzo[d]isoxazol-3-amine (Intermediate of EXAMPLE 3);
7-(3-aminopyrrolidin-1-yl)benzo[d]isothiazol-3-amine (Intermediate of EXAMPLE 4);
7-(3-aminopyrrolidin-1-yl)isoxazolo[5,4-c]pyridin-3-amine (Intermediate of EXAMPLE 5);
7-(3-aminopyrrolidin-1-yl)-5-methylbenzo[d]isoxazol-3-amine (Intermediate of EXAMPLE 6);
7-(3-amino-3,4-dimethylpyrrolidin-1-yl)benzo[d]isoxazol-3-amine (Intermediate of EXAMPLE 7);
4-amino-1-(3-aminobenzo[d]isoxazol-7-yl)pyrrolidin-3-ol (Intermediate of EXAMPLE 8);
7-(3-aminopyrrolidin-1-yl)-4-chlorobenzo[d]isoxazol-3-amine (Intermediate of EXAMPLE 9, 18, 19, 23, 25, 26 or 53);
7-(3-aminopyrrolidin-1-yl)-5-chlorobenzo[d]isoxazol-3-amine (Intermediate of EXAMPLE 10, 16 or 17);
7-(3-aminopyrrolidin-1-yl)-4-chloroisoxazolo[5,4-c]pyridin-3-amine (Intermediate of EXAMPLE 11, 20, 21, 22, 24, 27, 28, 29, 30, 31, 32, 33, 35, 36, 37, 38, 40, 43, 44, 45, 46, 47, 48, 50, 51 or 52);
7-(3-aminopyrrolidin-1-yl)-4-chloro-5-methylbenzo[d]isoxazol-3-amine (Intermediate of EXAMPLE 12);
7-(3-aminopyrrolidin-1-yl)-4-fluorobenzo[d]isoxazol-3-amine (Intermediate of EXAMPLE 13);
7-(3-aminopyrrolidin-1-yl)-4,5-dichlorobenzo[d]isoxazol-3-amine (Intermediate of EXAMPLE 14);
7-(3-amino-3-methylpyrrolidin-1-yl)-5-chlorobenzo[d]isoxazol-3-amine (Intermediate of EXAMPLE 15);
3-amino-7-(3-aminopyrrolidin-1-yl)benzo[d]isoxazole-5-carbonitrile (Intermediate of EXAMPLE 34);
7-(3-aminopyrrolidin-1-yl)-5-(difluoromethyl)isoxazolo[5,4-c]pyridin-3-amine (Intermediate of EXAMPLE 39);
3-amino-7-(3-aminopyrrolidin-1-yl)isoxazolo[5,4-c]pyridine-5-carbonitrile (Intermediate of EXAMPLE 41) or
7-(3-aminopyrrolidin-1-yl)-5-methylisoxazolo[5,4-c]pyridin-3-amine (Intermediate of EXAMPLE 42 or 49).

In the sixth aspect, carboxylic acid compounds represented by the general formula CAs (CA-1 through CA-8) of the present invention are useful and novel as the intermediates of the compounds having FIXa inhibitory activities (for example, described in the EXAMPLES 2, 3, 4, 6, 7, 8, 16, 17, 18, 20, 21, 22, 23, 25, 26, 27, 28, 30, 31, 32, 42, 43, 45, 46, 47, 48, 49, 50, 51, 52 and 53).

Methods for Producing the Compounds of the Present Invention
General Methods

Methods for producing compounds of Formula (I) of the present invention will be described below.

The compounds represented by Formula (I) and salts thereof, which are the compounds of the present invention, can be readily produced from known compounds or commercially available compounds by, for example, known processes described in published documents, and produced by production processes described below. The present invention is not limited to the production processes described below.

Unless otherwise noted, m, n, o, p, q, r, s, $R^1$, $R^2$, $R^3$, $R^4$, $R^5$, X, Y, $Z^1$, $Z^2$, $Z^3$, $Z^4$, a substructure of bicycle represented by Formula (II) or Formula (VI), a substructure of ring A represented by Formula (III), a substructure of ring B represented by Formula (V) and a substructure of Het ring represented by Formula (IV) in the formulae shown in the description of the production method are as defined above for the Formula (I). The alkylene group in the side chain or ring of the compound may be substituted with the substituents defined for the Formula (I).

In the production methods, the definition of $R^A$ is a $C_{1-6}$ alkyl, $C_{6-14}$ aryl, or $C_{7-20}$ aralkyl unless otherwise specified.

In the production methods, the definition of $R^{3A}$ is a $C_{1-6}$ alkyl, $C_{6-14}$ aryl, $C_{7-20}$ alalkyl or heterocyclic group unless otherwise specified.

In the production methods, the definition of Z is a halogen atom, such as a fluoro atom, chloro atom, bromo atom and iodo atom, unless otherwise specified.

In the production methods, the definition of W is a boronic acid, a boronic acid ester, or a trifluoroborate salt unless otherwise specified.

In the production methods, the definition of $P^1$ is a protective group for a hydroxy group (—OH) or a thiol group (—SH) unless otherwise specified. Examples of the protective group for a hydroxy group include an alkoxyalkyl group such as a methoxymethyl group, a methoxyethoxymethyl group, and a tetrahydropyranyl group; an arylmethyl group such as a benzyl group and a triphenylmethyl group; a silyl group such as a triethylsilyl group and a t-butyldimethylsilyl group; an alkanoyl group such as an acetyl group; an aroyl group such as a benzoyl group; an alkylcarbonyl group such as a methoxycarbonyl group; and an arylmethylcarbonyl group such as a benzyloxycarbonyl group. Examples of the protective group for a thiol group include an arylmethyl group such as a benzyl group and a triphenylmethyl group; an alkanoyl group such as an acetyl group and a pivaloyl group; and an aroyl group such as a benzoyl group.

In the production methods, the definition of P² is a protective group for a phenolic hydroxy group unless otherwise specified. Examples of the protective group include an alkoxyalkyl group such as a methoxymethyl group, a methoxyethoxymethyl group, and a tetrahydropyranyl group; an arylmethyl group such as a benzyl group; a silyl group such as a trimethylsilyl group and a t-butyldimethylsilyl group; an alkanoyl group such as an acetyl group and a pivaloyl group; an aroyl group such as a benzoyl group; an alkylcarbonyl group such as a methoxycarbonyl group; and an arylmethylcarbonyl group such as a benzyloxycarbonyl group.

In the production methods, the definition of P³ is a protective group for an amino group (—$NH_2$) or an imino group (—NH—) unless otherwise specified. Examples of the protective group include an alkanoyl group such as an acetyl group; an arylmethyl group such as a benzyl group (Bn), 2,4-dimethoxybenzyl group (2,4-DMB) and a triphenylmethyl group (Tr); an alkoxyalkyl group such as a methoxymethyl group and a methoxyethoxymethyl group; an alkyl group such as a methyl group, an ethyl group and a tert-butyl group; an alkanoyl group such as an acetyl group; an alkoxycarbonyl group such as a methoxycarbonyl group, an ethoxycarbonyl group, and a tert-butoxycarbonyl group (Boc); an arylmethoxycarbonyl group such as a benzyloxycarbonyl group (Z), a para-methoxybenzyloxycarbonyl group, and a para-nitrobenzyloxycarbonyl group; an alkenyloxycarbonyl group such as a allyloxycarbonyl group (alloc), and an aroyl group such as a benzoyl group (Bz).

Deprotection methods of such protective groups are different depending on the chemical properties of a protected reactive group (a hydroxy group, a thiol group, or an imino group) and an employed protective group. For example, an acyl-type protective group such as an alkanoyl group, an alkoxycarbonyl group, and an aroyl group can be hydrolyzed using a suitable base such as an alkali metal hydroxide including lithium hydroxide, sodium hydroxide, and potassium hydroxide for the deprotection. An alkoxyalkyl-type protective group such as a methoxymethyl group, a methoxyethoxymethyl group, and a tetrahydropyranyl group, a substituted methoxycarbonyl-type protective group such as a t-butoxycarbonyl group and a para-methoxybenzyloxycarbonyl group, and a silyl-type protective group such as a triethylsilyl group and a t-butyldimethylsilyl group can be removed using a suitable acid such as acetic acid, hydrochloric acid, hydrobromic acid, sulfuric acid, phosphoric acid, trifluoroacetic acid, and trifluoromethanesulfonic acid or a combination of them. The silyl-type protective group can also be removed using a suitable fluorine ion ($F^-$) generating reagent such as tetrabutylammonium fluoride and hydrogen fluoride. An arylmethoxycarbonyl group such as a benzyloxycarbonyl group, a para-methoxybenzyloxycarbonyl group, and a para-nitrobenzyloxycarbonyl group and an arylmethyl group such as a benzyl group can be removed by hydrogenolysis using a palladium carbon catalyst. A benzyl group can be removed by Birch reduction using metallic sodium in liquid ammonia. A triphenylmethyl group can be removed using a suitable acid such as acetic acid, hydrochloric acid, hydrobromic acid, sulfuric acid, phosphoric acid, trifluoroacetic acid, and trifluoromethanesulfonic acid or a combination of them. It can also be removed by Birch reduction using metallic sodium in liquid ammonia and removed by hydrogenolysis using a palladium carbon catalyst.

During the production of the compound of Formula (I) of the present invention, when it has a reactive group such as a hydroxy group, an amino group, and a carboxy group, such group may be properly protected in any reaction step, and the protective group may be removed in a suitable step. Methods for introducing and removing such protective groups are properly employed depending on the type of a group to be protected or a protective group. For example, such introduction and removal can be performed by methods described in the review section of Greene, T. W., et. al., *Protective Groups in Organic Synthesis*, 2007, 4th Ed., Wiley, New York, or Kocienski, P., *Protecting Groups* 1994, Thieme.

The required starting materials, such as (A-1), (C-1), (C-2), (C-6), (I-1), (L-1), (L-3), (M-1), (N-1), (N-4), (P-8), (Q-1), (R-1) and (S-1) are either commercially available, or known compounds, or capable of being readily synthesized by the method commonly used in the organic chemistry from commercially available or known compounds. Unless otherwise noted, the reaction conditions employed in the production method are as described below:

Reaction conditions in the production methods are as follows unless otherwise specified. The reaction temperature is in a range from −78° C. to the reflux temperature of a solvent, and the reaction time is a time sufficient for a reaction. Examples of the reaction inert solvent include, but are not limited to, an aromatic hydrocarbon solvent such as toluene and benzene; a polar solvent such as water, methanol, N,N-dimethylformamide, dimethyl sulfoxide, and 1,3-dimethyl-2-imidazolidinone; a basic solvent such as triethylamine and pyridine; a halogenated solvent such as chloroform, methylene chloride, and 1,2-dichloroethane; an ether solvent such as diethyl ether, tetrahydrofuran, and dioxane; and a mixed solvent of them. Such solvents are properly selected depending on reaction conditions. Examples of the base include, but are not limited to, an inorganic base such as potassium carbonate, cesium carbonate, sodium hydroxide, potassium hydroxide, and sodium hydride; and an organic base such as triethylamine, pyridine, N,N-dialkylaniline, and lithium diisopropylamide. Examples of the acid include, but are not limited to, a mineral acid such as hydrochloric acid and sulfuric acid, and an organic acid such as methanesulfonic acid and p-toluenesulfonic acid. The base and the acid are not necessarily limited to those mentioned above.

Hereinafter, production methods will be described, but the present invention is not limited to these methods.

Scheme 1: Condensation of an amine represented by formula (AM) with a carboxylic acid represented by formula (CA).

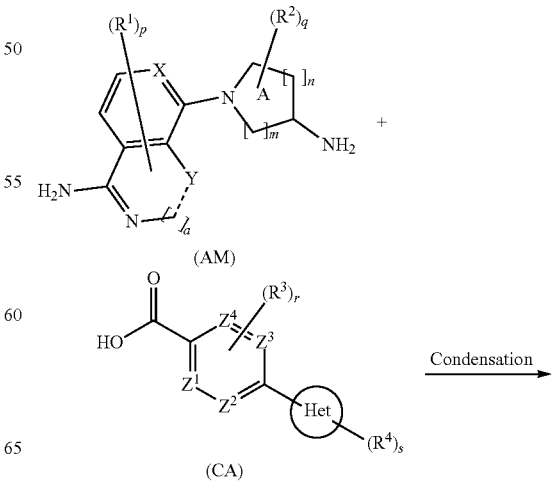

-continued

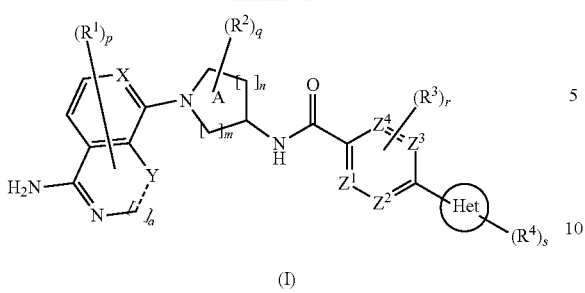

(I)

A compound represented by formula (I) can be produced by condensation of an amine represented by formula (AM) with a carboxylic acid represented by formula (CA).

Scheme 2: [Synthetic Procedure A] Synthetic route of an amine represented by (AM-1); in the case of n = 0, Y = O, X = CH, ----- = single bond at a compound represented by formula (AM).

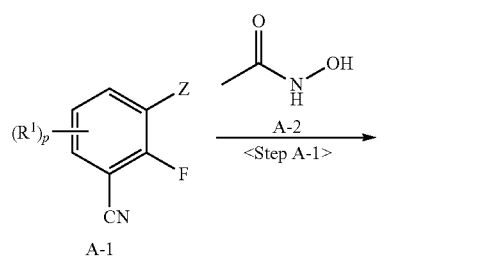

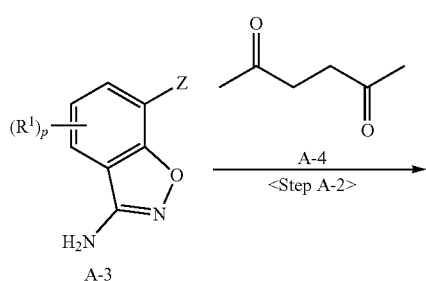

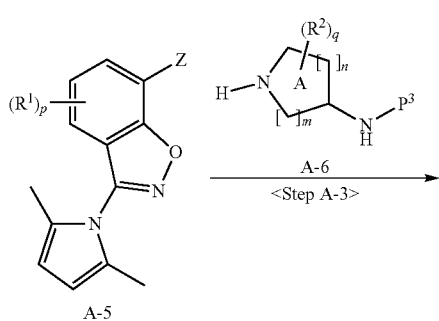

-continued

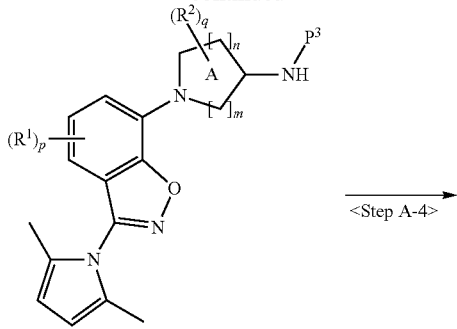

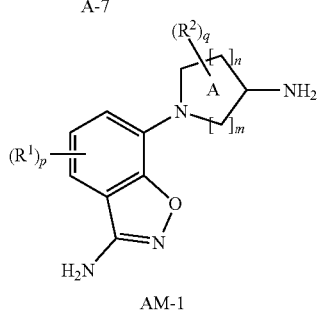

AM-1

Z = Halogen atom

<Step A-1>

In accordance with a similar process that described in published documents, for example, *Tetrahedron Letters*, 37(17), p 2885-2886, 1996, a compound represented by formula (A-3) can be produced from a compound represented by formula (A-1), which is commercially available or can be produced by various methods known in the published literature, to react with N-hydroxyacetamide represented by formula (A-2) in the presence of a base such as potassium tert-butoxide, sodium tert-butoxide, potassium carbonate, sodium carbonate, or cesium carbonate and in a solvent which is inactive to the reaction, such as diethyl ether, tetrahydrofuran, 1,2-dimethoxyethane, 1,4-dioxane, N,N-dimethylformamide, dimethyl sulfoxide, or a mixed solvent thereof at a temperature in the range of room temperature to the solvent-reflux temperature.

<Step A-2>

In accordance with a similar process that described in published documents, for example, *Journal of Medicinal Chemistry*, 51(24), p 7843-7854, 2008, a compound represented by formula (A-5) can be produced from a compound represented by formula (A-3) to react with 2,5-hexanedione represented by formula (A-4) in a solvent which is inactive to the reaction, such as acetic acid at a temperature in the range of room temperature to the solvent-reflux temperature.

<Step A-3>

In accordance with a similar process that described in published documents, for example, World Intellectual Property Organization (WIPO) publication, WO2009/059112, p 124, a compound represented by formula (A-7) can be produced from a compound represented by formula (A-5) to react with a compound represented by formula (A-6), which is commercially available or can be produced by various methods known in the published literature, in the presence of a base such as cesium carbonate, potassium carbonate, potassium phosphate, sodium tert-butoxide, triethyl amine, or N,N-diisopropylethylamine, in the presence of Pd-catalyst such as tris(dibenzylideneacetone)dipalladium ((dba)₃Pd₂), palladium(II) acetate (Pd(OAc)₂), and in the presence of phosphine ligand such as dicyclohexylphosphino-2',4',6'-triisopropylbiphenyl (X-phos), 4,5-Bis(diphenylphosphino)-9,9-dimethylxanthene (XANTPHOS), 2,2'-bis(diphenylphosphino)-1,1'-binaphthyl (BINAP) or [1,1'-biphenyl]-2-yl-bis(1,1-dimethylethyl)-phosphine (JohnPhos) in a solvent which is inactive to the reaction, such as toluene, N,N-dimethylformamide, N,N-dimethylacetamide, N-methylpyrrolidone, acetonitrile, acetonitrile/H₂O, dioxane, dioxane/H₂O, tetrahydrofuran, tetrahydrofuran/H₂O or a mixed solvent thereof at a temperature in the range of room temperature to the solvent-reflux temperature.

<Step A-4>

In accordance with a similar process that described in published documents, for example, Greene, T. W., et. al., *Protective Groups in Organic Synthesis* (2007), 4th Ed., a compound represented by formula (AM-1) can be produced from a compound represented by formula (A-7) in the presence of a acid such as hydrochloric acid, acetic acid, or trifluoroacetic acid, with or without a solvent which is inactive to the reaction, such as water, dichloromethane, dioxane, tetrahydrofuran, ethyl acetate, or a mixed solvent thereof at a temperature in the range of 0° C. to the solvent-reflux temperature.

Scheme 3: [Synthetic Procedure B] Alternative synthetic route of an amine represented by formula (AM-1).

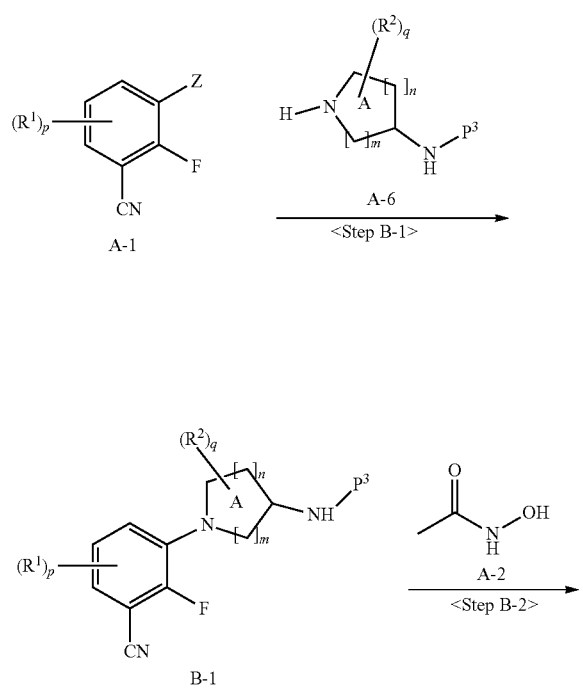

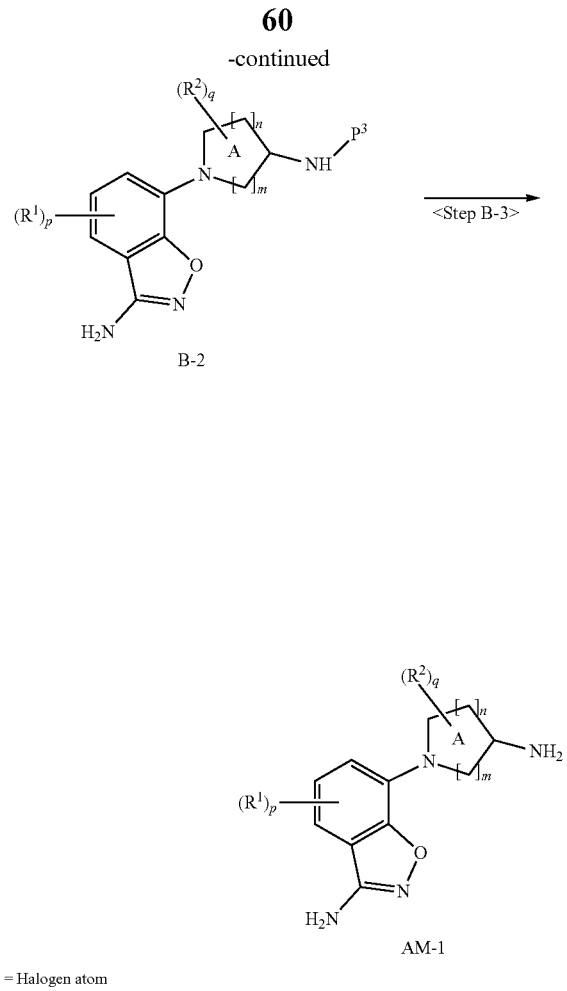

Z = Halogen atom

<Step B-1>

A compound represented by formula (B-1) can be produced by the similar process as that used in <Step A-3> of Reaction Scheme 2 using a compound represented by formula (A-1), which is commercially available or can be produced by various methods known in the published literature, and a compound represented by formula (A-6), which is commercially available or can be produced by various methods known in the published literature.

<Step B-2>

A compound represented by formula (B-2) can be produced by the similar process as that used in <Step A-1> of Reaction Scheme 2 using a compound represented by formula (B-1) and N-hydroxyacetamide represented by formula (A-2).

<Step B-3>

A compound represented by formula (AM-1) can be produced by the similar process as that used in <Step A-3> of Reaction Scheme 2 using a compound represented by formula (B-2).

Scheme 4: [Synthetic Procedure C] Synthetic route of an amine represented by formula (AM-2); in the case of n = 0, Y = O, X = N, ----- = single bond at an amine represented by formula (AM).

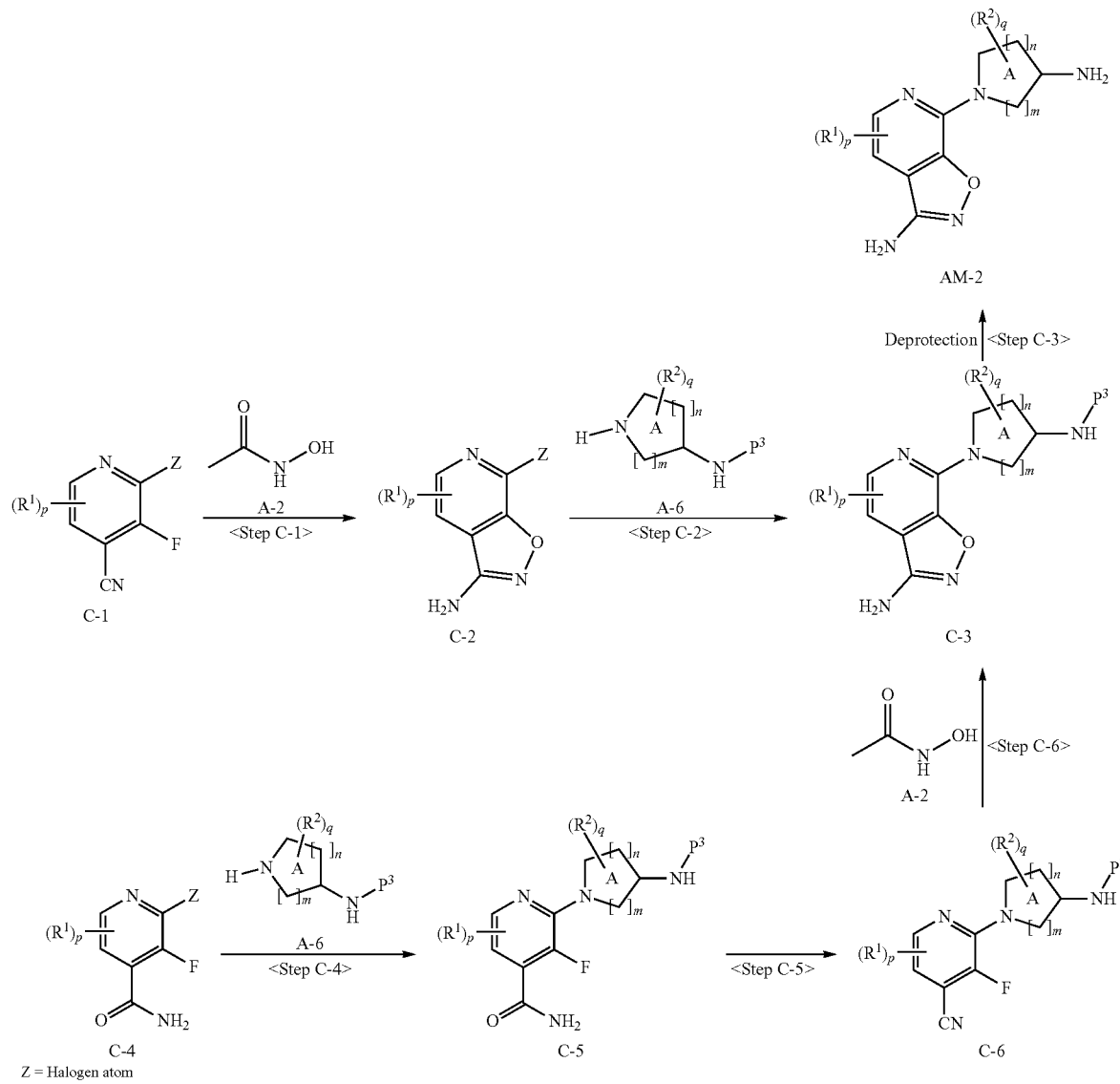

Z = Halogen atom

<Step C-1>
A compound represented by formula (C-2) can be produced by the similar process as that used in <Step A-1> of Reaction Scheme 2 using a compound represented by formula (C-1), which is commercially available or can be produced by various methods known in the published literature, and N-hydroxyacetamide represented by formula (A-2).

<Step C-2>
In accordance with a similar process that described in published documents, for example, *Bioorganic & Medicinal Chemistry Letters*, 16(12), p 3287-3291, 2006, a compound represented by formula (C-3) can be produced from a compound represented by formula (C-2) to react with a compound represented by formula (A-6), which is commercially available or can be produced by various methods known in the published literature, in the presence of a base such as potassium carbonate, sodium carbonate, cesium carbonate, triethyl amine, or N,N-diisopropylethylamine, in a solvent which is inactive to the reaction, such as dimethyl sulfoxide, N,N-dimethylformamide, N,N-dimethylacetamide, N-methylpyrrolidone, acetonitrile or a mixed solvent thereof at a temperature in the range of room temperature to the solvent-reflux temperature.

<Step C-3>
A compound represented by formula (AM-2) can be produced by the similar process as that used in <Step A-3> of Reaction Scheme 2 using a compound represented by formula (C-3).

<Step C-4>
A compound represented by formula (C-5) can be produced by the similar process as that used in <Step C-2> of Reaction Scheme 4 using a compound represented by formula (C-4), which is commercially available or can be produced by various methods known in the published literature, and a compound represented by formula (A-6), which is commercially available or can be produced by various methods known in the published literature.

<Step C-5>

In accordance with a similar process that described in published documents, for example, *Journal of Medicinal Chemistry*, 53(15), p 5422-5438, 2010, a compound represented by formula (C-6) can be produced from a compound represented by formula (C-5) to react with trifluoroacetic anhydride (TFAA) in the presence of a base such as triethyl amine, or N,N-diisopropylethylamine, in a solvent which is inactive to the reaction, such as dichloromethane, 1,2-dichloroethane or a mixed solvent thereof at a temperature in the range of 0° C. to the solvent-reflux temperature.

<Step C-6>

A compound represented by formula (C-3) can be produced by the similar process as that used in <Step A-1> of Reaction Scheme 2 using a compound represented by formula (C-6) and N-hydroxyacetamide represented by formula (A-2).

Scheme 5: [Synthetic Procedure D] Synthetic route of an amine represented by formula (AM-3); in the case of n = 0, Y = NH, X = CH or $CR^1$, ---- = single bond at an amine represented by formula (AM).

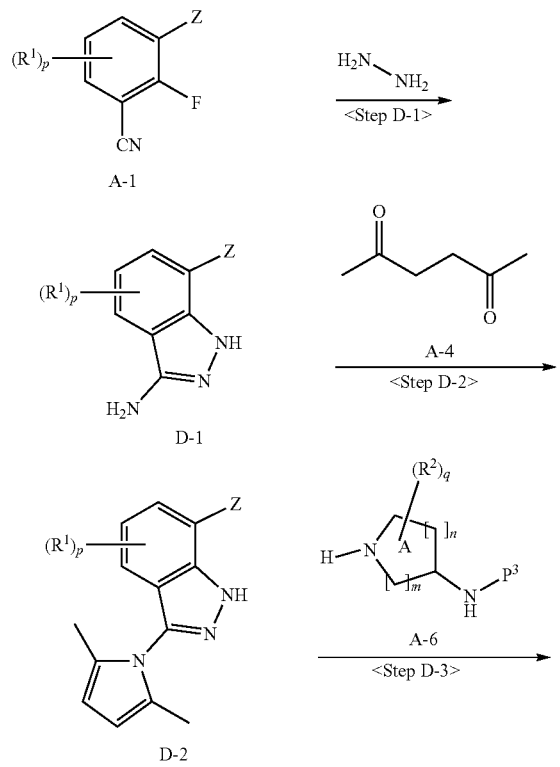

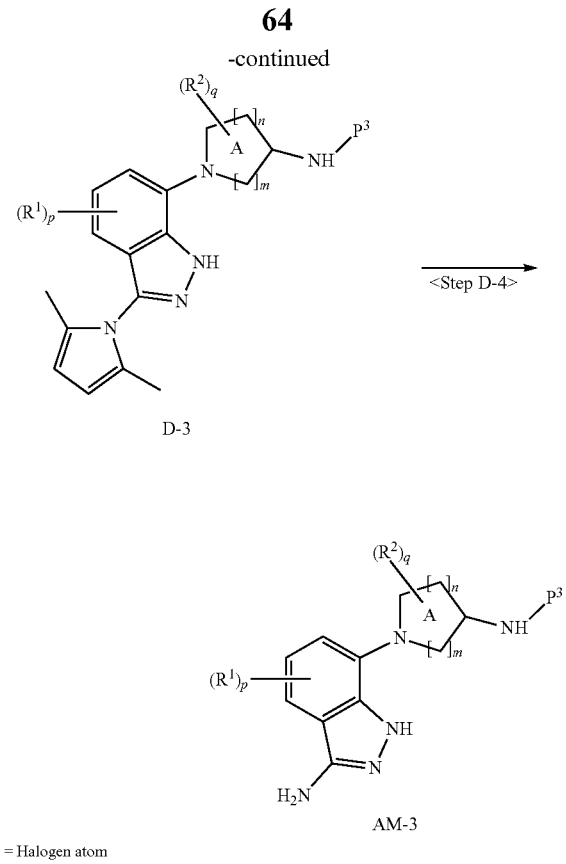

Z = Halogen atom

<Step D-1>

In accordance with a similar process that described in published documents, for example, *Bioorganic & Medicinal Chemistry*, 19(1), p 321-329, 2011, a compound represented by formula (D-1) can be produced from a compound represented by formula (A-1), which is commercially available or can be produced by various methods known in the published literature, to react with a hydrazine hydrate in a solvent which is inactive to the reaction, such as methanol, ethanol, 2-propanol, butanol or a mixed solvent thereof at a temperature in the range of room temperature to the solvent-reflux temperature.

<Step D-2>

A compound represented by formula (D-2) can be produced by the similar process as that used in <Step A-2> of Reaction Scheme 2 using a compound represented by formula (D-1) and 2,5-hexanedione represented by formula (A-4).

<Step D-3>

A compound represented by formula (D-3) can be produced by the similar process as that used in <Step A-3> of Reaction Scheme 2 using a compound represented by formula (D-2) and a compound represented by formula (A-6), which is commercially available or can be produced by various methods known in the published literature.

<Step D-4>

A compound represented by formula (AM-3) can be produced by the similar process as that used in <Step A-4> of Reaction Scheme 2 using a compound represented by formula (D-3).

Scheme 6: [Synthetic Procedure E] Alternative synthetic route of an amine represented by formula (AM-3).

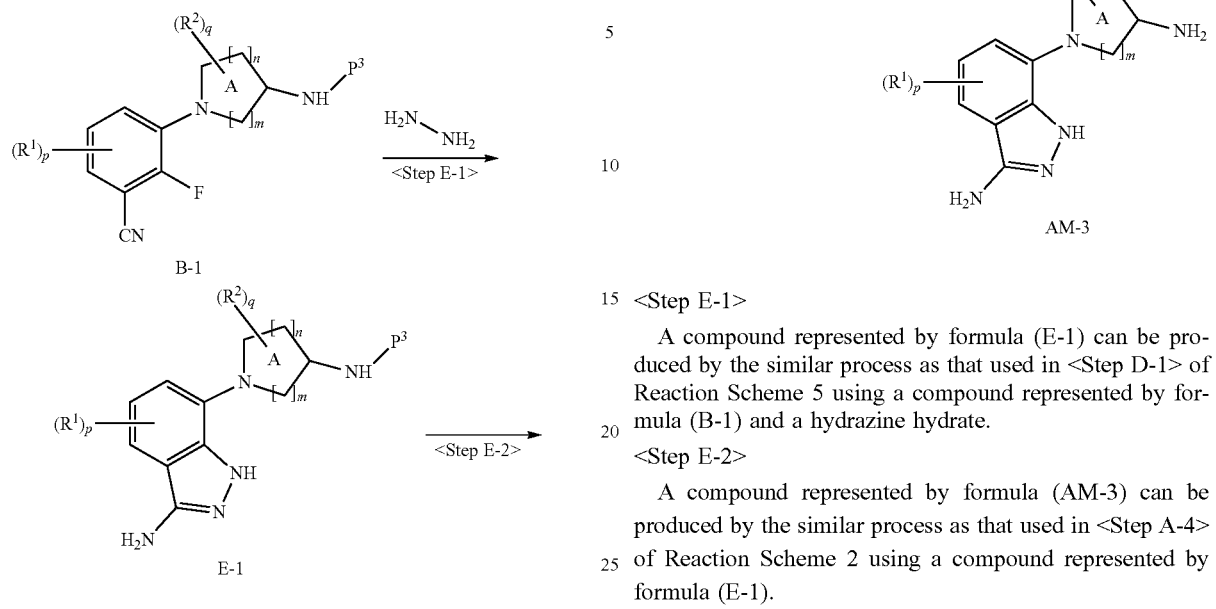

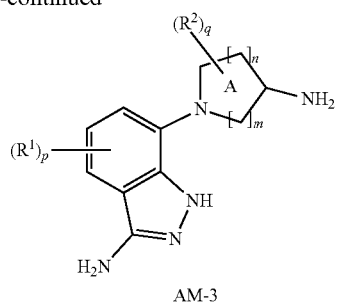

AM-3

<Step E-1>

A compound represented by formula (E-1) can be produced by the similar process as that used in <Step D-1> of Reaction Scheme 5 using a compound represented by formula (B-1) and a hydrazine hydrate.

<Step E-2>

A compound represented by formula (AM-3) can be produced by the similar process as that used in <Step A-4> of Reaction Scheme 2 using a compound represented by formula (E-1).

Scheme 7: [Synthetic Procedure F] Synthetic route of an amine represented by formula (AM-4); in the case of n = 0, Y = NH, X = N, ----- = single bond at an amine represented by formula (AM).

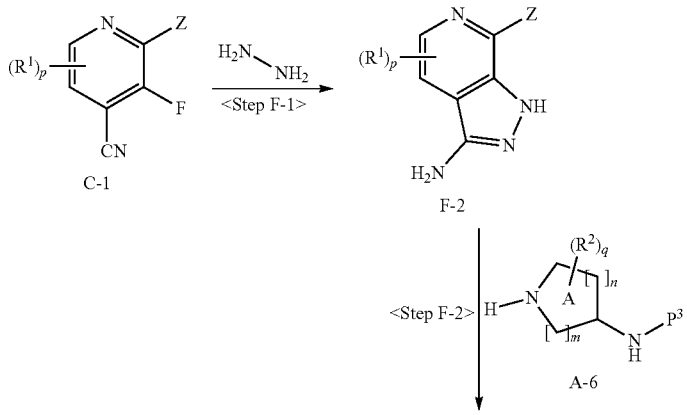

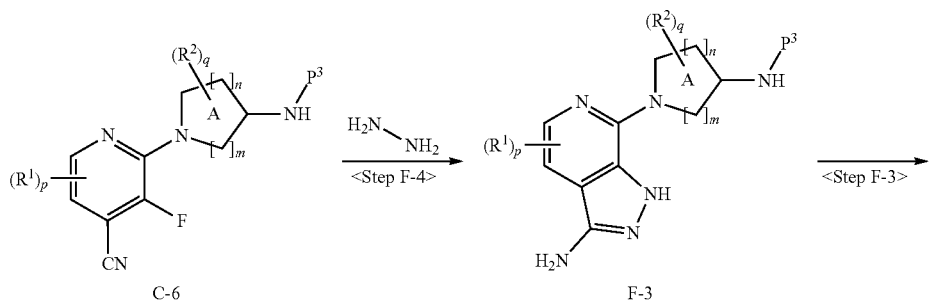

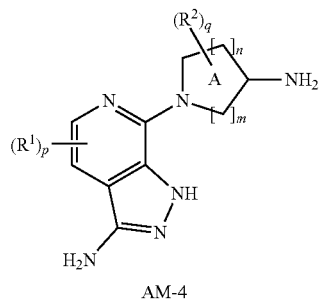

AM-4

Z = Halogen atom

<Step F-1>
In accordance with a similar process that described in published documents, for example, *Bioorganic & Medicinal Chemistry Letters*, 13(9), p 1581-1584, 2003, a compound represented by formula (F-1) can be produced from a compound represented by formula (C-1), which is commercially available or can be produced by various methods known in the published literature, to react with a hydrazine hydrate in a solvent which is inactive to the reaction, such as methanol, ethanol, 2-propanol, butanol or a mixed solvent thereof at a temperature in the range of room temperature to the solvent-reflux temperature.

<Step F-2>
A compound represented by formula (F-3) can be produced by the similar process as that used in <Step A-3> of Reaction Scheme 2 using a compound represented by formula (F-2) and a compound represented by formula (A-6), which is commercially available or can be produced by various methods known in the published literature.

<Step F-3>
A compound represented by formula (AM-4) can be produced by the similar process as that used in <Step A-4> of Reaction Scheme 2 using a compound represented by formula (F-3).

<Step F-4>
A compound represented by formula (F-3) can be produced by the similar process as that used in <Step F-1> of Reaction Scheme 7 using a compound represented by formula (C-6).

Scheme 8: [Synthetic Procedure G] Synthetic route of an amine represented by formula (AM-5); in the case of n = 0, Y = S, X = CH, ---- = single bond at an amine represented by formula (AM).

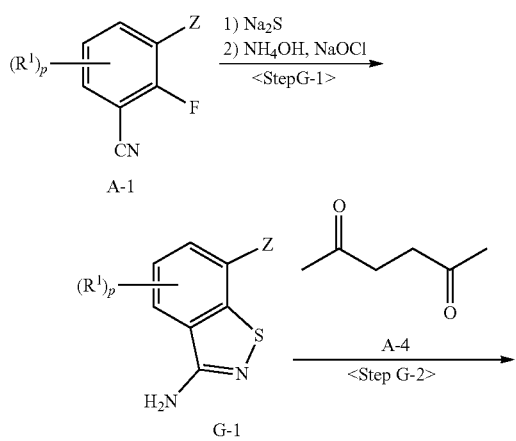

Z = Halogen atom

<Step G-1>
In accordance with a similar process that described in published documents, for example, World Intellectual Property Organization (WIPO) publication, WO2009/152200, p 73-74, a compound represented by formula (G-1) can be produced from a compound represented by formula (A-1), which is commercially available or can be produced by various methods known in the published literature, to react with a sodium sulfide in a solvent which is inactive to the reaction, such as dimethyl sulfoxide at a temperature in the range of room temperature to the solvent-reflux temperature, and then to react with sodium hypochlorite in the presence of ammonia water at a temperature in the range of 0° C. to room temperature.

<Step G-2>

A compound represented by formula (G-2) can be produced by the similar process as that used in <Step A-2> of Reaction Scheme 2 using a compound represented by formula (G-1) and 2,5-hexanedione represented by formula (A-4).

<Step G-3>

A compound represented by formula (G-3) can be produced by the similar process as that used in <Step A-3> of Reaction Scheme 2 using a compound represented by formula (G-2) and a compound represented by formula (A-6), which is commercially available or can be produced by various methods known in the published literature.

<Step G-4>

A compound represented by formula (AM-5) can be produced by the similar process as that used in <Step A-4> of Reaction Scheme 2 using a compound represented by formula (G-3).

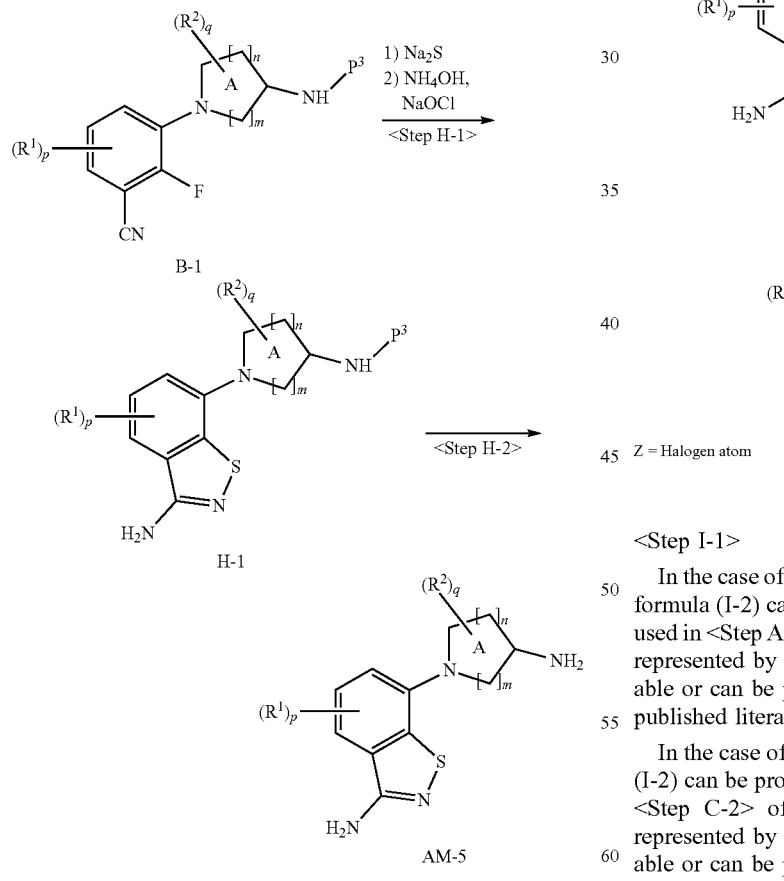

Scheme 9: [Synthetic Procedure H] Alternative synthetic route of an amine represented by formula (AM-5).

<Step H-1>

A compound represented by formula (H-1) can be produced by the similar process as that used in <Step G-1> of Reaction Scheme 8 using a compound represented by formula (B-1).

<Step H-2>

A compound represented by formula (AM-5) can be produced by the similar process as that used in <Step A-4> of Reaction Scheme 2 using a compound represented by formula (H-1).

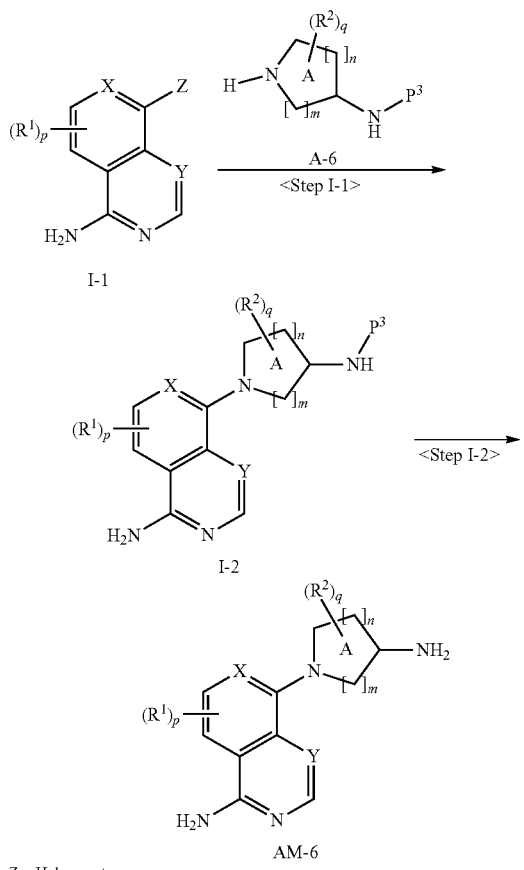

Scheme 10: [Synthetic Procedure I] Synthetic route of an amine represented by formula (AM-6); in the case of n = 1, Y = CH or N, X = CH or N, ----- = double bond at an amine represented by formula (AM).

<Step I-1>

In the case of X═CH or $CR^1$, a compound represented by formula (I-2) can be produced by the similar process as that used in <Step A-3> of Reaction Scheme 2 using a compound represented by formula (I-1) which is commercially available or can be produced by various methods known in the published literature.

In the case of X═N, a compound represented by formula (I-2) can be produced by the similar process as that used in <Step C-2> of Reaction Scheme 4 using a compound represented by formula (I-1) which is commercially available or can be produced by various methods known in the published literature.

<Step I-2>

A compound represented by formula (AM-6) can be produced by the similar process as that used in <Step A-4> of Reaction Scheme 2 using a compound represented by formula (I-2).

Scheme 11: [Synthetic Procedure L] Synthetic route of a carboxylic acid represented by formula (CA-1); in the case of a substructure of Het ring represented by Formula (IV) and Phenyl ring form C—C bond formation at a compound represented by formula (CA).

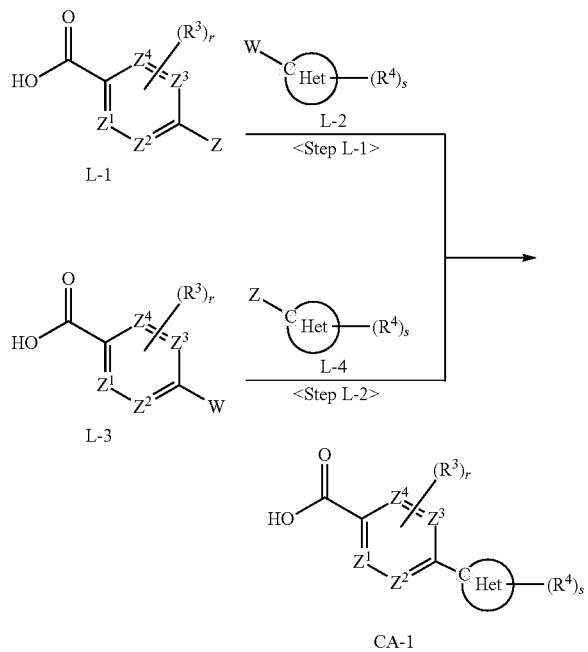

<Step L-1>

In accordance with a similar process that described in published documents, for example, *Jikken Kagaku Koza (Experimental Chemistry Series)*, 5th edition, 18, Organic synthesis VI, Organic synthesis by using Metal, pp. 327-352, 2004, Maruzen Co., Ltd., and *Journal of Medicinal Chemistry*, 48(20), pp. 6326-6339, 2005, a compound represented by formula (CA-1) can be produced from a compound represented by formula (L-1), which is commercially available or can be produced by various methods known in the published literature, to react with a compound represented by formula (L-2) which is commercially available or can be produced by various methods known in the published literature, in the presence of a base such as, cesium carbonate, potassium carbonate, potassium phosphate, triethyl amine, N,N-diisopropylethylamine, in the presence of Pd-catalyst such as, palladium(II) acetate (Pd(OAc)$_2$), tetrakis triphenylphosphine palladium (Pd(PPh$_3$)$_4$), tris(dibenzylideneacetone)dipalladium ((dba)$_3$Pd$_2$), bis(dibenzylideneacetone) palladium ((dba)$_2$Pd), [1,1'-bis(diphenylphosphino)ferrocene]dichloro palladium(II) (Pd(dppf)Cl$_2$) and in the presence of phosphine ligand, such as triphenylphosphine, tri(tert-butyl)phosphine, tri(o-tolyl)phosphine, 2-dicyclohexylphosphino-2',6'-dimethoxybiphenyl, dicyclohexylphosphino-2',4',6'-triisopropylbiphenyl (X-phos) in a solvent which is inactive to the reaction, such as, toluene, xylene, N,N-dimethylformamide, N,N-dimethylacetamide, dimethoxyethane, acetonitrile, acetonitrile/H$_2$O, dioxane, dioxane/H$_2$O, tetrahydrofuran, tetrahydrofuran/H$_2$O or a mixed solvent thereof at a temperature in the range of 0° C. to the solvent-reflux temperature, or can be produced in a similar way by using tetramethyl ammonium chloride, tetrabutyl ammonium chloride instead of phosphine ligand.

<Step L-2>

A compound represented by formula (CA-1) can be produced by the similar process as that used in <Step L-1> of Reaction Scheme 13 using a compound represented by formula (L-3) which is commercially available or can be produced by various methods known in the published literature, and a compound represented by (L-4) which is commercially available or can be produced by various methods known in the published literature.

Scheme 12: [Synthetic Procedure M] Synthetic route of a carboxylic acid represented by formula (CA-2); in the case of a substructure of Het ring represented by Formula (IV) is 1,3,4-triazole moiety at a compound represented by formula (CA).

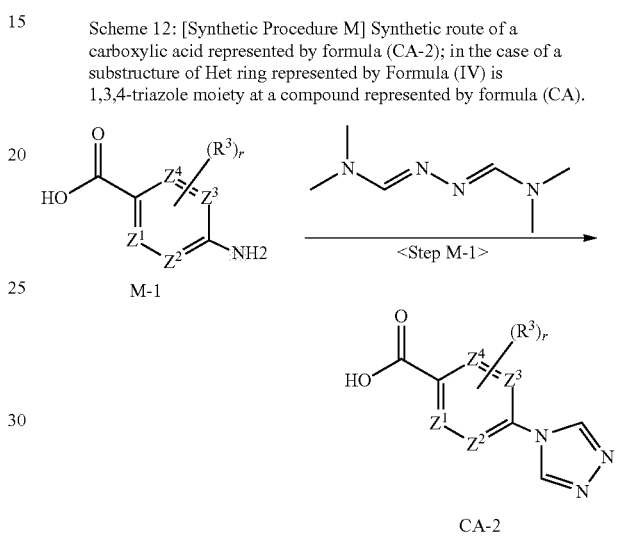

In accordance with a similar process that described in published documents, for example, *Tetrahedron Letters*, 51(4), p 653-656, 2010, a compound represented by formula (CA-2) can be produced from a compound represented by formula (M-1), which is commercially available or can be produced by various methods known in the published literature, to react with methanehydrazonamide in the presence of a acid such as, trifluoroacetic acid, acetic acid, p-toluensulfonic acid or hydrochloride, in a solvent which is inactive to the reaction, such as, benzene, toluene, xylene, or a mixed solvent thereof at a temperature in the range of 0° C. to the solvent-reflux temperature.

Scheme 13: [Synthetic Procedure N] Synthetic route of a carboxylic acid represented by formula (CA-3); in the case of a substructure of Het ring represented by Formula (IV) is substituted 1,3,4-triazole moiety at a compound represented by formula (CA).

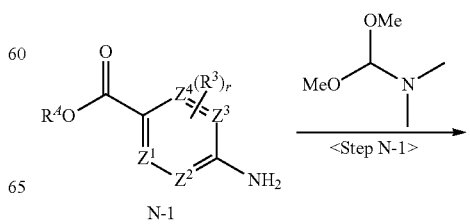

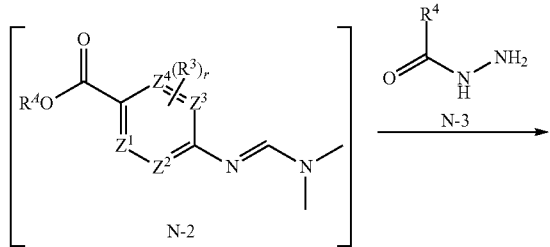

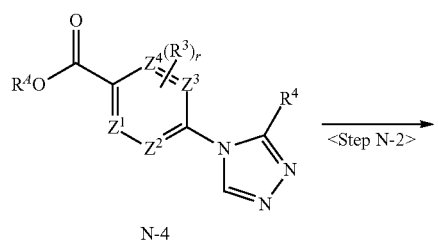

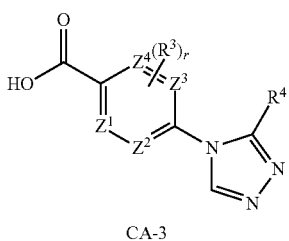

<Step N-1>

In accordance with a similar process that described in published documents, for example, *Organic Letters,* 6(17), p 2969-2971, 2004, an isolable compound represented by formula (N-2) can be produced from a compound represented by formula (N-1), which is commercially available or can be produced by various methods known in the published literature, to react with 1,1-dimethoxy-N,N-dimethylmethanamine in a solvent which is inactive to the reaction, such as, benzene, toluene, xylene, dichloromethane, acetonitrile, or a mixed solvent thereof at a temperature in the range of 0° C. to the solvent-reflux temperature, and then removing the reaction solvent. And then, in accordance with a similar process that described in published documents, for example, *Organic Letters,* 6(17), p 2969-2971, 2004, a compound represented by formula (N-4) can be produced from an isolable compound represented by formula (N-2) to react with 1,1-dimethoxy-N,N-dimethylmethanamine in acetic acid at a temperature in the range of room temperature to the solvent-reflux temperature.

<Step N-2>

In the case of $R^4=C_{1-6}$ alkyl group, e.g., methyl, ethyl, in accordance with a similar process that described in published documents, for example, "*Jikken Kagaku Koza (Experimental Chemistry Series)*, 4th edition, 22, Organic synthesis IV, Acids, amino acids, and peptides, pp. 1-43, 1992, Maruzen Co., Ltd.", a compound represented by formula (CA-3) can be produced from a compound represented by formula (N-4) in the presence of a base such as lithium hydroxide, sodium hydroxide, potassium hydroxide, lithium carbonate, sodium carbonate or potassium carbonate, in a solvent which is inactive to the reaction, such as water, methanol, ethanol, 2-propanol, N,N-dimethylformamide, dioxane, or tetrahydrofuran, or a mixed solvent thereof at a temperature in the range of 0° C. to the solvent-reflux temperature.

In the case of $R^4$=tert-butyl, in accordance with a similar process that described in published documents, for example, Greene, T. W., et. al., *Protective Groups in Organic Synthesis* (2007), 4th Ed., a compound represented by formula (CA-3) can be produced from a compound represented by formula (N-4) in the presence of a acid such as inorganic or organic acids such as hydrochloric acid, sulfuric acid, acetic acid or trifluoroacetic acid, with or without a solvent which is inactive to the reaction, such as water, methanol, ethanol, 2-propanol, dichloromethane, N,N-dimethylformamide, dioxane, or tetrahydrofuran, or a mixed solvent thereof at a temperature in the range of 0° C. to the solvent-reflux temperature.

In the case of $R^4$=alalkyl group, e.g., benzyl, a compound represented by formula (CA-3) can be produced by the similar process as that used in <Step J-1> of Reaction Scheme 11 using a compound represented by formula (N-4).

Scheme 14: [Synthetic Procedure O] Synthetic route of a carboxylic acid represented by formula (CA-3); in the case of R⁴ is difluoromethyl or trifluoromethyl at a compound represented by formula (CA-3).

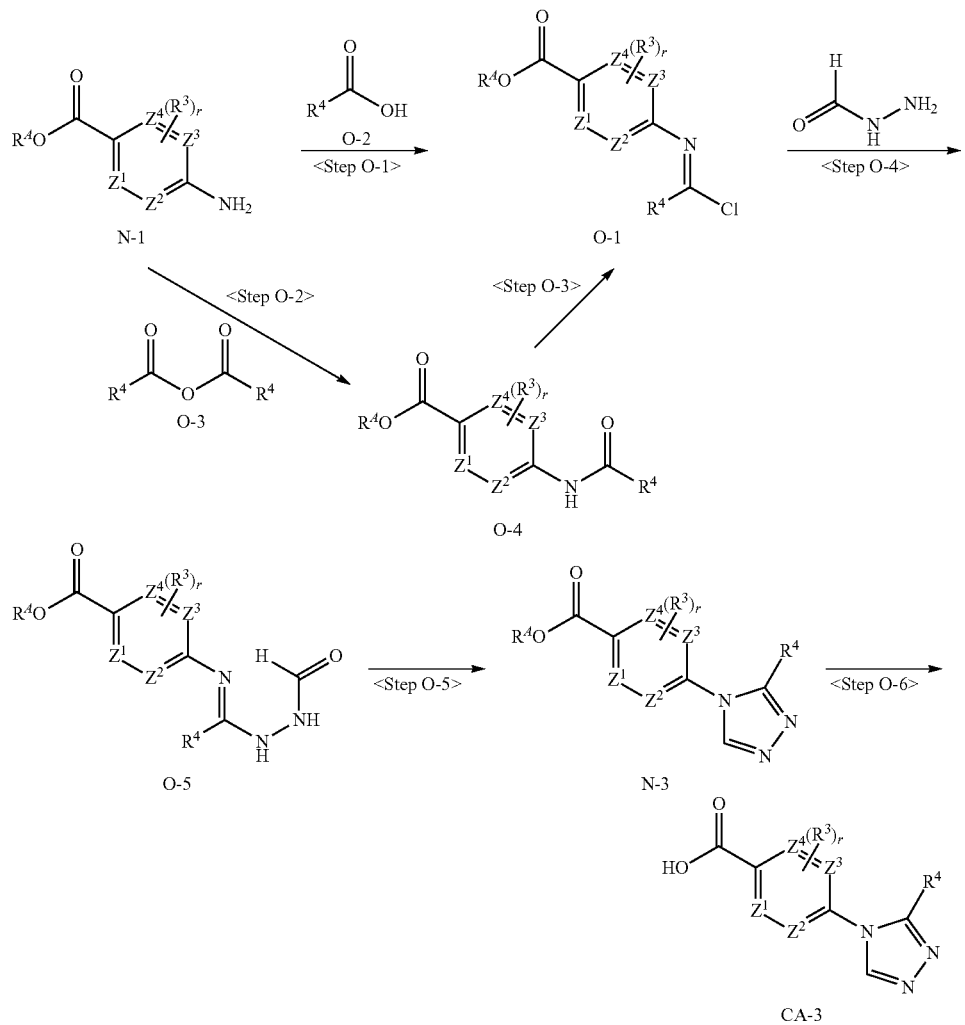

<Step O-1>

In accordance with a similar process that described in published documents, for example, *Synlett*, (3), p 447-450, 2007; *Journal of Agricultural and Food Chemistry*, 59(10), p 5671-5676, 2011, a compound represented by formula (O-1) can be produced from a compound represented by formula (N-1), which is commercially available or can be produced by various methods known in the published literature, to react with a carboxylic acid represented by formula (O-2), which is commercially available or can be produced by various methods known in the published literature, in the presence of a base such as triethylamine, N,N-diisopropylethylamine or pyridine and triphenylphosphine in a solvent which is inactive to the reaction, such as dichloromethane, chloroform, tetrachloromethane or a mixed solvent thereof at a temperature in the range of 0° C. to the solvent-reflux temperature.

<Step O-2>

In accordance with a similar process that described in published documents, for example, *Chemical & Pharmaceutical Bulletin*, 35(4), p 1397-404, 1987, a compound represented by formula (O-4) can be produced from a compound represented by formula (N-1), which is commercially available or can be produced by various methods known in the published literature, to react with a carboxylic acid anhydride represented by formula (O-3), which is commercially available or can be produced by various methods known in the published literature, in the presence of a base such as triethylamine, N,N-diisopropylethylamine or pyridine and triphenylphosphine in a solvent which is inactive to the reaction, such as dichloromethane, chloroform, or a mixed solvent thereof at a temperature in the range of 0° C. to the solvent-reflux temperature.

<Step O-3>

A compound represented by formula (O-1) can be produced by the similar process as that used in <Step O-1> of Reaction Scheme 16 using a compound represented by formula (O-4).

<Step O-4>

In accordance with a similar process that described in published documents, for example, *Tetrahedron Letters*, 31(19), pp. 2717-18, 1990, a compound represented by formula (O-5) can be produced from a compound represented by formula (O-4) to react with a formohydrazide in the presence of a base such as triethylamine, N,N-diisopropylethylamine or pyridine in a solvent which is inactive to the reaction, such as benzene, toluene, acetonitrilee, or a mixed solvent thereof at a temperature in the range of 0° C. to the solvent-reflux temperature.

<Step O-5>

A compound represented by formula (N-3) can be produced by the similar process as that used in <Step N-1> of (Reaction Scheme 15) using a compound represented by formula (O-5).

<Step O-6>

A compound represented by formula (CA-3) can be produced by the similar process as that used in <Step N-2> of (Reaction Scheme 15) using a compound represented by formula (N-3).

Scheme 15: [Synthetic Procedure P] Synthetic route of a carboxylic acid represented by formula (CA-4-1) and (CA-4-2); in the case of a substructure of Het ring represented by Formula (IV) is substituted 1,2,4-triazole moiety at a compound represented by formula (CA).

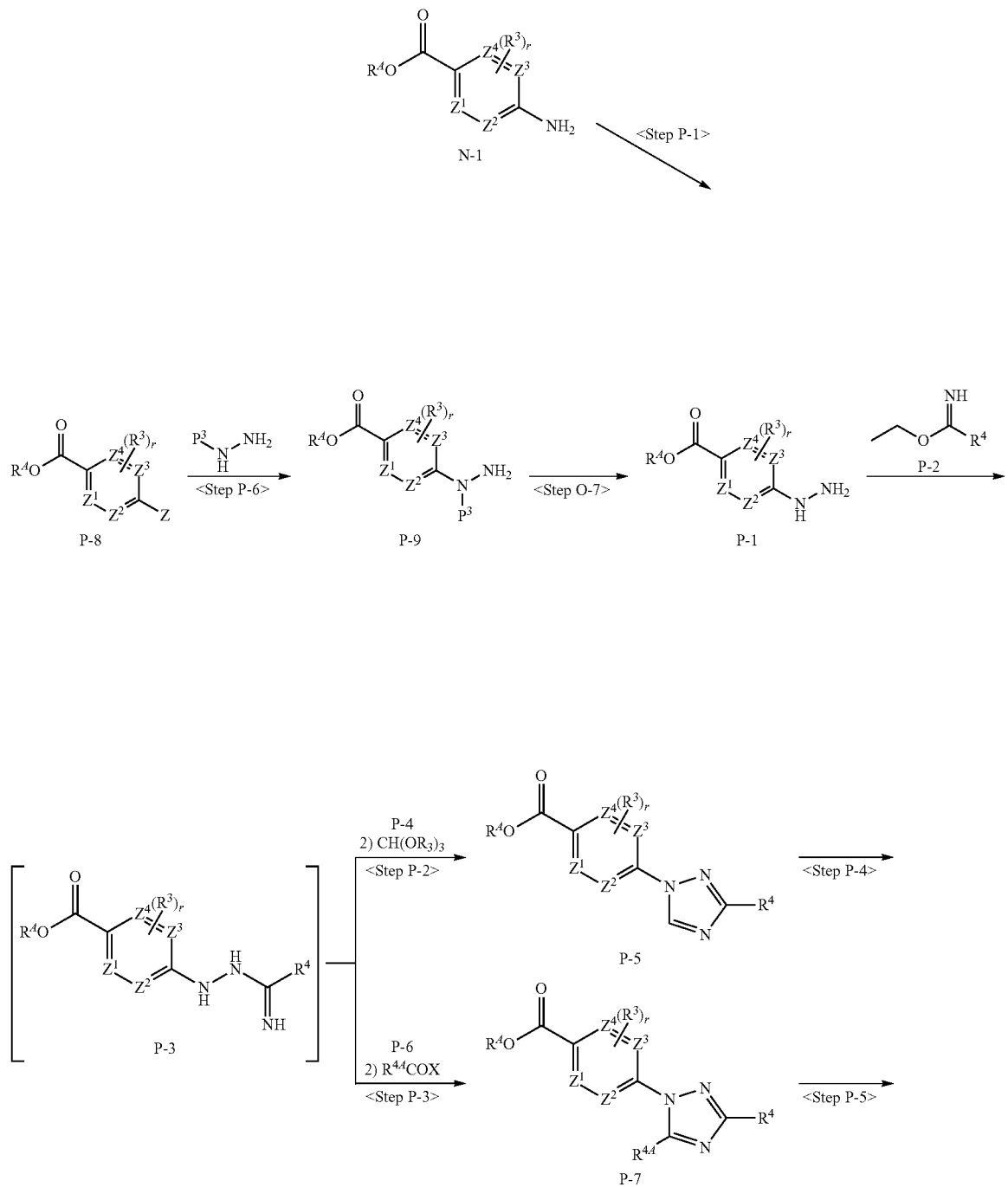

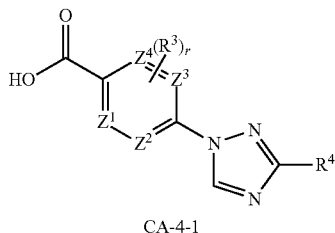

CA-4-1

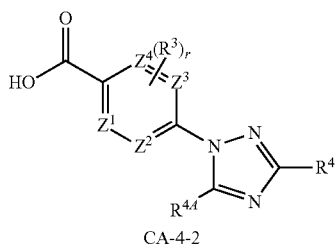

CA-4-2

<Step P-1>

In accordance with a similar process that described in published documents, for example, *Bioorganic & Medicinal Chemistry*, 11(13), pp. 2991-3013, 2003, a compound represented by formula (P-1) can be produced from a compound represented by formula (N-1), which is commercially available or can be produced by various methods known in the published literature, to react with sodium nitrite in 1N hydrochloric acid at a temperature of 0° C., and then to react with stannous chloride at a temperature in the range of 0° C. to room temperature.

<Step P-2>

In accordance with a similar process that described in published documents, for example, *Journal of Organic Chemistry*, 53(18), pp. 4349-53, 1988, and World Intellectual Property Organization (WIPO) publication WO2010/100606, a compound represented by formula (P-5) can be produced via intermediate represented by formula (P-3) from a compound represented by formula (P-1) to react with imidiate derivatives represented by formula (P-2), which is commercially available or can be produced by various methods known in the published literature, in the presence of a base such as triethylamine, N,N-diisopropylethylamine or pyridine in a solvent which is inactive to the reaction, such as methanol, ethanol, 2-propanol, acetonitrile, or a mixed solvent thereof at a temperature in the range of 0° C. to the solvent-reflux temperature, then after removing the reaction solvent and to react with trialkoxymethane represented by formula (P-3) without a solvent at a temperature in the range of room temperature to 100° C.

<Step P-3>

In accordance with a similar process that described in published documents, for example, *Journal of Organic Chemistry*, 53(18), p 4349-53, 1988, and World Intellectual Property Organization (WIPO) publication WO2010/100606, a compound represented by formula (P-7) can be produced via intermediate represented by formula (P-3) from a compound represented by formula (P-1) to react with imidiate derivatives represented by formula (P-2), which is commercially available or can be produced by various methods known in the published literature, in the presence of a base such as triethylamine, N,N-diisopropylethylamine or pyridine in a solvent which is inactive to the reaction, such as methanol, ethanol, 2-propanol, acetonitrile, or a mixed solvent thereof at a temperature in the range of 0° C. to the solvent-reflux temperature, then after removing the reaction solvent and to react with acidic halide represented by formula (P-6) in the presence of a base such as triethylamine, N,N-diisopropylethylamine or pyridine, with or without a solvent which is inactive to the reaction, such as dichlorometane, chloroform, tetrahydrofuran or a mixed solvent at a temperature in the range of 0° C. to the solvent-reflux temperature.

<Step P-4>

A compound represented by formula (CA-4-1) can be produced by the similar process as that used in <Step N-2> of Reaction Scheme 15 using a compound represented by formula (P-5).

<Step P-5>

A compound represented by formula (CA-4-2) can be produced by the similar process as that used in <Step N-2> of Reaction Scheme 15 using a compound represented by formula (P-7).

<Step P-6>

In accordance with a similar process that described in published documents, for example, *Tetrahedron Letters*, 40(18), p 3543-3546, 1999, a compound represented by formula (P-9) can be produced from a compound represented by formula (P-8), which is commercially available or can be produced by various methods known in the published literature, to react with tert-butyl hydrazinecarboxylate in the presence of a base, such as cesium carbonate, potassium carbonate, potassium phosphate, sodium tert-butoxide, triethyl amine or N,N-diisopropylethylamine, in the presence of Pd-catalyst, such as tris(dibenzylideneacetone)dipalladium ((dba)$_3$Pd$_2$) or palladium(II) acetate (Pd(OAc)$_2$), and in the presence of phosphine ligand, such as dicyclohexylphosphino-2',4',6'-triisopropylbiphenyl (X-phos), 4,5-Bis(diphenylphosphino)-9,9-dimethylxanthene (XANTPHOS), 2,2'-bis(diphenylphosphino)-1,1'-binaphthyl (BINAP), [1,1'-biphenyl]-2-yl-bis(1,1-dimethylethyl)-phosphine (JohnPhos) in a solvent which is inactive to the reaction, such as toluene, N,N-dimethylformamide, N,N-dimethylacetamide, N-methylpyrrolidone, acetonitrile, acetonitrile/H$_2$O, dioxane, dioxane/H$_2$O, tetrahydrofuran, tetrahydrofuran/H$_2$O or a mixed solvent thereof at a temperature in the range of room temperature to the solvent-reflux temperature.

<Step P-7>

A compound represented by formula (P-1) can be produced by the similar process as that used in <Step A-4> of (Reaction Scheme 2) using a compound represented by formula (P-9).

Scheme 16: [Synthetic Procedure Q] Synthetic route of a carboxylic acid represented by formula (CA-5); in the case of a substructure of Het ring represented by Formula (IV) and a phenyl ring form a C—N bond which is represented by a compound of formula (CA-5).

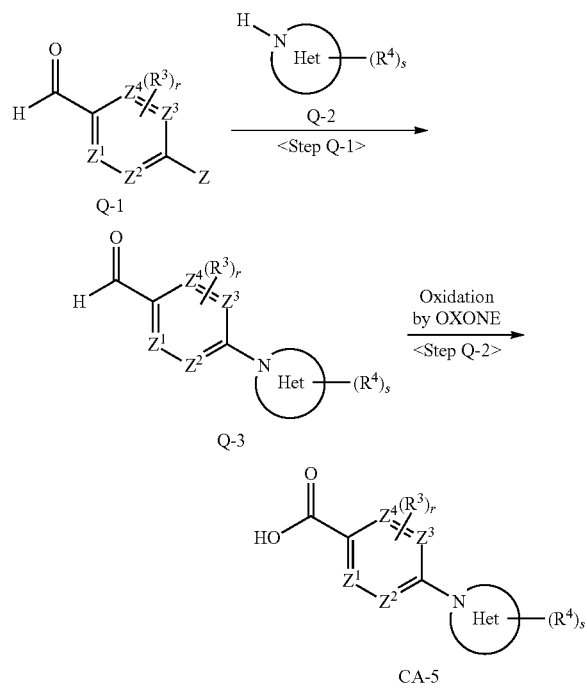

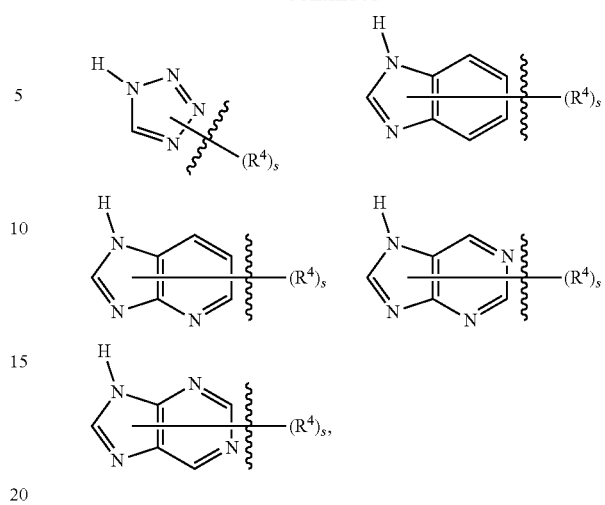

<Step Q-1>

In accordance with a similar process that described in published documents, for example, *European Journal of Medicinal Chemistry*, 46(9), p 4302-4310, 2011, a compound represented by formula (Q-3) can be produced from a compound represented by formula (Q-1), which is commercially available or can be produced by various methods known in the published literature, to react with a heteroaryl compound represented by formula (Q-2), for example, such as

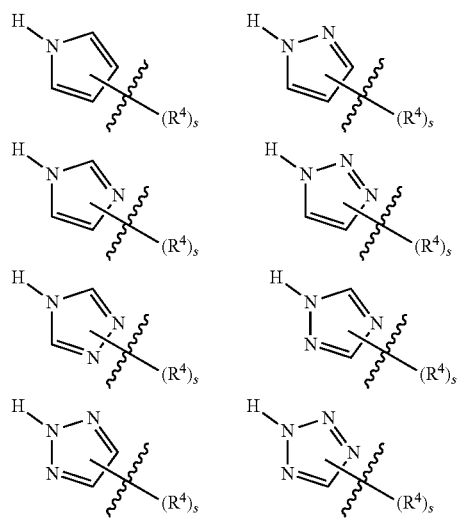

and the like which is commercially available or can be produced by various methods known in the published literature, in the presence of a base, such as sodium carbonate, cesium carbonate, potassium carbonate, sodium tert-butoxide, triethyl amine or N,N-diisopropylethylamine in the presence of a base, such as potassium carbonate, sodium carbonate, cesium carbonate, triethyl amine or N,N-diisopropylethylamine in a solvent which is inactive to the reaction, such as dimethyl sulfoxide, N,N-dimethylformamide, N,N-dimethylacetamide, N-methylpyrrolidone, acetonitrile, or a mixed solvent thereof at a temperature in the range of room temperature to the solvent-reflux temperature.

<Step Q-2>

In accordance with a similar process that described in published documents, for example, "*Organic Letters*, 5(7), p 1031-1034, 2003", a compound represented by formula (CA-5) can be produced from a compound represented by formula (Q-3) to react with OXONE® in a solvent which is inactive to the reaction, such as N,N-dimethylformamide, N,N-dimethylacetamide, N-methylpyrrolidone, or a mixed solvent thereof at a temperature in the range of 0° C. to the solvent-reflux temperature.

Scheme 17: [Synthetic Procedure R] Synthetic route of a carboxylic acid represented by formula (CA-6);

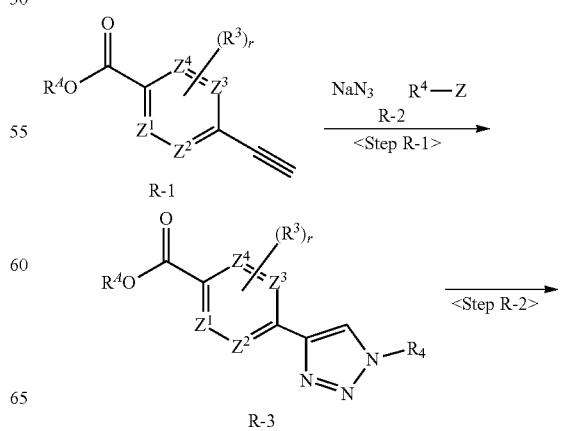

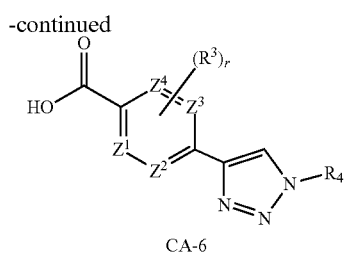

CA-6

<Step R-1>

In accordance with a similar process that described in published documents, for example, World Intellectual Property Organization (WIPO) publication WO2012/076590, a compound represented by formula (R-3) can be produced from a compound represented by formula (R-1), which is commercially available or can be produced by various methods known in the published literature, to react with sodium azide, in the presence of a halogenated compound represented by formula (R-2), copper catalyst such as CuI, and sodium ascorbate in a solvent which is inactive to the reaction, such as tetrahydrofuran, water, or a mixed solvent thereof at a temperature in the range of room temperature to the solvent-reflux temperature.

<Step R-2>

A compound represented by formula (CA-6) can be produced by the similar process as that used in <Step N-2> of (Reaction Scheme 15) using a compound represented by formula (R-3).

Scheme 18: [Synthetic Procedure R] Synthetic route of a carboxylic acid represented by formula (CA-7);

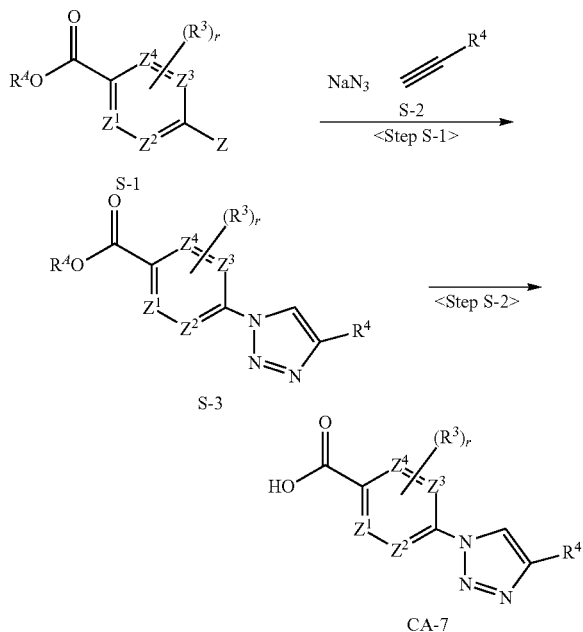

<Step S-1>

In accordance with a similar process that described in published documents, for example, *Journal of Organic Chemistry*, 76(8), p 2613-2618, 2011, a compound represented by formula (S-3) can be produced from a compound represented by formula (S-1), which is commercially available or can be produced by various methods known in the published literature, to react with sodium azide, in the presence of a halogenated compound represented by formula (S-2), copper catalyst such as CuI, and sodium ascorbate in a solvent which is inactive to the reaction, such as dimethyl sulfoxide, water, or a mixed solvent thereof at a temperature in the range of room temperature to the solvent-reflux temperature.

<Step S-2>

A compound represented by formula (CA-7) can be produced by the similar process as that used in <Step N-2> of (Reaction Scheme 15) using a compound represented by formula (S-3).

Scheme 19: [Synthetic Procedure U] Synthetic route of a compound represented by (I).

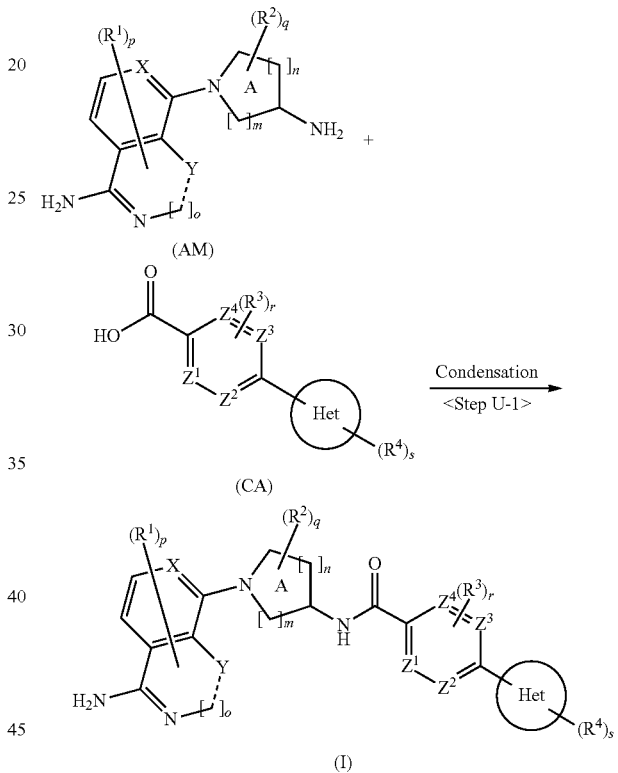

<Step U-1>

In accordance with a similar process that described in published documents, for example, *Jikken Kagaku Koza (Experimental Chemistry Series)*, 5th edition, 18, Organic synthesis IV, Acids, amino acids, and peptides, pp. 191-309, 1992, Maruzen Co., Ltd., a compound represented by formula (I) can be produced from a compound represented by formula (AM) (AM include formulas AM-1, AM-2, AM-3, AM-4, AM-5 and AM-6), to react with a compound represented by formula (CA) (CA include formulas CA-1, CA-2, CA-3, CA-4-1, CA-4-2, CA-5, CA-6, CA-7, CA-8 and CA') in the presence of a condensing agent such as 1,3-dicyclohexylcarbodiimide (DCC), 1-ethyl-3-(3'-dimethylaminopropyl)carbodiimide hydrochloride (WSC.HCl), benzotriazol-1-yloxy tris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP) or 4-(4,6-dimethoxy-1,3,5-triazin-2-yl)-4-methylmorpholinium chloride in a solvent which is inactive to the reaction, such as dichloromethane, chloroform, diethyl ether, tetrahydrofuran, toluene, benzene, N,N-dimethylformamide, N,N-dimethylacetamide, N-methylpyrrolidone, methanol, ethanol, 2-propanol, or a mixed solvent thereof, in the presence or absence of a base such as triethylamine, N,N-diisopropylethylamine or pyridine at a temperature in the range of 0° C. to the solvent-reflux temperature.

<Step V-1>

A compound represented by formula (V-1) can be produced by the similar process as that used in <Step U-1> of Reaction Scheme 22 using a compound represented by formula (AM) and a compound represented by formula (L-1), which is commercially available or can be produced by various methods known in the published literature.

Scheme 20: [Synthetic Procedure V] Synthetic route of a carboxylic acid represented by formula (I-2); in the case of a substructure of Het ring represented by Formula (IV) and Phenyl ring form C-C bond formation at a compound represented by formula (I).

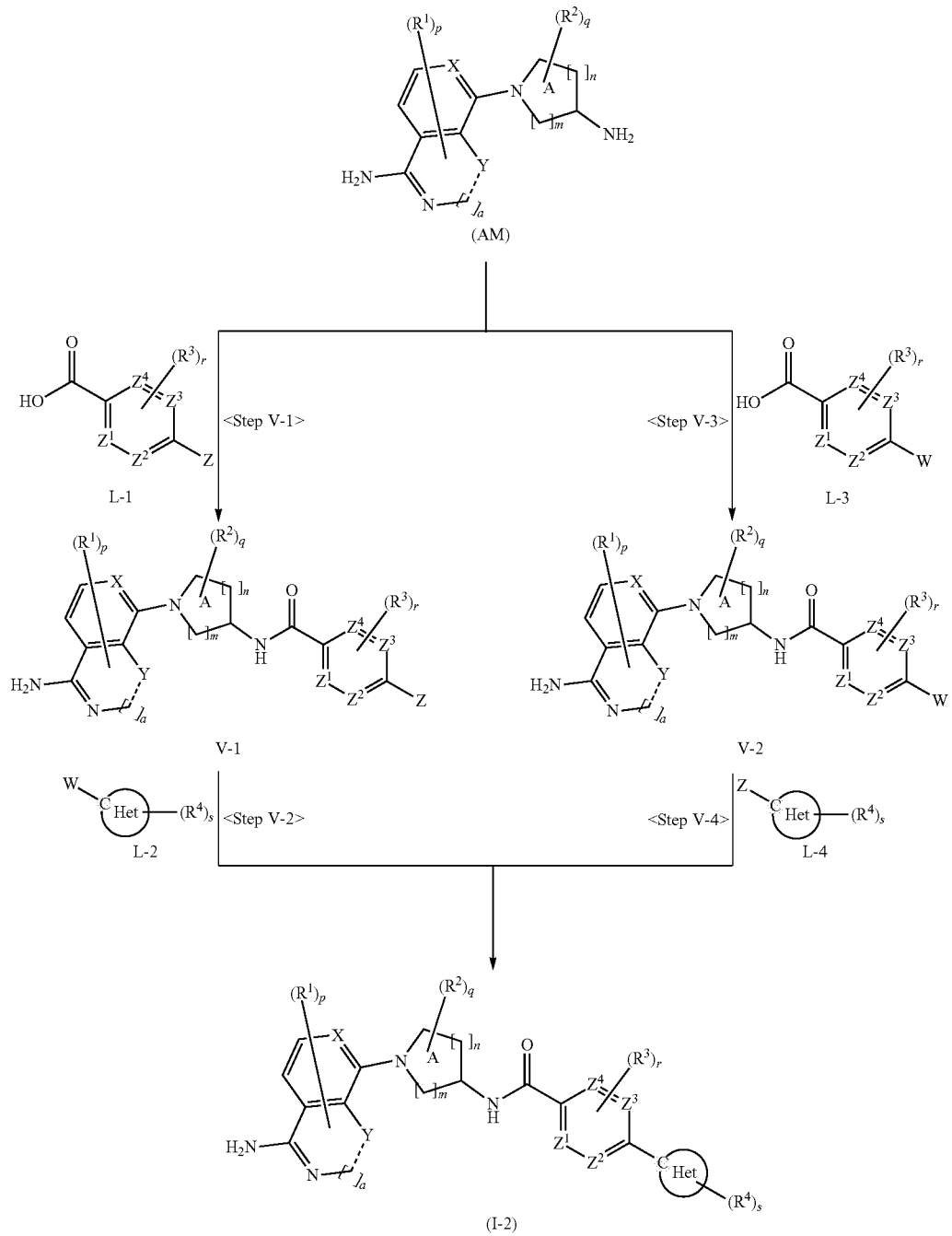

<Step V-2>

A compound represented by formula (I-2) can be produced by the similar process as that used in <Step L-1> of Reaction Scheme 13 using a compound represented by formula (V-1) and a compound represented by formula (L-2), which is commercially available or can be produced by various methods known in the published literature.

<Step V-3>

A compound represented by formula (V-2) can be produced by the similar process as that used in <Step U-1> of Reaction Scheme 22 using a compound represented by formula (AM) and a compound represented by formula (L-3), which is commercially available or can be produced by various methods known in the published literature.

<Step V-4>

A compound represented by formula (I-2) can be produced by the similar process as that used in <Step L-2> of Reaction Scheme 13 using a compound represented by formula (V-2) and a compound represented by formula (L-4), which is commercially available or can be produced by various methods known in the published literature.

Scheme 21: [Synthetic Procedure W] Synthetic route of a compound represented by (I-3); in the case of a substructure of Het ring represented by Formula (IV) and a phenyl ring form C-N bond, which is represented by a compound of formula (I).

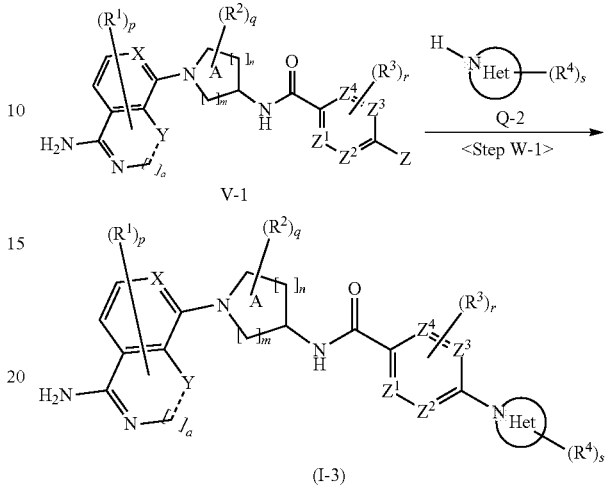

<Step W-1>

A compound represented by formula (I-3) can be produced by the similar process as that used in <Step Q-1> of Reaction Scheme 18 using a compound represented by formula (V-1) and a compound represented by formula (Q-2).

Scheme 22: [Synthetic Procedure X] Synthetic route of a compound represented by (I-a-2); in the case of bicycle heteroaryl group substituted with an aliphatic heteroring is a six-five ring system heteroaryl moiety, to give a compound represented by formula (I).

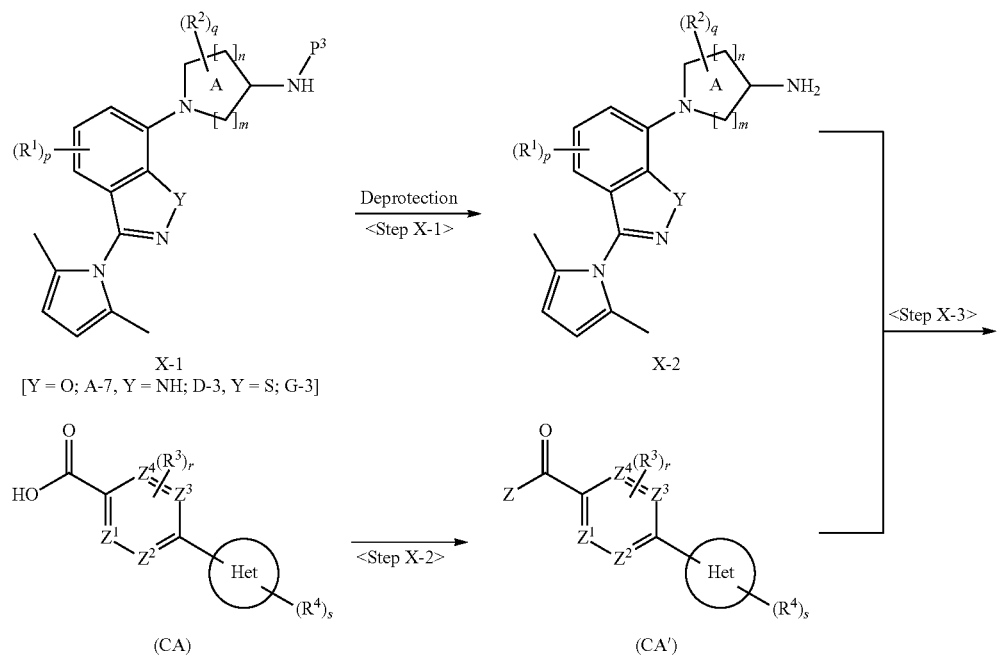

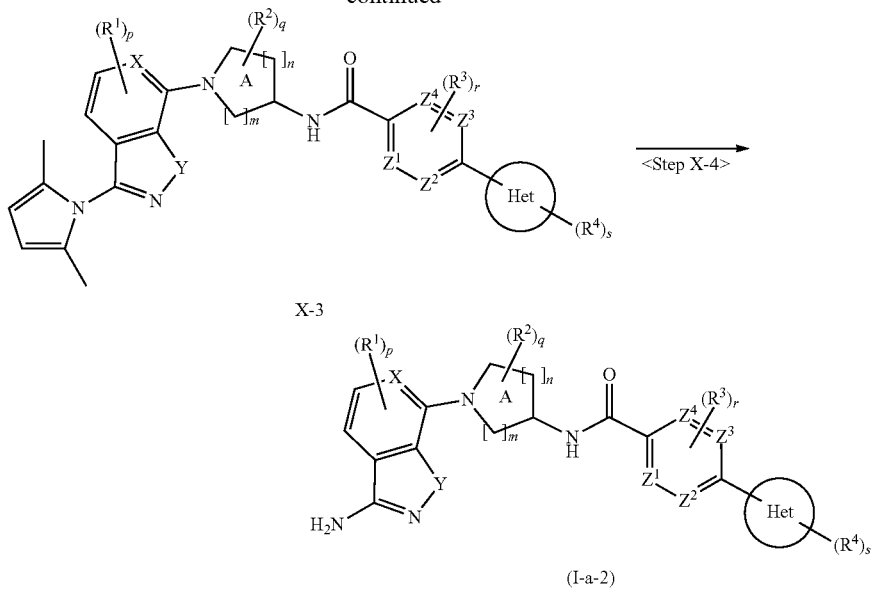

X-3

(I-a-2)

<Step X-1>

A compound represented by formula (X-2) can be produced by selective deprotection of the similar process as that used in <Step A-4> of Reaction Scheme 2 using a compound represented by formula (X-1) (in the case of Y=O, formula (X-1) is formula (A-7), in the case of Y=NH, formula (X-1) is formula (D-3), in the case of Y=S, formula (X-1) is formula (G-3)).

<Step X-2>

A compound represented by formula (CA') can be produced from a compound represented by formula (CA), which is commercially available or can be produced by various methods known in the published literature, to react with halogenation reagents such as thionyl chloride, oxalyl chloride, phosphoryl chloride, sulfuryl chloride, phosphorus trichloride, phosphorus pentachloride, phosphorus tribromide, by similar methods known that described in the published literature, according to a similar process that described in published documents (see for example, *Journal of the American Chemical Society*, 109(24), pp. 7488-7494, 1987) in the presence or absence of a base, such as triethylamine, N,N-diisopropylethylamine, pyridine or N,N-dimethylaminopyridine in a solvent which is inactive to the reaction, such as dichloromethane, 1,2-dichloroethane, chloroform, dioxane, tetrahydrofuran, benzene, toluene, or a mixed solvent thereof at a temperature in the range of room temperature to the solvent-reflux temperature.

<Step S-3>

A compound represented by formula (X-3) can be produced from a compound represented by formula (X-2) to react with a compound represented by formula (CA') according to a similar process that described in published documents (see for example, *Jikken Kagaku Koza* (*Experimental Chemistry Series*), 5th edition, 18, Organic synthesis IV, Acids, amino acids, and peptides, pp. 191-309, 1992, Maruzen Co., Ltd.) in the presence or absence of a base such as triethylamine, N,N-diisopropylethylamine or pyridine in a solvent which is inactive to the reaction, such as dichloromethane, chloroform, diethyl ether, tetrahydrofuran, toluene, benzene, or a mixed solvent thereof, at a temperature in the range of 0° C. to the solvent-reflux temperature.

<Step S-4>

A compound represented by formula (I-a-2) can be produced by the similar process as that used in <Step A-4> of (Reaction Scheme 2) using a compound represented by formula (X-3).

Scheme 23: [Synthetic Procedure Y] Synthetic route of a carboxylic acid represented by (CA-8);

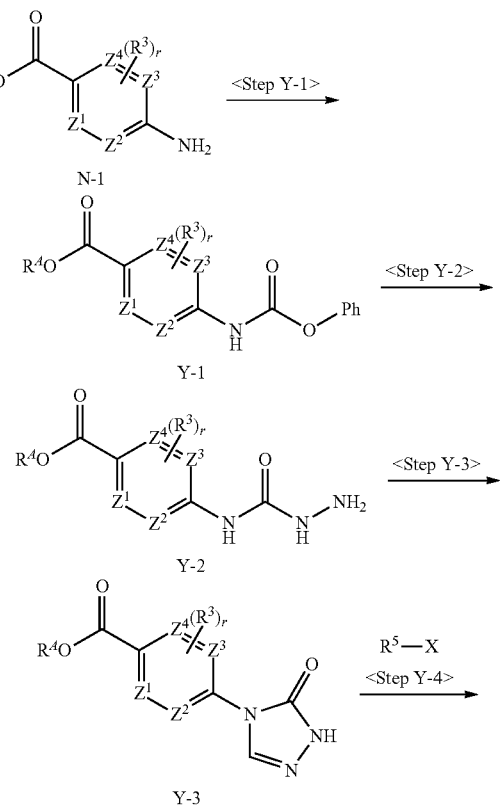

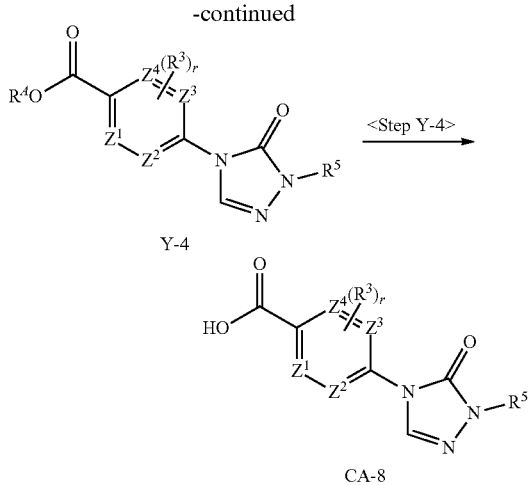

<Step Y-1>

In accordance with a similar process that described in published documents, for example, *Journal of Medicinal Chemistry*, 49(8), p 2512-2525, 2006, a compound represented by formula (Y-1) can be produced from a compound represented by formula (N-1), which is commercially available or can be produced by various methods known in the published literature, to react with phenyl chloroformate, in the presence of a amine such as pyridine, 2,6-lutidine, triethylamine, or N,N-diisopropylethylamine, in a solvent which is inactive to the reaction, such as dichloromethane, tetrahydrofuran, 1,4-dioxane, ethyl acetate, toluene, or a mixed solvent thereof at a temperature in the range of room temperature to the solvent-reflux temperature.

<Step Y-2>

In accordance with a similar process that described in published documents, for example, *Journal of Medicinal Chemistry*, 49(8), pp. 2512-2525, 2006, a compound represented by formula (Y-2) can be produced from a compound represented by formula (Y-1) to react with hydrazine hydrate in a solvent which is inactive to the reaction, such as tetrahydrofuran, 1,4-dioxane, dimethoxyethane, or a mixed solvent thereof at a temperature in the range of room temperature to the solvent-reflux temperature.

<Step Y-3>

In accordance with a similar process that described in published documents, for example, *Journal of Medicinal Chemistry*, 49(8), pp. 2512-2525, 2006, a compound represented by formula (Y3) can be produced from a compound represented by formula (Y-2) to react with formamidine acetate, in the presence of acetic acid, in a solvent which is inactive to the reaction, such as acetic acid, dimethylformamide, toluene or a mixed solvent thereof at a temperature in the range of room temperature to the solvent-reflux temperature.

<Step Y-4>

In accordance with a similar process that described in published documents, for example, *Journal of Medicinal Chemistry*, 49(8), pp. 2512-2525, 2006, a compound represented by formula (Y4) can be produced from a compound represented by formula (Y-3) to react with a halogenated reagent represented by $R^5$—X, in the presence of a base such as potassium carbonate, sodium carbonate, or cesium carbonate, in a solvent which is inactive to the reaction, such as dimethylformamide, tetrahydrofuran, toluene or a mixed solvent thereof at a temperature in the range of room temperature to the solvent-reflux temperature.

<Step Y-5>

A compound represented by formula (CA-8) can be produced by the similar process as that used in <Step N-2> of Reaction Scheme 15 using a compound represented by formula (Y-4).

(S) and (R) forms of compounds represented by Formula (I) can also be made from corresponding starting materials. The required starting materials for the synthesis of (S) and (R) isoforms of compound (A-6) are either commercially available, or capable of being readily synthesized by the method commonly used in the organic chemistry from commercially available products.

Acidic or basic products of the compound of the Formula (I) can be present in the form of their salts or in free form. Pharmacologically acceptable salts are preferred, for example alkali metal or alkaline earth metal salts such as hydrochlorides, hydrobromides, sulfates, hemisulfates, all possible phosphates, and salts of the amino acids, natural bases or carboxylic acids.

The preparation of pharmacologically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

EXAMPLES

The present invention will now be described in more detail using examples, but the present invention is not limited to the examples.

The measurement of nuclear magnetic resonance (NMR) spectrum (Table 2) was performed using a JEOL JNM-ECX300 FT-NMR (manufactured by JEOL Ltd.) or a JEOL JNM-ECX400 FT-NMR (manufactured by JEOL Ltd.).

Liquid chromatography-mass spectrometry (LC-MS, Table 3) was performed using a Waters FractionLynx MS system (manufactured by Waters Corporation) or a Waters Micromass ZQ Mass Spectromer/Agilent 1100 system. A SunFire Column™ (4.6 mm×5 cm, 5 micron) (manufactured by Waters Corporation) was used as an analytical column. A SunFire Column™ (19 mm×5 cm, 5 micron) (manufactured by Waters Corporation) was used as a preparative column. Methanol or MeCN and 0.05% aqueous acetic acid solution or 0.05% aqueous trifluoroacetic acid solution were used as the mobile phase. The analysis was performed under the following gradient conditions: Methanol or MeCN: 0.05% aqueous acetic acid solution or 0.05% aqueous trifluoroacetic acid solution=1:9 (0 min), 10:0 (5 min), and 10:0 (6 min). Liquid chromatography-mass spectrometry (UPLC-MS) was also performed using a ACQUITY UPLC+MS system (manufactured by Waters Corporation). A CAP- CELL Pak® C18 MGIII-H (2.0 mm×5 cm, 3 micron) (manufactured by Shiseido Co., Ltd.) was used as an analytical column. Methanol and 0.05% aqueous trifluoroacetic acid solution were used as the mobile phase. The analysis was performed under the following gradient conditions: Methanol: 0.05% aqueous trifluoroacetic acid solution=5:95 (0 min), 95:5 (1 min), 95:5 (1.6 min), and 5:95 (2 min). The solvent systems in Table 3 are described as the following: UPLC indicates UPLC-MS system and mobile phase is 0.05% aq. TFA, HPLC (TFA) indicates LC-MS system and mobile phase is 0.05% aq. TFA, HPLC (AcOH) indicates LC-MS system and mobile phase is 0.05% aq. AcOH.

"Celite®" (Fluka) diatomite is diatomaceous earth, and can be referred to as "celite".

Acronyms and abbreviations are as follows: acetic acid (AcOH); di-tert-butyldicarbonate ((Boc)₂O); butyl (Bu); diisopropylethylamine (DIPEA); 4-dimethylaminopyridine (DMAP); 1,2-dimethoxyethane (DME); dimethylformamide (DMF); ethanol (EtOH); dimethyl sulfoxide (DMSO); diphenylphosphorylazide (DPPA); 1,1'-bis(diphenylphosphino)ferrocene (Dppf); 1-ethyl-3-(3-dimethylaminopropyl)carbodiimide (EDCI); electrosprayionization (ESI); ethyl (Et); ethyl acetate (EtOAc); high performance liquid chromatography (HPLC); 0-(7-azabenzotriazol-1-yl)-N,N,N',N'-tetramethyluronium hexafluorophosphate (HATU); 1-hydroxy-7-azabenzotriazole (HOAt); 1-hydroxybenzotriazole (HOBt); liquid chromatography-mass spectrometry (LCMS); lithium diisopropylamide (LDA); methyl (Me); acetonitrile (MeCN); methanol (MeOH); mass spectrometry (MS); N-methylpyrrolidone (NMP); palladium on carbon (Pd/C); Tris(dibenzylideneacetone)dipalladium(0) (Pd₂(dba)₃); phenyl (Ph); 2-dicyclohexylphosphino-2',6'-dimethoxybiphenyl (SPhos); tetrabutylammonium fluoride (TBAF); tert-butylmethylether (TBME); trifluoroacetic acid (TFA); trifluoroacetic anhydride (TFAA); tetrahydrofuran (THF); 2-dicyclohexylphosphino-2',4',6'-triisopropylbiphenyl (XPhos); 4,5-bis(diphenylphosphino)-9,9-dimethylxanthene (Xantphos); catalyst (cat.); anhydrous (anh.); concentrated (conc.); saturated (sat.); room temperature (RT).

Example 1

N-(1-(3-Aminobenzo[d]isoxazol-7-yl)pyrrolidin-3-yl)-2-chloro-4-(4H-1,2,4-triazol-4-yl)benzamide

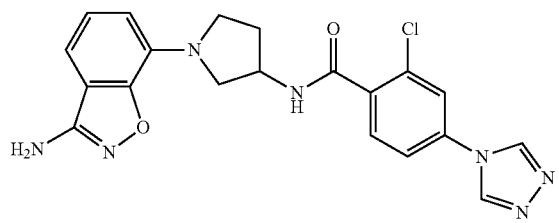 [SMILES: Nc1noc2c(N3CCC(NC(=O)c4ccc(-n5cnnc5)cc4Cl)C3)cccc12]

Step A. tert-Butyl (1-(3-cyano-2-fluorophenyl)pyrrolidin-3-yl)carbamate

To a solution of 3-bromo-2-fluorobenzonitrile (3.0 g, 15 mmol) in 1,4-dioxane (120 mL), tert-butyl pyrrolidin-3-ylcarbamate (2.8 g, 15 mmol), Pd₂(dba)₃ (1.4 g, 1.5 mmol), Xantphos (1.7 g, 3.0 mmol), and Cs₂CO₃ (9.8 g, 30 mmol) were added at RT. The mixture was stirred at 85° C. for 24 h. The mixture was filtered through a pad of Celite, treated with water (200 mL), extracted with EtOAc (100 mL×2). The combined organic layer was washed with brine, dried over Na₂SO₄, filtered, and concentrated in vacuo. The crude was purified by column chromatography (10-30% EtOAc in heptane) to give the title compound. MS (ESI) m/z=328 (M+Na)

Step B. tert-Butyl (1-(3-aminobenzo[d]isoxazol-7-yl)pyrrolidin-3-yl)carbamate

To a solution of tert-butyl (1-(3-cyano-2-fluorophenyl)pyrrolidin-3-yl)carbamate (8.5 mmol, 2.6 g) in DMF (80 mL) was added t-BuOK (77 mmol, 8.6 g) followed by N-hydroxyacetamide (77 mmol, 5.8 g) at RT. The reaction mixture was stirred at 90° C. for 18 h. The mixture was filtered through a pad of Celite, treated with water (200 mL), extracted with EtOAc (100 mL×2). The combined organic layer was washed with brine, dried over Na₂SO₄, filtered, and concentrated in vacuo. The crude was purified by column chromatography (10-30% EtOAc in heptane) to give the title compound.

MS (ESI) m/z=341 (M+Na)

Step C. 7-(3-Aminopyrrolidin-1-yl)benzo[d]isoxazol-3-amine dihydrochloride

A mixture of tert-butyl (1-(3-aminobenzo[d]isoxazol-7-yl)pyrrolidin-3-yl)carbamate (5.3 mmol, 1.7 g) and 4N HCl in 1,4-dioxane (150 mL) was stirred at RT for 2 h. The mixture was concentrated in vacuo to give the title compound. MS (ESI) m/z=219 (M+H)

¹H NMR (300 MHz, DMSO-d₆) δ (ppm): 8.35 (2H, brs), 7.13-7.04 (2H, m), 6.56 (1H, dd, J=7.4, 1.2 Hz), 5.05 (4H, brs), 3.97-3.86 (1H, m), 3.81-3.63 (3H, m), 3.51-3.41 (1H, m), 2.39-2.25 (1H, m), 2.14-2.01 (1H, m)

Step D. 2-Chloro-4-(4H-1,2,4-triazol-4-yl)benzoic acid

A suspension of 4-amino-2-chlorobenzoic acid (117 mmol, 20 g), (1E,N'E)-N'-((dimethylamino)methylene)-N,N-dimethylformohydrazonamide (140 mmol, 20 g), and TFA (30 mL) in toluene (300 mL) was refluxed for 8 h. The mixture was cooled to RT. The suspension was filtered and the solid product was washed with methanol to give the title compound. MS (ESI) m/z=224, 226 (M+H)

¹H NMR (400 MHz, DMSO-d₆) δ (ppm): 9.26 (2H, s), 8.06 (1H, d, J=2.3 Hz), 7.97 (1H, d, J=8.7 Hz), 7.81 (1H, dd, J=8.7, 2.3 Hz)

Step E

N-(1-(3-Aminobenzo[d]isoxazol-7-yl)pyrrolidin-3-yl)-2-chloro-4-(4H-1,2,4-triazol-4-yl)benzamide To a mixture of 7-(3-aminopyrrolidin-1-yl)benzo[d]isoxazol-3-amine dihydrochloride (72 mg, 0.25 mmol), 2-chloro-4-(4H-1,2,4-triazol-4-yl)benzoic acid (55 mg, 0.25 mmol), HOAt (84 mg, 0.61 mmol) and Et₃N (72 μL, 0.52 mmol) in DMF (3.0 mL) was added EDCI (0.12 g, 0.61 mmol) at RT. The mixture was stirred for 15 h. The mixture was purified by HPLC to give the title compound.

Example 2

N-(1-(3-Aminobenzo[d]isoxazol-7-yl)-3-methylpyrrolidin-3-yl)-2,6-dichloro-4-(4H-1,2,4-triazol-4-yl)benzamide

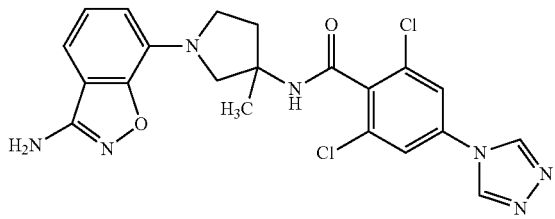 [SMILES: Nc1noc2c(N3CCC(NC(=O)c4c(Cl)cc(-n5cnnc5)cc4Cl)(c4ccccc4)C3)cccc12]

Step A. tert-Butyl (1-(3-aminobenzo[d]isoxazol-7-yl)-3-methylpyrrolidin-3-yl)carbamate Following the procedure of EXAMPLE 1 (Step A-B), 3-bromo-2-fluorobenzonitrile (0.55 g, 2.8 mmol) and tert-butyl (3-methylpyrrolidin-3-yl)carbamate (0.5 g, 2.5 mmol, WO2007117482) were converted to the title compound. MS (ESI) m/z=333 (M+H)
$^1$H NMR (400 MHz, CDCl$_3$) δ (ppm): 7.09 (1H, dd, J=7.8, 7.8 Hz), 6.77 (1H, d, J=7.8 Hz), 6.47 (1H, d, J=7.3 Hz), 4.70 (1H, s), 4.28 (2H, s), 3.83 (1H, d, J=10.1 Hz), 3.81-3.56 (3H, m), 2.55-2.38 (1H, m), 2.02-1.90 (1H, m), 1.55 (3H, s), 1.44 (9H, s)

Step B. 7-(3-Amino-3-methylpyrrolidin-1-yl)benzo[d]isoxazol-3-amine

Following the procedure of EXAMPLE 1 (Step C), tert-butyl (1-(3-aminobenzo[d]isoxazol-7-yl)-3-methylpyrrolidin-3-yl)carbamate was converted to the title compound. MS (ESI) m/z=233 (M+H)

Step C. Methyl 4-amino-2,6-dichlorobenzoate

A mixture of methyl 2,4,6-trichlorobenzoate (10 g, 42 mmol), benzophenone imine (9.1 g, 50 mmol), Cs$_2$CO$_3$ (41 g, 125 mmol), Pd$_2$(dba)$_3$ (0.47 g, 2.1 mmol), and Xantphos (1.8 g, 3.1 mmol) in toluene (100 mL) degassed under reduced pressure and backfilled in nitrogen. The mixture was stirred at 120° C. for 16 h. The mixture was cooled to RT, treated with water, extracted with ethyl acetate twice. The combined extract was dried over Na$_2$SO$_4$, filtered, and concentrated in vacuo. The residue was dissolved with THF (60 mL) and 2N aq. HCl (60 mL) was added. The mixture was stirred at RT for 2 h, then neutralized with aq. NaOH. It was extracted with ethyl acetate, dried over Na$_2$SO$_4$, filtered, and concentrated in vacuo. The crude was purified by column chromatography (0-30% EtOAc in heptane) to give the title compound. MS (ESI) m/z=220, 222 (M+H)

Step D. Methyl 2,6-dichloro-4-(4H-1,2,4-triazol-4-yl)benzoate

To a solution of methyl 4-amino-2,6-dichlorobenzoate (18 mmol, 4.0 g) in toluene, 1,1-dimethoxy-N,N-dimethylmethanamine (27 mmol, 3.6 mL) was added and the mixture was stirred at 120° C. for 2 h. The mixture was concentrated in vacuo. The residue was dissolved with AcOH, added formohydrazide (18 mmol, 1.1 g), then the mixture was stirred at 80° C. for 4 h. The mixture was concentrated in vacuo. The crude was purified by column chromatography (0-15% MeOH in EtOAc) to give the title compound. MS (ESI) m/z=272, 274 (M+H)

Step E. 2,6-Dichloro-4-(4H-1,2,4-triazol-4-yl)benzoic acid

A mixture of methyl 2,6-dichloro-4-(4H-1,2,4-triazol-4-yl)benzoate (12 mmol, 3.2 g) and lithium hydroxide monohydrate (59 mmol, 2.5 g) in MeOH (30 mL), THF (2 mL), and water (10 mL) was stirred at 80° C. for 6 h. The mixture was cooled to 0° C., neutralized with conc. HCl (5.0 mL), concentrated in vacuo. The crude was triturated with cold ethanol, filtered to give the title compound. MS (ESI) m/z=258, 260 (M+H)
$^1$H NMR (400 MHz, DMSO-d$_6$) δ (ppm): 9.23 (2.1H, s), 8.07 (2.0H, s) (CO$_2$H was not observed.)

Step F

N-(1-(3-Aminobenzo[d]isoxazol-7-yl)-3-methylpyrrolidin-3-yl)-2,6-dichloro-4-(4H-1,2,4-triazol-4-yl)benzamide Following the procedure of EXAMPLE 1 (Step E), 7-(3-amino-3-methylpyrrolidin-1-yl)benzo[d]isoxazol-3-amine (30 mg) and 2,6-dichloro-4-(4H-1,2,4-triazol-4-yl)benzoic acid (40 mg) were converted to the title compound.

Example 3

N-(1-(3-Aminobenzo[d]isoxazol-7-yl)-3-phenylpyrrolidin-3-yl)-2,6-dichloro-4-(4H-1,2,4-triazol-4-yl)benzamide

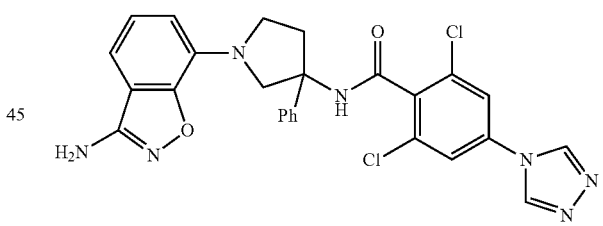

Step A. Ethyl 1-benzyl-3-phenylpyrrolidine-3-carboxylate

To a mixture of ethyl 2-phenylacrylate (0.50 g, 3.1 mmol) and TFA (20 µL, 0.31 mmol) in CH$_2$Cl$_2$ (18 mL) was added N-benzyl-1-methoxy-N-((trimethylsilyl)methyl)methanamine (0.87 mL, 3.4 mmol) in CH$_2$Cl$_2$ (18 mL) at 0° C. The mixture was stirred at RT overnight. The mixture was concentrated in vacuo and the residue was purified by column chromatography (0-20% EtOAc in heptane) to give the title compound. MS (ESI) m/z=310 (M+H)

Step B. Ethyl 3-phenylpyrrolidine-3-carboxylate

To the solution of ethyl 1-benzyl-3-phenylpyrrolidine-3-carboxylate (3.7 g, 12 mmol) in MeOH (15 mL), was added palladium hydroxide on carbon (0.37 g). The suspension was stirred under H₂ atmosphere at RT for 6 h. The mixture was filtrated through Celite, and the filtrate was concentrated in vacuo to obtain the title compound. MS (ESI) m/z=220 (M+H)

Step C. 1-Benzyl 3-ethyl 3-phenylpyrrolidine-1,3-dicarboxylate

To the solution of ethyl 3-phenylpyrrolidine-3-carboxylate (2.6 g, 12 mmol) and pyridine (1.9 mL, 23 mmol) in CH₂Cl₂ (50 mL), was added benzyl chloroformate (1.8 mL, 13 mmol) at 0° C. The solution was stirred at RT overnight. The mixture was diluted with H₂O and extracted with EtOAc. The organic layer was washed with brine, dried over Na₂SO₄, filtrated, and concentrated in vacuo. The residue was purified by column chromatography (silica-gel, 0-20% EtOAc in heptane) to give the title compound. MS (ESI) m/z=376 (M+Na)

Step D. 1-((Benzyloxy)carbonyl)-3-phenylpyrrolidine-3-carboxylic acid

To the solution of 1-benzyl 3-ethyl 3-phenylpyrrolidine-1,3-dicarboxylate (3.0 g, 8.5 mmol) in MeOH/H₂O (5 mL/2.5 mL) was added lithium hydroxide monohydrate (0.53 g, 13 mmol) at RT. The solution was stirred at RT overnight. The mixture was quenched with sat. aq. NH₄Cl and extracted with EtOAc. The organic layer was washed with brine, dried over Na₂SO₄, filtrated, and concentrated in vacuo to give the title compound. MS (ESI) m/z=348 (M+Na)

Step E. Benzyl 3-((tert-butoxycarbonyl)amino)-3-phenylpyrrolidine-1-carboxylate To the solution of 1-((benzyloxy)carbonyl)-3-phenylpyrrolidine-3-carboxylic acid (2.1 g, 6.5 mmol) and Et₃N (1.2 mL, 8.4 mmol) in acetone (60 mL), was added ethyl chloroformate (0.69 mL, 7.1 mmol) at 0° C. The solution was stirred at 0° C. for 1 h and then was added sodium azide (0.63 g, 9.7 mmol) at 0° C. The mixture was stirred at 0° C. for 3 h. The mixture was diluted with H₂O and extracted with EtOAc. The organic layer was washed with brine, dried over Na₂SO₄, filtrated, and concentrated in vacuo. The residue was dissolved in t-BuOH (60 mL) and stirred at 110° C. overnight. The mixture was diluted with H₂O and extracted with EtOAc. The organic layer was washed with brine, dried over Na₂SO₄, filtrated, and concentrated in vacuo. The residue was purified by column chromatography (20-70% EtOAc in heptane) to give the title compound. MS (ESI) m/z=419 (M+Na)

Step F. tert-Butyl (3-phenylpyrrolidin-3-yl)carbamate

To the solution of benzyl 3-((tert-butoxycarbonyl)amino)-3-phenylpyrrolidine-1-carboxylate (1.9 g, 4.7 mmol) in MeOH (20 mL) was added 10% Pd/C (0.37 g) at RT. The suspension was stirred at RT for 3 days. The mixture was filtrated through a pad of Celite and the filtrate was concentrated in vacuo to obtain the title compound. MS (ESI) m/z=263 (M+H)

Step G. 7-(3-Amino-3-phenylpyrrolidin-1-yl)benzo[d]isoxazol-3-amine dihydrochloride Following the procedures of EXAMPLE 1 (Step A-C), tert-butyl (3-phenylpyrrolidin-3-yl)carbamate was converted to the title compound (27 mg) as a brown powder over 3 steps. MS (ESI) m/z=317 (M+Na)
¹H NMR (400 MHz, DMSO-d₆) δ (ppm): 8.71 (3H, brs), 7.62 (2H, d, J=7.8 Hz), 7.53-7.41 (3H, m), 7.16-7.07 (2H, m), 6.67 (1H, d, J=7.3 Hz), 4.36 (1H, d, J=11.0 Hz), 3.98-3.88 (2H, m), 2.69-2.45 (3H, m) (one NH₂ group was not observed)

Step H

N-(1-(3-Aminobenzo[d]isoxazol-7-yl)-3-phenylpyrrolidin-3-yl)-2,6-dichloro-4-(4H-1,2,4-triazol-4-yl)benzamide Following the procedure of EXAMPLE 1 (Step E), 7-(3-amino-3-phenylpyrrolidin-1-yl)benzo[d]isoxazol-3-amine dihydrochloride (25 mg, 0.07 mmol) and 2,6-dichloro-4-(4H-1,2,4-triazol-4-yl)benzoic acid (18 mg, 0.07 mmol, EXAMPLE 2, Step D) were converted to the title compound.

Example 4

N-(1-(3-Aminobenzo[d]isothiazol-7-yl)pyrrolidin-3-yl)-2,6-dichloro-4-(4H-1,2,4-triazol-4-yl)benzamide

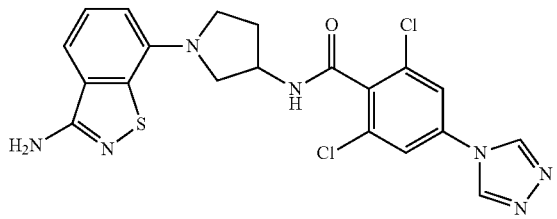 [SMILES: Nc1nsc2c(N3CCC(NC(=O)c4c(Cl)cc(-n5cnnc5)cc4Cl)C3)cccc12]

Step A. 7-Bromobenzo[d]isothiazol-3-amine

The mixture of 3-bromo-2-fluorobenzonitrile (5.0 mmol, 1.0 g) and sodium sulfide nonahydrate (6.0 mmol, 1.4 g) was dissolved in DMSO (50 mL) and heated at 70° C. overnight. The mixture was placed in an ice-water bath and treated with 28% aq. ammonia (6 mL) and aq. sodium hypochlorite (6 mL). The reaction mixture was allowed to warm to RT and stirred for 1 h. The mixture was diluted with TBME (50 mL) and washed with water (50 mL×2) and brine (50 mL). The organic layer was dried over Na₂SO₄, filtered, and concentrated in vacuo. The residue was triturated by EtOAc to give the title compound. MS (ESI) m/z=229, 231 (M+H)

Step B. 7-Bromo-3-(2,5-dimethyl-1H-pyrrol-1-yl)benzo[d]isothiazole

A mixture of hexane-2,5-dione (1.7 mmol, 0.20 g) and 7-bromobenzo[d]isothiazol-3-amine (1.4 mmol, 0.33 g) in acetic acid (10 mL) was stirred at 130° C. for 18 h. The mixture was concentrated in vacuo. The residue was purified by silica-gel column chromatography (0-33% EtOAc in heptane) to afford the title compound. MS (ESI) m/z=307, 309 (M+H)

Step C. tert-Butyl (1-(3-(2,5-dimethyl-1H-pyrrol-1-yl)benzo[d]isothiazol-7-yl)pyrrolidin-3-yl)carbamate To a mixture of 7-bromo-3-(2,5-dimethyl-1H-pyrrol-1-yl)benzo[d]isothiazole (1.2 mmol, 375 mg), tert-butyl pyrrolidin-3-ylcarbamate (1.8 mmol, 341 mg) in toluene, Pd$_2$(dba)$_3$ (0.12 mmol, 112 mg), XPhos (0.31 mmol, 145 mg), and t-BuONa (3.7 mmol, 352 mg) were added. The mixture was degassed under reduced pressure and backfilled with nitrogen. The mixture was stirred at 110° C. for 2 h, concentrated in vacuo, purified by silica-gel column chromatography (0-100% ethyl acetate in heptane) to afford the title compound. MS (ESI) m/z=413 (M+H)

Step D. 1-(3-(2,5-Dimethyl-1H-pyrrol-1-yl)benzo[d] isothiazol-7-yl)pyrrolidin-3-amine 4N HCl in EtOAc (3.0 mL) was added to tert-butyl (1-(3-(2,5-dimethyl-1H-pyrrol-1-yl)benzo[d]isothiazol-7-yl)pyrrolidin-3-yl)carbamate (0.57 mmol, 235 mg). The mixture was stirred at RT for 1 h. The mixture was neutralized with sat. aq. NaHCO$_3$ (3 mL) and diluted with CH$_2$Cl$_2$ (5 mL). The aqueous layer was extracted with CH$_2$Cl$_2$ (5 mL). The organic phases was dried over Na$_2$SO$_4$, filtered, and concentrated in vacuo to give the title compound. MS (ESI) m/z=313 (M+H)

$^1$H NMR (300 MHz, CDCl$_3$) δ (ppm): 7.26 (1H, dd, J=8.6, 7.2 Hz), 6.87 (1H, d, J=7.9 Hz), 6.49 (1H, d, J=7.6 Hz), 5.95 (2H, s), 3.95-3.72 (4H, m), 3.44 (1H, dd, J=8.8, 4.6 Hz), 2.35-2.29 (1H, m), 2.03 (6H, s), 1.97-1.87 (1H, m)

Step E 2,6-Dichloro-N-(1-(3-(2,5-dimethyl-1H-pyrrol-1-yl) benzo[d]isothiazol-7-yl)pyrrolidin-3-yl)-4-(4H-1,2, 4-triazol-4-yl)benzamide Following the procedure of EXAMPLE 1 (Step E), 1-(3-(2,5-dimethyl-1H-pyrrol-1-yl)benzo[d]isothiazol-7-yl)pyrrolidin-3-amine (0.08 mmol, 25 mg) and 2,6-dichloro-4-(4H-1,2,4-triazol-4-yl)benzoic acid (0.08 mmol, 20.6 mg, EXAMPLE 2, Step D) were converted to the title compound. MS (ESI) m/z=552 (M+H)

Step F

N-(1-(3-Aminobenzo[d]isothiazol-7-yl)pyrrolidin-3-yl)-2,6-dichloro-4-(4H-1,2,4-triazol-4-yl)benzamide TFA (1.0 mL) was added to 2,6-dichloro-N-(1-(3-(2,5-dimethyl-1H-pyrrol-1-yl)benzo[d]isothiazol-7-yl)pyrrolidin-3-yl)-4-(4H-1,2,4-triazol-4-yl)benzamide (0.03 mmol, 18 mg) in water (0.5 mL). The mixture was stirred at 50° C. for 1 h. The reaction mixture was neutralized with sat. aq. NaHCO$_3$ (2 mL) and diluted with CH$_2$Cl$_2$ (2 mL). The aqueous layer was extracted with CH$_2$Cl$_2$ (2 mL) and washed with water (2 mL). The organic layer was dried over Na$_2$SO$_4$, filtered, and concentrated in vacuo. The residue was purified by NH column chromatography (0-10% MeOH in EtOAc) to give the title compound.

Example 5

N-(1-(3-Aminoisoxazolo[5,4-c]pyridin-7-yl)pyrrolidin-3-yl)-2-chloro-4-(4H-1,2,4-triazol-4-yl)benzamide

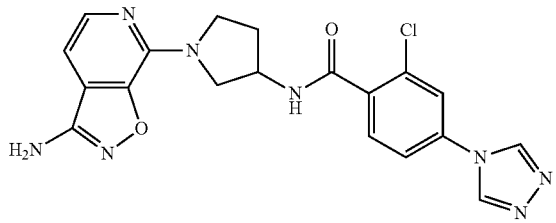 [SMILES: Nc1noc2c(N3CCC(NC(=O)c4ccc(-n5cnnc5)cc4Cl)C3)nccc12]

Step A. 2,3-Difluoroisonicotinamide

To a solution of 2,3-difluoroisonicotinic acid (50 mg, 0.31 mmol), NH$_4$Cl (179 mg, 0.94 mmol) and HATU (179 mg, 0.47 mmol) in DMF (1.0 mL) was added DIPEA (165 µL, 0.94 mmol). The mixture was stirred at RT for 1 h. The reaction mixture was diluted with H$_2$O. The mixture was extracted with EtOAc and the extract was washed with brine, dried over Na$_2$SO$_4$, filtered and concentrated in vacuo to afford a crude compound. The residue was purified by SiO$_2$ column chromatography (heptane:EtOAc=95:5 to 40:60) to give the title compound. MS (ESI) m/z=159 (M+H)

Step B. tert-Butyl (1-(4-carbamoyl-3-fluoropyridin-2-yl)pyrrolidin-3-yl)carbamate A suspension of 2,3-difluoroisonicotinamide (37 mg, 0.23 mmol), tert-butyl pyrrolidin-3-ylcarbamate (52 mg, 0.28 mmol) and K$_2$CO$_3$ (65 mg, 0.47 mmol) in DMF (1.1 mL) was stirred at 120° C. for 13 h. After cooled to RT, the reaction mixture was diluted with H$_2$O. The mixture was extracted with EtOAc and the extract was washed with brine, dried over Na$_2$SO$_4$, filtered and concentrated in vacuo to afford a crude compound. The residue was purified by NH—SiO$_2$ column chromatography (heptane:EtOAc=95:5 to 30:70) to give the title compound. MS (ESI) m/z=347 (M+Na)

Step C. tert-Butyl (1-(4-cyano-3-fluoropyridin-2-yl) pyrrolidin-3-yl)carbamate

To a suspension of tert-butyl (1-(4-carbamoyl-3-fluoropyridin-2-yl)pyrrolidin-3-yl)carbamate (58 mg, 0.18 mmol) and triethylamine (75 µL, 0.53 mmol) in CH$_2$Cl$_2$ (1.7 mL) was added TFAA (38 µL, 0.27 mmol) at 0° C. The reaction mixture was stirred at the same temperature for 30 minutes. The solvent was almost removed, then the residue was purified by NH—SiO$_2$ column chromatography (heptane: EtOAc=100:0 to 70:30) to give the title compound. MS (ESI) m/z=329 (M+Na)

Step D. tert-Butyl (1-(3-aminoisoxazolo[5,4-c]pyridin-7-yl)pyrrolidin-3-yl)carbamate To a solution of tert-butyl (1-(4-cyano-3-fluoropyridin-2-yl)pyrrolidin-3-yl)carbamate (40 mg, 0.13 mmol) in DMF (1.2 mL) was added N-hydroxyacetamide (88 mg, 1.18 mmol) and t-BuOK (132 mg, 1.18 mmol). The reaction mixture was stirred at 90° C. for 2 h. The reaction mixture was diluted with H₂O. The mixture was extracted with EtOAc and the extract was washed with brine, dried over Na₂SO₄, filtered and concentrated in vacuo to afford a crude compound. The residue was purified by SiO₂ column chromatography (heptane:EtOAc=80:20 to 30:70) to give the title compound.

MS (ESI) m/z=342 (M+Na)

Step E. 7-(3-Aminopyrrolidin-1-yl)isoxazolo[5,4-c]pyridin-3-amine trihydrochloride A solution of tert-butyl (1-(3-aminoisoxazolo[5,4-c]pyridin-7-yl)pyrrolidin-3-yl)carbamate (28 mg, 0.09 mmol) in 4N HCl in 1,4-dioxane (0.8 mL) was stirred at RT for 15 h. The reaction mixture was concentrated in vacuo to give the title compound.

¹H NMR (300 MHz, DMSO-d₆) δ (ppm): 8.37-8.20 (3H, m), 7.81 (1H, d, J=5.8 Hz), 7.13 (1H, d, J=6.5 Hz), 4.10-3.83 (5H, m), 2.41-2.25 (1H, m), 2.23-2.10 (1H, m)

MS (ESI) m/z=220 (M+H)

Step F

N-(1-(3-Aminoisoxazolo[5,4-c]pyridin-7-yl)pyrrolidin-3-yl)-2-chloro-4-(4H-1,2,4-triazol-4-yl)benzamide To a suspension of 7-(3-aminopyrrolidin-1-yl)isoxazolo[5,4-c]pyridin-3-amine trihydrochloride (28 mg, 0.08 mmol), 2-chloro-4-(4H-1,2,4-triazol-4-yl)benzoic acid (23 mg, 0.1 mmol, EXAMPLE 1, Step D) and HATU (48 mg, 0.13 mmol) in DMF (1.0 mL) was added DIPEA (59 μL, 0.34 mmol). The reaction mixture was stirred at RT for 18 h. The solution was purified by HPLC to give the title compound.

Example 6

N-(1-(3-Amino-5-methylbenzo[d]isoxazol-7-yl)pyrrolidin-3-yl)-2,6-dichloro-4-(3-methyl-1H-1,2,4-triazol-1-yl)benzamide

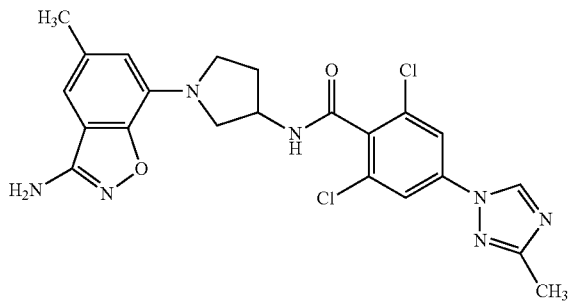 [SMILES: Cc1cc(N2CCC(NC(=O)c3c(Cl)cc(-n4cnc(C)n4)cc3Cl)C2)c2onc(N)c2c1]

Step A. 3-Bromo-2-fluoro-5-methylbenzoic acid

To a solution of diisopropylamine (3.6 mL, 25 mmol) in THF (60 mL) was added n-BuLi (2.6 molar, 8.95 mL, 23.3 mmol) at 0° C., it was stirred at the same temperature for 20 minutes. The mixture was cooled to −78° C. and 2-bromo-1-fluoro-4-methylbenzene (4.0 g, 21 mmol) in THF (20 mL) was added. The mixture was stirred at −78° C. for 25 minutes, then dry-ice was added to the reaction. The mixture was stirred at −78° C. for 1 h and at RT for 30 minutes. THF was almost removed and it was diluted with CH₂Cl₂ and 1N aq. NaOH. The mixture was extracted with CH₂Cl₂. The aqueous layer was acidified with 1N aq. HCl to pH 1, and it was extracted with EtOAc. The extract was washed with water and brine, and dried over Na₂SO₄, filtered, and concentrated in vacuo to give the title compound.

MS (ESI) m/z=233, 235 (M+H)

Step B. 3-Bromo-2-fluoro-5-methylbenzamide

To a suspension of 3-bromo-2-fluoro-5-methylbenzoic acid (1.15 g, 4.93 mmol), ammonium chloride (0.79 g, 15 mmol), HOAt (0.07 g, 0.49 mmol) in DMF (23 mL), EDCI (1.4 g, 7.4 mmol) and DIPEA (1.7 mL, 9.9 mmol) were added. The mixture was stirred at RT for 20 h. The mixture was diluted with EtOAc and water, extracted with EtOAc. The extract was washed with 1N aq. HCl, sat. aq. NaHCO₃, and brine. The organic layer was dried over Na₂SO₄, filtered, and concentrated in vacuo to give the title compound. MS (ESI) m/z=232, 234 (M+H)

Step C. 3-Bromo-2-fluoro-5-methylbenzonitrile

Following the procedure of EXAMPLE 5 (Step C), 3-bromo-2-fluoro-5-methylbenzamide (0.70 g, 2.65 mmol) was converted to the title compound. MS (ESI) m/z=214, 216 (M+H)

Step D. 7-Bromo-5-methylbenzo[d]isoxazol-3-amine

Following the procedure of EXAMPLE 5 (Step D), 3-bromo-2-fluoro-5-methylbenzonitrile (403 mg, 1.88 mmol) was converted to the title compound. MS (ESI) m/z=227, 229 (M+H)

Step E. 7-Bromo-3-(2,5-dimethyl-1H-pyrrol-1-yl)-5-methylbenzo[d]isoxazole

To a solution of 7-bromo-5-methylbenzo[d]isoxazol-3-amine (200 mg, 0.88 mmol) in AcOH (1.0 mL) was added hexane-2,5-dione (134 μL, 1.15 mmol). The reaction mixture was stirred at 120° C. for 7 h. The mixture was concentrated in vacuo to afford a crude compound. The residue was purified by NH—SiO₂ column chromatography (heptane:EtOAc 100:0 to 70:30) to give the title compound. MS (ESI) m/z=305, 307 (M+H)

Step F. tert-Butyl (1-(3-(2,5-dimethyl-1H-pyrrol-1-yl)-5-methylbenzo[d]isoxazol-7-yl)pyrrolidin-3-yl)carbamate A suspension of 7-bromo-3-(2,5-dimethyl-1H-pyrrol-1-yl)-5-methylbenzo[d]isoxazole (226 mg, 0.74 mmol), tert-butyl pyrrolidin-3-ylcarbamate (166 mg, 0.89 mmol), Pd₂(dba)₃ (68 mg, 0.07 mmol), Xphos (71 mg, 0.15 mmol) and Cs₂CO₃ (724 mg, 2.22 mmol) in toluene (6.8 mL) was stirred at 100° C. for 15 hours. The reaction mixture was diluted with H₂O. The mixture was extracted with EtOAc and the extract was washed with brine, dried over Na₂SO₄, filtered and concentrated in vacuo to afford a crude compound. The residue was purified by NH—SiO₂ column chromatography (heptane:EtOAc=100:0 to 80:20) to give the title compound.

MS (ESI) m/z=411 (M+H)

Step G. 7-(3-Aminopyrrolidin-1-yl)-5-methylbenzo[d]isoxazol-3-amine

A solution of tert-butyl (1-(3-(2,5-dimethyl-1H-pyrrol-1-yl)-5-methylbenzo[d]isoxazol-7-yl)pyrrolidin-3-yl)carbamate (160 mg, 0.39 mmol) in TFA (2.0 mL) and H₂O (1.0 mL) was stirred at 60° C. for 2 hours. The solvent was removed, then the residue was purified by NH—SiO₂ column chromatography (EtOAc:MeOH=100:0 to 95:5) to give the title compound. MS (ESI) m/z=233 (M+H)

$^1$H NMR (300 MHz, DMSO-$d_6$) δ (ppm): 6.77 (1H, s), 6.28 (1H, s), 6.10 (2H, s), 3.72-3.52 (3H, m), 3.50-3.21 (2H, m), 2.30 (3H, s), 2.16-2.02 (1H, m), 1.79-1.66 (1H, m)

Step H. tert-Butyl 1-(3,5-dichloro-4-(methoxycarbonyl)phenyl)hydrazinecarboxylate A mixture of palladium acetate (1.5 mmol, 0.34 g) and Xantphos (3.0 mmol, 1.7 g) in toluene (6 mL) was stirred under nitrogen for 10 min. In another flask, methyl 2,4,6-trichlorobenzoate (30 mmol, 7.2 g), tert-butyl hydrazinecarboxylate (36 mmol, 4.8 g), and K₂CO₃ (12 g, 90 mmol) in toluene (60 mL) were placed. To the mixture, catalyst suspension was added. The mixture was degassed under reduced pressure, then backfilled with nitrogen. The reaction mixture was stirred at 100° C. for 16 h. The mixture was cooled to RT, added water, and extracted with EtOAc. The extract was dried over Na₂SO₄, filtered, and concentrated in vacuo. The crude was purified by column chromatography (silica-gel, 0-30% EtOAc in heptane) to give the title compound. MS (ESI) m/z=357, 359 (M+Na)

Step I. Methyl 2,6-dichloro-4-hydrazinylbenzoate hydrochloride

A mixture of tert-butyl 1-(3,5-dichloro-4-(methoxycarbonyl)phenyl)hydrazinecarboxylate (12 mmol, 4.1 g) and 4N HCl in ethyl acetate (61 mmol, 15 mL) was stirred at RT for 3 h. The mixture was cooled to 0° C., filtered, washed with cold EtOAc to give the title compound.

MS (ESI) m/z=235, 237 (M+H)

Step J. Methyl 2,6-dichloro-4-(3-methyl-1H-1,2,4-triazol-1-yl)benzoate

To a solution of ethyl acetimidate hydrochloride (21 mmol, 2.6 g) in ethanol (22 mL) at 0° C., Et₃N (21 mmol, 3.0 mL) was added. In the other flask, to a solution of methyl 2,6-dichloro-4-hydrazinylbenzoate hydrochloride (11 mmol, 2.9 g) in ethanol (22 mL) at 0° C., Et₃N (21 mmol, 3.0 mL) was added. The solution of methyl 2,6-dichloro-4-hydrazinylbenzoate was added dropwise into the suspension of ethyl acetimidate. The mixture was stirred at the same temperature for 10 min and then at RT for 1 h. To the mixture, trimethyl orthoformate (214 mmol, 23 mL) was added, concentrated in vacuo, added trimethyl orthoformate (23 mL) again, then stirred at 100° C. for 4 h. The mixture was diluted with ethyl acetate, washed with water, dried over Na₂SO₄, filtered, concentrated in vacuo. The crude was purified by flash chromatography (silica-gel, 0-80% EtOAc in heptane) to give the title compound.

MS (ESI) m/z=286, 288 (M+H)

Step K. 2,6-Dichloro-4-(3-methyl-1H-1,2,4-triazol-1-yl)benzoic acid

A mixture of methyl 2,6-dichloro-4-(3-methyl-1H-1,2,4-triazol-1-yl)benzoate (9.4 mmol, 2.7 g) and lithium hydroxide monohydrate (47 mmol, 2.0 g) in MeOH (30 mL)-THF (10 mL)-water (2.0 mL) was stirred at 70° C. for 16 h. The mixture was cooled to 0° C., quenched with c.HCl (3.8 mL), partially concentrated in vacuo. The residue was triturated with cold ethanol-water (2:1) to give the desired product (1.6 g, 1st crop). The mother liquid was partially concentrated, triturated with cold THF (~5 mL), filtered, and washed with cold ethanol (2nd crop). The 1st and 2nd crops were combined and dried in vacuo to give the desired product. MS (ESI) m/z=272, 274 (M+H) $^1$H NMR (300 MHz, DMSO-$d_6$) δ (ppm): 9.26 (1H, s), 7.96 (2H, s), 2.38 (3H, s)

Step L

N-(1-(3-Amino-5-methylbenzo[d]isoxazol-7-yl)pyrrolidin-3-yl)-2,6-dichloro-4-(3-methyl-1H-1,2,4-triazol-1-yl)benzamide Following the procedure of EXAMPLE 5 (Step F), 7-(3-aminopyrrolidin-1-yl)-5-methylbenzo[d]isoxazol-3-amine (14 mg, 0.06 mmol) and 2,6-dichloro-4-(3-methyl-1H-1,2,4-triazol-1-yl)benzoic acid (18 mg, 0.07 mmol) were converted to the title compound.

Example 7

N-((3R*,4S*)-1-(3-Aminobenzo[d]isoxazol-7-yl)-3,4-dimethylpyrrolidin-3-yl)-2,6-dichloro-4-(4H-1,2,4-triazol-4-yl)benzamide

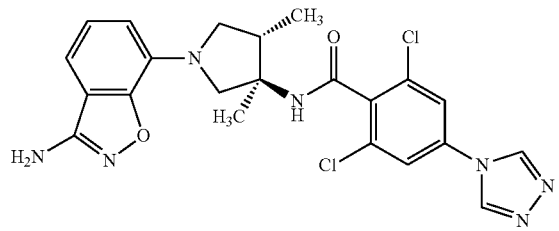 [SMILES: C[C@H]1CN(c2cccc3c(N)noc23)C[C@]1(C)NC(=O)c1c(Cl)cc(-n2cnnc2)cc1Cl]

Step A. (3R*,4R*)-Ethyl 1-benzyl-3,4-dimethylpyrrolidine-3-carboxylate

To a mixture of (E)-ethyl 2-methylbut-2-enoate (3.0 g, 23 mmol) and TFA (0.18 mL, 2.3 mmol) in CH₂Cl₂ (45 mL) was added N-benzyl-1-methoxy-N-((trimethylsilyl)methyl)methanamine (6.6 mL, 26 mmol) at 0° C. The mixture was stirred at RT overnight. The mixture was concentrated in vacuo and the residue was purified by column chromatography (silica-gel, 0-30% EtOAc in heptane) to give the title compound. MS (ESI) m/z=262 (M+H)

Step B. (3R*,4R*)-Ethyl 3,4-dimethylpyrrolidine-3-carboxylate

Following the procedure of EXAMPLE 3 (Step B), (3R*,4R*)-ethyl 1-benzyl-3,4-dimethylpyrrolidine-3-carboxylate (1.0 g, 3.8 mmol) was converted to the title compound. MS (ESI) m/z=172 (M+H)

Step C. (3R*,4R*)-Ethyl 1-(3-(2,5-dimethyl-1H-pyrrol-1-yl)benzo[d]isoxazol-7-yl)-3,4-dimethylpyrrolidine-3-carboxylate Following the procedure of EXAMPLE 6 (Step F), 7-bromo-3-(2,5-dimethyl-1H-pyrrol-1-yl)benzo[d]isoxazole (0.84 g, 2.9 mmol) and (3R*,4R*)-ethyl 3,4-dimethylpyrrolidine-3-carboxylate (0.54 g, 3.2 mmol) were converted to the title compound. MS (ESI) m/z=404 (M+Na)

Step D

(3R*,4R*)-1-(3-(2,5-Dimethyl-1H-pyrrol-1-yl)benzo[d]isoxazol-7-yl)-3,4-dimethylpyrrolidine-3-carboxylic acid To the solution of (3R*,4R*)-ethyl 1-(3-(2,5-dimethyl-1H-pyrrol-1-yl)benzo[d]isoxazol-7-yl)-3,4-dimethylpyrrolidine-3-carboxylat e (0.55 g, 1.4 mmol) in THF/H$_2$O (10 mL/2 mL) was added lithium hydroxide hydrate (67 mg, 1.6 mmol) at RT. The mixture was stirred at 50° C. for 3 h. To the mixture was added 1N aq. NaOH (3 mL) and MeOH (5 mL) and stirred at 50° C. for 2 h, then the mixture was diluted with sat. aq. NH$_4$Cl and extracted with EtOAc. The organic layer was washed with brine, dried over Na$_2$SO$_4$, filtrated, and concentrated in vacuo to give the title compound. MS (ESI) m/z=354 (M+H)

Step E. tert-Butyl ((3R*,4S*)-1-(3-(2,5-dimethyl-1H-pyrrol-1-yl)benzo[d]isoxazol-7-yl)-3,4-dimethylpyrrolidin-3-yl)carbamate A mixture of (3R*,4R*)-1-(3-(2,5-dimethyl-1H-pyrrol-1-yl)benzo[d]isoxazol-7-yl)-3,4-dimethylpyrrolidine-3-carboxylic acid (0.50 g, 1.4 mmol), DPPA (0.46 mL, 2.1 mmol), Et$_3$N (0.59 mL, 4.2 mmol), and molecular sieves 4 A (1.0 g) in t-BuOH (10 mL) was stirred at 110° C. for 5 h. The suspension was filtered through a pad of Celite and concentrated in vacuo. The residue was purified by column chromatography (silica-gel, 0-10% EtOAc in heptane) to give the title compound. MS (ESI) m/z=425 (M+H)

$^1$H NMR (400 MHz, CDCl$_3$) δ (ppm): 7.16 (1H, dd, J=7.8, 7.8 Hz), 6.70 (1H, d, J=7.3 Hz), 6.51 (1H, d, J=7.8 Hz), 5.98 (2H, s), 4.70 (1H, brs), 4.05 (1H, dd, J=8.7, 8.7 Hz), 3.88 (2H, brs), 3.47 (1H, dd, J=9.1, 9.1 Hz), 2.75-2.60 (1H, m), 2.13 (6H, s), 1.47 (9H, s), 1.39 (3H, s), 1.09 (3H, d, J=7.3 Hz)

Step F

(3R*,4S*)-1-(3-(2,5-Dimethyl-1H-pyrrol-1-yl)benzo[d]isoxazol-7-yl)-3,4-dimethylpyrrolidin-3-amine To a solution of tert-butyl ((3R*,4S*)-1-(3-(2,5-dimethyl-1H-pyrrol-1-yl)benzo[d]isoxazol-7-yl)-3,4-dimethylpyrrolidin-3-yl)carbamate (0.48 g, 1.1 mmol) in CH$_2$Cl$_2$ (2 mL), TFA (3 mL) was added. The mixture was stirred at RT for 1 h. The mixture was quenched with 1N aq. NaOH (15 mL) and extracted with ethyl acetate. The extract was washed with brine, dried over Na$_2$SO$_4$, filtered, and concentrated in vacuo to give the title compound. MS (ESI) m/z=325 (M+H)

Step G

N-((3R*,4S*)-1-(3-Aminobenzo[d]isoxazol-7-yl)-3,4-dimethylpyrrolidin-3-yl)-2,6-dichloro-4-(4H-1,2,4-triazol-4-yl)benzamide Following the procedures of EXAMPLE 1 (Step E) and EXAMPLE 4 (Step F), (3R*,4S*)-1-(3-(2,5-dimethyl-1H-pyrrol-1-yl)benzo[d]isoxazol-7-yl)-3,4-dimethylpyrrolidin-3-amine (0.31 mmol, 0.10 g) and 2-chloro-4-(4H-1,2,4-triazol-4-yl)benzoic acid (0.46 mmol, 119 mg, EXAMPLE 1, Step D) were converted to the title compound.

Example 8

N-((3S*,4S*)-1-(3-Aminobenzo[d]isoxazol-7-yl)-4-hydroxypyrrolidin-3-yl)-2,6-dichloro-4-(4H-1,2,4-triazol-4-yl)benzamide

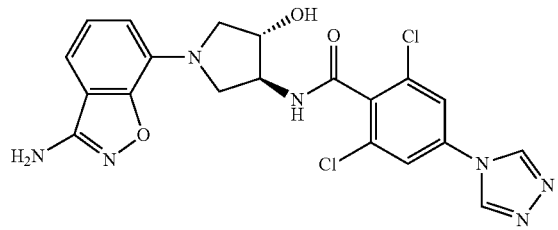 [SMILES: Nc1noc2c(N3C[C@H](NC(=O)c4c(Cl)cc(-n5cnnc5)cc4Cl)[C@@H](O)C3)cccc12]

Step A. Benzyl 6-oxa-3-azabicyclo[3.1.0]hexane-3-carboxylate

To a solution of benzyl 2,5-dihydro-1H-pyrrole-1-carboxylate (4.9 mmol, 1.0 g) in CH$_2$Cl$_2$ (30 mL) at 0° C. was added m-CPBA (20 mmol, 3.4 g) in portions. The reaction was stirred at RT for 18 h. The mixture was filtered and the filtrate was washed with aqueous NaHCO$_3$ and brine. The organic layer was dried over Na$_2$SO$_4$ and purified by silica gel chromatography (heptane/EtOAc=90/10 to 0/100) to afford the title compound. MS (ESI) m/z=242 (M+Na)

Step B. (3S*,4S*)-Benzyl 3-amino-4-hydroxypyrrolidine-1-carboxylate

The mixture of benzyl 6-oxa-3-azabicyclo[3.1.0]hexane-3-carboxylate (4.33 mmol, 950 mg) and ammonium hydroxide (4.0 mL), MeOH (2.0 mL) was heated in a sealed tube at 60° C. for 18 h. The reaction was concentrated in vacuo to afford the title compound.

MS (ESI) m/z=237 (M+H)

Step C. (3S*,4S*)-Benzyl 3-((tert-butoxycarbonyl)amino)-4-hydroxypyrrolidine-1-carboxylate To a solution of (3S*,4S*)-benzyl 3-amino-4-hydroxypyrrolidine-1-carboxylate (4.2 mmol, 1.0 g) in THF (10 mL) was added Et$_3$N (5.5 mmol, 0.77 mL). The reaction mixture was cooled to 0° C. and (Boc)$_2$O (5.5 mmol, 1.2 g) was added portionwise. The mixture was stirred at 0° C. for 15 min and at RT for 1.5 h, then diluted with EtOAc, and washed with water and brine. The organic layer was dried over Na$_2$SO$_4$, filtered, and concentrated in vacuo. The crude was purified by silica-gel column chromatography (heptane/EtOAc=66/34 to 0/100) to give the title compound.

MS (ESI) m/z=337 (M+H)

Step D. (3S*,4S*)-Benzyl 3-((tert-butoxycarbonyl)amino)-4-((tert-butyldiphenylsilyl)oxy)pyrrolidine-1-carboxylate To a solution of (3S*,4S*)-benzyl 3-((tert-butoxycarbonyl)amino)-4-hydroxypyrrolidine-1-carboxylate (0.24 mmol, 80 mg) in CH$_2$Cl$_2$ (0.80 mL) was added imidazole (0.48 mmol, 32.3 mg) and tert-butylchlorodiphenylsilane (0.36 mmol, 98.0 mg). The solution was stirred at RT for 3 h. The solvent was removed under reduced pressure and the crude product was purified by column chromatography (silica gel, heptane/EtOAc 100:0 to 67:33) to give the title compound. MS (ESI) m/z=575 (M+H)

Step E. tert-Butyl ((3S*,4S*)-4-((tert-butyldiphenyl-silyl)oxy)pyrrolidin-3-yl)carbamate To a solution of (3S*,4S*)-benzyl 3-((tert-butoxycarbonyl)amino)-4-((tert-butyldiphenylsilyl)oxy)pyrrolidine-1-carboxylate (0.21 mmol, 120 mg) in MeOH (1.2 mL) was added 10% Pd/C (0.11 mmol, 12 mg) at RT. The reaction mixture was stirred at RT for 18 h under H$_2$ (1 atm). The reaction mixture was filtered through a pad of Celite, and concentrated in vacuo. The crude product was used in the next step without further purification. MS (ESI) m/z=441 (M+H)

Step F. tert-Butyl ((3S*,4S*)-4-((tert-butyldiphenyl-silyl)oxy)-1-(3-(2,5-dimethyl-1H-pyrrol-1-yl)benzo[d]isoxazol-7-yl)pyrrolidin-3-yl)carbamate Following the procedure of EXAMPLE 4 (Step C), 7-bromo-3-(2,5-dimethyl-1H-pyrrol-1-yl)benzo[d]isoxazole (0.21 mmol, 60 mg) and tert-butyl ((3S*,4S*)-4-((tert-butyldiphenylsilyl)oxy)pyrrolidin-3-yl)carbamate (0.21 mmol, 91 mg) were converted to the title compound. MS (ESI) m/z=651 (M+H)

Step G. (3S*,4S*)-4-Amino-1-(3-aminobenzo[d]isoxazol-7-yl)pyrrolidin-3-ol

A solution of tert-butyl ((3S*,4S*)-4-((tert-butyldiphenyl-silyl)oxy)-1-(3-(2,5-dimethyl-1H-pyrrol-1-yl)benzo[d]isoxazol-7-yl)pyrrolidin-3-yl)carbamate (0.11 mmol, 70 mg) in TFA (2.0 mL) and water (1.0 mL) was stirred for 6 h at 60° C. The solvent was removed, then the residue was purified by SiO$_2$ column chromatography (EtOAc:MeOH=90:10 to 70:30) to give the title compound. MS (ESI) m/z=235 (M+H)

$^1$H NMR (300 MHz, CD$_3$OD) δ (ppm): 7.12-6.97 (2H, m), 6.60 (1H, d, J=7.6 Hz), 4.26-4.22 (1H, m), 4.02-3.92 (2H, m), 3.61-3.50 (3H, m)

Step H

N-((3S*,4S*)-1-(3-Aminobenzo[d]isoxazol-7-yl)-4-hydroxypyrrolidin-3-yl)-2,6-dichloro-4-(4H-1,2,4-triazol-4-yl)benzamide Following the procedure of EXAMPLE 1 (Step E), (3S*,4S*)-4-amino-1-(3-aminobenzo[d]isoxazol-7-yl)pyrrolidin-3-ol (0.09 mmol, 20.8 mg) and 2,6-dichloro-4-(4H-1,2,4-triazol-4-yl)benzoic acid (0.09 mmol, 23 mg, EXAMPLE 2, Step D) were converted to the title compound.

Example 9

(R)—N-(1-(3-Amino-4-chlorobenzo[d]isoxazol-7-yl)pyrrolidin-3-yl)-2-chloro-4-(4H-1,2,4-triazol-4-yl)benzamide

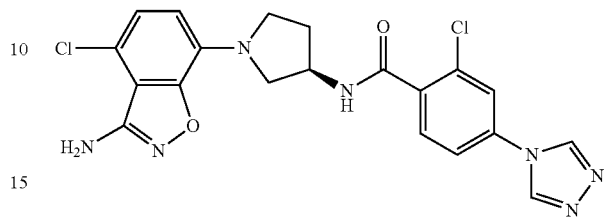

Step A. (R)-7-(3-Aminopyrrolidin-1-yl)-4-chlorobenzo[d]isoxazol-3-amine

Following the procedures of EXAMPLE 6 (Step A-G), 1-bromo-4-chloro-2-fluorobenzene was converted to the title compound over 7 steps. MS (ESI) m/z=253, 255 (M+H)

$^1$H NMR (400 MHz, CDCl$_3$) δ (ppm): 6.96 (1H, d, J=8.7 Hz), 6.34 (1H, d, J=8.2 Hz), 4.77 (2H, s), 3.84-3.70 (3H, m), 3.63-3.55 (1H, m), 3.41-3.35 (1H, m), 2.29-2.16 (1H, m), 1.88-1.77 (1H, m)

Step B

(R)—N-(1-(3-Amino-4-chlorobenzo[d]isoxazol-7-yl)pyrrolidin-3-yl)-2-chloro-4-(4H-1,2,4-triazol-4-yl)benzamide Following the procedure of EXAMPLE 5 (Step F), (R)-7-(3-aminopyrrolidin-1-yl)-4-chlorobenzo[d]isoxazol-3-amine (109 mg, 0.43 mmol) and 2-chloro-4-(4H-1,2,4-triazol-4-yl)benzoic acid (116 mg, 0.52 mmol, EXAMPLE 1, Step D) were converted to the title compound.

Example 10

(R)—N-(1-(3-Amino-5-chlorobenzo[d]isoxazol-7-yl)pyrrolidin-3-yl)-2-chloro-4-(4H-1,2,4-triazol-4-yl)benzamide

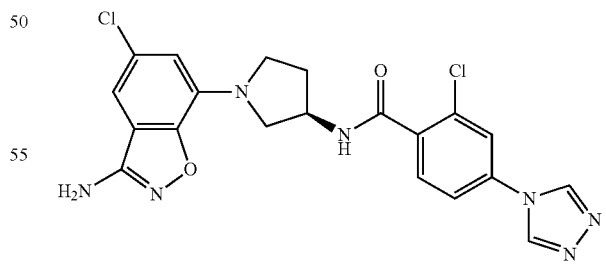

Step A. 3-Bromo-5-chloro-2-fluorobenzonitrile

To 1M lithium magnesium 2,2,6,6-tetramethylpiperidin-1-ide dichloride in THF (77 mmol, 77 mL) was added 5-chloro-2-fluorobenzonitrile (64 mmol, 10 g) in THF (70 mL) at −78° C. The reaction mixture was stirred at 0° C. for 1 h. To the mixture was added bromine (193 mmol, 30.8 g, 9.9 mL) at −78° C., and stirred for 1 h at −78° C. The reaction was quenched with sat. aq. NH₄Cl (400 mL), and extracted with EtOAc (200 mL, twice). The combined organic layer was washed with brine, dried over Na₂SO₄, filtrated, and concentrated in vacuo to give the title compound.

¹H NMR (300 MHz, CDCl₃) δ (ppm): 7.82 (1H, dd, J=5.7, 2.6 Hz), 7.57 (1H, dd, J=5.0, 2.6 Hz)

Step B. 7-Bromo-5-chlorobenzo[d]isoxazol-3-amine

Following the procedure of EXAMPLE 5 (Step D), 3-bromo-5-chloro-2-fluorobenzonitrile (4.6 mmol, 1.1 g) was converted to the title compound. MS (ESI) m/z=247, 249 (M+H)

Step C. 7-Bromo-5-chloro-3-(2,5-dimethyl-1H-pyrrol-1-yl)benzo[d]isoxazole

Following the procedure of EXAMPLE 6 (Step E), 7-bromo-5-chlorobenzo[d]isoxazol-3-amine (1.9 mmol, 0.46 g) was converted to the title compound. MS (ESI) m/z=325, 327 (M+H)

Step D. tert-Butyl (1-(5-chloro-3-(2,5-dimethyl-1H-pyrrol-1-yl)benzo[d]isoxazol-7-yl)pyrrolidin-3-yl)carbamate Following the procedure of EXAMPLE 6 (Step F), 7-bromo-5-chloro-3-(2,5-dimethyl-1H-pyrrol-1-yl)benzo[d]isoxazole (1.6 mmol, 0.53 g) and (R)-tert-butyl pyrrolidin-3-ylcarbamate (1.8 mmol, 0.33 g) were converted to the title compound. MS (ESI) m/z=431, 433 (M+H)

Step E

(R)-1-(5-chloro-3-(2,5-dimethyl-1H-pyrrol-1-yl)benzo[d]isoxazol-7-yl)pyrrolidin-3-amine hydrochloride Following the procedure of EXAMPLE 1 (Step C), (R)-tert-butyl (1-(5-chloro-3-(2,5-dimethyl-1H-pyrrol-1-yl)benzo[d]isoxazol-7-yl)pyrrolidin-3-yl)carbamate (0.71 mmol, 0.31 g) was converted to the title compound. MS (ESI) m/z=331, 333 (M+H) ¹H NMR (300 MHz, CD₃OD) δ (ppm): 6.73 (1H, d, J=1.7 Hz), 6.72 (1H, d, J=1.7 Hz), 5.97 (2H, s), 4.16-3.88 (4H, m), 3.78-3.68 (1H, m), 2.62-2.48 (1H, m), 2.30-2.17 (1H, m), 2.07 (6H, s)

Step F

(R)—N-(1-(3-Amino-5-chlorobenzo[d]isoxazol-7-yl)pyrrolidin-3-yl)-2-chloro-4-(4H-1,2,4-triazol-4-yl)benzamide Following the procedures of EXAMPLE 1 (Step E) and EXAMPLE 4 (Step F), (R)-1-(5-chloro-3-(2,5-dimethyl-1H-pyrrol-1-yl)benzo[d]isoxazol-7-yl)pyrrolidin-3-amine hydrochloride and 2-chloro-4-(4H-1,2,4-triazol-4-yl)benzoic acid (EXAMPLE 1, Step D) were converted to the title compound over 2 steps.

Example 11

(R)—N-(1-(3-Amino-4-chloroisoxazolo[5,4-c]pyridin-7-yl)pyrrolidin-3-yl)-2-chloro-4-(3-methyl-1H-1,2,4-triazol-1-yl)benzamide

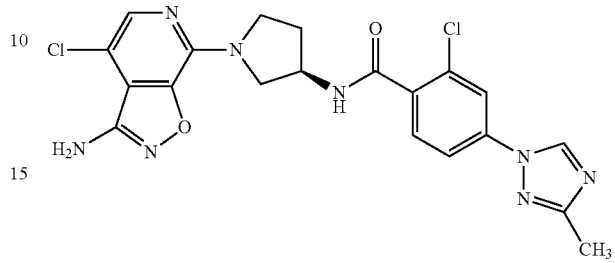

Step A. 2-Chloro-4-(3-methyl-1H-1,2,4-triazol-1-yl)benzaldehyde

To a solution of 2-chloro-4-fluorobenzaldehyde (95 mmol, 15 g) and 3-methyl-1H-1,2,4-triazole (114 mmol, 9.4 g) in CH₃CN (300 mL) was added K₂CO₃ (142 mmol, 20 g) and stirred at 60° C. After 24 h, the reaction mixture was added water and extracted with EtOAc. The organic extracts washed with saturated aq. NaCl, dried over Na₂SO₄, and filtered and concentrated in vacuo. The crude was purified by column chromatography (heptane:EtOAc=20:80-10:90) to give the title compound. MS (ESI) m/z=222, 224 (M+H)
¹H NMR (300 MHz, CDCl₃) δ (ppm): 10.45 (1H, s), 8.55 (1H, s), 8.06 (1H, d, J=8.6 Hz), 7.87 (1H, d, J=2.1 Hz), 7.68 (1H, dd, J=8.6, 2.1 Hz), 2.51 (3H, s).

Step B. 2-Chloro-4-(3-methyl-1H-1,2,4-triazol-1-yl)benzoic acid

To a solution of 2-chloro-4-(3-methyl-1H-1,2,4-triazol-1-yl)benzaldehyde (1.8 mmol, 400 mg) in DMF (4.0 mL) was added Oxone® (2.7 mmol, 1.7 g) and stirred at RT. After 16 h, the reaction mixture was added sat. aq. Na₂S₂O₃ and diluted with EtOAc. The mixture was filtered through Celite and extracted with EtOAc. The organic layer was dried over Na₂SO₄. The solvent was removed to give the title compound. MS (ESI) m/z=238, 240 (M+H)
¹H NMR (400 MHz, DMSO-d₆) δ (ppm): 9.31 (1H, s), 8.05 (1H, s), 7.96 (1H, d, J=8.7 Hz), 7.88 (1H, d, J=8.2 Hz), 2.37 (3H, s)

Step C. 5-Chloro-2,3-difluoroisonicotinic acid

Following the procedure of EXAMPLE 6 (Step A), 5-chloro-2,3-difluoropyridine (3.0 g, 20 mmol) was converted to the title compound.
¹H NMR (400 MHz, DMSO-d₆) δ (ppm): 8.31 (1H, s)

Step D. 5-Chloro-2,3-difluoroisonicotinamide

To a mixture of 5-chloro-2,3-difluoroisonicotinic acid (1.0 g, 5.2 mmol) and oxalyl chloride (0.9 mL, 10 mmol) in CH₂Cl₂ (10 mL) at 0° C., catalytic amount of DMF was added. The mixture was stirred at RT for 1 h, then concentrated in vacuo. The residue in CH₂Cl₂ (20 mL) was added dropwise into an 8M NH₃ in methanol (20 mL) at 0° C. The mixture was stirred at the same temperature for 1 h. The mixture was treated with water and extracted with CH$_2$Cl$_2$. The extract was washed with brine, dried over Na$_2$SO$_4$, filtered, and concentrated in vacuo to give the desired product.

MS (ESI) m/z=193 (M+H)

Step E. (R)-7-(3-Aminopyrrolidin-1-yl)-4-chloroisoxazolo[5,4-c]pyridin-3-amine dihydrochloride Following the procedures of EXAMPLE 5 (Step B-E), 5-chloro-2,3-difluoroisonicotinamide was converted to the title compound over 4 steps.

MS (ESI) m/z=254 (M+H)
$^1$H NMR (400 MHz, CD$_3$OD) δ (ppm): 7.77 (1H, s), 4.15-3.89 (5H, m), 2.57-2.45 (1H, m), 2.27-2.14 (1H, m). (NH$_2$ were not observed.)

Step F (R)—N-(1-(3-Amino-4-chloroisoxazolo[5,4-c]pyridin-7-yl)pyrrolidin-3-yl)-2-chloro-4-(3-methyl-1H-1,2,4-triazol-1-yl)benzamide Following the procedure of EXAMPLE 1 (Step E), (R)-7-(3-aminopyrrolidin-1-yl)-4-chloroisoxazolo[5,4-c]pyridin-3-amine dihydrochloride (60 mg) and 2-chloro-4-(3-methyl-1H-1,2,4-triazol-1-yl)benzoic acid (62 mg) were converted to the title compound.

Example 12

(R)—N-(1-(3-Amino-4-chloro-5-methylbenzo[d]isoxazol-7-yl)pyrrolidin-3-yl)-2-chloro-4-(4H-1,2,4-triazol-4-yl)benzamide

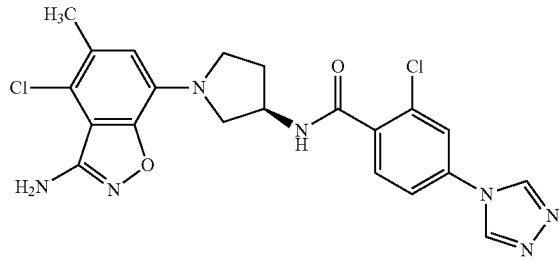 [SMILES: Cc1cc(N2CC[C@@H](NC(=O)c3ccc(-n4cnnc4)cc3Cl)C2)c2onc(N)c2c1Cl]

Step A. 3-Bromo-6-chloro-2-fluoro-5-methylbenzoic acid

Following the procedure of EXAMPLE 6 (Step A), 1-bromo-4-chloro-2-fluoro-5-methylbenzene (18 mmol, 4.0 g) was converted to the title compound.
$^1$H NMR (300 MHz, CD$_3$OD) δ (ppm): 7.67 (1H, d, J=7.6 Hz), 2.38 (3H, s)

Step B. 3-Bromo-6-chloro-2-fluoro-5-methylbenzamide

Following the procedure of EXAMPLE 11 (Step B), 3-bromo-6-chloro-2-fluoro-5-methylbenzoic acid (12 mmol, 3.2 g) was converted to the title compound. MS (ESI) m/z=266, 268 (M+H)

Step C. 3-Bromo-6-chloro-2-fluoro-5-methylbenzonitrile

Following the procedure of EXAMPLE 5 (Step C), 3-bromo-6-chloro-2-fluoro-5-methylbenzamide (12 mmol, 3.2 g) was converted to the title compound. MS (ESI) m/z=248, 250 (M+H)

Step D. 7-Bromo-4-chloro-5-methylbenzo[d]isoxazol-3-amine

Following the procedure of EXAMPLE 5 (Step D), 3-bromo-6-chloro-2-fluoro-5-methylbenzonitrile (11 mmol, 2.8 g) was converted to the title compound. MS (ESI) m/z=261, 263 (M+H)

Step E. 7-Bromo-4-chloro-3-(2,5-dimethyl-1H-pyrrol-1-yl)-5-methylbenzo[d]isoxazole Following the procedure of EXAMPLE 6 (Step E), 7-bromo-4-chloro-5-methylbenzo[d]isoxazol-3-amine (9.6 mmol, 2.5 g) was converted to the title compound. MS (ESI) m/z=339, 341 (M+H)

Step F. (R)-tert-Butyl (1-(4-chloro-3-(2,5-dimethyl-1H-pyrrol-1-yl)-5-methylbenzo[d]isoxazol-7-yl)pyrrolidin-3-yl)carbamate Following the procedure of EXAMPLE 6 (Step F), 7-bromo-4-chloro-3-(2,5-dimethyl-1H-pyrrol-1-yl)-5-methylbenzo[d]isoxazole (0.59 mmol, 200 mg) was converted to the title compound. MS (ESI) m/z=445, 447 (M+H)

Step G (R)-1-(4-Chloro-3-(2,5-dimethyl-1H-pyrrol-1-yl)-5-methylbenzo[d]isoxazol-7-yl)pyrrolidin-3-amine hydrochloride Following the procedure of EXAMPLE 4 (Step D), (R)-tert-butyl (1-(4-chloro-3-(2,5-dimethyl-1H-pyrrol-1-yl)-5-methylbenzo[d]isoxazol-7-yl)pyrrolidin-3-yl)carbamate (0.3 mmol, 135 mg) was converted to the title compound.

MS (ESI) m/z=345, 347 (M+H)
$^1$H NMR (300 MHz, CD$_3$OD) δ (ppm): 6.74 (1H, s), 5.92 (2H, s), 4.14-4.05 (1H, m), 3.97-3.89 (3H, m), 3.70-3.60 (1H, m), 2.61-2.49 (1H, m), 2.40 (3H, s), 2.26-2.15 (1H, m), 2.00 (6H, s)

Step H (R)-2-Chloro-N-(1-(4-chloro-3-(2,5-dimethyl-1H-pyrrol-1-yl)-5-methylbenzo[d]isoxazol-7-yl)pyrrolidin-3-yl)-4-(4H-1,2,4-triazol-4-yl)benzamide Following the procedure of EXAMPLE 1 (Step E), (R)-1-(4-chloro-3-(2,5-dimethyl-1H-pyrrol-1-yl)-5-methylbenzo[d]isoxazol-7-yl)pyrrolidin-3-amine hydrochloride (0.14 mmol, 55 mg) and 2-chloro-4-(4H-1,2,4-triazol-4-yl) benzoic acid (0.14 mmol, 32 mg, EXAMPLE 1, Step D) were converted to the title compound. MS (ESI) m/z=550, 552 (M+H)

Step I (R)—N-(1-(3-Amino-4-chloro-5-methylbenzo[d]isoxazol-7-yl)pyrrolidin-3-yl)-2-chloro-4-(4H-1,2,4-triazol-4-yl)benzamide Following the procedure of EXAMPLE 4 (Step F), (R)-2-chloro-N-(1-(4-chloro-3-(2,5-dimethyl-1H-pyrrol-1-yl)-5-methylbenzo[d]isoxazol-7-yl)pyrrolidin-3-yl)-4-(4H-1,2,4-triazol-4-yl)benzamide (0.13 mmol, 70 mg) was converted to the title compound.

Example 13

(R)—N-(1-(3-Amino-4-fluorobenzo[d]isoxazol-7-yl)pyrrolidin-3-yl)-2-chloro-4-(4H-1,2,4-triazol-4-yl)benzamide

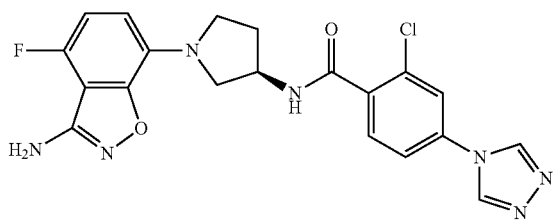 [SMILES: Nc1noc2c(N3CC[C@@H](NC(=O)c4ccc(-n5cnnc5)cc4Cl)C3)ccc(F)c12]

Step A. 4-Fluorobenzo[d]isoxazol-3-amine

Following the procedure of EXAMPLE 5 (Step D), 2,6-difluorobenzonitrile (7.2 mmol, 1 g) was converted to the title compound. MS (ESI) m/z=153 (M+H)

Step B. 7-Bromo-4-fluorobenzo[d]isoxazol-3-amine

Following the procedure of EXAMPLE 14 (Step B), 4-fluorobenzo[d]isoxazol-3-amine (2.2 mmol, 0.34 g) was converted to the title compound (contained 5-bromo-4-fluorobenzo[d]isoxazol-3-amine). MS (ESI) m/z=231, 233 (M+H)

Step C. 7-Bromo-3-(2,5-dimethyl-1H-pyrrol-1-yl)-4-fluorobenzo[d]isoxazole

Following the procedure of EXAMPLE 6 (Step E), 7-bromo-4-fluorobenzo[d]isoxazol-3-amine (1.9 mmol, 0.43 g) was converted to the title compound (78%, contained 5-bromo-3-(2,5-dimethyl-1H-pyrrol-1-yl)-4-fluorobenzo[d]isoxazole).

MS (ESI) m/z=309, 311 (M+H)

Step D. (R)-tert-Butyl (1-(3-(2,5-dimethyl-1H-pyrrol-1-yl)-4-fluorobenzo[d]isoxazol-7-yl)pyrrolidin-3-yl)carbamate Following the procedure of EXAMPLE 6 (Step F), 7-bromo-3-(2,5-dimethyl-1H-pyrrol-1-yl)-4-fluorobenzo[d]isoxazole (1.42 mmol, 440 mg) was converted to the title compound. MS (ESI) m/z=415 (M+H)

Step E (R)-1-(3-(2,5-Dimethyl-1H-pyrrol-1-yl)-4-fluorobenzo[d]isoxazol-7-yl)pyrrolidin-3-amine hydrochloride Following the procedure of EXAMPLE 4 (Step D), (R)-tert-butyl (1-(3-(2,5-dimethyl-1H-pyrrol-1-yl)-4-fluorobenzo[d]isoxazol-7-yl)pyrrolidin-3-yl)carbamate (0.21 mmol, 86 mg) was converted to the title compound. MS (ESI) m/z=315 (M+H)

$^1$H NMR (300 MHz, CD$_3$OD) δ (ppm): 7.00 (1H, t, J=8.8 Hz), 6.76 (1H, dd, J=8.6, 3.8 Hz), 5.93 (2H, s), 4.05-3.96 (1H, m), 3.93-3.77 (3H, m), 3.67-3.54 (1H, m), 2.56-2.44 (1H, m), 2.19-2.05 (1H, m), 2.09 (6H, s)

Step F (R)-2-Chloro-N-(1-(3-(2,5-dimethyl-1H-pyrrol-1-yl)-4-fluorobenzo[d]isoxazol-7-yl)pyrrolidin-3-yl)-4-(4H-1,2,4-triazol-4-yl)benzamide Following the procedure of EXAMPLE 1 (Step E), (R)-1-(3-(2,5-dimethyl-1H-pyrrol-1-yl)-4-fluorobenzo[d]isoxazol-7-yl)pyrrolidin-3-amine hydrochloride (0.1 mmol, 35 mg) and 2-chloro-4-(4H-1,2,4-triazol-4-yl)benzoic acid (0.1 mmol, 22 mg) were converted to the title compound. MS (ESI) m/z=520 (M+H)

Step G (R)—N-(1-(3-Amino-4-fluorobenzo[d]isoxazol-7-yl)pyrrolidin-3-yl)-2-chloro-4-(4H-1,2,4-triazol-4-yl)benzamide Following the procedure of EXAMPLE 4 (Step F), (R)-2-chloro-N-(1-(3-(2,5-dimethyl-1H-pyrrol-1-yl)-4-fluorobenzo[d]isoxazol-7-yl)pyrrolidin-3-yl)-4-(4H-1,2,4-triazol-4-yl)benzamide (0.08 mmol, 40 mg) was converted to the title compound.

Example 14

(R)—N-(1-(3-Amino-4,5-dichlorobenzo[d]isoxazol-7-yl)pyrrolidin-3-yl)-2-chloro-4-(4H-1,2,4-triazol-4-yl)benzamide

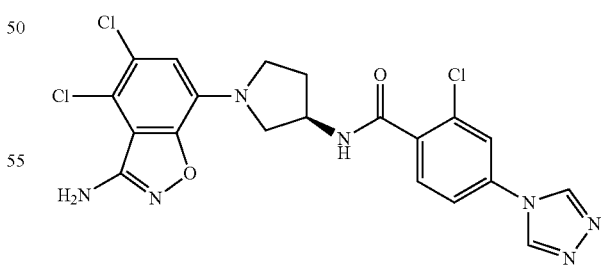

Step A. 4,5-Dichlorobenzo[d]isoxazol-3-amine

Following the procedure of EXAMPLE 5 (Step D), of 2,3-dichloro-6-fluorobenzonitrile (11 mmol, 2.0 g) was converted to the title compound. MS (ESI) m/z=203, 205 (M+H)

Step B. 7-Bromo-4,5-dichlorobenzo[d]isoxazol-3-amine

To a solution of 4,5-dichlorobenzo[d]isoxazol-3-amine (7.1 mmol, 1.5 g) in conc. H₂SO₄ (7.0 mL) was added N-bromosuccinimide (7.5 mmol, 1.3 g) at RT. The reaction mixture was stirred for 1 h. The reaction was quenched with water (50 mL), filtered, washed with water to give the title compound. MS (ESI) m/z=281, 283, 285 (M+H)

Step C

(R)—N-(1-(3-Amino-4,5-dichlorobenzo[d]isoxazol-7-yl)pyrrolidin-3-yl)-2-chloro-4-(4H-1,2,4-triazol-4-yl)benzamide Following the procedures of EXAMPLE 4 (Step D,F), EXAMPLE 5 (Step F), and EXAMPLE 6 (Step E,F), 7-bromo-4,5-dichlorobenzo[d]isoxazol-3-amine was converted to the title compound over 5 steps.

Example 15

N-(1-(3-Amino-5-chlorobenzo[d]isoxazol-7-yl)-3-methylpyrrolidin-3-yl)-2-chloro-4-(3-methyl-1H-1,2,4-triazol-1-yl)benzamide

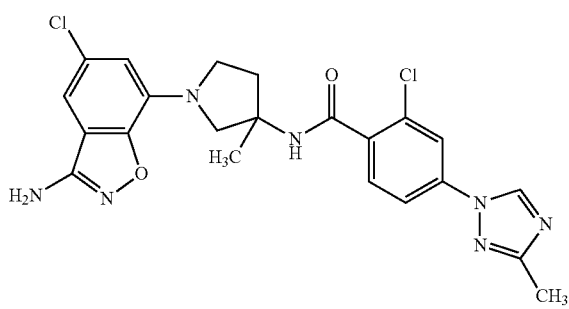 [SMILES: Cc1ncn(-c2ccc(C(=O)NC3(C)CCN(c4cc(Cl)cc5c(N)noc45)C3)c(Cl)c2)n1]

Step A. tert-Butyl (1-(5-chloro-3-(2,5-dimethyl-1H-pyrrol-1-yl)benzo[d]isoxazol-7-yl)-3-methylpyrrolidin-3-yl)carbamate Following the procedure of EXAMPLE 6 (Step F), 7-bromo-5-chloro-3-(2,5-dimethyl-1H-pyrrol-1-yl)benzo[d]isoxazole (50 mg, 0.15 mmol, EXAMPLE 10, Step C) and tert-butyl (3-methylpyrrolidin-3-yl)carbamate (34 mg, 0.17 mmol) were converted to the title compound. MS (ESI) m/z=445 (M+H)

¹H NMR (400 MHz, CDCl₃) δ (ppm): 6.66 (1H, d, J=1.8 Hz), 6.46 (1H, d, J=1.4 Hz), 5.97 (2H, s), 4.70 (1H, brs), 3.94 (1H, d, J=10.1 Hz), 3.91-3.74 (2H, m), 3.68 (1H, d, J=10.5 Hz), 2.50 (1H, s), 2.12 (6H, s), 2.08-1.94 (1H, m), 1.57 (3H, s), 1.45 (9H, s)

Step B

N-(1-(3-Amino-5-chlorobenzo[d]isoxazol-7-yl)-3-methylpyrrolidin-3-yl)-2-chloro-4-(3-methyl-1H-1,2,4-triazol-1-yl)benzamide Following the procedures of EXAMPLE 1 (Step E) and EXAMPLE 4 (Step D, F), (1-(5-chloro-3-(2,5-dimethyl-1H-pyrrol-1-yl)benzo[d]isoxazol-7-yl)-3-methylpyrrolidin-3-yl)carbamate was converted to the title compound over 3 steps.

Example 16

(R)—N-(1-(3-Amino-5-chlorobenzo[d]isoxazol-7-yl)pyrrolidin-3-yl)-2-chloro-4-(3-(hydroxymethyl)-1H-1,2,4-triazol-1-yl)benzamide

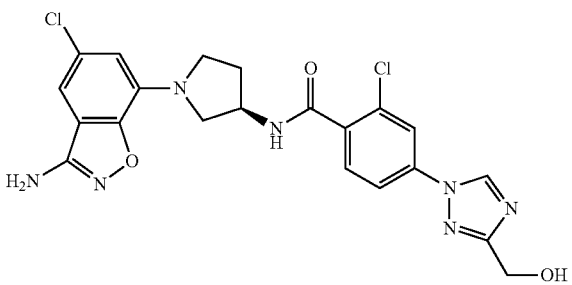 [SMILES: Nc1noc2c(N3CC[C@@H](NC(=O)c4ccc(-n5cnc(CO)n5)cc4Cl)C3)cc(Cl)cc12]

Step A. Methyl 1-(3-Chloro-4-formylphenyl)-1H-1,2,4-triazole-3-carboxylate

To a solution of 2-chloro-4-fluorobenzaldehyde (25 mmol, 4.0 g) and methyl 1H-1,2,4-triazole-3-carboxylate (38 mmol, 4.8 g) in NMP (80 mL) was added K₃PO₄ (38 mmol, 8.0 g) and stirred at 60° C. After 24 h, the reaction mixture was added water and extracted with EtOAc. The organic extract was washed with saturated NaCl, dried over Na₂SO₄, and filtered and concentrated in vacuo. The crude residue was purified by silica-gel column chromatography (heptane:EtOAc=70:30-30:70) to give the title compound. MS (ESI) m/z=266, 268 (M+H)

Step B. 2-Chloro-4-(3-(methoxycarbonyl)-1H-1,2,4-triazol-1-yl)benzoic acid

Following the procedure of EXAMPLE 11 (Step B), methyl 1-(3-chloro-4-formylphenyl)-1H-1,2,4-triazole-3-carboxylate (25 mmol, 9.6 g) was converted to the title compound. MS (ESI) m/z=282, 284 (M+H)

Step C. Methyl 1-(4-(tert-butoxycarbonyl)-3-chlorophenyl)-1H-1,2,4-triazole-3-carboxylate To a solution of 2-chloro-4-(3-(methoxycarbonyl)-1H-1,2,4-triazol-1-yl)benzoic acid (8.2 mmol, 2.3 g) in t-BuOH (46 mL)/CH₂Cl₂ (46 mL) was added DMAP (2.5 mmol, 0.30 g) and (Boc)₂O (33 mmol, 7.6 mL) at 40° C. After 2 h, (Boc)₂O (1.0 eq.) was added. After 1 h, the reaction mixture was diluted with EtOAc and H₂O, then extracted with EtOAc. The organic layer was washed with brine, dried over Na₂SO₄, then the solvent was removed. The residue was purified by SiO₂ column chromatography (heptane:EtOAc=60:40 to 60:40) to give the title compound. MS (ESI) m/z=338, 340 (M+H)

Step D. tert-Butyl 2-chloro-4-(3-(hydroxymethyl)-1H-1,2,4-triazol-1-yl)benzoate To a solution of methyl 1-(4-(tert-butoxycarbonyl)-3-chlorophenyl)-1H-1,2,4-triazole-3-carboxylate (1.2 mmol, 400 mg) in THF (8.0 mL)/MeOH (8.0 mL) was added calcium chloride (4.7 mmol, 526 mg) and NaBH$_4$ (4.7 mmol, 179 mg) at RT. After 1.5 h, calcium chloride (4.7 mmol, 525 mg) and NaBH$_4$ (4.7 mmol, 179 mg) were added again. After 1 h, NaBH$_4$ (8 eq.) was added. After 15 h, the reaction mixture was poured into water, extracted with EtOAc, the organic extracts washed with saturated aq. NaCl, dried over Na$_2$SO$_4$, and filtered and concentrated in vacuo. The crude residue was purified by silica-gel column chromatography (hepane:EtOAc=20:80-80:20) to give the title compound. MS (ESI) m/z=254, 256 (M-C$_4$H$_8$+H)

Step E. 2-Chloro-4-(3-(hydroxymethyl)-1H-1,2,4-triazol-1-yl)benzoic acid

4N HCl-dioxane (10 mL) was added to tert-butyl 2-chloro-4-(3-(hydroxymethyl)-1H-1,2,4-triazol-1-yl)benzoate (0.19 mmol, 60 mg). The mixture was stirred at RT for 3 days. The solvent was removed under vacuum to give the title compound.
$^1$H NMR (300 MHz, CD$_3$OD) δ (ppm): 9.29 (1H, s), 8.07 (1H, d, J=2.1 Hz), 8.05 (1H, d, J=8.6 Hz), 7.89 (1H, dd, J=8.6, 2.1 Hz), 4.73 (2H, s) MS (ESI) m/z=254, 256 (M+H)

Step F

(R)-2-Chloro-N-(1-(5-chloro-3-(2,5-dimethyl-1H-pyrrol-1-yl)benzo[d]isoxazol-7-yl)pyrrolidin-3-yl)-4-(3-(hydroxymethyl)-1H-1,2,4-triazol-1-yl)benzamide Following the procedure of EXAMPLE 1 (Step E), (R)-1-(5-chloro-3-(2,5-dimethyl-1H-pyrrol-1-yl)benzo[d]isoxazol-7-yl)pyrrolidin-3-amine dihydrochloride (0.10 mmol, 40 mg, EXAMPLE 10, Step E) and 2-chloro-4-(3-(hydroxymethyl)-1H-1,2,4-triazol-1-yl)benzoic acid (0.11 mmol, 28 mg) were converted to the title compound. MS (ESI) m/z=566, 568 (M+H)

Step G

(R)—N-(1-(3-Amino-5-chlorobenzo[d]isoxazol-7-yl)pyrrolidin-3-yl)-2-chloro-4-(3-(hydroxymethyl)-1H-1,2,4-triazol-1-yl)benzamide A solution of (R)-2-chloro-N-(1-(5-chloro-3-(2,5-dimethyl-1H-pyrrol-1-yl)benzo[d]isoxazol-7-yl)pyrrolidin-3-yl)-4-(3-(hydroxymethyl)-1H-1,2,4-triazol-1-yl)benzamide (9.0 mg, 0.020 mmol) in TFA (1.0 mL) and H$_2$O (0.50 mL) was stirred for 2 h at 60° C. To the reaction mixture was added sat. aq. NaHCO$_3$ and extracted with EtOAc. The organic layer was washed with sat. aq. NaHCO$_3$ and brine, then dried over Na$_2$SO$_4$. The solvent was removed, then the residue was triturated (MeOH:EtOH=1:1). The crude was purified by HPLC to give the title compound. MS (ESI) m/z=488, 490 (M+H)

Example 17

(R)—N-(1-(3-Amino-5-chlorobenzo[d]isoxazol-7-yl)pyrrolidin-3-yl)-2-chloro-4-(3-cyclopropyl-1H-1,2,4-triazol-1-yl)benzamide

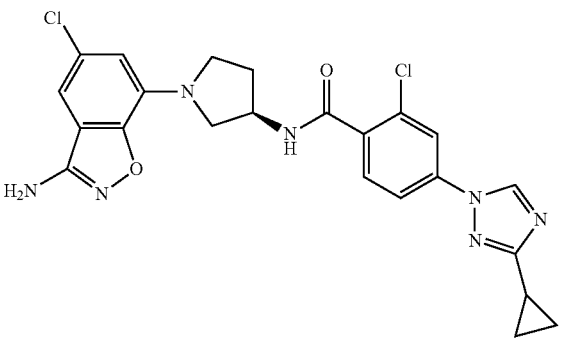 [SMILES: Nc1noc2c(N3CC[C@@H](NC(=O)c4ccc(-n5cnc(C6CC6)n5)cc4Cl)C3)cc(Cl)cc12]

Step A. 2-Chloro-4-(3-cyclopropyl-1H-1,2,4-triazol-1-yl)benzoic acid

Following the procedures of EXAMPLE 11 (A-B), 3-cyclopropyl-1H-1,2,4-triazole was converted to the title compound. MS (ESI) m/z=264, 266 (M+H)
$^1$H NMR (300 MHz, DMSO-d$_6$) δ: 9.26 (1H, s), 8.05 (1H, d, J=2.1 Hz), 7.97 (1H, d, J=8.6 Hz), 7.88 (1H, dd, J=8.6, 2.1 Hz), 5.76 (1H, s), 2.16-2.04 (1H, m), 1.03-0.96 (2H, m), 0.93-0.86 (2H, m)

Step B

(R)-2-Chloro-N-(1-(5-chloro-3-(2,5-dimethyl-1H-pyrrol-1-yl)benzo[d]isoxazol-7-yl)pyrrolidin-3-yl)-4-(3-cyclopropyl-1H-1,2,4-triazol-1-yl)benzamide Following the procedure of EXAMPLE 5 (Step F), (R)-1-(5-chloro-3-(2,5-dimethyl-1H-pyrrol-1-yl)benzo[d]isoxazol-7-yl)pyrrolidin-3-amine hydrochloride (0.090 mmol, 33 mg, EXAMPLE 10, Step E) and 2-chloro-4-(3-cyclopropyl-1H-1,2,4-triazol-1-yl)benzoic acid (0.14 mmol, 36 mg) were converted to the title compound. MS (ESI) m/z=576, 578 (M+H)

Step C

(R)—N-(1-(3-Amino-5-chlorobenzo[d]isoxazol-7-yl)pyrrolidin-3-yl)-2-chloro-4-(3-cyclopropyl-1H-1,2,4-triazol-1-yl)benzamide The solution of (R)-2-chloro-N-(1-(5-chloro-3-(2,5-dimethyl-1H-pyrrol-1-yl)benzo[d]isoxazol-7-yl)pyrrolidin-3-yl)-4-(3-cyclopropyl-1H-1,2,4-triazol-1-yl)benzamide (0.06 mmol, 37 mg) in TFA (740 μL) and water (370 μL) was stirred for at 60° C. for 2 h. The reaction mixture was diluted with DMSO and purified by HPLC to give the title compound.

Example 18

(R)—N-(1-(3-Amino-4-chlorobenzo[d]isoxazol-7-yl)pyrrolidin-3-yl)-2-fluoro-4-(1H-1,2,4-triazol-1-yl)benzamide

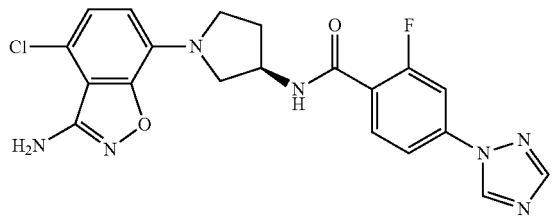 [SMILES: Nc1noc2c(N3CC[C@@H](NC(=O)c4ccc(-n5cncn5)cc4F)C3)ccc(Cl)c12]

Step A. 2-Fluoro-4-(1H-1,2,4-triazol-1-yl)benzoic acid

Following the procedure of EXAMPLE 11 (Step A-B), 2,4-difluorobenzaldehyde and 4H-1,2,4-triazole were converted to the title compound over 2 steps. MS (ESI) m/z=208 (M+H)

$^1$H NMR (400 MHz, DMSO-d$_6$) δ (ppm): 13.43 (1H, br s), 9.46 (1H, s), 8.32 (1H, s), 8.06 (1H, t, J=8.2 Hz), 7.93 (1H, dd, J=11.9, 2.3 Hz), 7.85 (1H, dd, J=8.5, 2.1 Hz)

Step B (R)—N-(1-(3-Amino-4-chlorobenzo[d]isoxazol-7-yl)pyrrolidin-3-yl)-2-fluoro-4-(1H-1,2,4-triazol-1-yl)benzamide Following the procedure of EXAMPLE 5 (Step F), 2-fluoro-4-(1H-1,2,4-triazol-1-yl)benzoic acid (24 mg) and (R)-7-(3-aminopyrrolidin-1-yl)-4-chlorobenzo[d]isoxazol-3-amine (30 mg, EXAMPLE 9, Step A) were converted to the title compound.

Example 19

(R)—N-(1-(3-Amino-4-chlorobenzo[d]isoxazol-7-yl)pyrrolidin-3-yl)-2-methyl-4-(1H-1,2,4-triazol-1-yl)benzamide

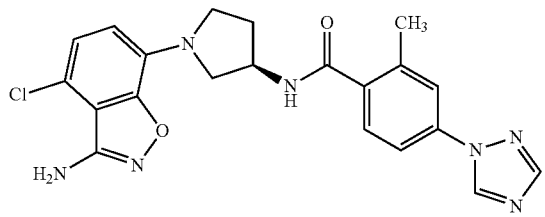 [SMILES: Cc1cc(-n2cncn2)ccc1C(=O)N[C@@H]1CCN(c2ccc(Cl)c3c(N)noc23)C1]

Following the procedure of EXAMPLE 5 (Step F), 2-methyl-4-(1H-1,2,4-triazol-1-yl)benzoic acid (23 mg) and (R)-7-(3-aminopyrrolidin-1-yl)-4-chlorobenzo[d]isoxazol-3-amine (30 mg, EXAMPLE 9, Step A) were converted to the title compound.

Example 20

(R)—N-(1-(3-Amino-4-chloroisoxazolo[5,4-c]pyridin-7-yl)pyrrolidin-3-yl)-2-chloro-4-(pyrimidin-5-yl)benzamide

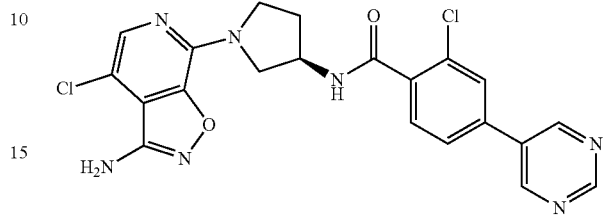

Step A. Methyl 2-chloro-4-(pyrimidin-5-yl)benzoate

To a mixture of (3-chloro-4-(methoxycarbonyl)phenyl)boronic acid (9.3 mmol, 2.0 g) and 5-bromopyrimidine (9.3 mmol, 1.5 g) in dioxane/water (30/105 mL), XPhos (1.9 mmol, 0.89 g), Cs$_2$CO$_3$ (28 mmol, 9.1 g), and Pd$_2$(dba)$_3$ (0.93 mmol, 0.85 g) were added. The mixture was degassed with nitrogen and heated at 100° C. for 3 h. The mixture was poured into water and extracted with ethyl acetate. The extract was washed with water, dried with magnesium sulfate, filtered, and concentrated under reduced pressure. The residue was purified by column chromatography (silica-gel, ethyl acetate-heptane (20:80)) to give the title compound. MS (ESI) m/z=249, 251 (M+H)

Step B. 2-Chloro-4-(pyrimidin-5-yl)benzoic acid

To a solution of methyl 2-chloro-4-(pyrimidin-5-yl)benzoate (4.0 mmol, 1.0 g) in MeOH (5 mL) and water (2.5 mL) at RT was added lithium hydroxide monohydrate (8.0 mmol, 0.34 g). The mixture was stirred at 60° C. for 21 h. The mixture was adjusted to pH 3 with 1N aq. HCl and extracted with EtOAc. The extract was washed with brine, dried over Na$_2$SO$_4$, filtered, and concentrated in vacuo to give the title compound. MS (ESI) m/z=235, 237 (M+H)

$^1$H NMR (400 MHz, DMSO-d$_6$) δ (ppm): 9.23-9.18 (3H, m), 7.99 (1H, s), 7.84 (2H, s)

Step C (R)—N-(1-(3-Amino-4-chloroisoxazolo[5,4-c]pyridin-7-yl)pyrrolidin-3-yl)-2-chloro-4-(pyrimidin-5-yl)benzamide Following the procedure of EXAMPLE 1 (Step E), (R)-7-(3-aminopyrrolidin-1-yl)-4-chloroisoxazolo[5,4-c]pyridin-3-amine dihydrochloride (30 mg, EXAMPLE 11, Step E) and 2-chloro-4-(pyrimidin-5-yl)benzoic acid (28 mg) were converted to the title compound.

Example 21

(R)—N-(1-(3-Amino-4-chloroisoxazolo[5,4-c]pyridin-7-yl)pyrrolidin-3-yl)-2-chloro-4-(2-methoxypyrimidin-5-yl)benzamide

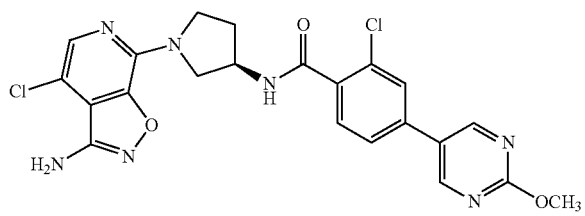 [SMILES: COc1ncc(-c2ccc(C(=O)N[C@@H]3CCN(c4ncc(Cl)c5c(N)noc45)C3)c(Cl)c2)cn1]

Step A.
2-Chloro-4-(2-methoxypyrimidin-5-yl)benzoic acid

A suspension of 2-chloro-4-iodobenzoic acid (300 mg, 1.1 mmol), (2-methoxypyrimidin-5-yl)boronic acid (330 mg, 2.1 mmol), Pd(PPh$_3$)$_4$ (120 mg, 0.11 mmol) and K$_2$CO$_3$ (0.44 g, 3.2 mmol) in DMF (3.6 mL) and H$_2$O (0.6 mL) was stirred at 100° C. for 14 hours. The reaction was cooled to RT and filtered with Celite and it was washed with water. The filtrate was washed with dichloromethane. The aqueous layer was neutralized by 1N aq. HCl to pH 7 to afford a precipitate. The precipitate was collected and dried to give the title compound. MS (ESI) m/z=265, 267 (M+H)

$^1$H NMR (400 MHz, DMSO-d$_6$) δ: 9.03 (2H, s), 7.97 (1H, d, J=1.8 Hz), 7.88 (1H, d, J=8.2 Hz), 7.80 (1H, dd, J=7.8, 1.8 Hz), 3.98 (3H, s)

Step B (R)—N-(1-(3-Amino-4-chloroisoxazolo[5,4-c]pyridin-7-yl)pyrrolidin-3-yl)-2-chloro-4-(2-methoxypyrimidin-5-yl)benzamide Following the procedure of EXAMPLE 5 (Step F), 2-chloro-4-(2-methoxypyrimidin-5-yl)benzoic acid (29 mg, 0.11 mmol) and (R)-7-(3-aminopyrrolidin-1-yl)-4-chloroisoxazolo[5,4-c]pyridin-3-amine dihydrochloride (30 mg, 0.09 mmol, EXAMPLE 11, Step E) were converted to the title compound.

Example 22

(R)—N-(1-(3-Amino-4-chloroisoxazolo[5,4-c]pyridin-7-yl)pyrrolidin-3-yl)-2-chloro-4-(2-cyanopyrimidin-5-yl)benzamide

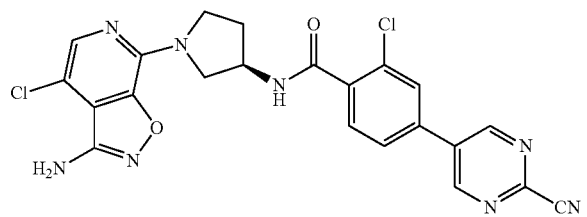 [SMILES: N#Cc1ncc(-c2ccc(C(=O)N[C@@H]3CCN(c4ncc(Cl)c5c(N)noc45)C3)c(Cl)c2)cn1]

Step A. 2-Chloro-4-(2-cyanopyrimidin-5-yl)benzoic acid

A mixture of 2-chloro-4-iodobenzoic acid (0.28 g, 0.99 mmol), 5-(4,4,5,5-tetramethyl-1,3,2-dioxaborolan-2-yl)pyrimidine-2-carbonitrile (0.41 g, 1.8 mmol), and K$_3$PO$_4$ (0.64 g, 3.0 mmol) in DME (4.2 mL) and water (1.4 mL) was stirred at 100° C. for 2 h. After cooling the mixture, it was diluted with water and CH2Cl2 and filtered. The aqueous layer was washed with CH$_2$Cl$_2$ and neutralized with 1N aq. HCl. The precipitate was collected and dried to give the title compound. MS (ESI) m/z=260, 262 (M+H)

$^1$H NMR (300 MHz, DMSO-d$_6$) δ (ppm): 9.46 (2H, s), 8.15 (1H, d, J=1.4 Hz), 8.00-7.89 (2H, m)

Step B (R)—N-(1-(3-Amino-4-chloroisoxazolo[5,4-c]pyridin-7-yl)pyrrolidin-3-yl)-2-chloro-4-(2-cyanopyrimidin-5-yl)benzamide Following the procedure of EXAMPLE 5 (Step F), 2-chloro-4-(2-cyanopyrimidin-5-yl)benzoic acid (29 mg, 0.11 mmol) and (R)-7-(3-aminopyrrolidin-1-yl)-4-chloroisoxazolo[5,4-c]pyridin-3-amine dihydrochloride (30 mg, 0.09 mmol, EXAMPLE 11, Step E) were converted to the title compound.

Example 23

(R)—N-(1-(3-Amino-4-chlorobenzo[d]isoxazol-7-yl)pyrrolidin-3-yl)-2-chloro-4-(3-(2-hydroxyethyl)-1H-1,2,4-triazol-1-yl)benzamide

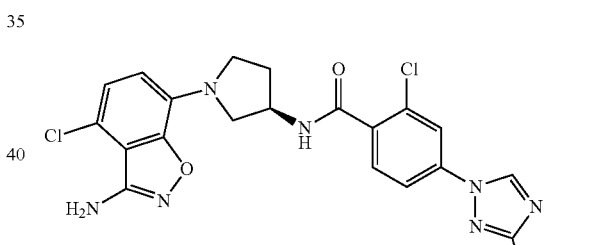

Step A. 2-Chloro-4-hydrazinylbenzoic acid

To a suspension of 4-amino-2-chlorobenzoic acid (53 mmol, 9.0 g) in 1N aq. HCl (90 mmol, 90 mL) at 0° C. was added a solution of sodium nitrite (55 mmol, 3.8 g) in water (5.0 mL) over 5 min and the reaction mixture maintained at 0° C. for 5 h. The resulting mixture was treated with stannous chloride (157 mmol, 30 g) in 1N aq. HCl (180 mmol, 180 mL) and was warmed to RT for 16 h. The resulting thick precipitate which formed was isolated by filtration, washed with ethanol and ether and was dried in vacuo to give the title compound (contained starting material). This material was used in the next step without further purification. MS (ESI) m/z=187, 189 (M+H)

Step B. 2-Chloro-4-(3-(2-ethoxy-2-oxoethyl)-1H-1,2,4-triazol-1-yl)benzoic acid To a solution of 2-chloro-4-hydrazinylbenzoic acid (1.8 mmol, 500 mg) and ethyl 3-ethoxy-3-iminopropanoate (2.7 mmol, 422 mg) in EtOH (6.6 mL) was added Et₃N (5.3 mmol, 0.74 mL). The mixture was stirred for 30 min at RT and then the solvent was removed under reduced pressure. The crude product in EtOH was stirred together with triethyl orthoformate (18 mmol, 2.9 mL) and ammonium formate (3.5 mmol, 223 mg) for 6 h at 80° C. The solvents are distilled off in vacuum and EtOAc and sat. aq. NaHCO₃ were added. The aqueous layer was washed with EtOAc and acidified to pH 1 with 1N aq. HCl. The aqueous layer was extracted by EtOAc and the organic layer was washed with brine, dried over Na₂SO₄, filtered, and concentrated in vacuo to give the title compound. MS (ESI) m/z=310, 312 (M+H)

Step C. tert-Butyl 2-chloro-4-(3-(2-ethoxy-2-oxo-ethyl)-1H-1,2,4-triazol-1-yl)benzoate Following the procedure of EXAMPLE 16 (Step C), 2-chloro-4-(3-(2-ethoxy-2-oxoethyl)-1H-1,2,4-triazol-1-yl) benzoic acid (1.4 mmol, 443 mg) was converted to the title compound. MS (ESI) m/z=366, 368 (M+H)

Step D. tert-Butyl 2-chloro-4-(3-(2-hydroxyethyl)-1H-1,2,4-triazol-1-yl)benzoate To a solution of tert-butyl 2-chloro-4-(3-(2-ethoxy-2-oxoethyl)-1H-1,2,4-triazol-1-yl)benzoate (0.25 mmol, 90 mg) in THF (3.6 mL) was added lithium tri-sec-butylborohydride (1M in THF, 0.74 mmol, 0.74 mL) at 0° C. After 30 min, the reaction mixture was added lithium tri-sec-butylborohydride (1M in THF, 1.3 mmol, 1.3 mL). After 1 h, to the mixture was added MeOH and water, and it was extracted with EtOAc, dried over Na₂SO₄. After concentration, resulting residue was purified by silica-gel column chromatography (heptane:EtOAc=85:15 to 100:0, then EtOAc:MeOH=95:5) to give the title compound. MS (ESI) m/z=324, 326 (M+H)

Step E. 2-Chloro-4-(3-(2-hydroxyethyl)-1H-1,2,4-triazol-1-yl)benzoic acid

Following the procedure of EXAMPLE 16 (Step E), tert-butyl 2-chloro-4-(3-(2-hydroxyethyl)-1H-1,2,4-triazol-1-yl)benzoate (56 mg, 0.17 mmol) was converted to the title compound. MS (ESI) m/z=268, 270 (M+H)

¹H NMR (400 MHz, CD₃OD) δ (ppm): 9.12 (1H, s), 8.03 (1H, d, J=2.3 Hz), 8.02 (1H, d, J=8.7 Hz), 7.85 (1H, dd, J=8.7, 2.3 Hz), 3.97 (2H, t, J=6.6 Hz), 3.01 (2H, t, J=6.9 Hz)

Step F

(R)—N-(1-(3-Amino-4-chlorobenzo[d]isoxazol-7-yl)pyrrolidin-3-yl)-2-chloro-4-(3-(2-hydroxyethyl)-1H-1,2,4-triazol-1-yl)benzamide Following the procedure of EXAMPLE 5 (Step F), (R)-7-(3-aminopyrrolidin-1-yl)-4-chlorobenzo[d]isoxazol-3-amine (29 mg, 0.10 mmol, EXAMPLE 9, Step A) and 2-chloro-4-(3-(2-hydroxyethyl)-1H-1,2,4-triazol-1-yl)benzoic acid (27 mg, 0.10 mmol) were converted to the title compound.

Example 24

(R)—N-(1-(3-Amino-4-chloroisoxazolo[5,4-c]pyridin-7-yl)pyrrolidin-3-yl)-2-chloro-4-(1H-1,2,4-triazol-1-yl)benzamide

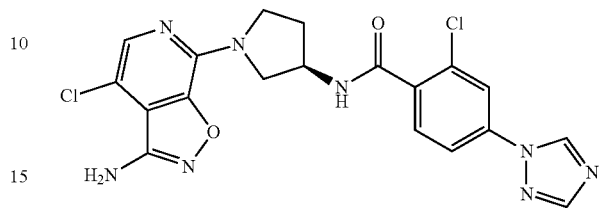

Following the procedure of EXAMPLE 5 (Step F), (R)-7-(3-aminopyrrolidin-1-yl)-4-chloroisoxazolo[5,4-c]pyridin-3-amine dihydrochloride (50 mg, EXAMPLE 11, Step E) and 2-chloro-4-(1H-1,2,4-triazol-1-yl)benzoic acid (48 mg) were converted to the title compound.

Example 25

(R)—N-(1-(3-Amino-4-chlorobenzo[d]isoxazol-7-yl)pyrrolidin-3-yl)-2-chloro-4-(5-(hydroxymethyl)pyridin-3-yl)benzamide

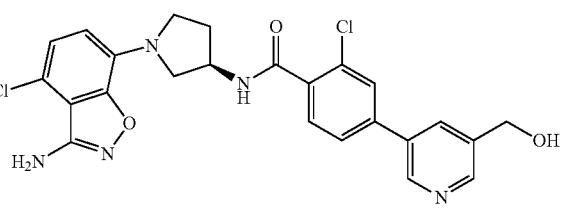

Step A. Methyl 2-chloro-4-(5-(hydroxymethyl)pyridin-3-yl)benzoate

To a solution of (3-chloro-4-(methoxycarbonyl)phenyl) boronic acid (100 mg, 0.47 mmol) and (5-bromopyridin-3-yl)methanol (88 mg, 0.47 mmol) in 1,4-dioxane (2.0 mL) and water (0.4 mL) was added Cs₂CO₃ (304 mg, 0.93 mmol) and 1,1'-bis(diphenylphosphino)ferrocene-palladium(II) dichloride dichloromethane complex (38 mg, 0.047 mmol) and stirred at 80° C. After 2 h, the reaction mixture was diluted with water and EtOAc and extracted with EtOAc. The organic layer was dried over Na₂SO₄, filtered and concentrated. The crude residue was purified by column chromatography (NH—SiO₂, heptane:EtOAc=50:50 to 0:100) to give the title compound. MS (ESI) m/z=278, 280 (M+H)

Step B. Sodium 2-chloro-4-(5-(hydroxymethyl)pyridin-3-yl)benzoate

To a solution of methyl 2-chloro-4-(5-(hydroxymethyl) pyridin-3-yl)benzoate (69 mg, 0.25 mmol) in MeOH (2.0 mL) was added 1N aq. sodium hydroxide (1.3 mL, 1.3 mmol) and stirred at 30° C. After 40 h, the reaction mixture was concentrated in vacuo to give the title compound. MS (ESI) m/z=264, 266 (M+H)

¹H NMR (300 MHz, DMSO-d₆) δ (ppm): 8.65 (1H, s), 8.46 (1H, d, J=1.7 Hz), 7.97-7.94 (1H, m), 7.54 (1H, d, J=1.7 Hz), 7.48 (1H, dd, J=7.9, 1.7 Hz), 7.36 (1H, d, J=7.9 Hz), 4.68 (2H, s)

Step C (R)—N-(1-(3-Amino-4-chlorobenzo[d]isoxazol-7-yl)pyrrolidin-3-yl)-2-chloro-4-(5-(hydroxymethyl)pyridin-3-yl)benzamide Following the procedure of EXAMPLE 5 (Step F), (R)-7-(3-aminopyrrolidin-1-yl)-4-chlorobenzo[d]isoxazol-3-amine (20 mg, 0.079 mmol, EXAMPLE 9, Step A) and sodium 2-chloro-4-(5-(hydroxymethyl)pyridin-3-yl)benzoate (22 mg, 0.080 mmol) were converted to the title compound.

Example 26

(R)—N-(1-(3-Amino-4-chlorobenzo[d]isoxazol-7-yl)pyrrolidin-3-yl)-2-chloro-4-(4-(2-hydroxyethyl)-1H-pyrazol-1-yl)benzamide

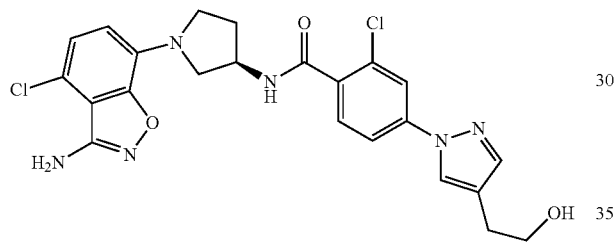

Step A. tert-Butyl 2-chloro-4-iodobenzoate

To a solution of 2-chloro-4-iodobenzoic acid (3.5 mmol, 1.0 g) in DMF (5 mL) was added CDI (5.3 mmol, 0.86 g) and the mixture was stirred at 40° C. for 30 min. To the mixture, t-BuOH (11 mmol, 1.0 mL) and 1,8-diazabicyclo[5.4.0]undec-7-ene (5.3 mmol, 0.8 mL) were added and the mixture was stirred at 40° C. overnight. The mixture was diluted with TBME, and washed with water and brine. The mixture was dried over Na₂SO₄, and the solvent was removed under reduced pressure. The residue was purified by silica-gel column chromatography (0-15% EtOAc in heptane) to give the title compound. MS (ESI) m/z=361, 363 (M+Na)

Step B. tert-Butyl 2-chloro-4-(4-(2-hydroxyethyl)-1H-pyrazol-1-yl)benzoate

To a suspension of tert-butyl 2-chloro-4-iodobenzoate (0.44 mmol, 150 mg), copper(I) iodide (0.44 mmol, 84 mg), 2-(1H-pyrazol-4-yl)ethanol (0.44 mmol, 50 mg) and tripotassium phosphate (1.33 mmol, 282 mg) in DMSO (2 mL), trans-N,N'-dimethylcyclohexane-1,2-diamine (0.89 mmol, 126 mg) was added at RT and the mixture was degassed under nitrogen atmosphere. The mixture was stirred at 50° C. for 1 h. The reaction mixture was quenched with water and extracted with EtOAc, washed with water, and concentrated in vacuo. The crude was purified by column chromatography on silica gel EtOAc/CH₂Cl₂ (5/95) to give the title compound.
MS (ESI) m/z=345, 347 (M+Na)

Step C. 2-Chloro-4-(4-(2-hydroxyethyl)-1H-pyrazol-1-yl)benzoic acid

4N HCl-dioxane (3 mL) was added to the tert-butyl 2-chloro-4-(4-(2-hydroxyethyl)-1H-pyrazol-1-yl)benzoate (0.26 mmol, 85 mg). The reaction mixture was stirred at 70° C. for 3 h. The solvent was removed under vacuum to give the title compound. MS (ESI) m/z=267, 269 (M+H)
¹H NMR (300 MHz, DMSO-d₆) δ (ppm): 8.47 (1H, s), 7.98 (1H, d, J=2.1 Hz), 7.94 (1H, d, J=8.6 Hz), 7.86 (1H, dd, J=8.6, 2.1 Hz), 7.70 (1H, s), 3.59 (2H, t, J=5.6 Hz), 2.63 (2H, t, J=6.9 Hz)

Step D (R)—N-(1-(3-Amino-4-chlorobenzo[d]isoxazol-7-yl)pyrrolidin-3-yl)-2-chloro-4-(4-(2-hydroxyethyl)-1H-pyrazol-1-yl)benzamide Following the procedure of EXAMPLE 5 (Step F), 2-chloro-4-(4-(2-hydroxyethyl)-1H-pyrazol-1-yl)benzoic acid (0.09 mmol, 24 mg) and (R)-7-(3-aminopyrrolidin-1-yl)-4-chlorobenzo[d]isoxazol-3-amine (0.09 mmol, 23 mg, EXAMPLE 9, Step A) were converted to the title compound.

Example 27

(R)—N-(1-(3-Amino-4-chloroisoxazolo[5,4-c]pyridin-7-yl)pyrrolidin-3-yl)-2-chloro-4-(4-(2-hydroxyethyl)-1H-imidazol-1-yl)benzamide

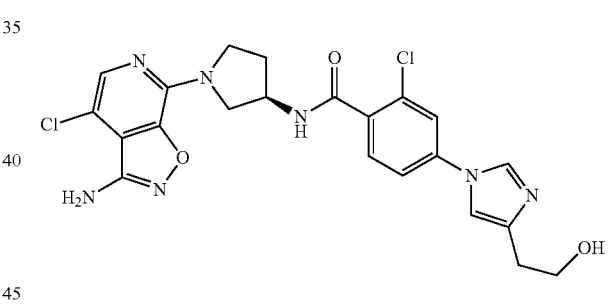

Step A. tert-Butyl 2-chloro-4-(4-(2-hydroxyethyl)-1H-imidazol-1-yl)benzoate

Following the procedure of EXAMPLE 26 (Step B), tert-butyl 2-chloro-4-iodobenzoate (0.44 mmol, 150 mg, EXAMPLE 26, Step A) and 2-(1H-imidazol-4-yl)ethanol (0.44 mmol, 50 mg) were converted to the title compound.
¹H NMR (300 MHz, CDCl₃) δ (ppm): 7.88 (1H, d, J=8.2 Hz), 7.83 (1H, d, J=1.4 Hz), 7.46 (1H, d, J=2.4 Hz), 7.31 (1H, dd, J=8.4, 2.2 Hz), 7.12 (1H, t, J=0.7 Hz), 3.95 (2H, t, J=5.7 Hz), 2.87 (2H, t, J=5.3 Hz), 1.63 (9H, d, J=2.7 Hz)

Step B. 2-Chloro-4-(4-(2-hydroxyethyl)-1H-imidazol-1-yl)benzoic acid hydrochloride Following the procedure of EXAMPLE 26 (Step C), tert-butyl 2-chloro-4-(4-(2-hydroxyethyl)-1H-imidazol-1-yl)benzoate (0.19 mmol, 62 mg) was converted to the title compound. MS (ESI) m/z=267, 269 (M+H)
¹H NMR (400 MHz, DMSO-d₆) δ (ppm): 13.72 (1H, br s), 9.37 (1H, br s), 8.07 (1H, d, J=2.3 Hz), 8.06-8.01 (1H, m), 8.01 (1H, d, J=8.2 Hz), 7.83 (1H, dd, J=8.7, 2.3 Hz), 3.70 (2H, t, J=6.4 Hz), 2.79 (2H, t, J=6.4 Hz)

Step C (R)—N-(1-(3-Amino-4-chloroisoxazolo[5,4-c]pyridin-7-yl)pyrrolidin-3-yl)-2-chloro-4-(4-(2-hydroxyethyl)-1H-imidazol-1-yl)benzamide Following the procedure of EXAMPLE 5 (Step F), 2-chloro-4-(4-(2-hydroxyethyl)-1H-imidazol-1-yl)benzoic acid hydrochloride (0.09 mmol, 27 mg) and (R)-7-(3-aminopyrrolidin-1-yl)-4-chloroisoxazolo[5,4-c]pyridin-3-amine (0.09 mmol, 23 mg, EXAMPLE 11, Step E) were converted to the title compound.

Example 28

(R)—N-(1-(3-Amino-4-chloroisoxazolo[5,4-c]pyridin-7-yl)pyrrolidin-3-yl)-2-chloro-4-(3-(difluoromethyl)-4H-1,2,4-triazol-4-yl)benzamide

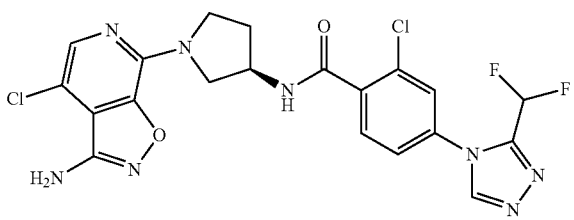 [SMILES: Nc1noc2c(N3CC[C@@H](NC(=O)c4ccc(-n5cnnc5C(F)F)cc4Cl)C3)ncc(Cl)c12]

Step A. Methyl 2-chloro-4-(3-(difluoromethyl)-4H-1,2,4-triazol-4-yl)benzoate

To CCl$_4$ (2.0 mL) in a flask at 0° C., Ph$_3$P (12 mmol, 3.2 g), Et$_3$N (4.8 mmol, 0.67 mL), and 2,2-difluoroacetic acid (4.0 mmol, 0.38 g) were sequentially added. The mixture was stirred at the same temperature for 10 min. To the mixture, methyl 4-amino-2-chlorobenzoate (4.0 mmol, 0.74 g) in CCl$_4$ (2.0 mL) was added dropwise, then stirred at 80° C. for 16 h. The mixture was diluted with heptane-ethyl acetate (3:1) and filtered. The filtrate was concentrated in vacuo and the residue was dissolved with toluene. To the solution at 0° C., Et$_3$N (4.8 mmol, 0.67 mL) and formylhydrazine (4.0 mmol, 0.24 g) were added. The mixture was stirred at 120° C. for 4 h. The mixture was concentrated in vacuo. The crude product was purified by column chromatography (silica-gel, 10-90% ethyl acetate in heptane) to give the title compound.
MS (ESI) m/z=288, 290 (M+H)

Step B. 2-Chloro-4-(3-(difluoromethyl)-4H-1,2,4-triazol-4-yl)benzoic acid

To a solution of methyl 2-chloro-4-(3-(difluoromethyl)-4H-1,2,4-triazol-4-yl)benzoate (0.79 mmol, 0.23 g) in 1,4-dioxane (1.0 mL), lithium hydroxide monohydrate (0.82 mmol, 35 mg) in water (0.5 mL) was added. The mixture was stirred at RT for 4 h. The mixture was concentrated, added 4N HCl in dioxane (0.21 mL), concentrated in vacuo, and crystallized from methanol to give the title compound.
MS (ESI) m/z=274, 276 (M+H)

$^1$H NMR (400 MHz, DMSO-d$_6$) δ (ppm): 13.81 (1H, brs), 9.08 (1H, s), 7.97 (1H, d, J=8.2 Hz), 7.91 (1H, d, J=2.3 Hz), 7.65 (1H, dd, J=8.2, 2.3 Hz), 7.42 (1H, t, J=51.5 Hz)

Step C (R)—N-(1-(3-Amino-4-chloroisoxazolo[5,4-c]pyridin-7-yl)pyrrolidin-3-yl)-2-chloro-4-(3-(difluoromethyl)-4H-1,2,4-triazol-4-yl)benzamide Following the procedure of EXAMPLE 5 (Step F), 2-chloro-4-(3-(difluoromethyl)-4H-1,2,4-triazol-4-yl)benzoic acid (12 mg, 0.04 mmol) and (R)-7-(3-aminopyrrolidin-1-yl)-4-chloroisoxazolo[5,4-c]pyridin-3-amine dihydrochloride (14 mg, 0.04 mmol, EXAMPLE 11, Step E) were converted to the title compound.

Example 29

(R)—N-(1-(3-Amino-4-chloroisoxazolo[5,4-c]pyridin-7-yl)pyrrolidin-3-yl)-4-(1H-benzo[d]imidazol-1-yl)-2-chlorobenzamide

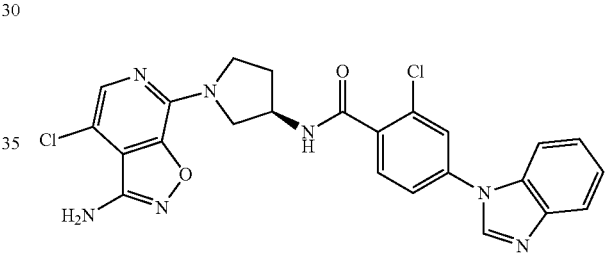

Step A. 4-(1H-Benzo[d]imidazol-1-yl)-2-chlorobenzoic acid

Following the procedures of EXAMPLE 11 (Step A-B), 1H-benzo[d]imidazole was converted to the title compound over 2 steps. MS (ESI) m/z=273, 275 (M+H)

$^1$H NMR (300 MHz, DMSO-d$_6$) δ (ppm): 8.83 (1H, s), 8.04 (1H, d, J=8.6 Hz), 7.97 (1H, d, J=2.1 Hz), 7.84-7.78 (2H, m), 7.76-7.71 (1H, m), 7.44-7.34 (2H, m)

Step B (R)—N-(1-(3-Amino-4-chloroisoxazolo[5,4-c]pyridin-7-yl)pyrrolidin-3-yl)-4-(1H-benzo[d]imidazol-1-yl)-2-chlorobenzamide Following the procedure of EXAMPLE 5 (Step F), 4-(1H-benzo[d]imidazol-1-yl)-2-chlorobenzoic acid (0.090 mmol, 25 mg) and (R)-7-(3-aminopyrrolidin-1-yl)-4-chlorobenzo[d]isoxazol-3-amine (0.09 mmol, 23 mg, EXAMPLE 11, Step E) were converted to the title compound.

Example 30

(R)—N-(1-(3-Amino-4-chloroisoxazolo[5,4-c]pyridin-7-yl)pyrrolidin-3-yl)-2-chloro-4-(pyridazin-4-yl)benzamide

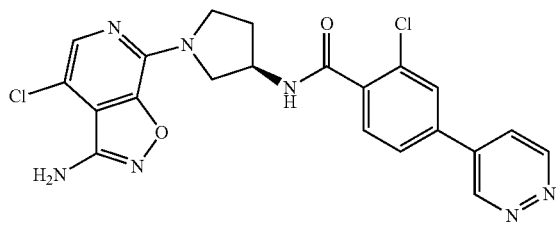 [SMILES: Nc1noc2c(N3CC[C@@H](NC(=O)c4ccc(-c5ccnnc5)cc4Cl)C3)ncc(Cl)c12]

Step A. 2-Chloro-4-(pyridazin-4-yl)benzoic acid

The mixture of 2-chloro-4-(4,4,5,5-tetramethyl-1,3,2-dioxaborolan-2-yl)benzoic acid (2.3 mmol, 650 mg), 4-bromopyridazine hydrobromide (2.1 mmol, 500 mg), PdCl$_2$(dppf) (0.1 mmol, 76 mg), Cs$_2$CO$_3$ (10 mmol, 3.4 g) in 1,4-dioxane/water (15 mL/15 mL) was degassed and heated at 90° C. for 2 h. The reaction mixture was poured into water (50 mL), washed with EtOAc (30 mL). The aqueous layer was adjusted to pH 3 using 1N aq. HCl and then the precipitate was filtered to give the title compound. MS (ESI) m/z=235, 237 (M+H)

$^1$H NMR (DMSO-d$_6$) δ (ppm): 9.71 (1H, dd, J=2.5, 1.1 Hz), 9.34 (1H, dd, J=5.5, 0.9 Hz), 8.14 (1H, d, J=1.4 Hz), 8.11 (1H, dd, J=5.5, 2.7 Hz), 7.98 (1H, dd, J=8.0, 1.6 Hz), 7.93 (1H, d, J=8.2 Hz)

Step B (R)—N-(1-(3-Amino-4-chloroisoxazolo[5,4-c]pyridin-7-yl)pyrrolidin-3-yl)-2-chloro-4-(pyridazin-4-yl)benzamide Following the procedure of EXAMPLE 5 (Step F), (R)-7-(3-aminopyrrolidin-1-yl)-4-chloroisoxazolo[5,4-c]pyridin-3-amine (0.079 mmol, 20 mg, EXAMPLE 11, Step E) and 2-chloro-4-(pyridazin-4-yl)benzoic acid (0.079 mmol, 19 mg) were converted to the title compound.

Example 31

(R)—N-(1-(3-Amino-4-chloroisoxazolo[5,4-c]pyridin-7-yl)pyrrolidin-3-yl)-2-chloro-4-(5-(2-hydroxyethyl)pyridin-3-yl)benzamide

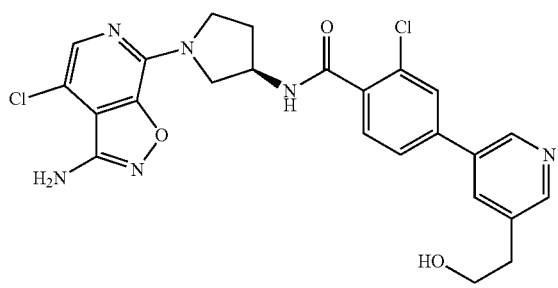 [SMILES: Nc1noc2c(N3CC[C@@H](NC(=O)c4ccc(-c5cncc(CCO)c5)cc4Cl)C3)ncc(Cl)c12]

Step A. 2-(5-Bromopyridin-3-yl)ethanol

To a solution of 2-(5-bromopyridin-3-yl)acetic acid (0.22 g, 1.0 mmol) in THF (20 mL) was added borane-tetrahydrofuran complex (4.0 mL, 4.0 mmol) at 0° C. and warmed to RT gradually. After 1 h, the reaction mixture was added 1N aq. HCl and extracted with EtOAc. The organic layer was washed with brine, dried over Na$_2$SO$_4$, then the solvent was removed. The residue was purified by NH—SiO$_2$ column chromatography (heptane:EtOAc=50:50 to 10:90) to give the title compound. MS (ESI) m/z=202, 204 (M+H)

Step B. Methyl 2-chloro-4-(5-(2-hydroxyethyl)pyridin-3-yl)benzoate

Following the procedure of EXAMPLE 25 (Step A), (3-chloro-4-(methoxycarbonyl)phenyl)boronic acid (150 mg, 0.70 mmol) and 2-(5-bromopyridin-3-yl)ethanol (141 mg, 0.70 mmol) were converted to the title compound. MS (ESI) m/z=292, 294 (M+H).

Step C. 2-Chloro-4-(5-(2-hydroxyethyl)pyridin-3-yl)benzoic acid

Following the procedure of EXAMPLE 25 (Step B), methyl 2-chloro-4-(5-(2-hydroxyethyl)pyridin-3-yl)benzoate (146 mg, 0.50 mmol) was converted to the title compound. MS (ESI) m/z=278, 280 (M+H)

$^1$H NMR (300 MHz, DMSO-d$_6$) δ (ppm): 13.49 (1H, s), 8.92 (1H, s), 8.59 (1H, s), 8.28 (1H, s), 8.00 (1H, s), 7.93 (1H, d, J=8.2 Hz), 7.84 (1H, d, J=7.9 Hz), 3.71 (2H, t, J=6.4 Hz), 2.87 (2H, t, J=6.4 Hz)

Step D (R)—N-(1-(3-Amino-4-chloroisoxazolo[5,4-c]pyridin-7-yl)pyrrolidin-3-yl)-2-chloro-4-(5-(2-hydroxyethyl)pyridin-3-yl)benzamide Following the procedure of EXAMPLE 10, (R)-7-(3-aminopyrrolidin-1-yl)-4-chloroisoxazolo[5,4-c]pyridin-3-amine (0.079 mmol, 20 mg, EXAMPLE 11, Step E) and 2-chloro-4-(5-(2-hydroxyethyl)pyridin-3-yl)benzoic acid (0.079 mmol, 22 mg) were converted to the title compound.

Example 32

(R)—N-(1-(3-Amino-4-chloroisoxazolo[5,4-c]pyridin-7-yl)pyrrolidin-3-yl)-2-chloro-4-(1H-imidazo[4,5-b]pyridin-1-yl)benzamide

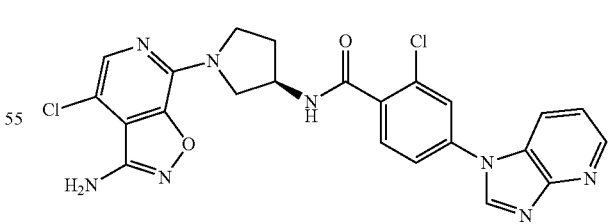

Step A. 2-Chloro-4-(1H-imidazo[4,5-b]pyridin-1-yl)benzoic acid

Following the procedure of EXAMPLE 11 (Step A-B), 1H-imidazo[4,5-b]pyridine was converted to the title compound.

$^1$H NMR (300 MHz, DMSO-d$_6$) δ (ppm): 13.62 (1H, brs), 8.96 (1H, s), 8.53 (1H, dd, J=4.8, 1.6 Hz), 8.19 (1H, dd, J=8.0, 1 Hz), 8.01 (1H, d, J=8.2 Hz), 7.99 (1H, d, J=1.8 Hz), 7.81 (1H, dd, J=8.2, 2.3 Hz), 7.40 (1H, dd, J=8.2, 4.6 Hz) MS (ESI) m/z=274, 276 (M+H)

Step B (R)—N-(1-(3-Amino-4-chloroisoxazolo[5,4-c]pyridin-7-yl)pyrrolidin-3-yl)-2-chloro-4-(1H-imidazo[4,5-b]pyridin-1-yl)benzamide Following the procedure of EXAMPLE 5 (Step F), 2-chloro-4-(1H-imidazo[4,5-b]pyridin-1-yl)benzoic acid (0.090 mmol, 25 mg) and (R)-7-(3-aminopyrrolidin-1-yl)-4-chloroisoxazolo[5,4-c]pyridin-3-amine (0.090 mmol, 23 mg, EXAMPLE 11, Step E) were converted to the title compound.

Example 33

(R)—N-(1-(3-Amino-4-chloroisoxazolo[5,4-c]pyridin-7-yl)pyrrolidin-3-yl)-2-chloro-4-(pyrazin-2-yl)benzamide

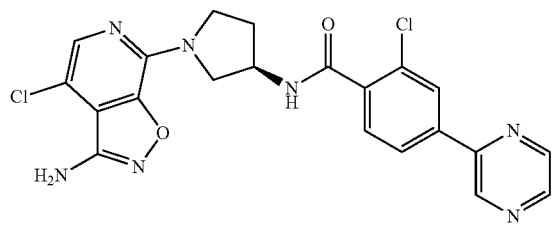 [SMILES: Nc1noc2c(N3CC[C@@H](NC(=O)c4ccc(-c5cnccn5)cc4Cl)C3)ncc(Cl)c12]

Step A (R)—N-(1-(3-Amino-4-chloroisoxazolo[5,4-c]pyridin-7-yl)pyrrolidin-3-yl)-2-chloro-4-(4,4,5,5-tetramethyl-1,3,2-dioxaborolan-2-yl)benzamide To a solution of (R)-7-(3-aminopyrrolidin-1-yl)-4-chloroisoxazolo[5,4-c]pyridin-3-amine dihydrochloride (0.92 mmol, 300 mg, EXAMPLE 11, Step E) and 2-chloro-4-(4,4,5,5-tetramethyl-1,3,2-dioxaborolan-2-yl)benzoic acid (1.0 mmol, 285 mg) in CH$_2$Cl$_2$ (6.0 mL) was added HATU (1.4 mmol, 524 mg) and DIPEA (2.8 mmol, 0.48 mL). The reaction mixture was stirred at 40° C. for 6 h. Then the mixture was diluted with MeOH. The crude mixture was purified by SiO$_2$ column chromatography (heptane: EtOAc=50:50 to 0:100) to give the title compound.
$^1$H NMR (400 MHz, DMSO-d$_6$) δ (ppm): 8.83 (1H, d, J=6.4 Hz), 7.78 (1H, s), 7.62-7.59 (2H, m), 7.44 (1H, d, J=7.3 Hz), 6.21 (2H, s), 4.58-4.50 (1H, m), 3.99-3.93 (1H, m), 3.87-3.74 (3H, m), 2.28-2.18 (1H, m), 2.09-2.00 (1H, m), 1.29 (12H, s) MS (ESI) m/z=518, 520 (M+H)

Step B (R)—N-(1-(3-Amino-4-chloroisoxazolo[5,4-c]pyridin-7-yl)pyrrolidin-3-yl)-2-chloro-4-(pyrazin-2-yl)benzamide To a solution of (R)—N-(1-(3-amino-4-chloroisoxazolo[5,4-c]pyridin-7-yl)pyrrolidin-3-yl)-2-chloro-4-(4,4,5,5-tetramethyl-1,3,2-dioxaborolan-2-yl)benzamide (0.048 mmol, 25 mg), 2-chloropyrazine (0.053 mmol, 6.0 mg) and Cs$_2$CO$_3$ (0.15 mmol, 47 mg) in 1,4-dioxane (2.0 mL) and water (0.40 mL) was added 1,1'-bis(diphenylphosphino)ferrocene-palladium(II) dichloride dichloromethane complex (0.010 mmol, 9.5 mg) and it was sonicated under nitrogen. The mixture was stirred at 90° C. for 2 h. It was cooled to RT and purified by HPLC to give the title compound.

Example 34

(R)—N-(1-(3-Amino-5-cyanobenzo[d]isoxazol-7-yl)pyrrolidin-3-yl)-2-chloro-4-(3-methyl-1H-1,2,4-triazol-1-yl)benzamide

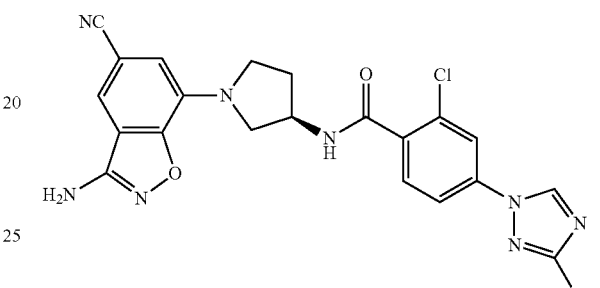

Step A. 2-Chloro-3-cyano-6-fluorobenzoic acid

Following the procedure of EXAMPLE 6 (Step A), 2-chloro-4-fluorobenzonitrile was converted to the title compound. MS (ESI) m/z=200 (M+H)

Step B. 2-Chloro-3-cyano-6-fluorobenzamide

Following the procedure of EXAMPLE 11 (Step D), 2-chloro-3-cyano-6-fluorobenzoic acid (17 mmol, 3.4 g) was converted to the title compound. MS (ESI) m/z=199, 201 (M+H)

Step C. 5-Cyano-2-fluorobenzamide

A mixture of 2-chloro-3-cyano-6-fluorobenzamide (13 mmol, 2.6 g), potassium acetate (26 mmol, 2.6 g), and 10% Pd—C (0.26 g) in MeOH (52 mL) was stirred under H$_2$ at RT for 1.5 h. The mixture was filtered through a pad of Celite and the filtrate was concentrated in vacuo. The residue was dissolved with EtOAc and washed with water and brine. The organic layer was dried over Na$_2$SO$_4$, filtered, and concentrated in vacuo to give the title compound. MS (ESI) m/z=165 (M+H)

Step D. 4-Fluoroisophthalonitrile

Following the procedure of EXAMPLE 5 (Step C), 5-cyano-2-fluorobenzamide (8.53 mmol, 1.4 g) was converted to the title compound.
$^1$H NMR (300 MHz, CDCl$_3$) δ: 8.01-7.91 (2H, m), 7.41 (1H, t, J=8.2 Hz)

Step E. 3-Aminobenzo[d]isoxazole-5-carbonitrile

To a solution of 4-fluoroisophthalonitrile (2.5 mmol, 0.36 g) in DMF (7.2 mL), N-hydroxyacetamide (7.4 mmol, 0.55 g) and K$_2$CO$_3$ (7.4 mmol, 1.0 g) were added.

The reaction mixture was stirred at RT for 5 h, then diluted with EtOAc, washed with water and brine. The organic layer was dried over $Na_2SO_4$, filtered, and concentrated in vacuo. The crude was purified by silica-gel column chromatography (0-50% EtOAc in heptane) to give the title compound. MS (ESI) m/z=160 (M+H)

Step F. 3-Amino-7-bromobenzo[d]isoxazole-5-carboxamide

Following the procedure of EXAMPLE 14 (Step B), 3-aminobenzo[d]isoxazole-5-carbonitrile (0.38 mmol, 60 mg) was converted to the title compound. MS (ESI) m/z=256, 258 (M+H)

Step G. 3-Amino-7-bromobenzo[d]isoxazole-5-carbonitrile

Following the procedure of EXAMPLE 5 (Step C), 3-amino-7-bromobenzo[d]isoxazole-5-carboxamide (0.35 mmol, 90 mg) was converted to the title compound. MS (ESI) m/z=238, 240 (M+H)

Step H. 7-Bromo-3-(2,5-dimethyl-1H-pyrrol-1-yl)benzo[d]isoxazole-5-carbonitrile

Following the procedure of EXAMPLE 6 (Step E), 3-amino-7-bromobenzo[d]isoxazole-5-carbonitrile (0.12 mmol, 28 mg) was converted to the title compound. MS (ESI) m/z=316, 318 (M+H)

Step I. (R)-tert-Butyl (1-(5-cyano-3-(2,5-dimethyl-1H-pyrrol-1-yl)benzo[d]isoxazol-7-yl)pyrrolidin-3-yl)carbamate Following the procedure of EXAMPLE 6 (Step F), 7-bromo-3-(2,5-dimethyl-1H-pyrrol-1-yl)benzo[d]isoxazole-5-carbonitrile (0.05 mmol, 15 mg) was converted to the title compound. MS (ESI) m/z=444 (M+Na)

Step J (R)-7-(3-Aminopyrrolidin-1-yl)-3-(2,5-dimethyl-1H-pyrrol-1-yl)benzo[d]isoxazole-5-carbonitrile hydrochloride Following the procedure of EXAMPLE 4 (Step D), (R)-tert-butyl(1-(5-cyano-3-(2,5-dimethyl-1H-pyrrol-1-yl)benzo[d]isoxazol-7-yl)pyrrolidin-3-yl) carbamate (0.03 mmol, 12 mg) was converted to the title compound.
MS (ESI) m/z=322 (M+H)
$^1$H NMR (300 MHz, $CD_3OD$) δ (ppm): 7.20 (1H, d, J=1.0 Hz), 6.95 (1H, d, J=1.0 Hz), 6.00 (2H, s), 4.08-3.75 (5H, m), 2.56-2.43 (1H, m), 2.22-2.04 (1H, m), 2.09 (6H, s)

Step K (R)—N-(1-(3-Amino-5-cyanobenzo[d]isoxazol-7-yl)pyrrolidin-3-yl)-2-chloro-4-(3-methyl-1H-1,2,4-triazol-1-yl)benzamide Following the procedures of EXAMPLE 1 (Step E) and EXAMPLE 4 (Step F), (R)-7-(3-aminopyrrolidin-1-yl)-3-(2,5-dimethyl-1H-pyrrol-1-yl)benzo[d]isoxazole-5-carbonitrile hydrochloride (0.07 mmol, 25 mg) and 2-chloro-4-(3-methyl-1H-1,2,4-triazol-1-yl)benzoic acid (0.07 mmol, 17 mg, EXAMPLE 11, Step B) were converted to the title compound over 2 steps.

Example 35

(R)—N-(1-(3-Amino-4-chloroisoxazolo[5,4-c]pyridin-7-yl)pyrrolidin-3-yl)-2-chloro-4-(6-oxo-1-(2,2,2-trifluoroethyl)-1,6-dihydropyridin-3-yl)benzamide

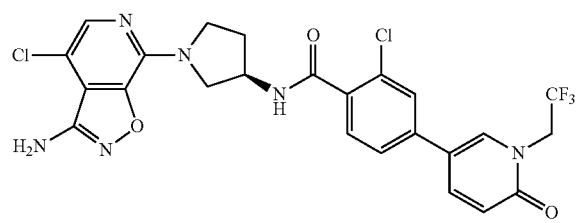 [SMILES: Nc1noc2c(N3CC[C@@H](NC(=O)c4ccc(-c5ccc(=O)n(CC(F)(F)F)c5)cc4Cl)C3)ncc(Cl)c12]

Following the procedure of EXAMPLE 33 (Step B), (R)—N-(1-(3-amino-4-chloroisoxazolo[5,4-c]pyridin-7-yl)pyrrolidin-3-yl)-2-chloro-4-(4,4,5,5-tetramethyl-1,3,2-dioxaborolan-2-yl)benzamide (0.048 mmol, 25 mg, EXAMPLE 33, Step A) and 5-bromo-1-(2,2,2-trifluoroethyl)pyridin-2(1H)-one (0.096 mmol, 25 mg) were converted to the title compound.

Example 36

(R)—N-(1-(3-Amino-4-chloroisoxazolo[5,4-c]pyridin-7-yl)pyrrolidin-3-yl)-4-(4H-1,2,4-triazol-4-yl)benzamide

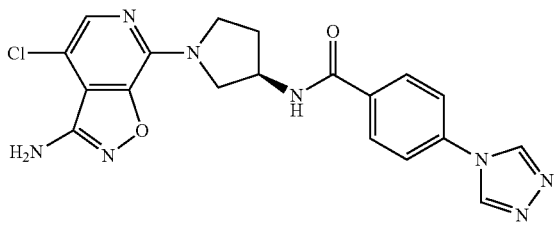 [SMILES: Nc1noc2c(N3CC[C@@H](NC(=O)c4ccc(-n5cnnc5)cc4)C3)ncc(Cl)c12]

Following the procedure of EXAMPLE 5 (Step F), 4-(4H-1,2,4-triazol-4-yl)benzoic acid (0.053 mmol, 10 mg) and (R)-7-(3-aminopyrrolidin-1-yl)-4-chloroisoxazolo[5,4-c]pyridin-3-amine (0.053 mmol, 13 mg, EXAMPLE 11, Step E) were converted to the title compound.

Example 37

(R)—N-(1-(3-Amino-4-chloroisoxazolo[5,4-c]pyridin-7-yl)pyrrolidin-3-yl)-2-chloro-4-(1-(difluoromethyl)-6-oxo-1,6-dihydropyridin-3-yl)benzamide

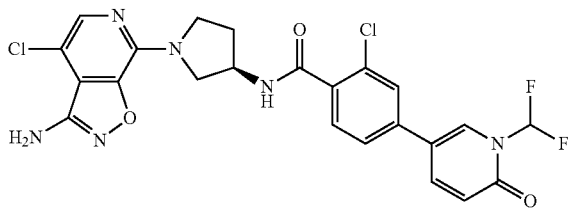 [SMILES: Nc1noc2c(N3CC[C@@H](NC(=O)c4ccc(-c5ccc(=O)n(C(F)F)c5)cc4Cl)C3)ncc(Cl)c12]

Following the procedure of EXAMPLE 33 (Step B), (R)—N-(1-(3-amino-4-chloroisoxazolo[5,4-c]pyridin-7-yl)pyrrolidin-3-yl)-2-chloro-4-(4,4,5,5-tetramethyl-1,3,2-dioxaborolan-2-yl)benzamide (0.05 mmol, 25 mg, EXAMPLE 33, Step A) and 5-bromo-1-(difluoromethyl)pyridin-2(1H)-one (0.07 mmol, 16 mg) were converted to the title compound.

Example 38

(R)-4-([1,2,4]Triazolo[4,3-a]pyridin-6-yl)-N-(1-(3-amino-4-chloroisoxazolo[5,4-c]pyridin-7-yl)pyrrolidin-3-yl)-2-chlorobenzamide

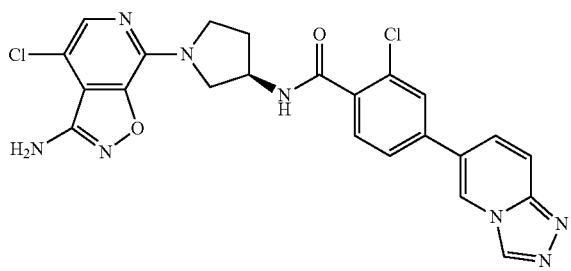 [SMILES: Nc1noc2c(N3CC[C@@H](NC(=O)c4ccc(-c5ccc6nncn6c5)cc4Cl)C3)ncc(Cl)c12]

Following the procedure of EXAMPLE 33 (Step B), (R)—N-(1-(3-amino-4-chloroisoxazolo[5,4-c]pyridin-7-yl)pyrrolidin-3-yl)-2-chloro-4-(4,4,5,5-tetramethyl-1,3,2-dioxaborolan-2-yl)benzamide (0.06 mmol, 30 mg, EXAMPLE 33, Step A) and 6-bromo-[1,2,4]triazolo[4,3-a]pyridine (0.09 mmol, 17 mg) were converted to the title compound.

Example 39

(R)—N-(1-(3-Amino-5-(difluoromethyl)isoxazolo[5,4-c]pyridin-7-yl)pyrrolidin-3-yl)-2-chloro-4-(3-methyl-1H-1,2,4-triazol-1-yl)benzamide

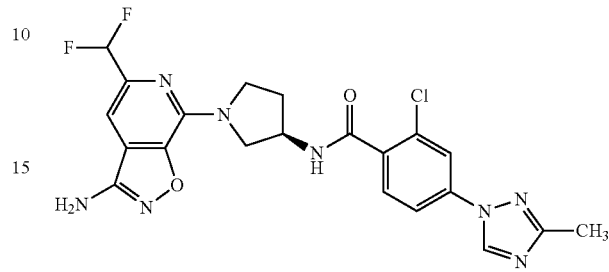

Step A.
2-Bromo-6-(dibromomethyl)-3-fluoropyridine

To a solution of 2-bromo-3-fluoro-6-methylpyridine (52.6 mmol, 10 g) in $CCl_4$ (200 mL) was added N-Bromosuccinimide (105 mmol, 18.7 g), Benzoyl peroxide (8.42 mmol, 2.0 g), it was stirred for 3 h at 80° C. N-Bromosuccinimide (5 g), Benzoyl peroxide (200 mg) was added twice. The reaction mixture was stirred for 18 h at 80° C. The reaction mixture was filtered, and then solvent was removed. The residue was purified by column (heptane/EtOAc=90/10-50/50) to give the title compound.
MS (ESI) m/z=346, 348, 350 (M+H)

Step B. 6-Bromo-5-fluoropicolinaldehyde

Calcium carbonate (95 mmol, 9.5 g) was added to a solution of 2-bromo-6-(dibromomethyl)-3-fluoropyridine (43 mmol, 15 g) in DMSO (120 mL). The mixture was stirred at 150° C. for 4 h. The mixture was diluted with EtOAc and washed with water and brine. The organic extract was dried over $Na_2SO_4$, filtered and concentrated in vacuo to give the crude product. MS (ESI) m/z=204, 206 (M+H)

Step C.
2-Bromo-6-(dimethoxymethyl)-3-fluoropyridine

A solution of 6-bromo-5-fluoropicolinaldehyde (32 mmol, 6.5 g), p-toluenesulfonic acid monohydrate (0.64 mmol, 0.12 g) and trimethyl orthoformate (127 mmol, 13.5 g, 14.1 mL) in MeOH was refluxed for 2 h. After concentration in vacuo, the residue was purified by column chromatography (heptane/EtOAc=100/0-50/50) to give the title compound. MS (ESI) m/z=272, 274 (M+H)

Step D.
2-Bromo-6-(dimethoxymethyl)-3-fluoroisonicotinic acid

Following the procedure of EXAMPLE 6 (Step A), 2-bromo-6-(dimethoxymethyl)-3-fluoropyridine (22 mmol, 5.5 g) was converted to the title compound. MS (ESI) m/z=316, 318 (M+Na)

Step E. 2-Bromo-6-(dimethoxymethyl)-3-fluoroisonicotinamide

Following the procedure of EXAMPLE 11 (Step D), 2-bromo-6-(dimethoxymethyl)-3-fluoroisonicotinic acid (2.4 mmol, 0.70 g) was converted to the title compound. MS (ESI) m/z=315, 317 (M+Na)

Step F. (R)-tert-Butyl (1-(4-carbamoyl-6-(dimethoxymethyl)-3-fluoropyridin-2-yl)pyrrolidin-3-yl)carbamate Following the procedure of EXAMPLE 5 (Step B, by using NMP instead of DMF), 2-bromo-6-(dimethoxymethyl)-3-fluoroisonicotinamide (1.88 mmol, 550 mg) was converted to the title compound. MS (ESI) m/z=399 (M+H)

Step G. (R)-2-(3-Aminopyrrolidin-1-yl)-6-(dimethoxymethyl)-3-fluoroisonicotinamide hydrochloride Following the procedure of EXAMPLE 4 (Step D), (R)-tert-butyl (1-(4-carbamoyl-6-(dimethoxymethyl)-3-fluoropyridin-2-yl)pyrrolidin-3-yl)carbamate (1.61 mmol, 640 mg) was converted to the title compound. MS (ESI) m/z=321 (M+Na)

Step H (R)-2-(3-(2-Chloro-4-(3-methyl-1H-1,2,4-triazol-1-yl)benzamido)pyrrolidin-1-yl)-6-(dimethoxymethyl)-3-fluoroisonicotinamide Following the procedure of EXAMPLE 1 (Step E), (R)-2-(3-aminopyrrolidin-1-yl)-6-(dimethoxymethyl)-3-fluoroisonicotinamide hydrochloride (1.58 mmol, 530 mg) and 2-chloro-4-(3-methyl-1H-1,2,4-triazol-1-yl)benzoic acid (1.58 mmol, 376 mg, EXAMPLE 11, Step B) were converted to the title compound.
MS (ESI) m/z=540 (M+Na)

Step I (R)-2-(3-(2-Chloro-4-(3-methyl-1H-1,2,4-triazol-1-yl)benzamido)pyrrolidin-1-yl)-3-fluoro-6-formylisonicotinamide To a suspension of (R)-2-(3-(2-chloro-4-(3-methyl-1H-1,2,4-triazol-1-yl)benzamido)pyrrolidin-1-yl)-6-(dimethoxymethyl)-3-fluoroisonicotinamide (0.19 mmol, 100 mg) in THF (1 mL), hydrochloric acid (100 µL) was added at RT. The mixture was stirred at 50° C. for 3 h. The reaction mixture was diluted with EtOAc and basified by sat. aq. NaHCO$_3$. The mixture was extracted with EtOAc. Then the solution was dried over Na$_2$SO$_4$, filtered and concentrated in vacuo to afford a crude compound. MS (ESI) m/z=472, 474 (M+H)

Step J (R)-2-(3-(2-Chloro-4-(3-methyl-1H-1,2,4-triazol-1-yl)benzamido)pyrrolidin-1-yl)-6-(difluoromethyl)-3-fluoroisonicotinamide To a suspension of (R)-2-(3-(2-chloro-4-(3-methyl-1H-1,2,4-triazol-1-yl)benzamido)pyrrolidin-1-yl)-3-fluoro-6-formylisonicotinamide (0.19 mmol, 90 mg) in CH$_2$Cl$_2$ (2.0 mL), DAST (0.95 mmol, 126 µL) was added at RT. The mixture was stirred at RT for 18 h. The reaction mixture was diluted with EtOAc and basified by aq. NaHCO$_3$. Precipitate appeared. This precipitate was filtered. The filtrate was extracted with CH$_2$Cl$_2$-MeOH. Then the solution was dried over Na$_2$SO$_4$, filtered and concentrated in vacuo to afford a crude compound. The residue was purified by NH column chromatography (EtOAc/MeOH=100/0-90/10) to give the title compound. MS (ESI) m/z=494, 496 (M+H)

Step K (R)-2-Chloro-N-(1-(4-cyano-6-(difluoromethyl)-3-fluoropyridin-2-yl)pyrrolidin-3-yl)-4-(3-methyl-1H-1,2,4-triazol-1-yl)benzamide Following the procedure of EXAMPLE 5 (Step C), (R)-2-(3-(2-chloro-4-(3-methyl-1H-1,2,4-triazol-1-yl)benzamido)pyrrolidin-1-yl)-6-(difluoromethyl)-3-fluoroisonicotinamide (0.02 mmol, 10 mg) was converted to the title compound. MS (ESI) m/z=476, 478 (M+H)

Step L (R)—N-(1-(3-Amino-5-(difluoromethyl)isoxazolo[5,4-c]pyridin-7-yl)pyrrolidin-3-yl)-2-chloro-4-(3-methyl-1H-1,2,4-triazol-1-yl)benzamide Following the procedure of EXAMPLE 34 (Step E), (R)-2-chloro-N-(1-(4-cyano-6-(difluoromethyl)-3-fluoropyridin-2-yl)pyrrolidin-3-yl)-4-(3-methyl-1H-1,2,4-triazol-1-yl)benzamide (0.0063 mmol, 3 mg) was converted to the title compound.

Example 40

(R)—N-(1-(3-Amino-4-chloroisoxazolo[5,4-c]pyridin-7-yl)pyrrolidin-3-yl)-2-chloro-4-(1-methyl-6-oxo-1,6-dihydropyridazin-3-yl)benzamide

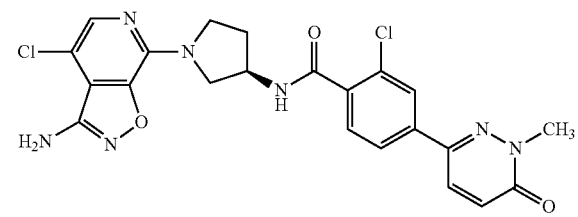 [SMILES: Cn1nc(-c2ccc(C(=O)N[C@@H]3CCN(c4ncc(Cl)c5c(N)noc45)C3)c(Cl)c2)ccc1=O]

Following the procedure of EXAMPLE 33 (Step B), (R)—N-(1-(3-amino-4-chloroisoxazolo[5,4-c]pyridin-7-yl)pyrrolidin-3-yl)-2-chloro-4-(4,4,5,5-tetramethyl-1,3,2-dioxaborolan-2-yl)benzamide (0.058 mmol, 30 mg, EXAMPLE 33, Step A) and 6-chloro-2-methylpyridazin-3(2H)-one (0.07 mmol, 10 mg) were converted to the title compound.

Example 41

(R)—N-(1-(3-Amino-5-cyanoisoxazolo[5,4-c]pyridin-7-yl)pyrrolidin-3-yl)-2-chloro-4-(3-methyl-1H-1,2,4-triazol-1-yl)benzamide

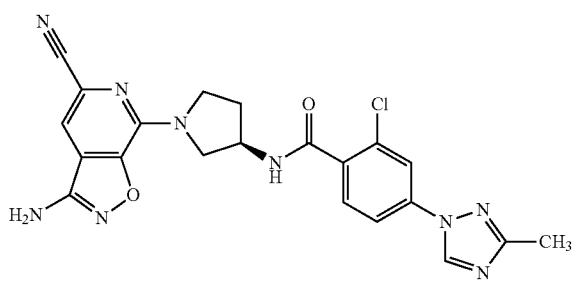 [SMILES: Cc1ncn(-c2ccc(C(=O)N[C@@H]3CCN(c4nc(C#N)cc5c(N)noc45)C3)c(Cl)c2)n1]

Step A (R)-2-(3-(2-Chloro-4-(3-methyl-1H-1,2,4-triazol-1-yl)benzamido)pyrrolidin-1-yl)-6-cyano-3-fluoroisonicotinamide To a solution of (R)-2-(3-(2-chloro-4-(3-methyl-1H-1,2,4-triazol-1-yl)benzamido)pyrrolidin-1-yl)-3-fluoro-6-formylisonicotinamide (0.06 mmol, 26 mg, EXAMPLE 39, Step I) in ammonium hydroxide (260 µL) and THF (260 µL) was added iodine (0.06 mmol, 15 mg) at RT. The mixture was stirred for 5 h at the same temperature. The mixture was diluted with water, extracted with EtOAc, washed with aq. Na$_2$S$_2$O$_3$ and brine, dried over Na$_2$SO$_4$, filtered, and concentrated in vacuo. The residue was purified by SiO$_2$ column chromatography (EtOAc/MeOH=100:0 to 90:10) to give the title compound.

MS (ESI) m/z=469 (M+H)

Step B (R)-2-Chloro-N-(1-(4,6-dicyano-3-fluoropyridin-2-yl)pyrrolidin-3-yl)-4-(3-methyl-1H-1,2,4-triazol-1-yl)benzamide Following the procedure of EXAMPLE 5 (Step C), (R)-2-(3-(2-chloro-4-(3-methyl-1H-1,2,4-triazol-1-yl)benzamido)pyrrolidin-1-yl)-6-cyano-3-fluoroisonicotinamide (0.04 mmol, 20 mg) was converted to the title compound.

MS (ESI) m/z=451, 453 (M+H)

Step C (R)—N-(1-(3-Amino-5-cyanoisoxazolo[5,4-c]pyridin-7-yl)pyrrolidin-3-yl)-2-chloro-4-(3-methyl-1H-1,2,4-triazol-1-yl)benzamide Following the procedure of EXAMPLE 34 (Step E), (R)-2-chloro-N-(1-(4,6-dicyano-3-fluoropyridin-2-yl)pyrrolidin-3-yl)-4-(3-methyl-1H-1,2,4-triazol-1-yl)benzamide (0.03 mmol, 15 mg) was converted to the title compound.

Example 42

(R)—N-(1-(3-Amino-5-methylisoxazolo[5,4-c]pyridin-7-yl)pyrrolidin-3-yl)-2-chloro-4-(4-(2-hydroxyethyl)-1H-1,2,3-triazol-1-yl)benzamide

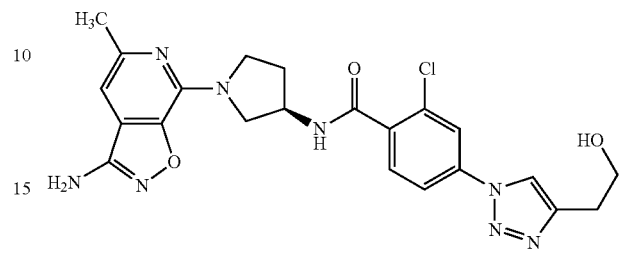

Step A.
2-Bromo-3-fluoro-6-methylisonicotinaldehyde

To a solution of diisopropylamine (3.6 mL, 25 mmol) in THF (65 mL) was added n-BuLi (1.64 M, 14 mL, 23 mmol) at 0° C., it was stirred at the same temperature for 20 min. The mixture was cooled to −78° C. and 2-bromo-3-fluoro-6-methylpyridine (4.0 g, 21 mmol) in THF (40 mL) was added. The mixture was stirred at −78° C. for 0.5 h. Then, DMF (2.0 mL, 25 mmol) was added to the reaction, and the mixture was warmed up to room temperature. To the reaction was added sat. aq. NH$_4$Cl and it was extracted with EtOAc. The extract was washed with brine, dried over Na$_2$SO$_4$, filtered and concentrated in vacuo to give the title compound. MS (ESI) m/z=218, 220 (M+H)

Step B. 2-Bromo-3-fluoro-6-methylisonicotinonitrile

To a solution of 2-bromo-3-fluoro-6-methylisonicotinaldehyde (4.6 g, 21 mmol) in NH$_4$OH (25%, 46 mL) and THF (46 mL) was added I$_2$ (5.8 g, 23 mmol) at RT, it was stirred at RT for 5 h. The reaction was diluted with H$_2$O. The mixture was extracted with EtOAc and it was washed with aq. Na$_2$S$_2$O$_3$, brine, dried over Na$_2$SO$_4$, filtered and concentrated in vacuo. The residue was purified by NH—SiO$_2$ column chromatography (heptane:EtOAc=100:0 to 50:50) to give the title compound. MS (ESI) m/z=215, 217 (M+H)

Step C. 7-Bromo-5-methylisoxazolo[5,4-c]pyridin-3-amine

A suspension of 2-bromo-3-fluoro-6-methylisonicotinonitrile (2.9 g, 14 mmol), N-hydroxyacetamide (1.5 g, 20 mmol) and K$_2$CO$_3$ (3.7 g, 27 mmol) in DMF (87 mL) was stirred at RT for 16 hours. N-hydroxyacetamide (0.5 g, 6.7 mmol) was added to the reaction, then the mixture was stirred at 40° C. for 1 h. The reaction mixture was diluted with H$_2$O and extracted with EtOAc. The extract was washed with sat. aq. NaHCO$_3$ and brine, dried over Na$_2$SO$_4$, filtered and concentrated in vacuo. The residue was triturated with heptane-CH$_2$Cl$_2$ to give the title compound. MS (ESI) m/z=228, 230 (M+H)

Step D. (R)-tert-Butyl (1-(3-amino-5-methylisoxazolo[5,4-c]pyridin-7-yl)pyrrolidin-3-yl)carbamate A mixture of 7-bromo-5-methylisoxazolo[5,4-c]pyridin-3-amine (13 mmol, 3 g), (R)-tert-butyl pyrrolidin-3-ylcarbamate (14 mmol, 2.7 g) and K$_2$CO$_3$ (26 mmol, 3.6 g) in NMP (90 mL) was stirred at 120° C. for 13 h. The mixture was diluted with EtOAc and H$_2$O, extracted with EtOAc. The extract was washed with brine, dried over Na$_2$SO$_4$, filtered, and concentrated in vacuo. The residue was purified by silica-gel column chromatography (heptane:EtOAc=95:5 to 0:100) to give the title compound.
MS (ESI) m/z=334 (M+H)

Step E. (R)-7-(3-Aminopyrrolidin-1-yl)-5-methyl-isoxazolo[5,4-c]pyridin-3-amine hydrochloride Following the procedure of EXAMPLE 5 (Step E), (R)-tert-butyl (1-(3-amino-5-methylisoxazolo[5,4-c]pyridin-7-yl)pyrrolidin-3-yl)carbamate (13 mmol, 4.2 g) was converted to the title compound. MS (ESI) m/z=234 (M+H)

Step F. tert-Butyl 2-chloro-4-(4-(2-hydroxyethyl)-1H-1,2,3-triazol-1-yl)benzoate Trans-N,N'-Dimethylcyclohexane-1,2-diamine (0.27 mmol, 38 mg) was added to the mixture of tert-butyl 2-chloro-4-iodobenzoate (1.8 mmol, 600 mg, EXAMPLE 26, Step A), sodium azide (2.13 mmol, 138 mg), but-3-yn-1-ol (2.0 mmol, 137 mg), copper(I) iodide (0.18 mmol, 34 mg), L-ascorbic acid sodium salt (0.18 mmol, 35 mg), DMSO (5 mL) and water (1 mL). The reaction mixture was degassed via under pressure and filled in N$_2$ gas. The mixture was stirred at RT for 15 h. NH$_4$OH and CH$_2$Cl$_2$ were added to the reaction mixture. The aqueous phase was extracted with CH$_2$Cl$_2$, and the combined organic extracts were washed with water. The organic extract was filtered through a pad of Celite and concentrated. Purified with column chromatography (silica-gel, heptane/EtOAc=9/1 to EtOAc) to give the title compound. MS (ESI) m/z=324, 326 (M+H)

Step G. 2-Chloro-4-(4-(2-hydroxyethyl)-1H-1,2,3-triazol-1-yl)benzoic acid

TFA (3 mL) was added to the solution of tert-butyl 2-chloro-4-(4-(2-hydroxyethyl)-1H-1,2,3-triazol-1-yl)benzoate (0.99 mmol, 320 mg) in CH$_2$Cl$_2$ (6 mL) and stirred at RT for 15 h. The reaction mixture was concentrated. The residue was dissolved with EtOH (5 mL). 1N aq. NaOH (2.5 mmol, 2.5 mL) was added to the solution and stirred at RT for 1 h. The reaction mixture was added 1N aq. HCl (2.5 mL) and extracted with EtOAc. The organic phase was washed with half-brine, concentrated in vacuo, to give the title compound. MS (ESI) m/z=268, 270 (M+H)
$^1$H NMR (300 MHz, DMSO-d$_6$) δ: 8.74 (1H, s), 8.11 (1H, s), 7.98 (2H, s), 4.78 (1H, t, J=5.7 Hz), 3.70 (2.0H, dt, J=11.9, 6.7 Hz), 2.86 (2.0H, t, J=6.9 Hz)

Step H (R)—N-(1-(3-Amino-5-methylisoxazolo[5,4-c]pyridin-7-yl)pyrrolidin-3-yl)-2-chloro-4-(4-(2-hydr oxy-ethyl)-1H-1,2,3-triazol-1-yl)benzamide Following the procedure of EXAMPLE 1 (Step E), (R)-7-(3-aminopyrrolidin-1-yl)-5-methylisoxazolo[5,4-c]pyridin-3-amine hydrochloride (0.11 mmol, 30 mg) and 2-chloro-4-(4-(2-hydroxyethyl)-1H-1,2,3-triazol-1-yl)benzoic acid (0.11 mmol, 30 mg) were converted to the title compound.

Example 43

(R)—N-(1-(3-Amino-4-chloroisoxazolo[5,4-c]pyridin-7-yl)pyrrolidin-3-yl)-2-chloro-4-(3-(trifluoromethyl)-4H-1,2,4-triazol-4-yl)benzamide

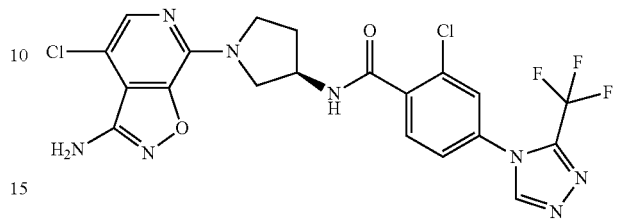

Step A. Methyl 2-chloro-4-(2,2,2-trifluoroacetamido)benzoate

To a mixture of methyl 4-amino-2-chlorobenzoate (5.0 mmol, 0.93 g) and Et$_3$N (7.0 mmol, 0.98 mL) in CH$_2$Cl$_2$ (20 mL) at 0° C., TFAA (6.0 mmol, 0.85 mL) was added dropwise. The mixture was stirred at RT for 1 h. The mixture was quenched with water, extracted with CH$_2$Cl$_2$. The extract was dried over Na$_2$SO$_4$, filtered, concentrated in vacuo. The crude was purified by column chromatography (silica-gel, 0-40% ethyl acetate in heptane) to give the title compound. MS (ESI) m/z=282, 284 (M+H)

Step B. Methyl 2-chloro-4-(3-(trifluoromethyl)-4H-1,2,4-triazol-4-yl)benzoate

A mixture of methyl 2-chloro-4-(2,2,2-trifluoroacetamido)benzoate (0.75 g, 2.7 mmol), Ph$_3$P (0.98 g, 3.7 mmol), CCl$_4$ (0.39 mL, 4.0 mmol) in CH$_2$Cl$_2$ (2.7 mL) was stirred at 50° C. for 3 h. The mixture was concentrated in vacuo, added heptane-ethyl acetate (1:1), cooled to 0° C., and filtered. The filtrate was concentrated in vacuo. To the residue in a flask at 0° C., pyridine (3 mL) was added. To the mixture, formylhydrazine (0.16 g, 2.7 mmol) in pyridine (2 mL) was added. The mixture was stirred at 110° C. for 5 h. The mixture was concentrated in vacuo. The residue was dissolved with ethyl acetate (100 mL), washed with 1N aq. HCl (30 mL, twice), sat. aq. NaHCO$_3$ (30 mL), dried over Na$_2$SO$_4$, filtered, and concentrated in vacuo. The crude was purified by column chromatography (silica-gel, 0-80% ethyl acetate in heptane) to give the title compound.
MS (ESI) m/z=306, 308 (M+H)

Step C. 2-Chloro-4-(3-(trifluoromethyl)-4H-1,2,4-triazol-4-yl)benzoic acid

Following the procedure of EXAMPLE 28 (Step B), methyl 2-chloro-4-(3-(trifluoromethyl)-4H-1,2,4-triazol-4-yl)benzoate (0.75 g, 0.25 mmol) was converted to the title compound. MS (ESI) m/z=292, 294 (M+H)
$^1$H NMR (400 MHz, DMSO-d$_6$) δ (ppm): 13.86 (1H, s), 9.19 (1H, s), 8.00 (1H, d, J=1.8 Hz), 7.98 (1H, d, J=8.2 Hz) 7.71 (1H, dd, J=8.2, 1.8 Hz)

Step D (R)—N-(1-(3-Amino-4-chloroisoxazolo[5,4-c]pyridin-7-yl)pyrrolidin-3-yl)-2-chloro-4-(3-(trifluoromethyl)-4H-1,2,4-triazol-4-yl)benzamide Following the procedure of EXAMPLE 5 (Step F), (R)-7-(3-aminopyrrolidin-1-yl)-4-chloroisoxazolo[5,4-c]pyridin-3-amine dihydrochloride (33 mg, 0.10 mmol, EXAMPLE 11, Step E) and 2-chloro-4-(3-(trifluoromethyl)-4H-1,2,4-triazol-4-yl)benzoic acid (29 mg, 0.10 mmol) were converted to the title compound.

Example 44

(R)—N-(1-(3-Amino-4-chloroisoxazolo[5,4-c]pyridin-7-yl)pyrrolidin-3-yl)-2-chloro-4-(1-methyl-2-oxo-1,2-dihydropyrimidin-5-yl)benzamide

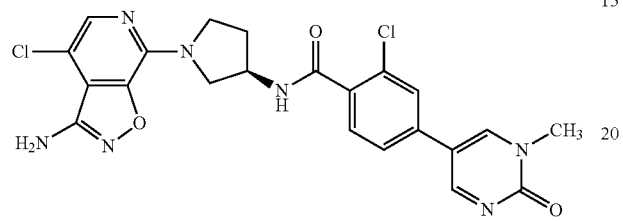

Step A. 5-Bromopyrimidin-2(1H)-one

To a solution of 5-bromopyrimidin-2-amine (11 mmol, 2.0 g) in acetic acid (35 mL) was added sodium nitrite (69 mmol, 4.8 g) in water (25 mL) at RT over 1.5 h. After 5 h, the reaction mixture was partly evaporated, the precipitate was filtered and washed with water to give the title compound. MS (ESI) m/z=175, 177 (M+H)

Step B. 5-Bromo-1-methylpyrimidin-2(1H)-one

To a solution of 5-bromopyrimidin-2(1H)-one (2.3 mmol, 400 mg) in DMF (12 mL) was added MeI (11 mmol, 0.71 mL) K$_2$CO$_3$ (4.6 mmol, 632 mg). After 16 h, the reaction mixture was diluted with water and extracted with EtOAc. The organic layer was dried over Na$_2$SO$_4$, filtered, concentrated. The crude was purified by trituration with EtOAc to give the title compound. MS (ESI) m/z=189, 191 (M+H)

Step C (R)—N-(1-(3-Amino-4-chloroisoxazolo[5,4-c]pyridin-7-yl)pyrrolidin-3-yl)-2-chloro-4-(1-methyl-2-oxo-1,2-dihydropyrimidin-5-yl)benzamide Following the procedure of EXAMPLE 33 (Step B), (R)—N-(1-(3-amino-4-chloroisoxazolo[5,4-c]pyridin-7-yl)pyrrolidin-3-yl)-2-chloro-4-(4,4,5,5-tetramethyl-1,3,2-dioxaborolan-2-yl)benzamide (0.048 mmol, 25 mg, EXAMPLE 33, Step A) and 5-bromo-1-methylpyrimidin-2(1H)-one (0.096 mmol, 18 mg) were converted to the title compound.

Example 45

(R)—N-(1-(3-Amino-4-chloroisoxazolo[5,4-c]pyridin-7-yl)pyrrolidin-3-yl)-2-chloro-4-(1-methyl-5-oxo-1,5-dihydro-4H-1,2,4-triazol-4-yl)benzamide

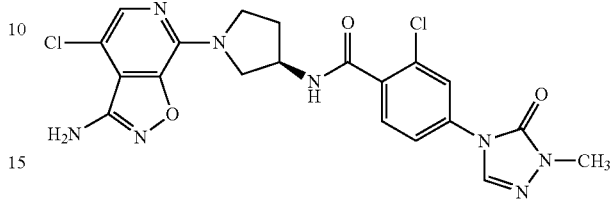

Step A. Methyl 2-chloro-4-(hydrazinecarboxamido)benzoate

To a mixture of methyl 4-amino-2-chlorobenzoate (30 mmol, 5.6 g) and 2,6-lutidine (33 mmol, 3.8 mL) in THF (60 mL) at 0° C., phenyl chloroformate (33 mmol, 4.2 mL) was added dropwise. The mixture was stirred at RT for 10 min, diluted with ethyl acetate, washed with 1N aq. HCl and sat. aq. NaHCO$_3$. The organic layer was dried over Na$_2$SO$_4$, filtered, and concentrated in vacuo. A mixture of the crude and hydrazine hydrate (90 mmol, 4.4 mL) in 1,4-dioxane (60 mL) was stirred at 100° C. for 2 h. The mixture was concentrated in vacuo. The residue was triturated with water, filtered to collect the title compound. MS (ESI) m/z=244, 246 (M+H)

Step B. Methyl 2-chloro-4-(5-oxo-1H-1,2,4-triazol-4(5H)-yl)benzoate

A mixture of methyl 2-chloro-4-(hydrazinecarboxamido)benzoate (5.1 g, 21 mmol) and formamidine acetate (6.5 g, 63 mmol) in acetic acid (42 mL) was stirred at 80° C. for 1 h. The mixture was cooled to RT, added water (84 mL), cooled with ice-water bath. The suspension was filtered, washed with water to give the desired product.

MS (ESI) m/z=254, 256 (M+H)

Step C. 2-Chloro-4-(1-methyl-5-oxo-1H-1,2,4-triazol-4(5H)-yl)benzoic acid

To a mixture of methyl 2-chloro-4-(5-oxo-1H-1,2,4-triazol-4(5H)-yl)benzoate (8.3 mmol, 2.1 g) and K$_2$CO$_3$ (25 mmol, 3.4 g) in DMF (17 ml) at RT, methyl iodide (17 mmol, 1.0 mL) was added. The mixture was stirred at RT for 16 h. The mixture was diluted with ethyl acetate, washed with sat. aq. NH$_4$Cl and water, dried over Na$_2$SO$_4$, filtered, and concentrated in vacuo. To the residue, 1,4-dioxane (8.0 mL) and lithium hydroxide monohydrate (9.1 mmol, 0.38 g) in water (4.0 mL) were added and the mixture was stirred at RT for 2 h. The mixture was acidified with 4N HCl in dioxane and concentrated in vacuo. The residue was washed with cold methanol to give the desired product. MS (ESI) m/z=254, 256 (M+H)

$^1$H NMR (400 MHz, DMSO-d$_6$) δ (ppm): 8.62 (1H, s), 8.01 (1H, d, J=2.3 Hz), 7.94 (1H, d, J=8.7 Hz), 7.85 (1H, dd, J=8.5, 2.1 Hz), 3.39 (4H, s)

Step D (R)—N-(1-(3-Amino-4-chloroisoxazolo[5,4-c]pyridin-7-yl)pyrrolidin-3-yl)-2-chloro-4-(1-methyl-5-oxo-1H-1,2,4-triazol-4(5H)-yl)benzamide Following the procedure of EXAMPLE 5 (Step F), (R)-7-(3-aminopyrrolidin-1-yl)-4-chloroisoxazolo[5,4-c]pyridin-3-amine dihydrochloride (33 mg, 0.10 mmol, EXAMPLE 11, Step E) and 2-chloro-4-(1-methyl-5-oxo-1H-1,2,4-triazol-4(5H)-yl)benzoic acid (25 mg, 0.10 mmol) were converted to the title compound. MS (ESI) m/z=489, 491 (M+H)

Example 46

(R)—N-(1-(3-Amino-4-chloroisoxazolo[5,4-c]pyridin-7-yl)pyrrolidin-3-yl)-2-chloro-4-(5-oxo-1,5-dihydro-4H-1,2,4-triazol-4-yl)benzamide

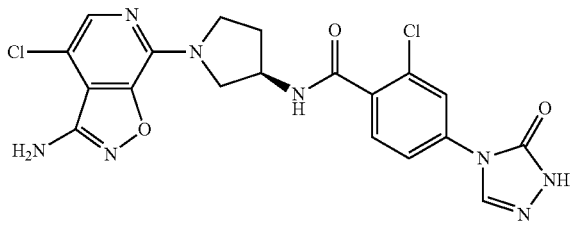 [SMILES: Nc1noc2c(N3CC[C@@H](NC(=O)c4ccc(-n5cn[nH]c5=O)cc4Cl)C3)ncc(Cl)c12]

Step A. Methyl 2-chloro-4-((phenoxycarbonyl)amino)benzoate

To a mixture of methyl 4-amino-2-chlorobenzoate (20 mmol, 3.7 g) and 2,6-lutidine (22 mmol, 2.6 mL) in THF (40 mL) at 0° C., phenyl chloroformate (22 mmol, 2.8 mL) was added dropwise. The mixture was stirred at RT for 10 min, then it was diluted with ethyl acetate, washed with 1N aq. HCl and sat. aq. NaHCO$_3$. The organic layer was dried over Na$_2$SO$_4$, filtered, and concentrated in vacuo. The crude was triturated with heptane-ethyl acetate (1:2) to give the title compound. MS (ESI) m/z=306, 308 (M+H)

Step B. 2-Chloro-4-(hydrazinecarboxamido)benzoic acid

A mixture of methyl 2-chloro-4-((phenoxycarbonyl)amino)benzoate (18 mmol, 5.6 g) and hydrazine hydrate (55 mmol, 2.7 mL) in 1,4-dioxane (37 mL) was stirred at 100° C. for 2 h. The mixture was concentrated in vacuo. To the residue, 1N aq. NaOH (40 mL) was added. The suspension was stirred at RT for 3 h, then acidified to pH 4 with c.HCl. The suspension was filtered to give the title compound. MS (ESI) m/z=230, 232 (M+H)

Step C. 2-Chloro-4-(5-oxo-1H-1,2,4-triazol-4(5H)-yl)benzoic acid

Following the procedure of EXAMPLE 45 (Step B), 2-chloro-4-(hydrazinecarboxamido)benzoic acid (0.84 g, 3.7 mmol) was converted to the title compound. MS (ESI) m/z=240, 242 (M+H) $^1$H NMR (400 MHz, DMSO-d$_6$) δ (ppm): 8.42 (1H, s), 7.82 (1H, s), 7.71 (1H, d, J=1.8 Hz), 7.55 (1H, dd, J=8.2, 1.8 Hz), 7.51 (1H, d, J=8.2 Hz), 1.76 (3H, s)

Step D (R)—N-(1-(3-Amino-4-chloroisoxazolo[5,4-c]pyridin-7-yl)pyrrolidin-3-yl)-2-chloro-4-(5-oxo-1H-1,2,4-triazol-4(5H)-yl)benzamide To a mixture of (R)-7-(3-aminopyrrolidin-1-yl)-4-chloroisoxazolo[5,4-c]pyridin-3-amine dihydrochloride (33 mg, 0.10 mmol, EXAMPLE 11, Step E), 2-chloro-4-(5-oxo-1H-1,2,4-triazol-4(5H)-yl)benzoic acid (24 mg, 0.10 mmol), and DIPEA (87 µL, 0.50 mmol) in DMF (0.5 mL), HATU (42 mg, 0.11 mmol) was added. After stirring at RT for 1 h, additional HATU (38 mg, 0.10 mmol) was added and stirred for 1 h. To the mixture, 1N aq. NaOH (0.5 mL) was added and the mixture was stirred for 16 h. It was purified by HPLC to give the title compound. MS (ESI) m/z=475, 477 (M+H)

Example 47

(R)—N-(1-(3-Amino-4-chloroisoxazolo[5,4-c]pyridin-7-yl)pyrrolidin-3-yl)-2-chloro-4-(1-(2-hydroxyethyl)-5-oxo-1,5-dihydro-4H-1,2,4-triazol-4-yl)benzamide

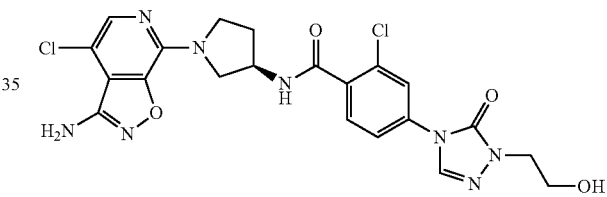

Step A. Methyl 4-(1-(2-((tert-butyldimethylsilyl)oxy)ethyl)-5-oxo-1H-1,2,4-triazol-4(5H)-yl)-2-chlorobenzoate To a mixture of methyl 2-chloro-4-(5-oxo-1H-1,2,4-triazol-4(5H)-yl)benzoate (1.0 mmol, 0.25 g, EXAMPLE 45, Step B) and K$_2$CO$_3$ (3 mmol, 0.41 g) in DMF (5.0 mL) at RT, (2-bromoethoxy)(tert-butyl)dimethylsilane (1.5 mmol, 0.36 g) was added. The mixture was stirred at RT for 16 h. The mixture was treated with sat. aq. NH$_4$Cl, diluted with ethyl acetate, washed with water. The organic layer was dried over Na$_2$SO$_4$, filtered, concentrated in vacuo. The crude was purified by silica-gel column chromatography (0-30% ethyl acetate in heptane) to give the title compound. MS (ESI) m/z=412, 414 (M+H)

Step B. 2-Chloro-4-(1-(2-hydroxyethyl)-5-oxo-1H-1,2,4-triazol-4(5H)-yl)benzoic acid To a solution of methyl 4-(1-(2-((tert-butyldimethylsilyl)oxy)ethyl)-5-oxo-1H-1,2,4-triazol-4(5H)-yl)-2-chlorobenzoate (0.75 mmol, 310 mg) in 1,4-dioxane (3.0 mL), lithium hydroxide monohydrate (0.83 mmol, 35 mg) in water (0.75 mL) was added. The mixture was stirred at RT for 2 h. Additional lithium hydroxide monohydrate (70 mg) was added and stirred at RT for 16 h and at 60° C. for 8 h. The mixture was cooled to 0° C., added 4N HCl in dioxane (0.6 mL), and concentrated in vacuo. The residue was triturated with cold methanol to give the desired product. MS (ESI) m/z=284, 286 (M+H)

Step C (R)—N-(1-(3-Amino-4-chloroisoxazolo[5,4-c]pyridin-7-yl)pyrrolidin-3-yl)-2-chloro-4-(1-(2-hydroxyethyl)-5-oxo-1H-1,2,4-triazol-4(5H)-yl)benzamide Following the procedure of EXAMPLE 5 (Step F), (R)-7-(3-aminopyrrolidin-1-yl)-4-chloroisoxazolo[5,4-c]pyridin-3-amine dihydrochloride (33 mg, 0.10 mmol, EXAMPLE 11, Step E) and 2-chloro-4-(1-(2-hydroxyethyl)-5-oxo-1H-1,2,4-triazol-4(5H)-yl)benzoic acid (28 mg, 0.10 mmol) were converted to the title compound. MS (ESI) m/z=519, 521 (M+H)

Example 48

(R)—N-(1-(3-Amino-4-chloroisoxazolo[5,4-c]pyridin-7-yl)pyrrolidin-3-yl)-2-chloro-4-(9H-purin-9-yl)benzamide

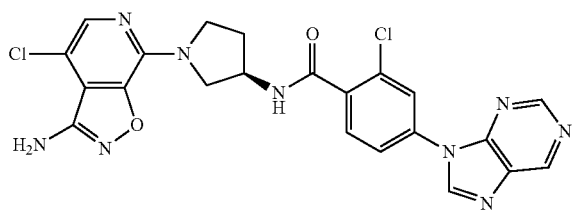 [SMILES: Nc1noc2c(N3CC[C@@H](NC(=O)c4ccc(-n5cnc6cncnc65)cc4Cl)C3)ncc(Cl)c12]

Step A. tert-Butyl 2-chloro-4-(9H-purin-9-yl)benzoate

To a mixture of copper(I) iodide (0.05 mmol, 10 mg), trans-N,N'-dimethylcyclohexane-1,2-diamine (0.07 mL), purine (2.1 mmol, 0.26 g), and Cs$_2$CO$_3$ (3.7 mmol, 1.2 g) in 1,4-dioxane (2 mL) was added tert-butyl 2-chloro-4-iodobenzoate (1.8 mmol, 0.60 g). The mixture was degassed under N$_2$ and stirred at 100° C. for 8 h. The reaction mixture was treated with water, extracted with EtOAc, washed with water and brine, dried over Na$_2$SO$_4$, filtered, and concentrated in vacuo. The crude was purified by silica-gel column chromatography (heptane/EtOAc=4:1-3:1) to give the title compound. MS (ESI) m/z=331, 333 (M+H)

Step B. 2-Chloro-4-(9H-purin-9-yl)benzoic acid

Following the procedure of EXAMPLE 26 (Step C), tert-butyl 2-chloro-4-(9H-purin-9-yl)benzoate (135 mg, 0.41 mmol) was converted to the title compound. $^1$H NMR (400 MHz, DMSO-d$_6$) δ (ppm): 9.35 (1H, s), 9.21 (1H, s), 9.11 (1H, s), 8.31 (1H, d, J=1.8 Hz), 8.13 (1H, dd, J=8.5, 2.1 Hz), 8.06 (1H, d, J=8.2 Hz)

Step C (R)—N-(1-(3-Amino-4-chloroisoxazolo[5,4-c]pyridin-7-yl)pyrrolidin-3-yl)-2-chloro-4-(9H-purin-9-yl)benzamide To a solution of 2-chloro-4-(9H-purin-9-yl)benzoic acid (0.05 mmol, 13 mg), (R)-7-(3-aminopyrrolidin-1-yl)-4-chloroisoxazolo[5,4-c]pyridin-3-amine (12 mg, 0.05 mmol, EXAMPLE 11, Step E), and DIPEA (0.14 mmol, 0.02 mL) in CH$_2$Cl$_2$ (1 mL), HATU (0.06 mmol, 23 mg) was added. The mixture was stirred at RT for 50 min. The solvent was removed and purified by HPLC to give the title compound. MS (ESI) m/z=510, 512 (M+H)

Example 49

(R)—N-(1-(3-Amino-5-methylisoxazolo[5,4-c]pyridin-7-yl)pyrrolidin-3-yl)-2,6-dichloro-4-(1-methyl-5-oxo-1,5-dihydro-4H-1,2,4-triazol-4-yl)benzamide

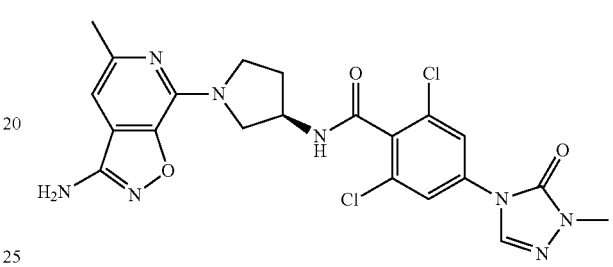

Step A. Methyl 2,6-dichloro-4-(5-oxo-1H-1,2,4-triazol-4(5H)-yl)benzoate

Following the procedures of EXAMPLE 45 (Step A-B), methyl 4-amino-2,6-dichlorobenzoate (15 mmol, 3.3 g, EXAMPLE 2, Step B) was converted to the title compound. MS (ESI) m/z=288, 290 (M+H)

Step B. 2,6-Dichloro-4-(1-methyl-5-oxo-1H-1,2,4-triazol-4(5H)-yl)benzoic acid

To a mixture of methyl 2,6-dichloro-4-(5-oxo-1H-1,2,4-triazol-4(5H)-yl)benzoate (9.7 mmol, 2.8 g) and K$_2$CO$_3$ (29 mmol, 4.0 g) in DMF (20 mL) at RT, methyl iodide (19 mmol, 1.2 mL) was added. The mixture was stirred at RT for 3 days. The mixture was diluted with ethyl acetate, washed with water, dried over Na$_2$SO$_4$, filtered, and concentrated in vacuo. To the residue, 1,4-dioxane (15 mL) and lithium hydroxide monohydrate (29 mmol, 1.2 g) in water (15 mL) were added and the mixture was stirred at 80° C. for 2 h. The mixture was cooled to 0° C., acidified to pH 4 with 4N HCl in dioxane and concentrated in vacuo. The crude was crystallized from acetonitrile-THF-MeOH (10:10:1) to give the desired product. MS (ESI) m/z=288, 290 (M+H)

$^1$H NMR (400 MHz, CD$_3$OD) δ (ppm): 8.25 (1H, s), 7.74 (2H, s), 3.48 (3H, s)

Step C. 2,6-Dichloro-4-(1-methyl-5-oxo-1H-1,2,4-triazol-4(5H)-yl)benzoyl chloride A mixture of 2,6-dichloro-4-(1-methyl-5-oxo-1H-1,2,4-triazol-4(5H)-yl)benzoic acid (5.2 mmol, 1.5 g) and SOCl$_2$ (10 mL) was stirred at 80° C. for 2 h. The mixture was concentrated in vacuo, triturated with cold CH$_2$Cl$_2$. The filtrate was concentrated in vacuo and the residue was triturated with cold ethyl acetate. Collected solid products were combined and the title compound was obtained. MS (ESI) m/z=306, 308 (M+H)

Step D (R)—N-(1-(3-Amino-5-methylisoxazolo[5,4-c]pyridin-7-yl)pyrrolidin-3-yl)-2,6-dichloro-4-(1-methyl-5-oxo-1,5-dihydro-4H-1,2,4-triazol-4-yl)benzamide To a mixture of (R)-7-(3-aminopyrrolidin-1-yl)-5-methylisoxazolo[5,4-c]pyridin-3-amine hydrochloride (27 mg, 0.10 mmol, EXAMPLE 42, Step E) and Et₃N (70 μL, 0.50 mmol) in CH₂Cl₂ (0.50 mL), 2,6-dichloro-4-(1-methyl-5-oxo-1H-1,2,4-triazol-4(5H)-yl)benzoyl chloride (31 mg, 0.10 mmol) was added. The mixture was stirred at RT for 1 h. The mixture was concentrated and purified by HPLC to give the title compound. MS (ESI) m/z=503, 505 (M+H)

Example 50

(R)—N-(1-(3-Amino-4-chloroisoxazolo[5,4-c]pyridin-7-yl)pyrrolidin-3-yl)-2-chloro-4-(5-oxo-1-(2,2,2-trifluoroethyl)-1,5-dihydro-4H-1,2,4-triazol-4-yl)benzamide

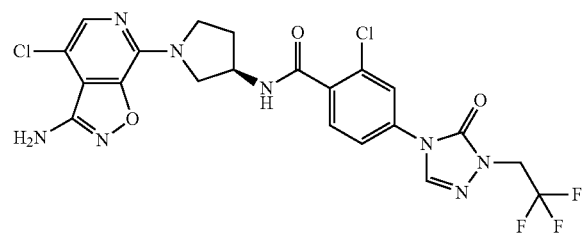 [SMILES: Nc1noc2c(N3CC[C@@H](NC(=O)c4ccc(-n5cnn(CC(F)(F)F)c5=O)cc4Cl)C3)ncc(Cl)c12]

Step A. 2-Chloro-4-(5-oxo-1-(2,2,2-trifluoroethyl)-1H-1,2,4-triazol-4(5H)-yl)benzoic acid Following the procedures of EXAMPLE 6 (Step H-J), methyl 2-chloro-4-(5-oxo-1H-1,2,4-triazol-4(5H)-yl)benzoate (2.0 mmol, 0.51 g, EXAMPLE 45, Step B) and 2,2,2-trifluoroethyl trifluoromethanesulfonate (4.0 mmol, 0.93 g) were converted to the title compound. MS (ESI) m/z=322, 324 (M+H)

¹H NMR (400 MHz, DMSO-d₆) δ (ppm): 8.76 (1H, s), 8.01 (1H, d, J=2.3 Hz), 7.96 (1H, d, J=8.7 Hz), 7.86 (1H, dd, J=8.5, 2.1 Hz), 4.72 (2H, q, J=9.1 Hz)

Step B (R)—N-(1-(3-Amino-4-chloroisoxazolo[5,4-c]pyridin-7-yl)pyrrolidin-3-yl)-2-chloro-4-(1-ethyl-5-oxo-1,5-dihydro-4H-1,2,4-triazol-4-yl)benzamide Following the procedure of EXAMPLE 5 (Step F), (R)-7-(3-aminopyrrolidin-1-yl)-4-chloroisoxazolo[5,4-c]pyridin-3-amine dihydrochloride (33 mg, 0.10 mmol, EXAMPLE 11, Step E) and 2-chloro-4-(5-oxo-1-(2,2,2-trifluoroethyl)-1H-1,2,4-triazol-4(5H)-yl)benzoic acid (32 mg, 0.10 mmol) were converted to the title compound. MS (ESI) m/z=557, 559 (M+H)

Example 51

(R)—N-(1-(3-Amino-4-chloroisoxazolo[5,4-c]pyridin-7-yl)pyrrolidin-3-yl)-2-chloro-4-(7H-purin-7-yl)benzamide

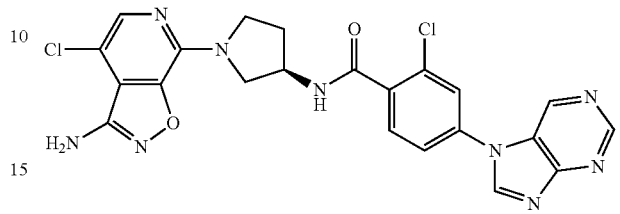

Step A. 2-Chloro-4-(7H-purin-7-yl)benzoic acid

Following the procedures of EXAMPLE 11 (Step A-B), purine was converted to the title compound. MS (ESI) m/z=275, 277 (M+H)

Step B (R)—N-(1-(3-Amino-4-chloroisoxazolo[5,4-c]pyridin-7-yl)pyrrolidin-3-yl)-2-chloro-4-(7H-purin-7-yl)benzamide Following the procedure of EXAMPLE 48 (Step C), 2-chloro-4-(7H-purin-7-yl)benzoic acid (0.07 mmol, 20 mg) was converted to the title compound. MS (ESI) m/z=510, 512 (M+H)

Example 52

(R)—N-(1-(3-Amino-4-chloroisoxazolo[5,4-c]pyridin-7-yl)pyrrolidin-3-yl)-3-chloro-5-(3-methyl-1H-1,2,4-triazol-1-yl)picolinamide

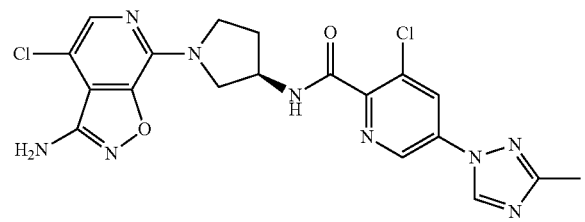 [SMILES: Cc1ncn(-c2cnc(C(=O)N[C@@H]3CCN(c4ncc(Cl)c5c(N)noc45)C3)c(Cl)c2)n1]

Step A. Methyl 5-bromo-3-chloropicolinate

To a round bottle flask with 5-bromo-3-chloropicolinic acid (4.2 mmol, 1.0 g) in MeOH (10 mL) was added SOCl₂ (5.1 mmol, 0.37 mL) dropwise at RT. The reaction mixture was refluxed for 1.5 h. After the solvent was removed, EtOAc was added to the residue, and the pH was adjusted to 7.0 by addition of sat. aq. NaHCO₃. The organic layer was dried over Na₂SO₄, filtered, and concentrated in vacuo to give the title compound. MS (ESI) m/z=250, 252 (M+H)

Step B. 3-Chloro-5-(3-methyl-1H-1,2,4-triazol-1-yl)picolinic acid

Following the procedures of EXAMPLE 6 (Step H-K), methyl 5-bromo-3-chloropicolinate (1.0 g) was converted to the title compound over 4 steps. MS (ESI) m/z=239, 241 (M+H)

$^1$H NMR (DMSO-d$_6$) δ (ppm): 9.24 (1H, s), 8.86 (1H, d, J=2.1 Hz), 8.31 (1H, d, J=2.1 Hz), 2.38 (3H, s)

Step C (R)—N-(1-(3-Amino-4-chloroisoxazolo[5,4-c]pyridin-7-yl)pyrrolidin-3-yl)-3-chloro-5-(3-methyl-1H-1,2,4-triazol-1-yl)picolinamide Following the procedure of EXAMPLE 1 (Step E), 3-chloro-5-(3-methyl-1H-1,2,4-triazol-1-yl)picolinic acid (21 mg, 0.09 mmol) and (R)-7-(3-aminopyrrolidin-1-yl)-4-chloroisoxazolo[5,4-c]pyridin-3-amine (20 mg, 0.08 mmol, EXAMPLE 11, Step E) were converted to the title compound.

MS (ESI) m/z=474, 476 (M+H)

Example 53

(R)—N-(1-(3-Amino-4-chlorobenzo[d]isoxazol-7-yl)pyrrolidin-3-yl)-2-chloro-4-(2-(hydroxymethyl)pyridin-4-yl)benzamide

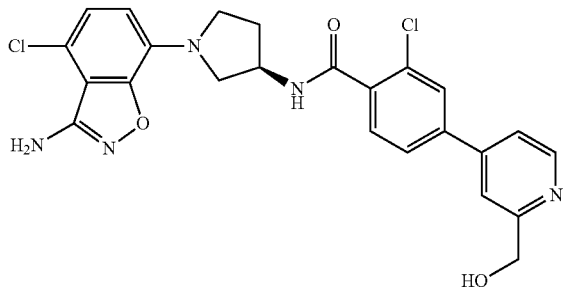 [SMILES: Nc1noc2c(N3CC[C@@H](NC(=O)c4ccc(-c5ccnc(CO)c5)cc4Cl)C3)ccc(Cl)c12]

Step A. Methyl 2-chloro-4-(2-(hydroxymethyl)pyridin-4-yl)benzoate

Following the procedure of EXAMPLE 25 (Step A), (3-chloro-4-(methoxycarbonyl)phenyl)boronic acid (150 mg, 0.70 mmol) and (4-bromopyridin-2-yl)methanol (132 mg, 0.70 mmol) were converted to the title compound. MS (ESI) m/z=278, 280 (M+H)

Step B. 2-Chloro-4-(2-(hydroxymethyl)pyridin-4-yl)benzoic acid

Following the procedure of EXAMPLE 25 (Step B), methyl 2-chloro-4-(2-(hydroxymethyl)pyridin-4-yl)benzoate (139 mg, 0.50 mmol) was converted to the title compound.

$^1$H NMR (300 MHz, DMSO-d$_6$) δ (ppm): 13.54 (1H, s), 8.59 (1H, dd, J=5.2, 0.7 Hz), 7.95 (1H, d, J=1.4 Hz), 7.94 (1H, d, J=7.9 Hz), 7.84 (1H, dd, J=8.1, 1.9 Hz), 7.79 (1H, d, J=1.0 Hz), 7.66 (1H, dd, J=5.2, 2.1 Hz), 5.51 (1H, s), 4.63 (2H, s)

MS (ESI) m/z=264, 266 (M+H)

Step C (R)—N-(1-(3-Amino-4-chlorobenzo[d]isoxazol-7-yl)pyrrolidin-3-yl)-2-chloro-4-(2-(hydroxymethyl)pyridin-4-yl)benzamide Following the procedure of EXAMPLE 5 (Step F), (R)-7-(3-aminopyrrolidin-1-yl)-4-chlorobenzo[d]isoxazol-3-amine (0.079 mmol, 20 mg, EXAMPLE 9, Step A) and 2-chloro-4-(2-(hydroxymethyl)pyridin-4-yl)benzoic acid (0.079 mmol, 21 mg) were converted to the title compound.

MS (ESI) m/z=498, 500 (M+H)

UTILITY

The invention also relates to medicaments which contain an efficacious amount of at least one compound of the Formula (I) and/or of a pharmaceutically acceptable salt of the compound of the Formula (I) and/or an optionally stereoisomeric form of the compound of the Formula (I), together with a pharmaceutically suitable and pharmaceutically acceptable vehicle, additive and/or other active substances and auxiliaries.

On account of their pharmacological properties, the compounds according to the invention are suitable, for example, for the prophylaxis, secondary prevention and therapy of all those diseases which are treatable by inhibition of blood clotting factor IXa. Thus, the compounds according to the invention are suitable as inhibitors both for prophylactic and for therapeutic administration to humans. They are suitable both for acute treatment and for long-term therapy. The compounds of the Formula (I) can be employed in patients who are suffering from disorders of well-being or diseases which accompany thromboses, embolisms, hypercoagulability or fibrotic changes. These include myocardial infarct, angina pectoris and all other forms of acute coronary syndrome, stroke, peripheral vascular diseases, deep vein thrombosis, pulmonary embolism, embolic or thrombotic events caused by cardiac arrhythmias, cardiovascular events such as restenosis after revascularization, angioplasty and similar interventions such as stent implantations and bypass operations. Furthermore, the compounds of the Formula (I) can be employed in all interventions which lead to contact of the blood with foreign surfaces, as in dialysis patients and patients with indwelling catheters. Compounds of the Formula (I) can also be employed in order to reduce the risk of thrombosis after surgical interventions such as in knee and hip joint operations.

Compounds of the Formula (I) are suitable for the treatment of patients with disseminated intravascular coagulation, sepsis and other intravascular events which accompany inflammation. Furthermore, compounds of the Formula (I) are suitable for the prophylaxis and treatment of patients with atherosclerosis, diabetes and the metabolic syndrome and their sequelae. Disorders of the hemostatic system (for example fibrin deposits) have been implicated in mechanisms which lead to tumor growth and tumor metastasis, and in the inflammatory and degenerative joint diseases such as rheumatoid arthritis and arthrosis. Compounds of the Formula (I) are suitable for the retardation or prevention of such processes.

Further indications for the use of the compounds of the Formula (I) are fibrotic changes of the lungs such as chronic obstructive pulmonary disease, adult respiratory distress syndrome (ARDS) and of the eye, such as fibrin deposits after eye operations. Compounds of the Formula (I) are also suitable for the prevention and/or treatment of scar formation.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates (including humans), sheep, horses, cattle, pigs, dogs, cats, rats, and mice.

Factor IXa inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the Factor IXa inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor IXa inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor IXa inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor IXa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula (I) can be administered both as a monotherapy and in combination or together with all antithrombotics (anticoagulants and platelet aggregation inhibitors), thrombolytics (plasminogen activators of any type), other profibrinolytically active substances, hypotensives, blood sugar regulators, lipid-lowering agents and antiarrhythmics.

The inhibitatory effectiveness of compounds of the present invention to the coagulation factors XIa, VIIa, IXa, Xa, plasma kallikrein or thrombin, can be determined using a relevant purified serine protease, respectively, and an appropriate synthetic substrate.

Pharmacological Examples (1) Determination of Inhibitory Activity Against Factor IXa Inhibitory activity against factor IXa was tested using the substrate SPECTROFLUOR FIXa (american diagnostica inc.; 500 West Avenue, Stamford, Conn. 06902 USA; Pr. No. 299F) and human factor IXa (american diagnostica inc.; Pr. No. 449b). Test substances were dissolved in buffer A (50 mM α,α,α-tris(hydroxymethyl) methylamine (Tris), 100 mM NaCl, 5 mM $CaCl_2$, 15% (v/v) ethylene glycol, pH 8.0) were mixed with factor IXa (0.1 µg/ml final concentration). The enzyme reaction was started by addition of SPECTROFLUOR FIXa (100 µM final concentration). After incubation for 60 minutes at room temperature, the reaction was stopped by the addition of 20% (v/v) acetic acid solution, and then the fluorescence value was measured (Excitation Wavelength: 355 nm, Emission Wavelength; 460 nm) in a microtiter plate reader (ARVO 1420 Multilabel Counter; PerkinElmer).

The $IC_{50}$ was calculated from a dilution series of the test substance with the aid of the software, Symyx Assay Explorer (Symyx Technologies, Inc.).

Table 1 shows the results of in vitro FIXa inhibition activity ($IC_{50}$) of Example compounds.

TABLE 1

| Ex No. | FIXa $IC_{50}$ [nM]# |
|---|---|
| 1 | A |
| 2 | A |
| 3 | A |
| 4 | B |
| 5 | A |
| 6 | A |
| 7 | A |
| 8 | A |
| 9 | A |
| 10 | A |
| 11 | A |
| 12 | A |
| 13 | B |
| 14 | A |
| 15 | A |
| 16 | A |
| 17 | A |
| 18 | B |
| 19 | B |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | B |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | B |
| 53 | A |

Factor IXa enzyme assay human $IC_{50}$ [nM]
Character of "A" in the column of FIXa $IC_{50}$ mean the range of $IC_{50} \leq 100$ nM.
Character of "B" in the column of FIXa $IC_{50}$ mean the range of $100$ nM $< IC_{50} \leq 1000$ nM.

In one embodiment, the compounds of the present invention were selective factor IXa inhibitors, i.e., selective for factor IXa over other coagulation factors, such as factor Xa.

(2) Determination of Inhibitory Activity Against Factor Xa

This measuring was performed as well as Factor IXa method excluding the following conditions. As substrate and enzyme, SPECTROFLUOR FXa (american diagnostica inc.; Pr. No. 222F, 100 µM final concentration) and human factor Xa (american diagnostica inc.; Pr. No. 526, 44 ng/ml final concentration) were used respectively. Test substances were dissolved in buffer B (20 mM Tris, 200 mM NaCl, 2.5 mM $CaCl_2$, pH 8.0).

Selectivity Calculation

Selectivity for Factor IXa activity over Factor Xa activity can be determined by the following calculation: ($IC_{50}$ Factor Xa)/(IC$_{50}$ Factor IXa). Similar calculations can be made for selectivity of compounds for Factor IXa compared to other coagulation factors.

These as well as other ways of minimizing contact between the components of combination products of the present invention, whether administered in a single dosage form or administered in separate forms but at the same time by the same manner, will be readily apparent to those skilled in the art, once armed with the present disclosure.

(3) Solubility Test (i) DMSO Precipitation Solubility (Kinetic Solubility)

A 10 mM solution of the compound of the invention in DMSO is added to 50 mM phosphate-buffered saline (pH 7.4) in a final concentration of 100 μM. The solution is incubated at room temperature for 1.5 hours while stirring at 600 rpm, and then filtered through a filter plate (4 μm, MultiScreen Solubility Filter Plate (Millipore)). Absorbance of the filtrate is measured on a plate reader (Powerscan HT (Dainippon Pharmaceutical Co., Ltd.)) at the maximum absorption wavelength. At the same time, solutions containing the test compound of known concentrations (1, 3, 10, 30 and 100 μM) are prepared as standard solutions for calibration; absorbance in each of the standard solutions in different concentrations is measured to prepare a calibration curve. The solubility (μM) of the compound is determined from the absorbance values of the filtrate and standard solutions.

(4) Metabolic Stability Test

A 10 mM solution of the compound of the invention in DMSO is added to a liver microsome solution (human, rat; XenoTech) and NADPH-regenerating solution (water containing β-NADP, glucose-6-phosphate, G-6-PDH(Y) and MgCl$_2$) in a final concentration of 1 μM. After incubation of the solution at 37° C. for 10 minutes or 20 minutes, the reaction is stopped by addition of acetonitrile. The reaction solution is centrifuged and filtered through a filter plate (MultiScreen HTS-HV Plate (Millipore)). A test compound in the filtrate is measured using liquid chromatography with tandem mass spectrometry (LC-MS/MS). Likewise, a sample with 0 reaction time is measured as a control, and the metabolic clearance (μL/min/mg protein) and the degradation rate (%) are determined by comparing the microsome reaction sample with the control.

(5) hERG Inhibitory Test by Patch Clamp Method

An effect on hERG (a human ether-a-go-go related gene) channel is measured with a fully automated patch-clamp system (Patchliner (Nanion) or QPatch HT (Sophion Bioscience)). To confirm the hERG I$_{Kr}$ current in cells, a depolarization pulse is applied on a regular basis, while membrane potential is clamped at −80 mV. After the generated current is stabilized, a test compound is added to a perfusate. The effect of the test compound on the hERG channel is confirmed by changes in tail current induced by applying depolarization pulses having a voltage of 40 mV (Patchliner) or 20 mV (QPAtch) and subsequent repolarization pulse having a voltage of −40 mV (Patchliner) or −50 mM (QPatch). The stimulus is given once every 10 seconds (Patchliner) or 15 seconds (QPatch). The measurement is performed at room temperature. The hERG channel inhibitory activity is calculated as a reduction ratio (suppression rate) of the tail current 2 minutes before addition of a test compound, when compared to the maximum tail current.

Calculation of this inhibitory activity enables to estimate the drug-induced QT prolongation and subsequent fatal adverse effects (ventricular tachycardia, sudden death, etc.).

The preferred compounds of the invention show the hERG (human ether-a-go-go related gene) inhibitory activity not less than 10 μM in terms of the IC$_{50}$ value.

(6) Plasma Protein Binding Rate Test

A 10 mM solution of the compound of the invention in DMSO is added to normal plasma (human, rat) in a final concentration of 10 μM. After dialysis at 37° C. for 4 hours with a rapid equilibrium dialysis device (RED Device (Linden Bioscience) or HTD96b (HTDialysis)), the solution of plasma side and the solution opposite to the dialysis membrane (PBS side) are subjected to LC-MS/MS to measure the test compound in the samples. The fraction unbound (%) is calculated from a ratio of the PBS side to the plasma side, and the plasma protein binding rate (%) is calculated from 100−the fraction unbound (%).

(7) Permeability in MDCKII Cell Monolayers

The permeability was evaluated by measuring transepithelial flux, using MDCKII cells. The cells were cultured for 3 days after seeding and grown to confluency on permeable polycarbonate membrane inserts, to permit flux experiments after loading on the apical side. The concentrations of the permeated compound of the invention were measured by LC-MS/MS. The flux across the MDCKII cell monolayers were linear with time for up to 1 h. 10 mM HEPES (pH 7.4) was used for loading buffer on the apical side and 10 mM HEPES (pH 7.4) containing 4% BSA was used for buffer on the basolateral side.

Pharmacological Experiment 7: Pharmacokinetics Test (Rat Cassette PK)

The compound of the invention is administering to male SD rats of 7 to 9 weeks old at a dose of 1 mg/kg (solvent for administration, DMSO: Tween 80: water=1:1:8, 10 mL/kg). Subsequently, blood is collected from the jugular vein 0.5, 1, 2 and 4 hours after the administration. Blood is centrifuged and plasma is obtained. The test compound in the plasma is extracted using organic solvents and measured using liquid chromatography/mass spectrometry. Likewise, concentrations (μg/mL) in the plasma is determined from a calibration curve prepared using standard solutions of the test compound having the known concentrations. The maximum plasma concentration is expressed as Cmax (μg/mL).

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

A number of references have been cited, the entire disclosures of which have been incorporated herein in their entirety.

The compounds of the present invention may also be useful as inhibitors of additional serine protease, notably human thrombin, human plasma kallikrein and human plasmin. Because of their inhibitory action, these compounds are indicated for use in the prevention or treatment of physiological reactions, as it were "Conditions" including thromboembolic disorder (arterial cardiovascular thromboembolic disorders, venous cardiovascular thromboembolic disorders, thromboembolic disorders in the chambers of the heart, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a)

prosthetic valves or other implants, (b) indwelling catheters, (c) stents, (d) cardiopulmonary bypass, (e) hemodialysis, or (f) other procedures in which blood is exposed to an artificial surface that promotes thrombosis), blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include antithrombotics (anti-coagulant or coagulation inhibitory agents anti-platelet or platelet inhibitory agents or platelet aggregation inhibitors), anti-inflammatory agents, thrombin inhibitors, thrombolytics (plasminogen activators) or fibrinolytic agents, other profibrinolytically active substances, thrombin receptor (PAR-1) antagonist, hypotensives, blood sugar regulators, lipid-lowering agents, antiarrhythmics, a factor IXa inhibitor different from the compound of claim 1, a factor VIIa inhibitor, a factor VIIIa inhibitor, a factor Xa inhibitor, factor XIa inhibitors, factor XIIa inhibitors, TAFI, adenosine diphosphate antiplatelet agents (e.g., P2Y12 antagonists), fibrinogen inhibitors (fibrinogen receptor antagonists) (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin.

For example, patients suffering from coronary artery disease, and patients subjected to angioplasty procedures, would benefit from coadministration of fibrinogen receptor antagonists and thrombin inhibitors. Factor IXa inhibitors may be administered first following thrombus formation, and tissue plasminogen activator or other plasminogen activator is administered thereafter.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as define below, to a mammal in a therapeutically effective amount. When administered in a combination, the combination of compounds in preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Compounds which can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVANO), aprotinin, synthetic pentasaccharide, direct acting thrombin inhibitors including hirudin and argatroban, as well as other factor VIIa inhibitor, VIIIa inhibitor, IXa inhibitor, Xa inhibitor, XIa inhibitor, thrombin inhibitor, fibrinogen inhibitors, TAFI, and known in the art. Factor IXa inhibitors different from the compounds of Formula (I) include synthetic active-site blocked competitive inhibitors, oral inhibitors and RNA aptamers. These are described in the previously cited Howard et al. reference (Howard, E L, Becker K C, Rusconi, C P, Becker R C. Factor IXa Inhibitors as Novel Anticoagulants. *Arterioscler Thromb Vasc Biol.* 2007; 27: 722-727.).

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors P2Y1 and P2Y12 with P2Y12 being even more preferred. Preferred P2Y12 receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-I and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptiders include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term "thrombin receptor antagonists", also known as protease activated receptor (PAR) antagonists or PAR-1 antagonists, are useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al, *J. Med. Chem.*, vol. 39, pp. 4879-4887 (1996), tetra- and pentapeptides are disclosed as being potent thrombin receptor antagonists, for example N-trans-cinnamoyl-p-fluoroPhe-p-guanidinoPhe-Leu-Arg-NH$_2$ and N-trans-cinnamoyl-p-fluoroPhe-p-guanidinoPhe-Leu-Arg-Arg-NH$_2$. Peptide thrombin receptor antagonists are also disclosed in WO 94/03479, published Feb. 17, 1994.

Substituted tricyclic thrombin receptor antagonists are disclosed in U.S. Pat. Nos. 6,063,847, 6,326,380 and WO 01/96330 and Ser. No. 10/271,715.

Other thrombin receptor antagonists include those disclosed in U.S. Pat. Nos. 7,1304,078; 7,235,567; 7,037,920; 6,645,987; and EP Patent Nos. EP1495018 and EP1294714.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complexes, including pharmaceutically acceptable salts or prodrugs thereof. The term anistreplase, as used herein, refers to anisoylated plasminogen streptokinase activator complexes, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvedilol and propranolol); Class III agents (such as sotalol, dofetilide, aminodarone, azimilide and ibutilide); Class IV agents (such as ditiazem and verapamil); K+ cannel openers such as IAch inhibitors, and IKur inhibitors (e.g., compounds such as those disclosed in WO01/40231).

The term antihypertensive agents, as used herein, include: alpha adrenergic blockers; beta adrenergic blockers; calcium channel blockers (e.g., diltiazem, verapamil nifedipine, amlodipine, felodipine, gallopamil, niludipine, nimodipine, nicardipine and mybefradil); diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamterene, amiloride, spironolactone); rennin inhibitors; angiotensin-converting enzyme (ACE) inhibitors (e.g., captopril, lisinopril, fosinopril, enalapril, ceranopril, cilazopril, delapril, pentopril, quinapril, ramipril, Lisinopril, alacepril, benazepril, enalaprilat, imidapril, moveltipril, spirapril, temocapril, or trandolapril); angiotensin-II-receptor antagonists (also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual CCE/NEP inhibitors, e.g., omapatrilat, gemopatrilat, nitrates); and β-blockers (e.g., propranolol, nadolol, or carvedilol).

Examples of suitable cardiac glycosides for use in combination with compounds of the present invention include digitalis and ouabain.

Examples of suitable mineralocorticoid receptor antagonists for use in combination with the compounds of the present invention include spironolactone and eplirinone.

Examples of suitable cholesterol/lipid lowering agents and lipid profile therapies for use in combination with the compounds of the present invention include: HMG-CoA reductase inhibitors (e.g., simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®), NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; cholesterol absorption inhibitors (e.g., ezetimibe (ZETIA®), and ezetimibe in combination with any other lipid lowering agents such as the HMG-CoA reductase inhibitors noted above and particularly with simvastatin (VYTORIN®) or with atorvastatin calcium); and cholesterol ester transfer protein inhibitors (e.g., CP-529414).

Examples of suitable anti-diabetic agents for use in combination with the compounds of the present invention include: biguanides (e.g., metformin); alpha glucosidase inhibitors (e.g., acarbose, miglitol); insulins (including insulin secretagogues or insulin sensitizers); meglitinides (e.g., repaglinide, nateglinide); sulfonylureas (e.g., chlorpropamide, tolazamide, tolbutamide, glimepiride, glyburide and glipizide); biguanide/glyburide combinations (e.g., glucovance), thiazolidinediones also referred to as glitazones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagons-like peptide-1 (GLP-1), and dipeptidyl peptidase IV (DPP4) inhibitors (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; piroxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., conjugated estrogens) and estradiol.

Examples of suitable anti-obesity agents for use in combination with the compounds of the present invention include orlistat and aP2 inhibitor (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporine A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Further more, examples of additional active agents which may be employed include but are not limited to potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxy-propoxy)-phenyl]-octanamid hemifumarate) SPP600, SPP630 and SPP635); endothelin receptor antagonists; vasodilators (e.g. nitroprusside); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists.

Typical doses of Factor IXa inhibitors of the invention in combination with other suitable anti-platelet agents, anticoagulation agents, or thrombolytic agents may be the same as those doses of Factor IXa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

TABLE 2

NMR Data of EXAMPLE Compounds

| Ex. No. | $^1$H NMR δ (ppm) |
|---|---|
| 5* | DMSO-$d_6$: 9.21 (2H, s), 8.89 (1H, d, J = 6.9 Hz), 7.99 (1H, d, J = 2.4 Hz), 7.80 (1H, d, J = 5.2 Hz), 7.76 (1H, dd, J = 8.2, 2.4 Hz), 7.63 (1H, d, J = 8.2 Hz), 6.94 (1H, d, J = 5.5 Hz), 6.42 (2H, s), 4.61-4.49 (1H, m), 4.05-3.96 (1H, m), 3.91-3.75 (3H, m), 2.32-2.19 (1H, m), 2.12-2.00 (1H, m) |
| 7* | CD$_3$OD: 9.05 (2H, s), 7.86 (2H, s), 7.06 (1H, dd, J = 7.6, 7.6 Hz), 6.94 (1H, d, J = 7.2 Hz), 6.51 (1H, d, J = 7.0 Hz), 4.00-3.81 (4H, m), 2.75-2.66 (1H, m), 1.43 (3H, s), 1.14 (3H, d, J = 6.9 Hz) (NH$_2$ and NH were not observed.) |
| 8* | CD$_3$OD: 9.08 (2H, s), 7.88 (2H, s), 7.09 (1H, t, J = 7.7 Hz), 7.00 (1H, d, J = 6.9 Hz), 6.61 (1H, d, J = 7.6 Hz), 4.52-4.49 (2H, m), 4.05-4.00 (2H, m), 3.78-3.73 (1H, m), 3.61-3.55 (1H, m), 3.16-3.13 (1H, m) |
| 9* | DMSO-$d_6$: 9.22 (2H, d, J = 3.1 Hz), 8.90 (1H, d, J = 6.9 Hz), 8.00 (1H, d, J = 2.4 Hz), 7.76 (1H, dd, J = 8.2, 2.1 Hz), 7.63 (1H, d, J = 8.2 Hz), 7.05 (1H, d, J = 8.6 Hz), 6.50 (1H, d, J = 8.2 Hz), 6.03 (2H, s), 4.61-4.50 (1H, m), 3.86 (1H, dd, J = 10.3, 6.5 Hz), 3.69-3.48 (3H, m), 2.34-2.21 (1H, m), 2.10-1.98 (1H, m) |
| 12 | CD$_3$OD: 9.08 (2H, s), 7.89 (1H, d, J = 1.8 Hz), 7.70-7.63 (2H, m), 6.51 (1H, s), 4.73-4.60 (2H, m), 3.90 (1H, dd, J = 10.3, 6.2 Hz), 3.80-3.58 (3H, m), 2.46-2.38 (1H, m), 2.36 (3H, s), 2.21-2.11 (1H, m) |
| 13 | DMSO-$d_6$: 9.26 (2H, s), 8.92 (1H, d, J = 6.9 Hz), 8.02 (1H, d, J = 2.3 Hz), 7.78 (1H, dd, J = 8.2, 2.3 Hz), 7.65 (1H, d, J = 8.2 Hz), 6.86 (1H, t, J = 8.9 Hz), 6.50 (1H, dd, J = 8.7, 4.1 Hz), 6.17 (2H, brs), 4.61-4.52 (1H, m), 3.82 (1H, dd, J = 10.1, 6.4 Hz), 3.68-3.31 (3H, m), 2.35-2.25 (1H, m), 2.07-1.99 (1H, m) |

TABLE 2-continued

NMR Data of EXAMPLE Compounds

| Ex. No. | $^1$H NMR δ (ppm) |
|---|---|
| 15* | CD$_3$OD: 9.04 (1H, s), 8.69 (1H, brs), 7.91 (1H, d, J = 2.1 Hz), 7.77 (1H, dd, J = 8.2, 2.1 Hz), 7.53 (1H, d, J = 8.2 Hz), 6.93 (1H, d, J = 2.1 Hz), 6.45 (1H, d, J = 1.7 Hz), 4.19 (1H, d, J = 10.3 Hz), 3.84-3.61 (2H, m), 3.68 (1H, d, J = 10.7 Hz), 2.68-2.51 (1H, m), 2.42 (3H, s), 2.18-2.04 (1H, m), 1.69 (3H, s) (NH$_2$ was not observed.) |
| 21* | DMSO-d$_6$: 8.99 (2H, s), 8.84 (1H, d, J = 6.9 Hz), 7.91 (1H, d, J = 1.7 Hz), 7.78 (1H, s), 7.75 (1H, dd, J = 7.9, 1.7 Hz), 7.54 (1H, d, J = 7.9 Hz), 6.21 (2H, brs), 4.60-4.50 (1H, m), 4.02-3.75 (7H, m), 2.32-2.17 (1H, m), 2.12-2.00 (1H, m) |
| 28* | DMSO-d$_6$: 9.04-8.96 (2H, m), 7.85 (1H, s), 7.79 (1H, d, J = 1.4 Hz), 7.69-7.59 (2H, m), 7.41 (1H, t, J = 52.2 Hz), 6.20 (2H, brs), 4.62-4.50 (1H, m), 4.03-3.76 (4H, m), 2.32-2.18 (1H, m), 2.16-2.02 (1H, m) |
| 33 | DMSO-d$_6$: 9.34 (1H, d, J = 1.4 Hz), 8.91 (1H, d, J = 6.4 Hz), 8.75 (1H, dd, J = 2.5, 1.6 Hz), 8.67 (1H, d, J = 2.3 Hz), 8.24 (1H, d, J = 1.8 Hz), 8.15 (1H, dd, J = 8.0, 1.6 Hz), 7.79 (1H, s), 7.60 (1H, d, J = 8.2 Hz), 6.22 (2H, brs), 4.60-4.52 (1H, m), 4.02-3.95 (1H, m), 3.90-3.77 (3H, m), 2.30-2.20 (1H, m), 2.12-2.02 (1H, m) |
| 35 | DMSO-d$_6$: 8.82 (1H, d, J = 6.9 Hz), 8.26 (1H, d, J = 2.3 Hz), 7.96 (1H, dd, J = 9.6, 2.7 Hz), 7.78 (1H, s), 7.70 (1H, d, J = 1.8 Hz), 7.57 (1H, dd, J = 8.2, 1.8 Hz), 7.50 (1H, d, J = 7.8 Hz), 6.60 (1H, d, J = 9.1 Hz), 6.22 (2H, brs), 4.89 (2H, q, J = 9.0 Hz), 4.60-4.48 (1H, m), 4.01-3.94 (1H, m), 3.90-3.75 (3H, m), 2.30-2.18 (1H, m), 2.10-2.00 (1H, m) |
| 41* | DMSO-d$_6$: 9.26 (1H, s), 8.87 (1H, d, J = 6.2 Hz), 8.00 (1H, d, J = 2.1 Hz), 7.83 (1H, dd, J = 8.4, 2.2 Hz), 7.62 (1H, d, J = 8.6 Hz), 7.58 (1H, s), 6.69 (2H, s), 4.59-4.51 (1H, m), 4.05-3.78 (4H, m), 2.36 (3H, s), 2.30-2.19 (1H, m), 2.13-2.02 (1H, m) |
| 45 | DMSO-d$_6$: 8.84 (1H, d, J = 6.9 Hz), 8.54 (1H, s), 7.89 (1H, d, J = 2.3 Hz), 7.76-7.73 (2H, m), 7.56 (1H, d, J = 8.7 Hz), 6.18 (2H, s), 4.56-4.48 (1H, m), 3.98-3.92 (1H, m), 3.86-3.73 (3H, m), 3.36 (3H, s), 2.27-2.17 (1H, m), 2.08-1.98 (1H, m) |
| 52* | DMSO-d$_6$: 9.32 (1H, s), 9.05 (1H, d, J = 6.9 Hz), 9.01 (1H, d, J = 2.1 Hz), 8.52 (1H, d, J = 2.1 Hz), 7.79 (1H, s), 6.21 (2H, brs), 4.63-4.52 (1H, m), 4.00 (1H, dd, J = 11.0, 5.8 Hz), 3.90-3.74 (3H, m), 2.39 (3H, s), 2.33-2.20 (1H, m), 2.16-2.02 (1H, m) |

No mark in Ex. No.: 400 MHz,
*300 MHz

TABLE 3

LC/MS Data of Example Compounds

| EX. No. | LC/MS m/z [M + H]$^+$ | LC/MS retention time min |
|---|---|---|
| 1[#] | 424, 426 | 4.13 |
| 2[#] | 472, 474 | 4.7 |
| 3 | 535 | 1.03 |
| 4[#] | 474, 476 | 4.38 |
| 5[##] | 425, 427 | 2.88 |
| 6[#] | 486, 488 | 5.2 |
| 7[#] | 486, 488 | 4.88 |
| 8[#] | 474, 476 | 3.63 |
| 9 | 458, 460 | 0.94 |
| 10[#] | 458, 460 | 4.83 |
| 11[#] | 473, 475 | 4.95 |
| 12[#] | 472, 474 | 5.12 |
| 13[#] | 442, 444 | 4.45 |
| 14[##] | 492, 494 | 5.25 |
| 15[#] | 486, 488 | 5.57 |
| 16 | 488, 490 | 0.96 |
| 17[#] | 498, 500 | 5.68 |
| 18 | 442, 444 | 1.00 |
| 19 | 438, 440 | 0.98 |
| 20 | 470, 472 | 0.92 |
| 21 | 500, 502 | 1.00 |
| 22 | 495, 497 | 0.99 |
| 23[#] | 502, 504 | 4.93 |
| 24[#] | 459, 461 | 4.60 |
| 25[#] | 498, 500 | 4.50 |
| 26[#] | 501, 503 | 5.17 |
| 27[###] | 502, 504 | 3.83 |
| 28 | 509, 511 | 0.91 |
| 29 | 508, 510 | 0.97 |
| 30 | 470, 472 | 0.90 |
| 31 | 513, 515 | 0.80 |
| 32 | 509, 511 | 0.92 |
| 33 | 470, 472 | 0.98 |
| 34 | 463, 465 | 0.95 |
| 35 | 567, 569 | 1.01 |
| 36 | 425, 427 | 0.84 |
| 37 | 535, 537 | 1.00 |
| 38 | 509, 511 | 0.92 |
| 39 | 489, 491 | 0.98 |
| 40 | 500, 502 | 0.97 |
| 41 | 464, 466 | 0.94 |
| 42[##] | 483, 485 | 3.41 |
| 43 | 527, 529 | 0.96 |
| 44 | 500, 502 | 0.87 |
| 45 | 489, 491 | 0.90 |
| 46 | 475, 477 | 0.86 |
| 47[###] | 519, 521 | 4.43 |
| 48 | 510, 512 | 0.92 |
| 49[#] | 503, 505 | 3.27 |
| 50 | 557, 559 | 0.96 |

TABLE 3-continued

| | LC/MS Data of Example Compounds | |
|---|---|---|
| | LC/MS | |
| EX. No. | m/z [M + H]⁺ | retention time min |
| 51 | 510, 512 | 0.87 |
| 52 | 474, 476 | 0.95 |
| 53 | 498, 500 | 0.89 |

No mark in Ex. No.: UPLC,
HPLC (TFA),
HPLC (AcOH)

What is claimed is:

1. A compound of the Formula (I)

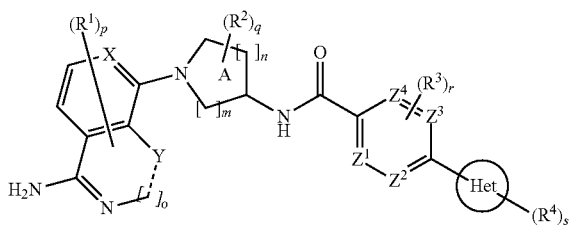

(I)

or a pharmaceutically acceptable salt thereof;

wherein: m is an integer of 1 to 2; n is an integer of 1 to 2; o is an integer of 0 or 1; p is an integer of 0 to 5; q is an integer of 0 to 4; r is an integer of 0 to 4; s is an integer of 0 to 4; X is a nitrogen atom or CH; Y is an oxygen atom, a sulfur atom or NH (when o=0), a nitrogen atom or CH (when o=1);

$Z_1$, $Z_2$, $Z_3$, $Z_4$ are each independently a nitrogen atom or CH;

each $R^1$ is independently a halogen atom, a cyano group, a $C_{1-6}$ alkyl group, a halogenated $C_{1-6}$ alkyl group, a hydroxyl $C_{1-6}$ alkyl group, a $C_{3-12}$ cycloalkyl group, a $C_{1-6}$ alkoxy group, a halogenated $C_{1-6}$ alkoxy group, a $C_{2-7}$ alkanoyl group or a group of —$NR^A R^B$;

$R^A$ and $R^B$ are each independently a hydrogen atom, a $C_{1-6}$ alkyl group or a $C_{2-7}$ alkanoyl group;

each $R^2$ is independently a hydroxyl group, a $C_{1-6}$ alkyl group, a halogenated $C_{1-6}$ alkyl group, a hydroxyl $C_{1-6}$ alkyl group, a $C_{1-6}$ alkoxy group, a halogenated $C_{1-6}$ alkoxy group, a $C_{6-14}$ aryl group, a heteroaryl group or oxo;

each $R^3$ is independently a halogen atom, a cyano group, a $C_{1-6}$ alkyl group, a halogenated $C_{1-6}$ alkyl group, a $C_{3-12}$ cycloalkyl group, a $C_{1-6}$ alkoxy group or a halogenated $C_{1-6}$ alkoxy group;

each $R^4$ is independently a halogen atom, a cyano group, a $C_{1-6}$ alkyl group, a $C_{3-12}$ cycloalkyl group, a halogenated $C_{1-6}$ alkyl group, a hydroxy $C_{1-6}$ alkyl group, a cyanated $C_{1-6}$ alkyl group, a $C_{1-6}$ alkoxy group, a $C_{1-6}$ alkoxy $C_{1-6}$ alkyl group, a halogenated $C_{1-6}$ alkoxy group, a $C_{2-7}$ alkanoyl group, a $C_{1-6}$ alkylthio group, a $C_{1-6}$ alkylsulfonyl group, a group of —$NR^A R^B$ or oxo;

a dotted line in a substructure of a bicycle represented by Formula (II):

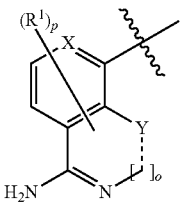

(II)

represents a single bond when o is 0 or a double bond when o is 1;

is heteroaryl.

2. The compound of claim 1, or a pharmaceutically acceptable salt thereof, wherein m is 1 and n is 1.

3. The compound of claim 1, or a pharmaceutically acceptable salt thereof, wherein o is 1.

4. The compound of claim 1, or a pharmaceutically acceptable salt thereof, wherein o is 0.

5. The compound of claim 1, or a pharmaceutically acceptable salt thereof, wherein p is an integer of 0 to 2, q is an integer of 0 to 2, r is an integer of 0 to 2 and s is 0 or 1.

6. The compound of claim 1, or a pharmaceutically acceptable salt thereof, wherein the substructure of Formula (V):

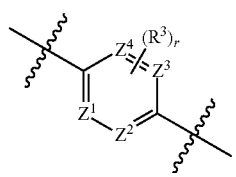

(V)

in Formula (I) is:

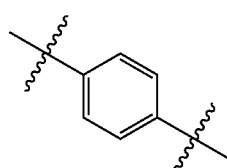 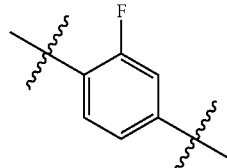

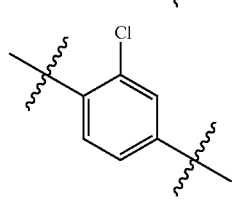 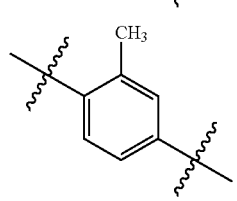

-continued
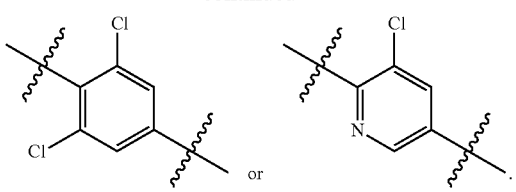 or 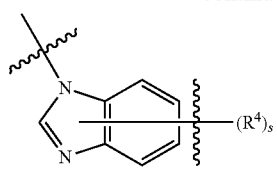.
7. The compound of claim 1, or a pharmaceutically acceptable salt thereof, wherein
(Het) is:
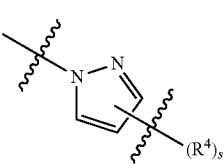
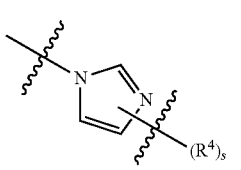
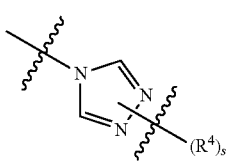
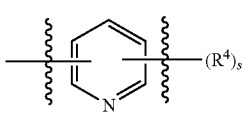
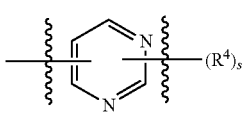
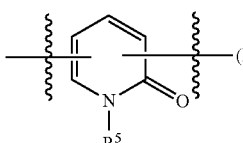
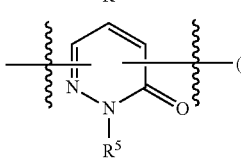
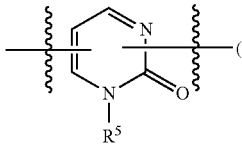
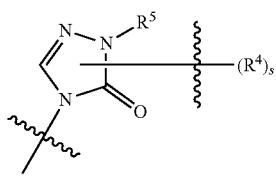
-continued
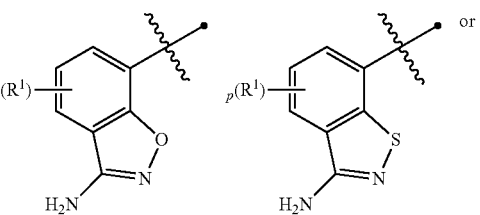
8. The compound of claim 1, or a pharmaceutically acceptable salt thereof, wherein the substructure of Formula (II):
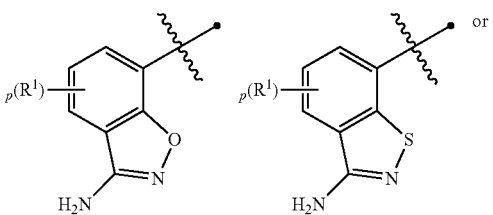
in Formula (I) is:

-continued

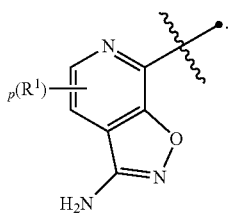

9. The compound of claim 8, or a pharmaceutically acceptable salt thereof, wherein a substructure of Formula (II):

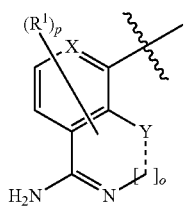

(II)

in Formula (I) is:

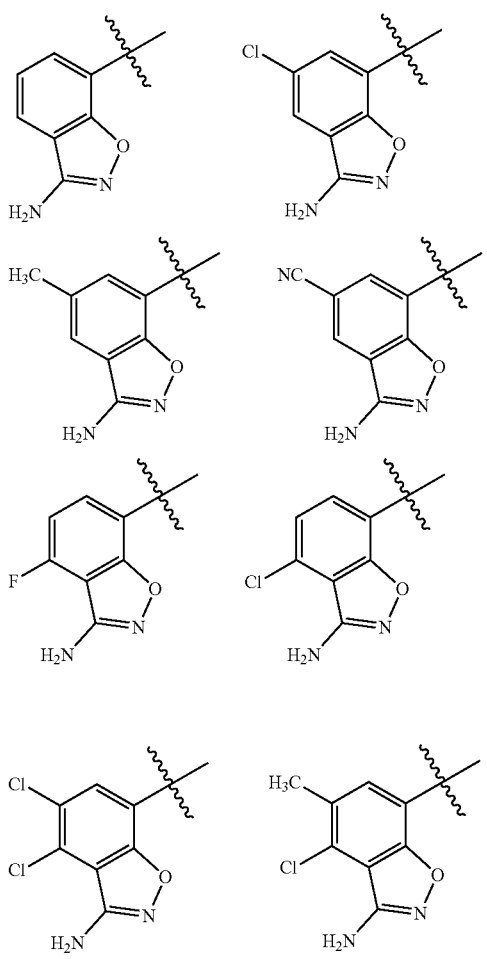

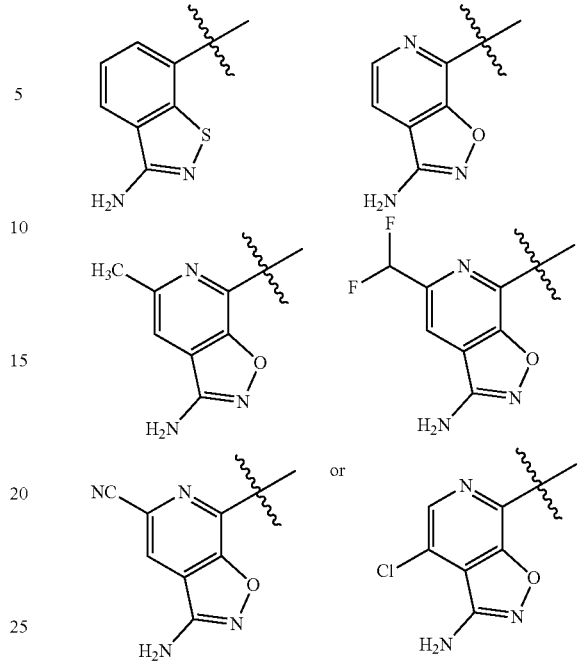

10. The compound of claim 1, or a pharmaceutically acceptable salt thereof, wherein: $R^1$ is a halogen atom, a cyano group, a $C_{1-6}$ alkyl group or a halogenated $C_{1-6}$ alkyl group.

11. The compound of claim 1, or a pharmaceutically acceptable salt thereof, wherein: $R^2$ is a hydroxyl group, a $C_{1-6}$ alkyl group or a $C_{6-14}$ aryl group.

12. The compound of claim 1, or a pharmaceutically acceptable salt thereof, wherein: $R^3$ is a halogen atom or a $C_{1-6}$ alkyl group.

13. The compound of claim 1, or a pharmaceutically acceptable salt thereof, wherein: $R^4$ is a cyano group, a $C_{1-6}$ alkyl group, a $C_{3-12}$ cycloalkyl group, a halogenated $C_{1-6}$ alkyl group, a hydroxy $C_{1-6}$ alkyl group, a $C_{1-6}$ alkoxy group or oxo.

14. The compound of claim 1, or a pharmaceutically acceptable salt thereof, which is:
N-(1-(3-Aminobenzo[d]isoxazol-7-yl)pyrrolidin-3-yl)-2-chloro-4-(4H-1,2,4-triazol-4-yl)benzamide;
N-(1-(3-Aminobenzo[d]isoxazol-7-yl)-3-methylpyrrolidin-3-yl)-2,6-dichloro-4-(4H-1,2,4-triazol-4-yl)benzamide;
N-(1-(3-Aminobenzo[d]isoxazol-7-yl)-3-phenylpyrrolidin-3-yl)-2,6-dichloro-4-(4H-1,2,4-triazol-4-yl)benzamide;
N-(1-(3-Aminobenzo[d]isothiazol-7-yl)pyrrolidin-3-yl)-2,6-dichloro-4-(4H-1,2,4-triazol-4-yl)benzamide;
N-(1-(3-Aminoisoxazolo[5,4-c]pyridin-7-yl)pyrrolidin-3-yl)-2-chloro-4-(4H-1,2,4-triazol-4-yl)benzamide;
N-(1-(3-Amino-5-methylbenzo[d]isoxazol-7-yl)pyrrolidin-3-yl)-2,6-dichloro-4-(3-methyl-1H-1,2,4-triazol-1-yl)benzamide;
N-((3R*,4S*)-1-(3-Aminobenzo[d]isoxazol-7-yl)-3,4-dimethylpyrrolidin-3-yl)-2,6-dichloro-4-(4H-1,2,4-triazol-4-yl)benzamide;
N-((3S*,4S*)-1-(3-Aminobenzo[d]isoxazol-7-yl)-4-hydroxypyrrolidin-3-yl)-2,6-dichloro-4-(4H-1,2,4-triazol-4-yl)benzamide;

(R)—N-(1-(3-Amino-4-chlorobenzo[d]isoxazol-7-yl)pyrrolidin-3-yl)-2-chloro-4-(4H-1,2,4-triazol-4-yl)benzamide;
(R)—N-(1-(3-Amino-5-chlorobenzo[d]isoxazol-7-yl)pyrrolidin-3-yl)-2-chloro-4-(4H-1,2,4-triazol-4-yl)benzamide;
(R)—N-(1-(3-Amino-4-chloroisoxazolo[5,4-c]pyridin-7-yl)pyrrolidin-3-yl)-2-chloro-4-(3-methyl-1H-1,2,4-triazol-1-yl)benzamide;
(R)—N-(1-(3-Amino-4-chloro-5-methylbenzo[d]isoxazol-7-yl)pyrrolidin-3-yl)-2-chloro-4-(4H-1,2,4-triazol-4-yl)benzamide;
(R)—N-(1-(3-Amino-4-fluorobenzo[d]isoxazol-7-yl)pyrrolidin-3-yl)-2-chloro-4-(4H-1,2,4-triazol-4-yl)benzamide;
(R)—N-(1-(3-Amino-4,5-dichlorobenzo[d]isoxazol-7-yl)pyrrolidin-3-yl)-2-chloro-4-(4H-1,2,4-triazol-4-yl)benzamide;
N-(1-(3-Amino-5-chlorobenzo[d]isoxazol-7-yl)-3-methylpyrrolidin-3-yl)-2-chloro-4-(3-methyl-1H-1,2,4-triazol-1-yl)benzamide;
(R)—N-(1-(3-Amino-5-chlorobenzo[d]isoxazol-7-yl)pyrrolidin-3-yl)-2-chloro-4-(3-(hydroxymethyl)-1H-1,2,4-triazol-1-yl)benzamide;
(R)—N-(1-(3-Amino-5-chlorobenzo[d]isoxazol-7-yl)pyrrolidin-3-yl)-2-chloro-4-(3-cyclopropyl-1H-1,2,4-triazol-1-yl)benzamide;
(R)—N-(1-(3-Amino-4-chlorobenzo[d]isoxazol-7-yl)pyrrolidin-3-yl)-2-fluoro-4-(1H-1,2,4-triazol-1-yl)benzamide;
(R)—N-(1-(3-Amino-4-chlorobenzo[d]isoxazol-7-yl)pyrrolidin-3-yl)-2-methyl-4-(1H-1,2,4-triazol-1-yl)benzamide;
(R)—N-(1-(3-Amino-4-chloroisoxazolo[5,4-c]pyridin-7-yl)pyrrolidin-3-yl)-2-chloro-4-(pyrimidin-5-yl)benzamide;
(R)—N-(1-(3-Amino-4-chloroisoxazolo[5,4-c]pyridin-7-yl)pyrrolidin-3-yl)-2-chloro-4-(2-methoxypyrimidin-5-yl)benzamide;
(R)—N-(1-(3-Amino-4-chloroisoxazolo[5,4-c]pyridin-7-yl)pyrrolidin-3-yl)-2-chloro-4-(2-cyanopyrimidin-5-yl)benzamide;
(R)—N-(1-(3-Amino-4-chlorobenzo[d]isoxazol-7-yl)pyrrolidin-3-yl)-2-chloro-4-(3-(2-hydroxyethyl)-1H-1,2,4-triazol-1-yl)benzamide;
(R)—N-(1-(3-Amino-4-chloroisoxazolo[5,4-c]pyridin-7-yl)pyrrolidin-3-yl)-2-chloro-4-(1H-1,2,4-triazol-1-yl)benzamide;
(R)—N-(1-(3-Amino-4-chlorobenzo[d]isoxazol-7-yl)pyrrolidin-3-yl)-2-chloro-4-(5-(hydroxymethyl)pyridin-3-yl)benzamide;
(R)—N-(1-(3-Amino-4-chlorobenzo[d]isoxazol-7-yl)pyrrolidin-3-yl)-2-chloro-4-(4-(2-hydroxyethyl)-1H-pyrazol-1-yl)benzamide;
(R)—N-(1-(3-Amino-4-chloroisoxazolo[5,4-c]pyridin-7-yl)pyrrolidin-3-yl)-2-chloro-4-(4-(2-hydroxyethyl)-1H-imidazol-1-yl)benzamide;
(R)—N-(1-(3-Amino-4-chloroisoxazolo[5,4-c]pyridin-7-yl)pyrrolidin-3-yl)-2-chloro-4-(3-(difluoromethyl)-4H-1,2,4-triazol-4-yl)benzamide;
(R)—N-(1-(3-Amino-4-chloroisoxazolo[5,4-c]pyridin-7-yl)pyrrolidin-3-yl)-4-(1H-benzo[d]imidazol-1-yl)-2-chlorobenzamide;
(R)—N-(1-(3-Amino-4-chloroisoxazolo[5,4-c]pyridin-7-yl)pyrrolidin-3-yl)-2-chloro-4-(pyridazin-4-yl)benzamide;
(R)—N-(1-(3-Amino-4-chloroisoxazolo[5,4-c]pyridin-7-yl)pyrrolidin-3-yl)-2-chloro-4-(5-(2-hydroxyethyl)pyridin-3-yl)benzamide;
(R)—N-(1-(3-Amino-4-chloroisoxazolo[5,4-c]pyridin-7-yl)pyrrolidin-3-yl)-2-chloro-4-(1H-imidazo[4,5-b]pyridin-1-yl)benzamide;
(R)—N-(1-(3-Amino-4-chloroisoxazolo[5,4-c]pyridin-7-yl)pyrrolidin-3-yl)-2-chloro-4-(pyrazin-2-yl)benzamide;
(R)—N-(1-(3-Amino-5-cyanobenzo[d]isoxazol-7-yl)pyrrolidin-3-yl)-2-chloro-4-(3-methyl-1H-1,2,4-triazol-1-yl)benzamide;
(R)—N-(1-(3-Amino-4-chloroisoxazolo[5,4-c]pyridin-7-yl)pyrrolidin-3-yl)-2-chloro-4-(6-oxo-1-(2,2,2-trifluoroethyl)-1, 6-dihydropyridin-3-yl)benzamide;
(R)—N-(1-(3-Amino-4-chloroisoxazolo[5,4-c]pyridin-7-yl)pyrrolidin-3-yl)-4-(4H-1,2,4-triazol-4-yl)benzamide;
(R)—N-(1-(3-Amino-4-chloroisoxazolo[5,4-c]pyridin-7-yl)pyrrolidin-3-yl)-2-chloro-4-(1-(difluoromethyl)-6-oxo-1, 6-dihydropyridin-3-yl)benzamide;
(R)-4-([1,2,4]Triazolo[4,3-a]pyridin-6-yl)-N-(1-(3-amino-4-chloroisoxazolo[5,4-c]pyridin-7-yl)pyrrolidin-3-yl)-2-chlorobenzamide;
(R)—N-(1-(3-Amino-5-(difluoromethyl)isoxazolo[5,4-c]pyridin-7-yl)pyrrolidin-3-yl)-2-chloro-4-(3-methyl-1H-1,2,4-triazol-1-yl)benzamide;
(R)—N-(1-(3-Amino-4-chloroisoxazolo[5,4-c]pyridin-7-yl)pyrrolidin-3-yl)-2-chloro-4-(1-methyl-6-oxo-1,6-dihydropyridazin-3-yl)benzamide;
(R)—N-(1-(3-Amino-5-cyanoisoxazolo[5,4-c]pyridin-7-yl)pyrrolidin-3-yl)-2-chloro-4-(3-methyl-1H-1,2,4-triazol-1-yl)benzamide;
(R)—N-(1-(3-Amino-5-methylisoxazolo[5,4-c]pyridin-7-yl)pyrrolidin-3-yl)-2-chloro-4-(4-(2-hydroxyethyl)-1H-1,2,3-triazol-1-yl)benzamide;
(R)—N-(1-(3-Amino-4-chloroisoxazolo[5,4-c]pyridin-7-yl)pyrrolidin-3-yl)-2-chloro-4-(3-(trifluoromethyl)-4H-1,2,4-triazol-4-yl)benzamide;
(R)—N-(1-(3-Amino-4-chloroisoxazolo[5,4-c]pyridin-7-yl)pyrrolidin-3-yl)-2-chloro-4-(1-methyl-2-oxo-1,2-dihydropyrimidin-5-yl)benzamide;
(R)—N-(1-(3-Amino-4-chloroisoxazolo[5,4-c]pyridin-7-yl)pyrrolidin-3-yl)-2-chloro-4-(1-methyl-5-oxo-1,5-dihydro-4H-1,2,4-triazol-4-yl)benzamide;
(R)—N-(1-(3-Amino-4-chloroisoxazolo[5,4-c]pyridin-7-yl)pyrrolidin-3-yl)-2-chloro-4-(5-oxo-1, 5-dihydro-4H-1,2,4-triazol-4-yl)benzamide;
(R)—N-(1-(3-Amino-4-chloroisoxazolo[5,4-c]pyridin-7-yl)pyrrolidin-3-yl)-2-chloro-4-(1-(2-hydroxyethyl)-5-oxo-1,5-dihydro-4H-1,2,4-triazol-4-yl)benzamide;
(R)—N-(1-(3-Amino-4-chloroisoxazolo[5,4-c]pyridin-7-yl)pyrrolidin-3-yl)-2-chloro-4-(9H-purin-9-yl)benzamide;
(R)—N-(1-(3-Amino-5-methylisoxazolo[5,4-c]pyridin-7-yl)pyrrolidin-3-yl)-2,6-dichloro-4-(1-methyl-5-oxo-1,5-dihydro-4H-1,2,4-triazol-4-yl)benzamide;
(R)—N-(1-(3-Amino-4-chloroisoxazolo[5,4-c]pyridin-7-yl)pyrrolidin-3-yl)-2-chloro-4-(5-oxo-1-(2,2,2-trifluoroethyl)-1,5-dihydro-4H-1,2,4-triazol-4-yl)benzamide;
(R)—N-(1-(3-Amino-4-chloroisoxazolo[5,4-c]pyridin-7-yl)pyrrolidin-3-yl)-2-chloro-4-(7H-purin-7-yl)benzamide;
(R)—N-(1-(3-Amino-4-chloroisoxazolo[5,4-c]pyridin-7-yl)pyrrolidin-3-yl)-3-chloro-5-(3-methyl-1H-1,2,4-triazol-1-yl)picolinamide or (R)—N-(1-(3-Amino-4-chlorobenzo[d]isoxazol-7-yl)pyrrolidin-3-yl)-2-chloro-4-(2-(hydroxymethyl)pyridin-4-yl)benzamide.

15. A pharmaceutical composition comprising at least one compound of claim 1, or a pharmaceutically acceptable salt thereof, and at least one pharmaceutically acceptable carrier.

16. A method of treating a thromboembolic disorder is selected from the group consisting of arterial cardiovascular thromboembolic disorders, venous cardiovascular thromboembolic disorders, thromboembolic disorders in the chambers of the heart, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis, comprising administering to a patient in need thereof a therapeutically effective amount of a compound of claim 1 or a pharmaceutically acceptable salt thereof.

17. The method of claim 16, further comprising administering to said patient at least one anticoagulant agent selected from the group consisting of a thrombin inhibitor, a thrombin receptor (PAR-1) antagonist, a factor VIIa inhibitor, factor VIIIa inhibitor, a factor IXa inhibitor different from the compound of claims 1-5, 6-15 and 16, a factor Xa inhibitor, a factor XIa inhibitor, TAFI or a fibrinogen inhibitor.

18. A pharmaceutical composition comprising:
a therapeutically effective amount of at least one compound of claim 1 or a pharmaceutically acceptable salt thereof, and at least one pharmaceutically acceptable carrier, and an effective amount of at least one agent which is: (a) an anticoagulant, (b) an anti-thrombin agent, (c) an anti-platelet agent, (d) a fibrinolytic, (e) a hypolipidemic agent, (f) an antihypertensive agent, and (g) an anti-ischemic agent.

19. A pharmaceutical composition comprising:
a therapeutically effective amount of at least one compound of claim 1 or a pharmaceutically acceptable salt thereof, and at least one pharmaceutically acceptable carrier, and an effective amount of at least one agent which is (a-1) warfarin, (a-2) heparin, (a-3) aprotinin, (a-4) synthetic pentasaccharide, (a-5) direct acting thrombin inhibitors, (a-6) a factor VIIa inhibitor, (a-7) a factor VIIIa inhibitor, (a-8) a second factor IXa inhibitor, (a-9) a factor Xa inhibitor, (a-10) a factor XIa inhibitor, (a-11) a thrombin inhibitor, (a-12) a TAFI, (a-13) a fibrinogen inhibitor, (b-1) a boroarginine derivative, (b-2) a boropeptide, (b-3) heparin, (b-4) hirudin, (b-5) argatroban, (c-1) a NSAID, (c-2) a IIb/IIIa antagonist, (c-3) a thromboxane-A2-receptor antagonist, (c-4) a thromboxane-A2-synthetase inhibitor, (c-5) a PDE-III inhibitor, (c-6) a PDE V inhibitor, (c-7) a ADP receptor antagonist, (c-8) an antagonist of the purinergic receptor P2Y1, (c-9) an antagonist of the purinergic receptor P2Y12, (d-1) tissue plasminogen activator (TPA, natural or recombinant) and modified forms thereof, (d-2) anistreplase, (d-3) urokinase, (d-4) streptokinase, (d-5) tenecteplase (TNK), (d-6) lanoteplase (nPA), (d-7) a factor VIIa inhibitor, (d-8) a PAI-I inhibitor, (d-9) an alpha-2-antiplasmin inhibitor, (d-10) an anisoylated plasminogen streptokinase activator complex, (e-1) a HMG-CoA reductase inhibitor, (e-2) a squalene synthetase inhibitor, (e-3) a fibrate, (e-4) a bile acid sequestrant, (e-5) an ACAT inhibitor, (e-6) a MTP inhibitor, (e-7) a lipooxygenase inhibitor, (e-8) a cholesterol absorption inhibitor, (e-9) a cholesterol ester transfer protein inhibitor, (f-1) an alpha adrenergic blocker, (f-2) a beta adrenergic blocker, (f-3) a calcium channel blocker, (f-4) a diuretics, (f-5) a renin inhibitor, (f-6) an angiotensin-converting enzyme inhibitor, (f-7) an angiotensin-II-receptor antagonist, (f-8) an ET receptor antagonist, (f-9) a Dual ET/AII antagonist, (f-10) a neutral endopeptidase inhibitors, (f-11) a vasopepsidase inhibitor, (g-1) a Class I agent, (g-2) a Class II agent, (g-3) a Class III agent, a (g-4) Class IV agent, (g-5) a K+ cannel opener, (g-6) an IKur inhibitor or (g-7) a cardiac glycoside.

20. A compound of the Formula (VII):

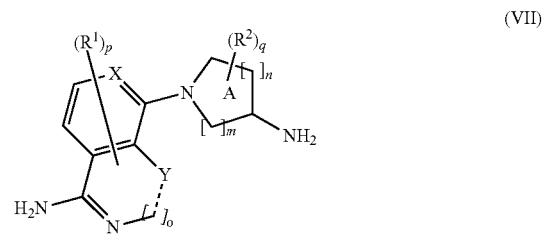

(VII)

or a pharmaceutically acceptable salt thereof; wherein:
m is an integer of 1 or 2; n is an integer of 1 or 2; o is an integer of 0 or 1; p is an integer of 0 to 5; q is an integer of 0 to 4; X is a nitrogen atom or CH; Y is an oxygen atom, a sulfur atom or NH (when o=0), Y is a nitrogen atom or CH (when o=1);
each $R^1$ is independently a halogen atom, a cyano group, a $C_{1-6}$ alkyl group, a halogenated $C_{1-6}$ alkyl group, a $C_{3-12}$ cycloalkyl group, a $C_{1-6}$ alkoxy group, a halogenated $C_{1-6}$ alkoxy group, a $C_{2-7}$ alkanoyl group, a $C_{1-6}$ alkylthio group, a $C_{1-6}$ alkylsulfonyl group or a group of —$NR^A R^B$;
$R^A$ and $R^B$ are each independently a hydrogen atom, a $C_{1-6}$ alkyl group or a $C_{2-7}$ alkanoyl group;
each $R^2$ is independently a hydroxyl group, a $C_{1-6}$ alkyl group, a halogenated $C_{1-6}$ alkyl group, a hydroxyl $C_{1-6}$ alkyl group, a $C_{1-6}$ alkoxy group, a halogenated $C_{1-6}$ alkoxy group, a $C_{6-14}$ aryl group, a heteroaryl group or oxo;
a dotted line in a substructure of a bicycle represented by Formula (II):

(II)

represents a single bond when o=0 or a double bond when o=1.

* * * * *